US006906046B2

(12) United States Patent
Jackson et al.

(10) Patent No.: US 6,906,046 B2
(45) Date of Patent: Jun. 14, 2005

(54) PHARMACEUTICAL USES AND SYNTHESIS OF BENZOBICYCLOOCTANES

(75) Inventors: Randy W. Jackson, Snohomish, WA (US); Ihab Darwish, Seattle, WA (US); Ted A. Baughman, Bothell, WA (US); J. Jeffry Howbert, Bellevue, WA (US)

(73) Assignee: Celltech R & D Inc., Bothell, WA (US)

( * ) Notice: Subject to any disclaimer, the term of this patent is extended or adjusted under 35 U.S.C. 154(b) by 61 days.

(21) Appl. No.: 10/015,828

(22) Filed: Dec. 11, 2001

(65) Prior Publication Data

US 2003/0069305 A1 Apr. 10, 2003

Related U.S. Application Data

(60) Provisional application No. 60/257,532, filed on Dec. 22, 2000.

(51) Int. Cl.$^7$ .................................................. C07F 7/02
(52) U.S. Cl. ..................... 514/63; 514/511; 544/155; 544/159; 544/380; 544/391; 546/285; 546/342; 548/127; 548/247; 548/537; 548/538; 548/573; 549/214; 556/404; 556/415; 556/418; 556/423; 556/440; 560/10; 560/36; 562/441
(58) Field of Search .................... 514/63, 511; 544/155, 544/159, 380, 391; 546/285, 342; 548/127, 247, 537, 538, 573; 549/214; 556/404, 415, 418, 423, 440; 560/10, 36; 562/441

(56) References Cited

U.S. PATENT DOCUMENTS

| | | | |
|---|---|---|---|
| 3,949,987 A | 4/1976 | Candor | |
| 4,655,451 A | 4/1987 | Townsley | |
| 4,666,157 A | 5/1987 | Bodine et al. | |
| 4,698,363 A | 10/1987 | Hart | 514/530 |
| 5,403,953 A | 4/1995 | de Nanteuil et al. | 562/466 |
| 5,558,333 A | 9/1996 | Kelson et al. | |
| 5,645,499 A | 7/1997 | Lewis | |
| 5,674,905 A | 10/1997 | Kalindjian et al. | 514/616 |
| 5,710,159 A | 1/1998 | Voss et al. | 514/275 |
| 5,739,163 A | 4/1998 | Cain et al. | 514/539 |
| 5,779,566 A | 7/1998 | Wilens | |
| 5,849,736 A | 12/1998 | Wityak et al. | 514/227.8 |
| 5,882,269 A | 3/1999 | Lewis | |
| 6,147,224 A | 11/2000 | Vuligonda et al. | 548/518 |
| 6,211,171 B1 | 4/2001 | Sawynok et al. | 514/211.13 |

OTHER PUBLICATIONS

Database CAPLUS on STN, Acc. No. 1970:414534, Takeda et al., Tetrahedron (1970), 26(6), p. 1435–51 (CAPLUS abstract).*

Database CAPLUS on STN, Acc. No. 1970:414534,Takeda et al, Tetrahedron (1970), 26(6), p. 1435–51 (abstract).*

Jackson, "A mild and selective method for the cleavage of tert–butyl esters," *Tetrahedron Letters* 42(31):5163–5165, Jul. 30, 2001.

Hagishita et al., "Optical Activity by βΓ–Unsaturated Ketones. Part 1. Effect of the Direction of the Electric Tansition Dipole Moment in the Aromatic Group in Benzobicyclo[2.2.2]ocen–2–one t Derivatives," *Journal of the Chemical Society Perkin Transactions* 2(14):1937–1941, 1977.

Karlsson et al., "Biosensor Analysis of Drug–Target Interactions: Direct and Competitive Binding Assays for Investigation of Interactions between Thrombin and Thrombin Inhibitors," *Anaylytical Biochemmistry* 278:1–13, 2000.

Shimizu et al., "High–performance affinity beads for identifying drup receptors," *Nature Biotechnology* 18(8):877–881, Aug. 2000.

Singh et al., "9,10–[1,4–Dihydrosubstituted–naphthalene–2–oxo–endo/exo–1,4–diyl]–N–arylsuccinimide : Congifurational Assignment by Pmr Spectroscopy," *Journal of the Indian Chemical Society* 67:818–820, Oct. 1990.

Takeda et al., "Diels–Alder Reaction. IX. Reaction of the 1,7–, 2,7–, 2,6– and 1,6–dihydroxynaphthalene and 6–bromo–2–naphthol with maleic anhydride and the resolution of some derivatives of the adducts," *Tetrahedron* 26:1435–1451, 1970.

Takeda et al., "Studies on Bis–quaternary Ammonium Salts of the Dibenzobicycol(2.2.2)octadienopyrrolidine Series. Part 1. Synthesis," *Shionogi Kenkyusho Nempo* 15:53–59, 1965.

Van Broeck et al., "Smooth Generation of 3H–2–Benzopyran–3–ones and their Diesl–Alder Reactions with Olefinic Dienophiles," *Journal of the Chemical Society, Perkin Transactions 1* 3:639–644, 1991.

* cited by examiner

*Primary Examiner*—Brian Davis
(74) *Attorney, Agent, or Firm*—Jane E. Rotter; Davis Wright Tremaine LLP

(57) ABSTRACT

Benzobicyclooctane compounds, their use in inhibiting cellular events involving TNF-α and IL-8, and in the treatment of inflammation events in general; a combinatorial library of diverse bicyclooctanes and process for their synthesis as a library and as individual compounds.

82 Claims, No Drawings

US 6,906,046 B2

PHARMACEUTICAL USES AND SYNTHESIS OF BENZOBICYCLOOCTANES

This application claims the benefit of U.S. Provisional Patent Application No. 60/257,532, filed Dec. 22, 2000, where this provisional application is incorporated herein by reference in its entirety.

TECHNICAL FIELD

The present invention is generally directed to benzobicyclooctanes, their use in inhibiting cellular events involving TNF-α or IL-8, and in the treatment of inflammation events in general; the application also provides a combinatorial library of diverse bicyclooctanes and methods for their synthesis in a library format as well as individual compounds.

BACKGROUND OF THE INVENTION

One process for discovering new therapeutically active compounds for a given indication involves the screening of all compounds from available compound collections. From the compounds tested, one or more structures is selected as a promising lead. A large number of related analogues are then synthesized in order to develop a structure-activity relationship (SAR). The SARs direct the development and then selection of one or more optimal compounds following traditional one-at-a-time synthesis and biological testing. This optimization process is long and labor intensive.

Adding significant numbers of new structures to the compound collections used in this initial screening step of the discovery and optimization process cannot be accomplished with traditional one-at-a-time synthesis methods, except over a time frame of months or even years. Faster methods are needed that allow for the preparation of libraries of related compounds in a matter of days or a few weeks. This need is particularly apparent when it comes to synthesizing more complex compounds.

Combinatorial approaches have recently been extended to "organic" or non-peptide, libraries. The organic libraries at present, however, are limited in diversity and generally relate to peptidomimetic compounds; in other words, organic molecules that repeat a peptide chain pharmacophore. There is a need in the art for additional approaches to the preparation of new organic libraries.

Cytokines are pleiotropic extracellular proteins that are released and recognized by a wide variety of cell types. Via a series of complex interactions they are responsible for regulating many of the events involved in growth and differentiation of an organism. Among the cytokines, tumor necrosis factor-α (TNF-α) has been shown to play an important role in the genesis of certain chronic inflammatory and autoimmune diseases. TNF-α is secreted mainly by macrophages and monocytes in response to a variety of inflammatory agents. Other cell types such as NK cells, T cells, B cells, Kupfer cells, and glial cells also produce TNF-α.

TNF-α is synthesized as an inactive 26 kDa pro-protein which is cleaved by the metalloprotease TNF-α Converting Enzyme (TACE) to afford the active 17 kDa cytokine protein. The cytokine exerts its biological effects by interacting with two high affinity receptors of molecular weights 55 kDa (TNFR1 or p55) and 75 kDa (TNFR2 or p75) found on the surface of most cell types. As a result of TNF-α binding to its receptors, a cascade of signaling events occurs within the cell. The exact nature and sequence of events is dependent upon cell type and receptor. Two of the most important physiological effects of TNF-α binding to its receptors are the upregulation of new genes by activation of the transcription factor NFκB, and induction of programmed cell death or apoptosis.

Apoptosis is a normal physiological process whereby incompetent cells become targeted for disposal by the immune system. The process involves a series of morphological changes to the apoptotic cell, including a change of surface chemistry. This change in surface chemistry is recognized by macrophages that rapidly phagocytose the cell. A number of stimuli can induce apoptosis, including DNA damage, UV radiation, growth factor deprivation, bacterial and viral infection, and ligation of cell surface receptors. TNF-α has been shown to induce apoptosis by binding to TNFR1. Under normal biochemical circumstances the process of apoptosis is integral in regulating the homeostatic balance between cell death and cell proliferation. However in many autoimmune diseases this balance is shifted; not only do unwanted cells undergo apoptosis but healthy cells as well. These diseases are often associated with increased levels of TNF-α. There is a need in the art for compounds that can modulate binding of TNF-α to cell receptors, and/or modulate the consequential intracellular events.

Transcription factors are a family of proteins that bind to DNA and serve to upregulate gene expression. Often they remain in an inactive form until acted upon by a biochemical signal. One such transcription factor is nuclear factor kappa B (NFκB), which can be activated by the binding of TNF-α to TNFR1 and/or TNFR2. NFκB regulates many of the cytokines and other proinflammatory molecules associated with inflammatory and autoimmune diseases. Classes of proteins subject to regulation by NFκB and which have been demonstrated to be involved with disease states are cytokines and growth factors, adhesion molecules, chemokines, and immunoreceptors.

The inhibition of TNF-α induced apoptosis and of NFκB activation is one means of preventing and/or treating autoimmune and inflammatory diseases including, but not limited to, rheumatoid arthritis, inflammatory bowel disease, psoriasis, atherosclerosis, asthma, reperfusion injury, ischemia, sepsis, graft vs. host disease, adult respiratory distress syndrome, multiple sclerosis, and a host of severe invasive infections such as fulminant hepatitis, AIDS and bacterial meningitis, and allergic inflammation of the lungs and airways.

Interleukin-8 (IL-8) is a chemokine (chemotactic cytokine) which plays an important role in the recruitment of neutrophils to sites of inflammation. It is a member of the CXC subfamily of chemokines, members of which contain a single amino acid residue between the first two cysteines. In addition to inducing the chemotaxis of neutrophils, IL-8 exerts other immunomodulatory effects such as release of superoxide, mobilization of intracellular Ca++, upregulation of cell surface integrins, and activation of phospholipase D. All of these cellular events are the result of IL-8 binding to one of its two high affinity receptors. The two receptors, known as IL8RA or CXCR1 and IL8RB or CXCR2, bind the ligand with a $K_d$ of ca. 2 nM.

Numerous reports in the literature have associated increased levels of IL-8 with the development of inflammatory and autoimmune diseases such as Inflammatory Bowel Disease (IBD), psoriasis, rheumatoid arthritis, Acute Respiratory Distress Syndrome (ARDS), cancer, atherosclerosis, reperfusion injury, and graft vs. host disease. The inhibition of IL-8 or other CXC chemokines from binding to CXCR1 and/or CXCR2 receptors is one means of preventing and/or treating these diseases.

Although treatment regimens are available for the symptomatic amelioration of some or all of these diseases, there still exists the need for compositions and methods for preventing and/or treating the inflammation which is often associated with the disease.

The present invention satisfies these needs and provides related advantages as well, as described more fully herein.

SUMMARY OF THE INVENTION

The present invention overcomes the known limitations to classical organic synthesis of bicyclooctanes, and the shortcomings in applying combinatorial chemistry to bicyclooctanes, as well as providing compounds which are useful in inhibiting TNF-α, IL-8, apoptotic-mediated processes, and inflammatory conditions. Moreover, the present invention provides a library of diverse bicyclooctanes useful in elucidating the structure-function relationship in biological processes, such as inflammation.

In one embodiment, the present invention provides a compound of formula (I)

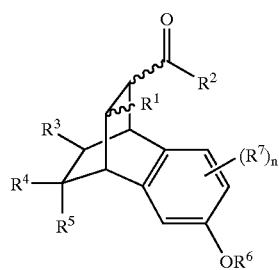

(I)

and optical isomers, diastereomers, enantiomers and pharmaceutically acceptable salts thereof in isolation or mixture, where, independently at each location:

$R^1$ is selected from the following six formulae:

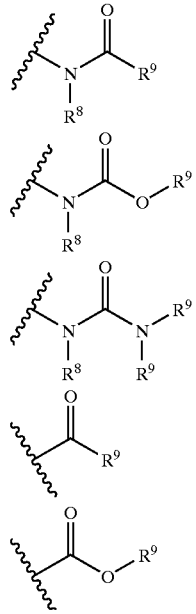

$R^2$ is —$OR^9$ or —$NR^9R^9$;

$R^3$ is selected from hydrogen, halogen, hydroxyl or protected hydroxyl, amino or protected amino, and $C_1$–$C_8$alkyl or $C_1$–$C_8$haloalkyl;

$R^4$ and $R^5$ are independently selected from $R^9$, —$OR^9$, —$NR^9R^9$ and —$N$=$N$—$R^9$, or $R^4$ and $R^5$ may together form a group selected from =O, =$CR^8R^8$ and =$NR^{10}$, or $R^4$ and $R^5$ may together with the carbon to which they are both attached form a spiro carbocyclic or heterocyclic ring;

$R^6$ is selected from hydrogen, inorganic groups having 1–8 atoms exclusively selected from boron, sulfur, phosphorous, silicon and hydrogen, and organic groups having 1–20 carbons and optionally containing 1–4 heteroatoms selected from nitrogen, oxygen and silicon;

$R^7$ is selected from halogen, hydroxyl or protected hydroxyl, amino or protected amino, and $C_1$–$C_8$alkyl or $C_1$–$C_8$haloalkyl;

$R^8$ is selected from hydrogen, alkyl, aryl and heteroalkyl;

$R^9$ is selected from hydrogen and organic groups having 1–30 carbons and optionally containing 1–4 heteroatoms selected from nitrogen, oxygen and silicon, with the provision that two $R^9$ groups both joined to a common atom may be joined together so as to form a ring with the common atom;

$R^{10}$ is selected from —$R^9$, —$OR^9$, —$NR^9R^9$, —NH—C(O)$R^9$; —NH—C(O)$OR^9$ and —NH—C(S)NH$R^9$; and n is 0, 1, 2 or 3;

with the proviso that when $R^6$ is hydrogen and $R^4$ and $R^5$ together form =O and $R^1$ is $CO_2R^9$, then $R^2$ is not $OCH_3$.

In one embodiment $R^1$ is

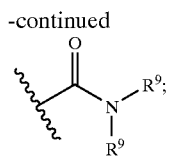

In one embodiment $R^1$ is

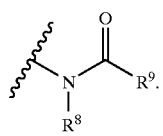

In one embodiment $R^1$ is

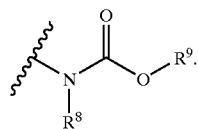

In one embodiment $R^1$ is

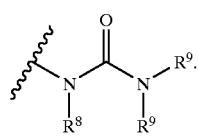

In any of the above embodiments, $R^8$ is, in one embodiment, selected from hydrogen and $C_1$–$C_8$ alkyl. In a further embodiment, $R^8$ is hydrogen.

In one embodiment R$^1$ is

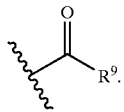

In one embodiment R$^1$ is

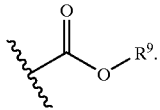

In one embodiment R$^1$ is

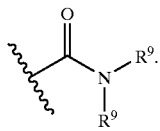

In one embodiment, R$^1$ is selected from the following five formulae:

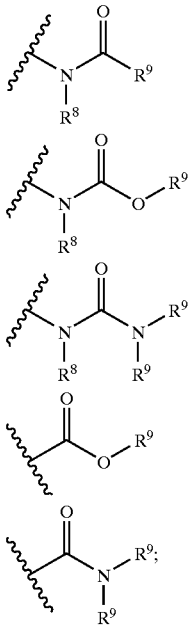

In one embodiment R$^1$ is selected from the following four formulae:

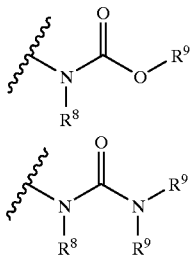

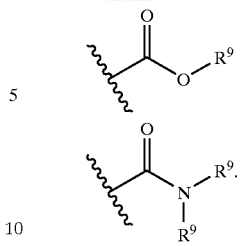

In any of the above embodiments, in a further embodiment, R$^9$ is independently selected at each occurrence from hydrogen, R$^{11}$, R$^{12}$, R$^{13}$, R$^{14}$ and R$^{15}$ where R$^{11}$ is selected from alkyl, heteroalkyl, aryl and heteroaryl; R$^{12}$ is selected from (R$^{11}$)$_p$-alkylene, (R$^{11}$)$_p$-heteroalkylene, (R$^{11}$)$_p$-arylene and (R$^{11}$)$_p$-heteroarylene; R$^{13}$ is selected from (R$^{12}$)$_p$-alkylene, (R$^{12}$)$_p$-heteroalkylene, (R$^{12}$)$_p$-arylene, and (R$^{12}$)$_p$-heteroarylene; R$^{14}$ is selected from (R$^{13}$)$_p$-alkylene, (R$^{13}$)$_p$-heteroalkylene, (R$^{13}$)$_p$-arylene, and (R$^{13}$)$_p$-heteroarylene, R$^{15}$ is selected from (R$^{14}$)$_p$-alkylene, (R$^{14}$)$_p$-heteroalkylene, (R$^{14}$)$_p$-arylene, and (R$^{14}$)$_p$-heteroarylene, and p is selected from 0, 1, 2, 3, 4 and 5, with the provision that two R$^9$ groups both joined to a common atom may be joined together so as to form a ring with the common atom.

In any of the above embodiments, in a further embodiment, R$^9$ is independently selected at each occurrence from R$^{11}$, R$^{12}$, R$^{13}$, R$^{14}$ and R$^{15}$ where R$^{11}$ is selected from alkyl, heteroalkyl, aryl and heteroaryl; R$^{12}$ is selected from (R$^{11}$)$_p$-alkylene, (R$^{11}$)$_p$-heteroalkylene, (R$^{11}$)$_p$-arylene and (R$^{11}$)$_p$-heteroarylene; R$^{13}$ is selected from (R$^{12}$)$_p$-alkylene, (R$^{12}$)$_p$-heteroalkylene, (R$^{12}$)$_p$-arylene, and (R$^{12}$)$_p$-heteroarylene; R$^{14}$ is selected from (R$^{13}$)$_p$-alkylene, (R$^{13}$)$_p$-heteroalkylene, (R$^{13}$)$_p$-arylene, and (R$^{13}$)$_p$-heteroarylene, R$^{15}$ is selected from (R$^{14}$)$_p$-alkylene, (R$^{14}$)$_p$-heteroalkylene, (R$^{14}$)$_p$-arylene, and (R$^{14}$)$_p$-heteroarylene, and p is selected from 0, 1, 2, 3, 4 and 5.

In any of the above embodiments, in a further embodiment, R$^9$ is selected from hydrogen, heteroalkyl, C$_1$–C$_{15}$alkyl, (heteroaryl)C$_1$–C$_{15}$alkylene, (C$_6$–C$_{10}$aryl)C$_1$–C$_{15}$alkylene, C$_6$–C$_{10}$aryl fused to C$_1$–C$_{15}$alkylene, (alkyl)$_p$(C$_6$–C$_{10}$arylene)C$_1$–C$_{15}$alkylene, (C$_6$–C$_{10}$aryl)(C$_6$–C$_{10}$arylene)C$_1$–C$_{15}$alkylene, (C$_1$–C$_{15}$alkyl)$_p$(heteroarylene)C$_1$–C$_{15}$alkylene, and (heteroalkyl)$_p$(C$_6$–C$_{10}$arylene)C$_1$–C$_{15}$alkylene, or two R$^9$ groups bonded to a common nitrogen of R$^1$ may be joined together to form a 5–8 membered heterocycle including the common nitrogen, where this 5–8 membered heterocycle may be substituted with 0–5 groups selected from alkyl and heteralkyl, where p is selected from 1, 2, 3, 4 and 5.

In any of the above embodiments, in a further embodiment, R$^9$ is selected from hydrogen, heteroalkyl, C$_1$–C$_{15}$alkyl, (C$_6$–C$_{10}$aryl)C$_1$–C$_{15}$alkylene, (heteroaryl)C$_1$–C$_{15}$alkylene, and (heteroalkyl)$_p$(C$_6$–C$_{10}$arylene)C$_1$–C$_{15}$alkylene, or the two R$^9$ groups joined to a common nitrogen of R$^1$ may be joined together to form a 5–8 membered heterocycle including the common nitrogen.

In any of the above embodiments, in a further embodiment, R$^9$ is selected from heteroalkyl, C$_1$–C$_{15}$alkyl, (C$_6$–C$_{10}$aryl)C$_1$–C$_{15}$alkylene, (C$_6$–C$_{10}$aryl)(C$_6$–C$_{10}$arylene)C$_1$–C$_{15}$alkylene, (C$_1$–C$_{15}$alkyl)$_p$(heteroarylene)C$_1$–C$_{15}$alkylene, and C$_6$–C$_{10}$aryl fused to C$_1$–C$_{15}$alkylene.

In any of the above embodiments, in a further embodiment, R$^9$ is selected from hydrogen, heteroalkyl, C$_1$–C$_{15}$alkyl, (C$_6$–C$_{10}$aryl)C$_1$–C$_{15}$alkylene, (C$_6$–C$_{10}$aryl)

($C_6$–$C_{10}$arylene)$C_1$–$C_{15}$alkylene, ($C_1$–$C_{15}$alkyl)$_p$(heteroarylene)$C_1$–$C_{15}$alkylene, and $C_6$–$C_{10}$aryl fused to $C_1$–$C_{15}$alkylene.

In any of the above embodiments, in a further embodiment, $R^9$ is selected from hydrogen, heteroalkyl, $C_1$–$C_{15}$alkyl, (heteroaryl)$C_1$–$C_{15}$alkylene, and (heteroalkyl)$_p$($C_6$–$C_{10}$arylene)$C_1$–$C_{15}$alkylene.

In any of the above embodiments, in a further embodiment, $R^9$ is selected from hydrogen, heteroalkyl, $C_1$–$C_{15}$alkyl, (heteroaryl)$C_1$–$C_{15}$alkylene, ($C_6$–$C_{10}$aryl)$C_1$–$C_{15}$alkylene, (alkyl)$_p$($C_6$–$C_{10}$arylene)$C_1$–$C_{15}$alkylene, or the two $R^9$ groups of $R^1$ may be joined together to form a 5–8 membered heterocycle including the common nitrogen, where this 5–8 membered heterocycle may be substituted with 0–5 groups selected from alkyl and heteralkyl.

In any of the above embodiments, in a further embodiment, $R^2$ is —$OR^9$.

In any of the above embodiments, in a further embodiment, $R^2$ is —$NR^9R^9$.

In any of the above embodiments, in a further embodiment, $R^9$ of $R^2$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from ($R^{11}$)$_p$-alkylene, ($R^{11}$)$_p$-heteroalkylene, ($R^{11}$)$_p$-arylene and ($R^{11}$)$_p$-heteroarylene; $R^{13}$ is selected from ($R^{12}$)$_p$-alkylene, ($R^{12}$)$_p$-heteroalkylene, ($R^{12}$)$_p$-arylene, and ($R^{12}$)$_p$-heteroarylene; $R^{14}$ is selected from ($R^{13}$)$_p$-alkylene, ($R^{13}$)$_p$-heteroalkylene, ($R^{13}$)$_p$-arylene, and ($R^{13}$)$_p$-heteroarylene, $R^{15}$ is selected from ($R^{14}$)$_p$-alkylene, ($R^{14}$)$_p$-heteroalkylene, ($R^{14}$)$_p$-arylene, and ($R^{14}$)$_p$-heteroarylene, and p is selected from 0, 1, 2, 3, 4 and 5.

In any of the above embodiments, in a further embodiment, $R^9$ of $R^2$ is selected from hydrogen, heteroalkyl, $C_1$–$C_{15}$alkyl, ($C_6$–$C_{10}$aryl)($C_6$–$C_{10}$arylene)$C_1$–$C_{15}$alkylene, ($C_1$–$C_{15}$alkyl)$_p$(heteroarylene)$C_1$–$C_{15}$alkylene, ($C_1$–$C_{15}$alkyl)$_p$(heteroarylene)-heteroalkylene, (heteroalkyl)$_p$($C_6$–$C_{10}$arylene)$C_1$–$C_{15}$alkylene, and ($C_1$–$C_{15}$alkyl)$_p$($C_6$–$C_{10}$arylene)heteroalkylene.

In any of the above embodiments unless otherwise inconsistent with a previous definition, in a further embodiment $R^2$ is —$OR^9$ where $R^9$ is selected from a heteroalkyl group having preferably 1–10 carbons and 1–4 heteroatoms selected from nitrogen, oxygen, silicon and sulfur.

In any of the above embodiments unless otherwise inconsistent with a previous definition, in a further embodiment $R^2$ is —$NR^9R^9$ and $R^9$ is selected from hydrogen, heteroalkyl, $C_1$–$C_{15}$alkyl, (heteroaryl)$C_1$–$C_{15}$alkylene, (heteroalkyl)$_p$(aryl)-heteroalkylene, (heteroalkyl)$_p$(aryl)$C_1$–$C_{15}$alkylene, and ($C_1$–$C_{15}$alkyl)$_p$($C_6$–$C_{10}$arylene)$C_1$–$C_{15}$alkylene.

In any of the above embodiments, in a further embodiment, $R^3$ is selected from hydrogen and alkyl.

In any of the above embodiments, in a further embodiment, $R^3$ is hydrogen.

In any of the above embodiments, in a further embodiment, $R^4$ and $R^5$ are independently selected from $R^9$, —$OR^9$, —$NR^9R^9$ and —N=N—$R^9$.

In any of the above embodiments, in a further embodiment, $R^9$ of $R^4$ and $R^5$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from ($R^{11}$)$_p$-alkylene, ($R^{11}$)$_p$-heteroalkylene, ($R^{11}$)$_p$-arylene and ($R^{11}$)$_p$-heteroarylene; $R^{13}$ is selected from ($R^{12}$)$_p$-alkylene, ($R^{12}$)$_p$-heteroalkylene, ($R^{12}$)$_p$-arylene, and ($R^{12}$)$_p$-heteroarylene; $R^{14}$ is selected from ($R^{13}$)$_p$-alkylene, ($R^{13}$)$_p$-heteroalkylene, ($R^{13}$)$_p$-arylene, and ($R^{13}$)$_p$-heteroarylene, $R^{15}$ is selected from ($R^{14}$)$_p$-alkylene, ($R^{14}$)$_p$-heteroalkylene, ($R^{14}$)$_p$-arylene, and ($R^{14}$)$_p$-heteroarylene, and p is selected from 0, 1, 2, 3, 4 and 5.

In any of the above embodiments, in a further embodiment, each of $R^4$ and $R^5$ is hydrogen.

In any of the above embodiments unless otherwise inconsistent with a previous definition, in a further embodiment, at least one of $R^4$ and $R^5$ is selected from $C_1$–$C_{15}$alkyl, heteroalkyl, and $C_6$–$C_{10}$aryl.

In any of the above embodiments unless otherwise inconsistent with a previous definition, in a further embodiment, one of $R^4$ and $R^5$ is hydrogen and the other of $R^4$ and $R^5$ is selected from hydrogen, —$OR^9$, —$NR^9R^9$ and —N=N—$R^9$ where the $R^9$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from ($R^{11}$)$_p$-alkylene, ($R^{11}$)$_p$-heteroalkylene, ($R^{11}$)$_p$-arylene and ($R^{11}$)$_p$-heteroarylene; $R^{13}$ is selected from ($R^{12}$)$_p$-alkylene, ($R^{12}$)$_p$-heteroalkylene, ($R^{12}$)$_p$-arylene, and ($R^{12}$)$_p$-heteroarylene; $R^{14}$ is selected from ($R^{13}$)$_p$-alkylene, ($R^{13}$)$_p$-heteroalkylene, ($R^{13}$)$_p$-arylene, and ($R^{13}$)$_p$-heteroarylene, $R^{15}$ is selected from ($R^{14}$)$_p$-alkylene, ($R^{14}$)$_p$-heteroalkylene, ($R^{14}$)$_p$-arylene, and ($R^{14}$)$_p$-heteroarylene, and p is selected from 0, 1, 2, 3, 4 and 5.

In any of the above embodiments unless otherwise inconsistent with a previous definition. in a further embodiment, $R^4$ and $R^5$ together form a group selected from =O, =$CR^8R^8$ and =$NR^{10}$.

In any of the above embodiments unless otherwise inconsistent with a previous definition, in a further embodiment $R^4$ and $R^5$ together form =O.

In any of the above embodiments unless otherwise inconsistent with a previous definition, in a further embodiment $R^4$ and $R^5$ together form =$NR^{10}$ and $R^{10}$ is —$OR^9$ where $R^9$ is selected from hydrogen, $C_6$–$C_{10}$aryl, $C_1$–$C_8$alkyl, heteroalkyl, ($C_6$–$C_{10}$aryl)heteroalkyl, ($C_6$–$C_{10}$aryl)$C_1$–$C_{15}$alkylene, (heteroalkyl)$_p$(heteroarylene)$C_1$–$C_{15}$alkylene, (heteroalkyl)$_p$($C_6$–$C_{10}$arylene)$C_1$–$C_{15}$alkylene, and ($C_1$–$C_{15}$alkyl)$_p$($C_6$–$C_{10}$arylene)heteroalkylene.

In any of the above embodiments unless otherwise inconsistent with a previous definition, in a further embodiment $R^4$ and $R^5$ together form =$NR^{10}$ and $R^{10}$ is —$N(R^9)(R^9)$ where $R^9$ is selected from hydrogen, $C_1$–$C_8$alkyl, heteroalkyl, $C_6$–$C_{10}$aryl, ($C_6$–$C_{10}$aryl)heteroalkylene, (heteroalkyl)$_p$$C_6$–$C_{10}$arylene, ($C_1$–$C_{15}$alkyl)$_p$$C_6$–$C_{10}$arylene, (heteroalkyl)$_p$($C_6$–$C_{10}$arylene)heteroalkylene, ($C_1$–$C_{15}$alkyl)$_p$($C_6$–$C_{10}$arylene)$C_1$–$C_{15}$alkylene, and ($C_1$–$C_{15}$alkyl)$_p$($C_6$–$C_{10}$arylene)$C_1$–$C_{15}$heteroalkylene.

In any of the above embodiments unless otherwise inconsistent with a previous definition, in a further embodiment $R^4$ and $R^5$ together form =$CR^8R^8$, and one of $R^8$ is hydrogen while the other $R^8$ is selected from hydrogen, $C_1$–$C_8$alkyl and heteroalkyl.

In any of the above embodiments unless otherwise inconsistent with a previous definition, in a further embodiment $R^8$ is selected from hydrogen and $C_1$–$C_8$alkyl, and $R^{10}$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from ($R^{11}$)$_p$-alkylene, ($R^{11}$)$_p$-heteroalkylene, ($R^{11}$)$_p$-arylene and ($R^{11}$)$_p$-heteroarylene; $R^{13}$ is selected from ($R^{12}$)$_p$-alkylene, ($R^{12}$)$_p$-heteroalkylene, ($R^{12}$)$_p$-arylene, and ($R^{12}$)$_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R\ 4)_p$-arylene, and $(R^{14})_p$-heteroarylene, and p is selected from 0, 1, 2, 3, 4 and 5.

In any of the above embodiments unless otherwise inconsistent with a previous definition, in a further embodiment $R^8$ is hydrogen.

In any of the above embodiments unless otherwise inconsistent with a previous definition, in a further embodiment $R^{10}$ is $R^{11}$.

In any of the above embodiments unless otherwise inconsistent with a previous definition, in a further embodiment $R^4$ and $R^5$ together with the carbon to which they are both attached form a spiro carbocyclic or heterocyclic ring.

In any of the above embodiments unless otherwise inconsistent with a previous definition, in a further embodiment $R^6$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5.

In any of the above embodiments unless otherwise inconsistent with a previous definition, in a further embodiment $R^6$ is selected from $C_1$–$C_{15}$alkyl, $C_1$–$C_{15}$heteroalkyl, $(C_6$–$C_{10}$aryl)$C_1$–$C_{15}$alkylene, $(C_6$aryl)($C_6$aryl)$C_1$–$C_{15}$alkylene, $(C_2$–$C_6$heteroaryl)$C_1$–$C_{15}$alkylene, $(C_6$–$C_{10}$aryl)$C_1$–$C_{15}$heteroalkylene, (heteroalkyl)$_p$ $(C_6$–$C_{10}$arylene)$C_1$–$C_{15}$alkylene, (heteroalkyl)$_p$ $(C_2$–$C_6$heteroarylene)$C_1$–$C_{15}$alkylene, and (heteroalkyl)$_p$ $(C_6$arylene)(heteroalkylene)($C_6$arylene)$C_1$–$C_{15}$alkylene.

In any of the above embodiments unless otherwise inconsistent with a previous definition, in a further embodiment $R^6$ is an inorganic group having 1–8 atoms exclusively selected from boron, sulfur, phosphorous, silicon and hydrogen. Separately, in any of the above embodiments, $R^6$ excludes inorganic group having 1–8 atoms exclusively selected from boron, sulfur, phosphorous, silicon and hydrogen.

In any of the above embodiments unless otherwise inconsistent with a previous definition, in a further embodiment $R^6$ is hydrogen.

In any of the above embodiments unless otherwise inconsistent with a previous definition, in a further embodiment n is 0.

In any of the above embodiments unless otherwise inconsistent with a previous definition, in a further embodiment n is 1.

In any of the above embodiments unless otherwise inconsistent with a previous definition, in a further embodiment $R^3$ is hydrogen; $R^4$ and $R^5$ are selected from (a) $R^4$ is hydrogen and $R^5$ is hydroxyl or protected hydroxyl and (b) $R^4$ and $R^5$ together form carbonyl; $R^6$ is hydrogen; and n is 0.

In any of the above embodiments unless otherwise inconsistent with a previous definition, in a further embodiment $R^2$ is —$OR^9$.

In any of the above embodiments unless otherwise inconsistent with a previous definition, in a further embodiment $R^2$ is —$OCH_2CH_2Si(CH_3)_3$.

In any of the above embodiments unless otherwise inconsistent with a previous definition, in a further embodiment $R^1$ is

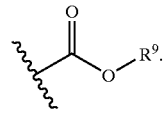

In any of the above embodiments unless otherwise inconsistent with a previous definition, in a further embodiment $R^9$ is a $C_1$–$C_6$ hydrocarbyl.

In any of the above embodiments unless otherwise inconsistent with a previous definition, in a further embodiment $R^9$ is selected from n-propyl and —$CH_2$—$CH$=$CH_2$.

In any of the above embodiments unless otherwise inconsistent with a previous definition, in a further embodiment $R^1$ is

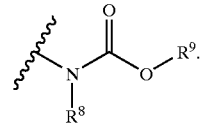

In any of the above embodiments unless otherwise inconsistent with a previous definition, in a further embodiment, $R^8$ is hydrogen and $R^9$ is $C_1$–$C_6$ hydrocarbyl.

In any of the above embodiments unless otherwise inconsistent with a previous definition, in a further embodiment, $R^9$ is —$CH_2$—$CH$=$CH_2$.

In any of the above embodiments unless otherwise inconsistent with a previous definition, in a further embodiment the stereochemistry of the $R^1$ and $C(=O)R^2$ groups being as shown in formula Ia, with $R^1$ and $C(=O)R^2$ in a cis arrangement, both over the benzo ring substituted with —$OR^6$ (Ia)

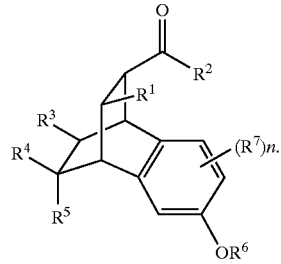

In any of the above embodiments unless otherwise inconsistent with a previous definition, in a further embodiment the stereochemistry of the $R^1$ and $C(=O)R^2$ groups being as shown in formula Ib, with $R^1$ and $C(=O)R^2$ in a trans arrangement, with only $C(=O)R^2$ over the benzo ring substituted with —$OR^6$

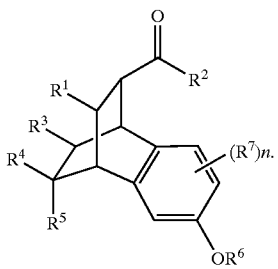

(Ib)

In any of the above embodiments unless otherwise inconsistent with a previous definition, in a further embodiment the stereochemistry of the $R^1$ and $C(=O)R^2$ groups being as shown in formula Ic, with $R^1$ and $C(=O)R^2$ in a trans arrangement, with only $R^1$ over the benzo ring substituted with $-OR^6$

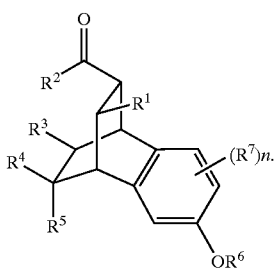

(Ic)

In any of the above embodiments unless otherwise inconsistent with a previous definition, in a further embodiment the stereochemistry of the $R^1$ and $C(=O)R^2$ groups being as shown in formula Id, with $R^1$ and $C(=O)R^2$ in a cis arrangement, with neither of the $R^1$ nor $C(=O)R^2$ groups being over the benzo ring substituted with $-OR^6$

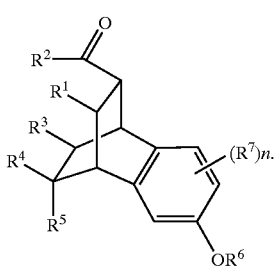

(Id)

In another embodiment, the present invention provides a composition comprising a compound, or a combination of compounds, according to any one of the above-described embodiments, and a pharmaceutically acceptable carrier, adjuvant or incipient.

In another embodiment, the present invention provides a method for inhibiting a TNF-α mediated processes, comprising administering to a patient in need thereof, through a therapeutically or prophylactically acceptable manner, a therapeutically or pharmaceutically effective amount of a composition comprising a compound or a mixture of compounds according to any of the above-described embodiments. In one embodiment, the administering is selected from transdermal, oral, intravenous, intramuscular, vaginal, rectal, pulmonary, subcutaneous, sublingual and transmucosal administration.

In another embodiment, the present invention provides a method for treating an inflammation event, comprising administering to a patient in need thereof, through a therapeutically or prophylactically acceptable manner, a therapeutically or pharmaceutically effective amount of a composition comprising a compound or a mixture of compounds according to any of the above-described embodiments. In one embodiment, the administering is selected from transdermal, oral, intravenous, intramuscular, vaginal, rectal, pulmonary, subcutaneous, sublingual and transmucosal administration.

In another embodiment, the present invention provides a library of benzobicyclooctane compounds where said library comprises a plurality of compounds each having a structure of formula (I) as describe above, including inventive embodiments thereof as set forth above, where diversity is present among the $R^1$, $R^2$, $R^3$, $R^4$, $R^5$, $R^6$, and $R^7$ groups.

In another embodiment, the present invention provides a process for preparing a combinatorial library of benzobicyclooctane compounds, wherein said library comprises a plurality of compounds of formula (I), including inventive embodiments thereof as set forth above, said process comprising the steps:

(a) providing a compound bound to a solid support according to formula (II)

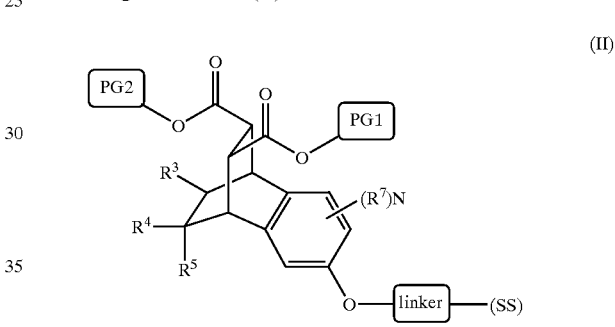

(II)

wherein PG1 and PG2 refer to first and second protecting groups, respectively, where the first protecting group can be removed in the continued presence of the second protecting group, and the second protecting group can be removed in the continued presence of the linker, and (SS) refers to a solid support;

(b) removing the first protecting group but not the second protecting group, to provide a first deprotected product;

(c) reacting the first deprotected product with a plurality of amines of the formula HNRR' to provide a plurality of compounds bound to a solid support, each according to formula (IIa)

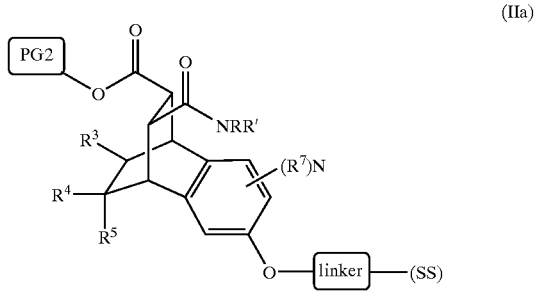

(IIa)

where R and R' are each independently selected from $R^9$;

(d) removing the second protecting group from (IIa) to provide a second deprotected product;

(e) reacting the second deprotected product with a plurality of amines of the formula HNR″R‴ to provide a plurality of compounds bound to a solid support, each according to formula (IIb)

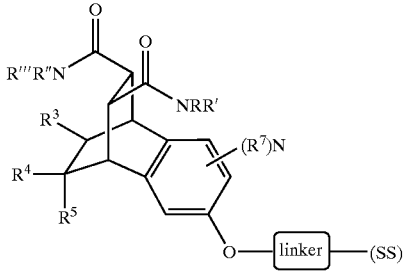

(IIb)

where R' and R‴ are each independently selected from $R^9$;

(f) removing the scaffold from the linker to provide a library of compounds according to formula (IIc)

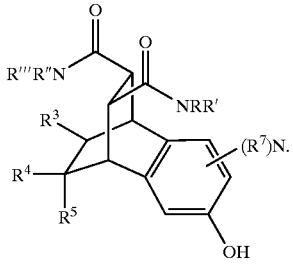

(IIc)

These and other embodiments of the present invention are described in further detail below.

DETAILED DESCRIPTION OF THE INVENTION

Before providing a detailed description of the invention, a number of terms as used herein are defined as follows:

Definition of Terms

As used herein, the following terms have the indicated meanings.

Unless otherwise indicated, the term "a" refers to one or more than one of the indicated items. For example, "a compound" includes one and more than one compound.

"Alkyl" is a saturated or unsaturated, straight or branched, hydrocarbon chain. In various embodiments, the alkyl group has 1–18 carbon atoms, i.e., is a C1–C18 group, or is a C1–C12 group, a C1–C6 group, or a C1–C4 group. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be substituted or unsubstituted. In one embodiment, the alkyl chains are unsubstituted. In another embodiment, the alkyl chain is substituted, e.g., with 1 substituent (i.e., the alkyl group is monosubstituted), or 1–2 substituents, or 1–3 substituents, or 1–4 substituents, etc.

"Aryl" is an aromatic hydrocarbon ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that make up the ring system. A C6 ring system, i.e., a phenyl ring, is a preferred aryl ring. In various embodiments, the polycyclic ring is a bicyclic aryl ring, where preferred bicyclic aryl rings are C8–C12, or C9–C10. A naphthyl ring, which has 10 carbon atoms, is a preferred polycyclic aryl ring. Aryl rings may be substituted or unsubstituted. In one embodiment, the aryl ring is unsubstituted. In another embodiment, the aryl ring is substituted with 1 substituent (i.e., the aryl ring is monosubstituted), or 1–2 substituents, or 1–3 substituents, or 1–4 substituents, etc.

"Carbocyclic aliphatic ring," also referred to as carbocycle, is a saturated or unsaturated, monocyclic or polycyclic (e.g., bicyclic, tricyclic, etc.) hydrocarbon ring. Carbocyclic aliphatic rings are not aromatic. A polycyclic hydrocarbon ring may include fused, spiro or bridged ring structures. In various embodiments, the monocyclic carbocyclic aliphatic ring is a C3–C10, or a C4–C7, or a C5–C6 ring system. In various embodiments, the polycyclic carbocyclic aliphatic ring is a C6–C12, or a C9–C10 ring system. In one embodiment, the polycyclic ring is bicyclic. In another embodiment, the polycyclic ring is bicyclic or tricyclic. Carbocyclic aliphatic rings include cyclopropyl, cyclopentyl, cyclohexyl, cyclohexenyl, cycloheptyl, and cyclooctyl. Carbocycles may be substituted or unsubstituted. In one embodiment, the carbocycle is unsubstituted. In another embodiment, the carbocycle is substituted with, e.g., 1 substituent (i.e., the alkyl group is monosubstituted), or 1–2 substituents, or 1–3 substituents, or 1–4 substituents, etc.

"Haloalkyl" is an alkyl chain substituted with one or more halogens. A preferred haloalkyl is trifluoromethyl.

"Heteroalkyl" is a saturated or unsaturated, straight or branched, chain containing carbon and at least one heteroatom. The heteroalkyl group may, in various embodiments, have one heteroatom, or 1–2 heteroatoms, or 1–3 heteroatoms, or 1–4 heteroatoms. Heteroalkyl chains may contain from 1 to 18 (i.e., 1–18) member atoms (carbon and heteroatoms) in the chain, and in various embodiments contain 1–12, or 1–6, or 1–4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., be monosubstituted), or may have 1–2 substituents, or 1–3 substituents, or 1–4 substituents, etc. Exemplary heteroalkyl groups include esters (—C(=O)—OR) and ketones (—C(=O)—).

"Heteroaryl" is an aromatic ring system or a semi-aromatic system of rings or a pseudo aromatic ring or rings containing carbon and at least one heteroatom in at least one of the rings. The heteroaryl group may, in various embodiments, have one heteroatom, or 1–2 heteroatoms, or 1–3 heteroatoms, or 1–4 heteroatoms in the ring. The heteroaryl group may further include more than one ring system, which in various embodiments may include one heteroatom or 1–2 heteroatoms, or 1–3 heteroatoms, or 1 heteroatom in each ring system, or 1–4 heteroatoms in each ring system. The heteroaryl group which comprises more than one ring system may, in various embodiments have one or more than one of the ring systems aromatic. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. The substituted heteroaryl ring may contain 1 substituent, or 1–2 substituents, or 1–3 substituents, or 1–4 substituents, etc. Exemplary heteroaryl rings include benzofuran, benzothiophene, furan, imidazole, indole, isothiazole, oxazole, pyrazine, pyrazole, pyridazine, pyridine, pyrimidine, pyrrole, quinoline, thiazole and thiophene.

"Heteroatom" is a nitrogen, sulfur, oxygen or silicon atom. Groups containing more than one heteroatom may contain different heteroatoms.

"Heterocyclic aliphatic ring," also referred to as "heterocyclyl", is a saturated or unsaturated, monocyclic or polycyclic (e.g., bicyclic, tricyclic, etc.) ring containing carbon and at least one heteroatom. Heterocyclic aliphatic rings are not aromatic per se but may be pseudo-aromatic and/or readily be made aromatic through methods known in the art. The heterocyclic aliphatic ring may, in various embodiments, have one heteroatom, or 1–2 heteroatoms, or 1–3 heteroatoms, or 1–4 heteroatoms, etc. In one embodiment, the heterocyclic aliphatic ring is monocyclic, where the monocyclic ring may have 3–10, or 4–7, or 5–6 member atoms. In another embodiment, the heterocyclic aliphatic ring is polycyclic, where in various embodiments, the ring may be bicyclic, or may be tricyclic, or may be either bicyclic or tricyclic. A polycyclic ring system may have one or more fused, spiro or bridged ring systems. The polycyclic heterocyclic aliphatic ring system may have 6–12, or 9–10 member atoms. The heterocyclic ring may be unsubstituted or substituted. In one embodiment, the heterocyclic ring is unsubstituted. In another embodiment, the heterocyclic ring is substituted. The substituted heterocyclic ring may contain 1 substituent, or 1–2 substituents, or 1–3 substituents, or 1–4 substituents, etc. Exemplary heterocyclic aliphatic rings include piperazyl, morpholinyl, tetrahydrofuranyl, tetrahydropyranyl and piperidyl.

"Inorganic groups having 1–8 atoms exclusively selected from boron, sulfur, phosphorous, silicon and hydrogen" refers to, for example, borates, sulfates, phosphates, silicates, and acids thereof.

"Lower alkyl" is an alkyl chain comprised of 1–6, preferably 1–4 carbon atoms.

"Pharmaceutically acceptable salt" and "salts thereof" means organic or inorganic salts of the pharmaceutically important molecule. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically important organic molecule may have more than one charged atom in its structure. Situations where multiple charged atoms are part of the molecule may have multiple counterions. Hence, the molecule of a pharmaceutically acceptable salt may contain one or more than one charged atoms and may also contain, one or more than one counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics.

"Substituents" replace a hydrogen atom with a non-hydrogen atom on an alkyl, heteroalkyl, aryl, heteroaryl, carbocycle, and/or heterocyclyl group as defined herein. Where the substituent contains a heteroatom, that heteroatom may be at any acceptable oxidation state for that particular atom, e.g., sulfur as part of a substituent may vary from an oxidation state of −2 to +8, and may be part of a complex or chelate as in a sulfoxide a mercapto-phosphine or metal chelated in a thia-crown ether. Suitable substituents that may be located on one or more of these groups include the following: hydroxy, alkoxy (i.e., alkyl-O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), sulfonamido (—N($R^9$)SO$_2$R$^9$ or —SO$_2$NR$^9$R$^9$), amino (e.g., amino, mono- and di-$C_1$–$C_3$ alkanylamino, methylphenylamino, methylbenzylamino, $C_1$–$C_3$ alkanylamido, acylamino, carbamamido, ureido, guanidino, nitro, cyano and imino). Moreover, any substituent may have from 1–5 further substituents attached thereto.

"Amino" means a nitrogen atom substituted with up to 4 groups, for instance, 2 or 3 alkyl groups as defined above, or 1 or 2 alkyl groups and a hydrogen group, or with one or two aryl groups and one or two alkyl groups so that the total number of groups is 2 or 3, or with two or three aryl groups, or with two or more hydrogen atoms or with other the substitution required to complete the nitrogen's valence requirements. "Amino" further includes amino salts where the nitrogen is hypervalent, having four bonds and may or may not have a charge and a counterion. The counterion, when present, may be an external inorganic and/or organic counterion and/or may be an internal counterion. Inorganic counterions include, for example, anions such as halo anions and other non-metal anions. Examples of organic counterions include, for example, anionic organic moieties such as acetate, citrate and other anionic organic moieties. Thus, amino refers to quaternary ammonium groups, tertiary amines and salts thereof, secondary amines and salts thereof, and primary amines and salts thereof.

As used herein and in the appended claims a "library" means a large number of chemical derivatives used in screening for biological activity or other activity. In general a library will have greater than 20 members, preferably the library will have at least 50 members, more preferably the library will have at least 96 members and most preferably the library will have at least 1000 members.

As used herein and in the appended claims "scaffold" means a common chemical structure found within a library of organic compounds. Similarly, within a combinatorial chemical library the scaffold forms the basis for a diverse series of chemical derivatization, additions and subtractions. Importantly, regardless of the extent of the chemical derivatization performed on the scaffold, the product is within the scope of the combinatorial library.

"Inflammation event" or "inflammation" or "swelling" are synonymous terms that mean an abnormal enlargement of a portion or tissue of an animal. The abnormal enlargement may be the normal, expected result of another event, such as, for example, sepsis, fever, trauma, shock, or injury. Non-limiting examples of some of these events include sepsis due to renal or liver failure, fever secondary to systemic infection, localized fever secondary to local infection, blunt force trauma or emotional trauma having physical manifestations, shock secondary to trauma and/or other events causing a pooling of body fluids and an injury causing release of cellular fluids initiating the inflammation cascade.

As used herein, "commercially available chemicals" and the chemicals used in the Examples set forth herein may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.),Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "compounds described in the chemical literature" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

As used herein "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

All other acronyms and abbreviations have the corresponding meaning as published in journals relative to the art of organic chemistry.

A. Compounds

In one aspect, the present invention provides benzobicyclooctane compounds of formula (I)

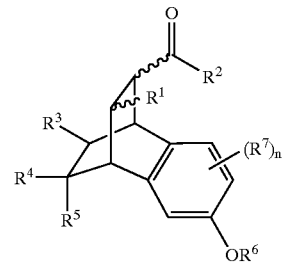

(I)

and optical isomers, diastereomers, enantiomers and pharmaceutically acceptable salts thereof in isolation (i.e., isolated from one another) or in mixture (i.e., two or more compounds in admixture with one another), where, independently at each location:

$R^1$ is selected from the following six formulae:

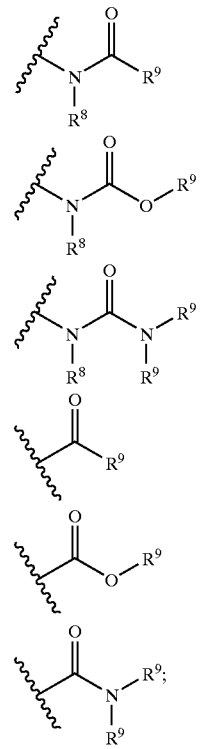

$R^2$ is —$OR^9$ or —$NR^9R^9$;

$R^3$ is selected from hydrogen, halogen, hydroxyl or protected hydroxyl, amino or protected amino, and $C_1$–$C_8$alkyl or $C_1$–$C_8$haloalkyl;

$R^4$ and $R^5$ are independently selected from $R^9$, —$OR^9$, —$NR^9R^9$ and —N=N—$R^9$, or $R^4$ and $R^5$ may together form a group selected from =O, =CR⁸R⁸ and =NR¹⁰, or R⁴ and R⁵ may together with the carbon to which they are both attached form a spiro carbocyclic or heterocyclic ring;

R⁶ is selected from hydrogen, inorganic groups having 1–8 atoms exclusively selected from boron, sulfur, phosphorous, silicon and hydrogen, and organic groups having 1–20 carbons and optionally containing 1–4 heteroatoms selected from nitrogen, oxygen and silicon;

R⁷ is selected from halogen, hydroxyl or protected hydroxyl, amino or protected amino, and C₁–C₈alkyl or C₁–C₈haloalkyl;

R⁸ is selected from hydrogen, alkyl (preferably C₁–C₈alkyl), aryl and heteroalkyl;

R⁹ is selected from hydrogen and organic groups having 1–30 carbons and optionally containing 1–4 heteroatoms selected from nitrogen, oxygen and silicon, with the proviso that two R⁹ groups both joined to a common atom may be joined together so as to form a ring with the common atom;

R¹⁰ is selected from —R⁹, —OR⁹, —NR⁹R⁹, —NH—C(O)R⁹; —NH—C(O)OR⁹ and —NH—C(S)NHR⁹; and n is 0, 1, 2 or 3.

In one embodiment, when R⁶ is hydrogen and R⁴ and R⁵ together form =O and R¹ is CO₂R⁹, then R² is not OCH₃. In one embodiment, R⁴ and R⁵ are both hydrogen, while in another embodiment R⁴ is not hydrogen when R⁵ is hydrogen.

In formula (1), the two wavy lines (one connected to R¹, the other connected to C(=O)R²) indicate that the invention provides any possible stereochemistry for the R¹ and C(=O)R² groups. In other words, the present invention provides benzobicyclooctanes having each of the four relative stereochemistries shown below as formulae (Ia), (Ib), (Ic) and (Id).

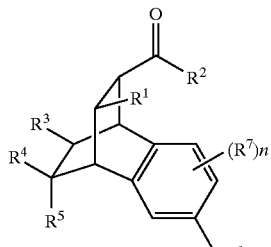

(Ia)

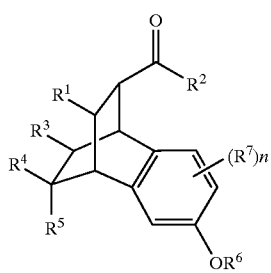

(Ib)

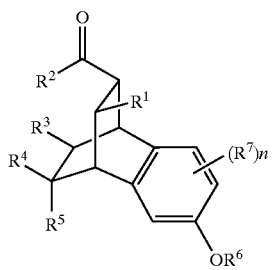

(Ic)

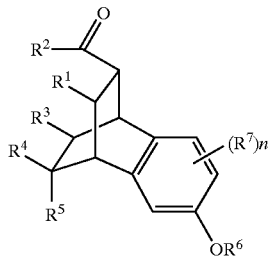

(Id)

In individual aspects the present invention provides compounds of formulae Ia through Io, where each of Ia through Io is made up of one or more of the compounds of formula Ia, Ib, Ic and Id. An "x" in a box to the right of the designation Ia through Io indicates which of Ia, Ib, Ic and Id is contained within the designated formula. Thus, for instance, the compounds of formula Ij contain the compounds within formulae Ic and Id (as an "x" is present in the columns designated Ic and Id), but do not include the compounds of formula Ia or Ib (as no "x" appears in the columns designated Ia and Ib) in the row designated formula Ij.

TABLE A

| Code | Formula | | | |
| No. | Ia | Ib | Ic | Id |
| --- | --- | --- | --- | --- |
| Ia | x | | | |
| Ib | | x | | |
| Ic | | | x | |
| Id | | | | x |
| Ie | x | x | | |
| If | x | | x | |
| Ig | x | | | x |
| Ih | | x | x | |
| Ii | | x | | x |
| Ij | | | x | x |
| Ik | x | x | x | |
| Il | x | x | | x |
| Im | x | | x | x |
| In | | x | x | x |
| Io | x | x | x | x |

Thus, as shown in Table A, in one aspect the present invention provides compounds of formula Ia, while in a separate aspect the present invention provides compounds of formula Ib; while in a still separate aspect the present invention provides compounds of formula Ic. In another aspect, the present invention provides compounds of formula Id, while in another aspect the present invention provides compounds of formula Ie (containing the set of compounds within formulae Ia and Ib), and in another aspect the present invention provides compounds of formula If (containing the set of compounds within formulae Ia and Ic). In still another aspect the present invention provides compounds of formula Ig, and in another aspect provides compounds of formula Ih, while in another aspect the invention provides compounds of formula Ii, and in yet another aspect the present invention provides compounds of formula Ij. In a separate aspect, the present invention provides compounds of formula Ik, while in another aspect the present invention provides compound of formula Il, and in still another aspect the invention provides compounds of formula Im. In addition, the present invention provides compounds of formula In, while in another aspect the present invention provides compounds of formula Io. Thus, using a convenient shorthand, it may be said that in various aspects the present invention provides benzybicyclooctane compounds of formulae: (Ia); (Ib); (Ic); (Id); (Ie); (If); (Ig); (Ih); (Ii); (Ij); (Ik); (Il); (Im); (In); (Io). In each of the above-listed aspects, the compounds include optical isomers, diastereomers, enantiomers and pharmaceutically acceptable salts thereof in isolation or mixture, where, independently at each location, the substituents $R^1$, $R^1$ etc. are as defined herein.

In the compounds of the present invention, $R^1$ is selected from the following six formulae, identified as R1a, R1b, R1c, R1d, R1e and R1f as defined below in Table B.

TABLE B

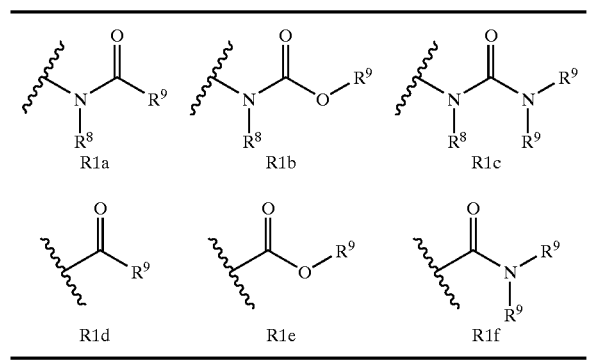

Thus, in compounds of the invention, $R^1$ may be one or more of R1a, R1b, R1c, R1d, R1e and R1f. Table C defines groups R1A through R1BJ, where each of R1A through R1BJ is composed of one or more of R1a, R1b, R1c, R1d, R1e and R1f. For example, as shown in Table C, R1A is defined as formula R1a but not any of R1b through R1f. As another example, R1G is defined as the sum of R1a and R1b, but does not include R1c through R1f. As a final example, R1BI is the sum of R1b through R1f, and excludes only R1a

TABLE C

| R1 | a | b | c | d | e | f |
|---|---|---|---|---|---|---|
| A | X | | | | | |
| B | | X | | | | |
| C | | | X | | | |
| D | | | | X | | |
| E | | | | | X | |
| F | | | | | | X |
| G | X | X | | | | |
| H | X | | X | | | |
| I | X | | | X | | |
| J | X | | | | X | |
| K | X | | | | | X |
| L | | X | X | | | |
| M | | X | | X | | |
| N | | X | | | X | |
| O | | X | | | | X |
| P | | | X | X | | |

TABLE C-continued

| R1 | a | b | c | d | e | f |
|---|---|---|---|---|---|---|
| Q | | | X | | X | |
| R | | | X | | | X |
| S | | | | X | X | |
| T | | | | X | | X |
| U | | | | | X | X |
| V | X | X | X | | | |
| W | X | X | | X | | |
| X | X | X | | | X | |
| Y | X | X | | | | X |
| Z | X | | X | X | | |
| AA | X | | X | | X | |
| AB | X | | X | | | X |
| AC | X | | | X | X | |
| AD | X | | | X | | X |
| AE | X | | | | X | X |
| AF | | X | X | X | | |
| AG | | X | X | | X | |
| AH | | X | X | | | X |
| AI | | X | | X | X | |
| AJ | | X | | X | | X |
| AK | | X | | | X | X |
| AL | | | X | X | X | |
| AM | | | X | X | | X |
| AN | | | X | | X | X |
| AO | | | | X | X | X |
| AP | X | X | X | X | | |
| AQ | X | X | X | | X | |
| AR | X | X | X | | | X |
| AS | X | X | | X | X | |
| AT | X | X | | X | | X |
| AU | X | X | | | X | X |
| AV | X | | X | X | X | |
| AW | X | | X | X | | X |
| AX | X | | X | | X | X |
| AY | X | | | X | X | X |
| AZ | | X | X | X | X | |
| BA | | X | X | X | | X |
| BB | | X | | X | X | X |
| BC | | | X | X | X | X |
| BD | X | X | X | X | X | |
| BE | X | X | X | X | | X |
| BF | X | X | X | | X | X |
| BG | X | X | | X | X | X |
| BH | X | | X | X | X | X |
| BI | | X | X | X | X | X |
| BJ | X | X | X | X | X | X |

Thus, in one aspect, the present invention provides compounds of formula (I) where $R^1$ is R1A. In another aspect, the invention provides compounds of formula (I) where $R^1$ is R1B. In another aspect, the invention provides compounds of formula (I) where $R^1$ is R1C. In another aspect, the invention provides compounds of formula (I) where $R^1$ is R1D. In another aspect, the invention provides compounds of formula (I) where $R^1$ is R1C. In another aspect, the invention provides compounds of formula (I) where $R^1$ is R1F. In other words, stated in a convenient shorthand nomenclature, in various aspects the present invention provides "Compounds of formula (I) where: $R^1$ is R1A; $R^1$ is R1B; $R^1$ is R1C; $R^1$ is R1D; $R^1$ is R1E; $R^1$ is R1F."

Using this same shorthand nomenclature, in various aspects the present invention provides compounds of formula (I) where: $R^1$ is R1G; $R^1$ is R1H; $R^1$ is R1I; $R^1$ is R1J; $R^1$ is R1K; $R^1$ is R1L; $R^1$ is R1M; $R^1$ is R1N; $R^1$ is R1O; $R^1$ is R1P; $R^1$ is R1Q; $R^1$ is R1R; $R^1$ is R1S; $R^1$ is R1T; $R^1$ is R1U; $R^1$ is R1V; $R^1$ is R1W; $R^1$ is R1X; $R^1$ is R1Y; $R^1$ is R1Z; $R^1$ is R1AA; $R^1$ is R1AB; $R^1$ is, R1AC; $R^1$ is R1AD; $R^1$ is R1AE; $R^1$ is R1AF; $R^1$ is R1AG; $R^1$ is R1AH; $R^1$ is R1AI; $R^1$ is R1AJ; $R^1$ is R1AK; $R^1$ is R1AL; $R^1$ is R1AM; $R^1$ is R1AN; $R^1$ is R1AO; $R^1$ is R1AP; $R^1$ is R1AQ; $R^1$ is R1AR; R¹ is R1AS; R¹ is R1AT; R¹ is R1AU; R¹ is R1AV; R¹ is R1AW; R¹ is R1AX; R¹ is R1AY; R¹ is R1AZ; R¹ is R1BA; R¹ is R1BB; R¹ is R1BC; R¹ is R1BD; R¹ is R1BE; R¹ is R1BF; R¹ is R1BG; R¹ is R1BH; R¹ is R1BI; R¹ is R1BJ.

In separate aspects, the present invention provides compounds of formulae (Ia)–(Io) as defined in Table B wherein R¹ is selected from R1A through R1BJ as defined in Table C. Each of these aspects is given a unique identifier, X1 through X937 in Table D, where each of X1 through X937 is a separate and unique aspect of the present invention. In each of X1 through X937, R² is —OR⁹ or NR⁹R⁹. The present invention also provides aspects Y1 through Y937 as defined in Table E, which are analogous to aspects X1 through X937 in terms of formula (Ia)–(Io) and R¹, however in aspects Y1 through Y937 R² is limited to —OR⁹. The present invention also provides aspects Z1 through Z937 as defined in Table F, which are analogous to aspects X1 through X937 in terms of formula (Ia)–(Io) and R¹, however in aspects Z1 through Z937 R² is limited to —NR⁹R⁹.

TABLE D

| R1 | Ia | Ib | Ic | Id | Ie | If | Ig | Ih | Ii | Ij | Ik | Il | Im | In | Io |
|---|---|---|---|---|---|---|---|---|---|---|---|---|---|---|---|
| A | X1 | X63 | X125 | X187 | X249 | X311 | X373 | X435 | X497 | X559 | X621 | X683 | X745 | X807 | X869 |
| B | X2 | X64 | X126 | X188 | X250 | X312 | X374 | X436 | X498 | X560 | X622 | X684 | X746 | X808 | X870 |
| C | X3 | X65 | X127 | X189 | X251 | X313 | X375 | X437 | X499 | X561 | X623 | X685 | X747 | X809 | X871 |
| D | X4 | X66 | X128 | X190 | X252 | X314 | X376 | X438 | X500 | X562 | X624 | X686 | X748 | X810 | X872 |
| E | X5 | X67 | X129 | X191 | X253 | X315 | X377 | X439 | X501 | X563 | X625 | X687 | X749 | X811 | X873 |
| F | X6 | X68 | X130 | X192 | X254 | X316 | X378 | X440 | X502 | X564 | X626 | X688 | X750 | X812 | X874 |
| G | X7 | X69 | X131 | X193 | X255 | X317 | X379 | X441 | X503 | X565 | X627 | X689 | X751 | X813 | X875 |
| H | X8 | X70 | X132 | X194 | X256 | X318 | X380 | X442 | X504 | X566 | X628 | X690 | X752 | X814 | X876 |
| I | X9 | X71 | X133 | X195 | X257 | X319 | X381 | X443 | X505 | X567 | X629 | X691 | X753 | X815 | X877 |
| J | X10 | X72 | X134 | X196 | X258 | X320 | X382 | X444 | X506 | X568 | X630 | X692 | X754 | X816 | X878 |
| K | X11 | X73 | X135 | X197 | X259 | X321 | X383 | X445 | X507 | X569 | X631 | X693 | X755 | X817 | X879 |
| L | X12 | X74 | X136 | X198 | X260 | X322 | X384 | X446 | X508 | X570 | X632 | X694 | X756 | X818 | X880 |
| M | X13 | X75 | X137 | X199 | X261 | X323 | X385 | X447 | X509 | X571 | X633 | X695 | X757 | X819 | X881 |
| N | X14 | X76 | X138 | X200 | X262 | X324 | X386 | X448 | X510 | X572 | X634 | X696 | X758 | X820 | X882 |
| O | X15 | X77 | X139 | X201 | X263 | X325 | X387 | X449 | X511 | X573 | X635 | X697 | X759 | X821 | X883 |
| P | X16 | X78 | X140 | X202 | X264 | X326 | X388 | X450 | X512 | X574 | X636 | X698 | X760 | X822 | X884 |
| Q | X17 | X79 | X141 | X203 | X265 | X327 | X389 | X451 | X513 | X575 | X637 | X699 | X761 | X823 | X885 |
| R | X18 | X80 | X142 | X204 | X266 | X328 | X390 | X452 | X514 | X576 | X638 | X700 | X762 | X824 | X886 |
| S | X19 | X81 | X143 | X205 | X267 | X329 | X391 | X453 | X515 | X577 | X639 | X701 | X763 | X825 | X887 |
| T | X20 | X82 | X144 | X206 | X268 | X330 | X392 | X454 | X516 | X578 | X640 | X702 | X764 | X826 | X888 |
| U | X21 | X83 | X145 | X207 | X269 | X331 | X393 | X455 | X517 | X579 | X641 | X703 | X765 | X827 | X889 |
| V | X22 | X84 | X146 | X208 | X270 | X332 | X394 | X456 | X518 | X580 | X642 | X704 | X766 | X828 | X890 |
| W | X23 | X85 | X147 | X209 | X271 | X333 | X395 | X457 | X519 | X581 | X643 | X705 | X767 | X829 | X891 |
| X | X24 | X86 | X148 | X210 | X272 | X334 | X396 | X458 | X520 | X582 | X644 | X706 | X768 | X830 | X892 |
| Y | X25 | X87 | X149 | X211 | X273 | X335 | X397 | X459 | X521 | X583 | X645 | X707 | X769 | X831 | X893 |
| Z | X26 | X88 | X150 | X212 | X274 | X336 | X398 | X460 | X522 | X584 | X646 | X708 | X770 | X832 | X894 |
| AA | X27 | X89 | X151 | X213 | X275 | X337 | X399 | X461 | X523 | X585 | X647 | X709 | X771 | X833 | X895 |
| AB | X28 | X90 | X152 | X214 | X276 | X338 | X400 | X462 | X524 | X586 | X648 | X710 | X772 | X834 | X896 |
| AC | X29 | X91 | X153 | X215 | X277 | X339 | X401 | X463 | X525 | X587 | X649 | X711 | X773 | X835 | X897 |
| AD | X30 | X92 | X154 | X216 | X278 | X340 | X402 | X464 | X526 | X588 | X650 | X712 | X774 | X836 | X898 |
| AE | X31 | X93 | X155 | X217 | X279 | X341 | X403 | X465 | X527 | X589 | X651 | X713 | X775 | X837 | X899 |
| AF | X32 | X94 | X156 | X218 | X280 | X342 | X404 | X466 | X528 | X590 | X652 | X714 | X776 | X838 | X900 |
| AG | X33 | X95 | X157 | X219 | X281 | X343 | X405 | X467 | X529 | X591 | X653 | X715 | X777 | X839 | X901 |
| AH | X34 | X96 | X158 | X220 | X282 | X344 | X406 | X468 | X530 | X592 | X654 | X716 | X778 | X840 | X902 |
| AI | X35 | X97 | X159 | X221 | X283 | X345 | X407 | X469 | X531 | X593 | X655 | X717 | X779 | X841 | X903 |
| AJ | X36 | X98 | X160 | X222 | X284 | X346 | X408 | X470 | X532 | X594 | X656 | X718 | X780 | X842 | X904 |
| AK | X37 | X99 | X161 | X223 | X285 | X347 | X409 | X471 | X533 | X595 | X657 | X719 | X781 | X843 | X905 |
| AL | X38 | X100 | X162 | X224 | X286 | X348 | X410 | X472 | X534 | X596 | X658 | X720 | X782 | X844 | X906 |
| AM | X39 | X101 | X163 | X225 | X287 | X349 | X411 | X473 | X535 | X597 | X659 | X721 | X783 | X845 | X907 |
| AN | X40 | X102 | X164 | X226 | X288 | X350 | X412 | X474 | X536 | X598 | X660 | X722 | X784 | X846 | X908 |
| AO | X41 | X103 | X165 | X227 | X289 | X351 | X413 | X475 | X537 | X599 | X661 | X723 | X785 | X847 | X909 |
| AP | X42 | X104 | X166 | X228 | X290 | X352 | X414 | X476 | X538 | X600 | X662 | X724 | X786 | X848 | X910 |
| AW | X43 | X105 | X167 | X229 | X291 | X353 | X415 | X477 | X539 | X601 | X663 | X725 | X787 | X849 | X911 |
| AR | X44 | X106 | X168 | X230 | X292 | X354 | X416 | X478 | X540 | X602 | X664 | X726 | X788 | X850 | X912 |
| AS | X45 | X107 | X169 | X231 | X293 | X355 | X417 | X479 | X541 | X603 | X665 | X727 | X789 | X851 | X913 |
| AT | X46 | X108 | X170 | X232 | X294 | X356 | X418 | X480 | X542 | X604 | X666 | X728 | X790 | X852 | X914 |
| AU | X47 | X109 | X171 | X233 | X295 | X357 | X419 | X481 | X543 | X605 | X667 | X729 | X791 | X853 | X915 |
| AV | X48 | X110 | X172 | X234 | X296 | X358 | X420 | X482 | X544 | X606 | X668 | X730 | X792 | X854 | X916 |
| AW | X49 | X111 | X173 | X235 | X297 | X259 | X421 | X483 | X545 | X607 | X669 | X731 | X793 | X855 | X917 |
| AX | X50 | X112 | X174 | X236 | X298 | X260 | X422 | X484 | X546 | X608 | X670 | X732 | X794 | X856 | X918 |
| AY | X51 | X113 | X175 | X237 | X299 | X261 | X423 | X485 | X547 | X609 | X671 | X733 | X795 | A857 | X919 |
| AZ | X52 | X114 | X176 | X238 | X300 | X362 | X424 | X486 | X548 | X610 | X672 | X734 | X796 | X858 | X920 |
| BA | X53 | X115 | X177 | X239 | X301 | X363 | X425 | X487 | X549 | X611 | X673 | X735 | X797 | X859 | X921 |
| BB | X54 | X116 | X178 | X240 | X302 | X364 | X426 | X488 | X550 | X612 | X674 | X736 | X798 | X860 | X922 |
| BC | X55 | X117 | X179 | X241 | X303 | X365 | X427 | X489 | X551 | X613 | X675 | X737 | X799 | X861 | X923 |
| BD | X56 | X118 | X180 | X242 | X304 | X366 | X428 | X490 | X552 | X614 | X676 | X738 | X800 | X862 | X924 |
| BE | X57 | X119 | X181 | X243 | X305 | X367 | X429 | X491 | X553 | X615 | X677 | X739 | X801 | X863 | X925 |
| BF | X58 | X120 | X182 | X244 | X306 | X368 | X430 | X492 | X554 | X616 | X678 | X740 | X802 | X864 | X926 |
| BG | X59 | X121 | X183 | X245 | X307 | X369 | X431 | X493 | X555 | X617 | X679 | X741 | X803 | X865 | X927 |
| BH | X60 | X122 | X184 | X246 | X308 | X370 | X432 | X494 | X556 | X618 | X680 | X742 | X804 | X866 | X928 |
| BI | X61 | X123 | X185 | X247 | X309 | X371 | X433 | X495 | X557 | X619 | X681 | X743 | X805 | X867 | X929 |
| BJ | X62 | X124 | X186 | X248 | X310 | X372 | X434 | X496 | X558 | X620 | X682 | X744 | X806 | X868 | X930 |

TABLE E

| R1 | Ia | Ib | Ic | Id | Ie | If | Ig | Ih | Ii | Ij | Ik | Il | Im | In | Io |
|---|---|---|---|---|---|---|---|---|---|---|---|---|---|---|---|
| A | Y1 | Y63 | Y125 | Y187 | Y249 | Y311 | Y373 | Y435 | Y497 | Y559 | Y621 | Y683 | Y745 | Y807 | Y869 |
| B | Y2 | Y64 | Y126 | Y188 | Y250 | Y312 | Y374 | Y436 | Y498 | Y560 | Y622 | Y684 | Y746 | Y808 | Y870 |
| C | Y3 | Y65 | Y127 | Y189 | Y251 | Y313 | Y375 | Y437 | Y499 | Y561 | Y623 | Y685 | Y747 | Y809 | Y871 |
| D | Y4 | Y66 | Y128 | Y190 | Y252 | Y314 | Y376 | Y438 | Y500 | Y562 | Y624 | Y686 | Y748 | Y810 | Y872 |
| E | Y5 | Y67 | Y129 | Y191 | Y253 | Y315 | Y377 | Y439 | Y501 | Y563 | Y625 | Y687 | Y749 | Y811 | Y873 |
| F | Y6 | Y68 | Y130 | Y192 | Y254 | Y316 | Y378 | Y440 | Y502 | Y564 | Y626 | Y688 | Y750 | Y812 | Y874 |
| G | Y7 | Y69 | Y131 | Y193 | Y255 | Y317 | Y379 | Y441 | Y503 | Y565 | Y627 | Y689 | Y751 | Y813 | Y875 |
| H | Y8 | Y70 | Y132 | Y194 | Y256 | Y318 | Y380 | Y442 | Y504 | Y566 | Y628 | Y690 | Y752 | Y814 | Y876 |
| I | Y9 | Y71 | Y133 | Y195 | Y257 | Y319 | Y381 | Y443 | Y505 | Y567 | Y629 | Y691 | Y753 | Y815 | Y877 |
| J | Y10 | Y72 | Y134 | Y196 | Y258 | Y320 | Y382 | Y444 | Y506 | Y568 | Y630 | Y692 | Y754 | Y816 | Y878 |
| K | Y11 | Y73 | Y135 | Y197 | Y259 | Y321 | Y383 | Y445 | Y507 | Y569 | Y631 | Y693 | Y755 | Y817 | Y879 |
| L | Y12 | Y74 | Y136 | Y198 | Y260 | Y322 | Y384 | Y446 | Y508 | Y570 | Y632 | Y694 | Y756 | Y818 | Y880 |
| M | Y13 | Y75 | Y137 | Y199 | Y261 | Y323 | Y385 | Y447 | Y509 | Y571 | Y633 | Y695 | Y757 | Y819 | Y881 |
| N | Y14 | Y76 | Y138 | Y200 | Y262 | Y324 | Y386 | Y448 | Y510 | Y572 | Y634 | Y696 | Y758 | Y820 | Y882 |
| O | Y15 | Y77 | Y139 | Y201 | Y263 | Y325 | Y387 | Y449 | Y511 | Y573 | Y635 | Y697 | Y759 | Y821 | Y883 |
| P | Y16 | Y78 | Y140 | Y202 | Y264 | Y326 | Y388 | Y450 | Y512 | Y574 | Y636 | Y698 | Y760 | Y822 | Y884 |
| Q | Y17 | Y79 | Y141 | Y203 | Y265 | Y327 | Y389 | Y451 | Y513 | Y575 | Y637 | Y699 | Y761 | Y823 | Y885 |
| R1 | Y18 | Y80 | Y142 | Y204 | Y266 | Y328 | Y390 | Y452 | Y514 | Y576 | Y638 | Y700 | Y762 | Y824 | Y886 |
| S | Y19 | Y81 | Y143 | Y205 | Y267 | Y329 | Y391 | Y453 | Y515 | Y577 | Y639 | Y701 | Y763 | Y825 | Y887 |
| T | Y20 | Y82 | Y144 | Y206 | Y268 | Y330 | Y392 | Y454 | Y516 | Y578 | Y640 | Y702 | Y764 | Y826 | Y888 |
| U | Y21 | Y83 | Y145 | Y207 | Y269 | Y331 | Y393 | Y455 | Y517 | Y579 | Y641 | Y703 | Y765 | Y827 | Y889 |
| V | Y22 | Y84 | Y146 | Y208 | Y270 | Y332 | Y394 | Y456 | Y518 | Y580 | Y642 | Y704 | Y766 | Y828 | Y890 |
| W | Y23 | Y85 | Y147 | Y209 | Y271 | Y333 | Y395 | Y457 | Y519 | Y581 | Y643 | Y705 | Y767 | Y829 | Y891 |
| X | Y24 | Y86 | Y148 | Y210 | Y272 | Y334 | Y396 | Y458 | Y520 | Y582 | Y644 | Y706 | Y768 | Y830 | Y892 |
| Y | Y25 | Y87 | Y149 | Y211 | Y273 | Y335 | Y397 | Y459 | Y521 | Y583 | Y645 | Y707 | Y769 | Y831 | Y893 |
| Z | Y26 | Y88 | Y150 | Y212 | Y274 | Y336 | Y398 | Y460 | Y522 | Y584 | Y646 | Y708 | Y770 | Y832 | Y894 |
| AA | Y27 | Y89 | Y151 | Y213 | Y275 | Y337 | Y399 | Y461 | Y523 | Y585 | Y647 | Y709 | Y771 | Y833 | Y895 |
| AB | Y28 | Y90 | Y152 | Y214 | Y276 | Y338 | Y400 | Y462 | Y524 | Y586 | Y648 | Y710 | Y772 | Y834 | Y896 |
| AC | Y29 | Y91 | Y153 | Y215 | Y277 | Y339 | Y401 | Y463 | Y525 | Y587 | Y649 | Y711 | Y773 | Y835 | Y897 |
| AD | Y30 | Y92 | Y154 | Y216 | Y278 | Y340 | Y402 | Y464 | Y526 | Y588 | Y650 | Y712 | Y774 | Y836 | Y898 |
| AE | Y31 | Y93 | Y155 | Y217 | Y279 | Y341 | Y403 | Y465 | Y527 | Y589 | Y651 | Y713 | Y775 | Y837 | Y899 |
| AF | Y32 | Y94 | Y156 | Y218 | Y280 | Y342 | Y404 | Y466 | Y528 | Y590 | Y652 | Y714 | Y776 | Y838 | Y900 |
| AG | Y33 | Y95 | Y157 | Y219 | Y281 | Y343 | Y405 | Y467 | Y529 | Y591 | Y653 | Y715 | Y777 | Y839 | Y901 |
| AH | Y34 | Y96 | Y158 | Y220 | Y282 | Y344 | Y406 | Y468 | Y530 | Y592 | Y654 | Y716 | Y778 | Y840 | Y902 |
| AI | Y35 | Y97 | Y159 | Y221 | Y283 | Y345 | Y407 | Y469 | Y531 | Y593 | Y655 | Y717 | Y779 | Y841 | Y903 |
| AJ | Y36 | Y98 | Y160 | Y222 | Y284 | Y346 | Y408 | Y470 | Y532 | Y594 | Y656 | Y718 | Y780 | Y842 | Y904 |
| AK | Y37 | Y99 | Y161 | Y223 | Y285 | Y347 | Y409 | Y471 | Y533 | Y595 | Y657 | Y719 | Y781 | Y843 | Y905 |
| AL | Y38 | Y100 | Y162 | Y224 | Y286 | Y348 | Y410 | Y472 | Y534 | Y596 | Y658 | Y720 | Y782 | Y844 | Y906 |
| AM | Y39 | Y101 | Y163 | Y225 | Y287 | Y349 | Y411 | Y473 | Y535 | Y597 | Y659 | Y721 | Y783 | Y845 | Y907 |
| AN | Y40 | Y102 | Y164 | Y226 | Y288 | Y350 | Y412 | Y474 | Y536 | Y598 | Y660 | Y722 | Y784 | Y846 | Y908 |
| AO | Y41 | Y103 | Y165 | Y227 | Y289 | Y351 | Y413 | Y475 | Y537 | Y599 | Y661 | Y723 | Y785 | Y847 | Y909 |
| AP | Y42 | Y104 | Y166 | Y228 | Y290 | Y352 | Y414 | Y476 | Y538 | Y600 | Y662 | Y724 | Y786 | Y848 | Y910 |
| AW | Y43 | Y105 | Y167 | Y229 | Y291 | Y353 | Y415 | Y477 | Y539 | Y601 | Y663 | Y725 | Y787 | Y849 | Y911 |
| AR | Y44 | Y106 | Y168 | Y230 | Y292 | Y354 | Y416 | Y478 | Y540 | Y602 | Y664 | Y726 | Y788 | Y850 | Y912 |
| AS | Y45 | Y107 | Y169 | Y231 | Y293 | Y355 | Y417 | Y479 | Y541 | Y603 | Y665 | Y727 | Y789 | Y851 | Y913 |
| AT | Y46 | Y108 | Y170 | Y232 | Y294 | Y356 | Y418 | Y480 | Y542 | Y604 | Y666 | Y728 | Y790 | Y852 | Y914 |
| AU | Y47 | Y109 | Y171 | Y233 | Y295 | Y357 | Y419 | Y481 | Y543 | Y605 | Y667 | Y729 | Y791 | Y853 | Y915 |
| AV | Y48 | Y110 | Y172 | Y234 | Y296 | Y358 | Y420 | Y482 | Y544 | Y606 | Y668 | Y730 | Y792 | Y854 | Y916 |
| AW | Y49 | Y111 | Y173 | Y235 | Y297 | Y359 | Y421 | Y483 | Y545 | Y607 | Y669 | Y731 | Y793 | Y855 | Y917 |
| AX | Y50 | Y112 | Y174 | Y236 | Y298 | Y360 | Y422 | Y484 | Y546 | Y608 | Y670 | Y732 | Y794 | Y856 | Y918 |
| AY | Y51 | Y113 | Y175 | Y237 | Y299 | Y361 | Y423 | Y485 | Y547 | Y609 | Y671 | Y733 | Y795 | Y857 | Y919 |
| AZ | Y52 | Y114 | Y176 | Y238 | Y300 | Y362 | Y424 | Y486 | Y548 | Y610 | Y672 | Y734 | Y796 | Y858 | Y920 |
| BA | Y53 | Y115 | Y177 | Y239 | Y301 | Y363 | Y425 | Y487 | Y549 | Y611 | Y673 | Y735 | Y797 | Y859 | Y921 |
| BB | Y54 | Y116 | Y178 | Y240 | Y302 | Y364 | Y426 | Y488 | Y550 | Y612 | Y674 | Y736 | Y798 | Y860 | Y922 |
| BC | Y55 | Y117 | Y179 | Y241 | Y303 | Y365 | Y427 | Y489 | Y551 | Y613 | Y675 | Y737 | Y799 | Y861 | Y923 |
| BD | Y56 | Y118 | Y180 | Y242 | Y304 | Y366 | Y428 | Y490 | Y552 | Y614 | Y676 | Y738 | Y800 | Y862 | Y924 |
| BE | Y57 | Y119 | Y181 | Y243 | Y305 | Y367 | Y429 | Y491 | Y553 | Y615 | Y677 | Y739 | Y801 | Y863 | Y925 |
| BF | Y58 | Y120 | Y182 | Y244 | Y306 | Y368 | Y430 | Y492 | Y554 | Y616 | Y678 | Y740 | Y802 | Y864 | Y926 |
| BG | Y59 | Y121 | Y183 | Y245 | Y307 | Y369 | Y431 | Y493 | Y555 | Y617 | Y679 | Y741 | Y803 | Y865 | Y927 |
| BH | Y60 | Y122 | Y184 | Y246 | Y308 | Y370 | Y432 | Y494 | Y556 | Y618 | Y680 | Y742 | Y804 | Y866 | Y928 |
| BI | Y61 | Y123 | Y185 | Y247 | Y309 | Y371 | Y433 | Y495 | Y557 | Y619 | Y681 | Y743 | Y805 | Y867 | Y929 |
| BJ | Y62 | Y124 | Y186 | Y248 | Y310 | Y372 | Y434 | Y496 | Y558 | Y620 | Y682 | Y744 | Y806 | Y868 | Y930 |

TABLE F

| R1 | Ia | Ib | Ic | Id | Ie | If | Ig | Ih | Ii | Ij | Ik | Il | Im | In | Io |
|---|---|---|---|---|---|---|---|---|---|---|---|---|---|---|---|
| A | Z1 | Z63 | Z125 | Z187 | Z249 | Z311 | Z373 | Z435 | Z497 | Z559 | Z621 | Z683 | Z745 | Z807 | Z869 |
| B | Z2 | Z64 | Z126 | Z188 | Z250 | Z312 | Z374 | Z436 | Z498 | Z560 | Z622 | Z684 | Z746 | Z808 | Z870 |
| C | Z3 | Z65 | Z127 | Z189 | Z251 | Z313 | Z375 | Z437 | Z499 | Z561 | Z623 | Z685 | Z747 | Z809 | Z871 |
| D | Z4 | Z66 | Z128 | Z190 | Z252 | Z314 | Z376 | Z438 | Z500 | Z562 | Z624 | Z686 | Z748 | Z810 | Z872 |
| E | Z5 | Z67 | Z129 | Z191 | Z253 | Z315 | Z377 | Z439 | Z501 | Z563 | Z625 | Z687 | Z749 | Z811 | Z873 |
| F | Z6 | Z68 | Z130 | Z192 | Z254 | Z316 | Z378 | Z440 | Z502 | Z564 | Z626 | Z688 | Z750 | Z812 | Z874 |
| G | Z7 | Z69 | Z131 | Z193 | Z255 | Z317 | Z379 | Z441 | Z503 | Z565 | Z627 | Z689 | Z751 | Z813 | Z875 |
| H | Z8 | Z70 | Z132 | Z194 | Z256 | Z318 | Z380 | Z442 | Z504 | Z566 | Z628 | Z690 | Z752 | Z814 | Z876 |
| I | Z9 | Z71 | Z133 | Z195 | Z257 | Z319 | Z381 | Z443 | Z505 | Z567 | Z629 | Z691 | Z753 | Z815 | Z877 |
| J | Z10 | Z72 | Z134 | Z196 | Z258 | Z320 | Z382 | Z444 | Z506 | Z568 | Z630 | Z692 | Z754 | Z816 | Z878 |
| K | Z11 | Z73 | Z135 | Z197 | Z259 | Z321 | Z383 | Z445 | Z507 | Z569 | Z631 | Z693 | Z755 | Z817 | Z879 |
| L | Z12 | Z74 | Z136 | Z198 | Z260 | Z322 | Z384 | Z446 | Z508 | Z570 | Z632 | Z694 | Z756 | Z818 | Z880 |
| M | Z13 | Z75 | Z137 | Z199 | Z261 | Z323 | Z385 | Z447 | Z509 | Z571 | Z633 | Z695 | Z757 | Z819 | Z881 |
| N | Z14 | Z76 | Z138 | Z200 | Z262 | Z324 | Z386 | Z448 | Z510 | Z572 | Z634 | Z696 | Z758 | Z820 | Z882 |
| O | Z15 | Z77 | Z139 | Z201 | Z263 | Z325 | Z387 | Z449 | Z511 | Z573 | Z635 | Z697 | Z759 | Z821 | Z883 |
| P | Z16 | Z78 | Z140 | Z202 | Z264 | Z326 | Z388 | Z450 | Z512 | Z574 | Z636 | Z698 | Z760 | Z822 | Z884 |
| Q | Z17 | Z79 | Z141 | Z203 | Z265 | Z327 | Z389 | Z451 | Z513 | Z575 | Z637 | Z699 | Z761 | Z823 | Z885 |
| R | Z18 | Z80 | Z142 | Z204 | Z266 | Z328 | Z390 | Z452 | Z514 | Z576 | Z638 | Z700 | Z762 | Z824 | Z886 |
| S | Z19 | Z81 | Z143 | Z205 | Z267 | Z329 | Z391 | Z453 | Z515 | Z577 | Z639 | Z701 | Z763 | Z825 | Z887 |
| T | Z20 | Z82 | Z144 | Z206 | Z268 | Z330 | Z392 | Z454 | Z516 | Z578 | Z640 | Z702 | Z764 | Z826 | Z888 |
| U | Z21 | Z83 | Z145 | Z207 | Z269 | Z331 | Z393 | Z455 | Z517 | Z579 | Z641 | Z703 | Z765 | Z827 | Z889 |
| V | Z22 | Z84 | Z146 | Z208 | Z270 | Z332 | Z394 | Z456 | Z518 | Z580 | Z642 | Z704 | Z766 | Z828 | Z890 |
| W | Z23 | Z85 | Z147 | Z209 | Z271 | Z333 | Z395 | Z457 | Z519 | Z581 | Z643 | Z705 | Z767 | Z829 | Z891 |
| X | Z24 | Z86 | Z148 | Z210 | Z272 | Z334 | Z396 | Z458 | Z520 | Z582 | Z644 | Z706 | Z768 | Z830 | Z892 |
| Y | Z25 | Z87 | Z149 | Z211 | Z273 | Z335 | Z397 | Z459 | Z521 | Z583 | Z645 | Z707 | Z769 | Z831 | Z893 |
| Z | Z26 | Z88 | Z150 | Z212 | Z274 | Z336 | Z398 | Z460 | Z522 | Z584 | Z646 | Z708 | Z770 | Z832 | Z894 |
| AA | Z27 | Z89 | Z151 | Z213 | Z275 | Z337 | Z399 | Z461 | Z523 | Z585 | Z647 | Z709 | Z771 | Z833 | Z895 |
| AB | Z28 | Z90 | Z152 | Z214 | Z276 | Z338 | Z400 | Z462 | Z524 | Z586 | Z648 | Z710 | Z772 | Z834 | Z896 |
| AC | Z29 | Z91 | Z153 | Z215 | Z277 | Z339 | Z401 | Z463 | Z525 | Z587 | Z649 | Z711 | Z773 | Z835 | Z897 |
| AD | Z30 | Z92 | Z154 | Z216 | Z278 | Z340 | Z402 | Z464 | Z526 | Z588 | Z650 | Z712 | Z774 | Z836 | Z898 |
| AE | Z31 | Z93 | Z155 | Z217 | Z279 | Z341 | Z403 | Z465 | Z527 | Z589 | Z651 | Z713 | Z775 | Z837 | Z899 |
| AF | Z32 | Z94 | Z156 | Z218 | Z280 | Z342 | Z404 | Z466 | Z528 | Z590 | Z652 | Z714 | Z776 | Z838 | Z900 |
| AG | Z33 | Z95 | Z157 | Z219 | Z281 | Z343 | Z405 | Z467 | Z529 | Z591 | Z653 | Z715 | Z777 | Z839 | Z901 |
| AH | Z34 | Z96 | Z158 | Z220 | Z282 | Z344 | Z406 | Z468 | Z530 | Z592 | Z654 | Z716 | Z778 | Z840 | Z902 |
| AI | Z35 | Z97 | Z159 | Z221 | Z283 | Z345 | Z407 | Z469 | Z531 | Z593 | Z655 | Z717 | Z779 | Z841 | Z903 |
| AJ | Z36 | Z98 | Z160 | Z222 | Z284 | Z346 | Z408 | Z470 | Z532 | Z594 | Z656 | Z718 | Z780 | Z842 | Z904 |
| AK | Z37 | Z99 | Z161 | Z223 | Z285 | Z347 | Z409 | Z471 | Z533 | Z595 | Z657 | Z719 | Z781 | Z843 | Z905 |
| AL | Z38 | Z100 | Z162 | Z224 | Z286 | Z348 | Z410 | Z472 | Z534 | Z596 | Z658 | Z720 | Z782 | Z844 | Z906 |
| AM | Z39 | Z101 | Z163 | Z225 | Z287 | Z349 | Z411 | Z473 | Z535 | Z597 | Z659 | Z721 | Z783 | Z845 | Z907 |
| AN | Z40 | Z102 | Z164 | Z226 | Z288 | Z350 | Z412 | Z474 | Z536 | Z598 | Z660 | Z722 | Z784 | Z846 | Z908 |
| AO | Z41 | Z103 | Z165 | Z227 | Z289 | Z351 | Z413 | Z475 | Z537 | Z599 | Z661 | Z723 | Z785 | Z847 | Z909 |
| AP | Z42 | Z104 | Z166 | Z228 | Z290 | Z352 | Z414 | Z476 | Z538 | Z600 | Z662 | Z724 | Z786 | Z848 | Z910 |
| AW | Z43 | Z105 | Z167 | Z229 | Z291 | Z353 | Z415 | Z477 | Z539 | Z601 | Z663 | Z725 | Z787 | Z849 | Z911 |
| AR | Z44 | Z106 | Z168 | Z230 | Z292 | Z354 | Z416 | Z478 | Z540 | Z602 | Z664 | Z726 | Z788 | Z850 | Z912 |
| AS | Z45 | Z107 | Z169 | Z231 | Z293 | Z355 | Z417 | Z479 | Z541 | Z603 | Z665 | Z727 | Z789 | Z851 | Z913 |
| AT | Z46 | Z108 | Z170 | Z232 | Z294 | Z356 | Z418 | Z480 | Z542 | Z604 | Z666 | Z728 | Z790 | Z852 | Z914 |
| AU | Z47 | Z109 | Z171 | Z233 | Z295 | Z357 | Z419 | Z481 | Z543 | Z605 | Z667 | Z729 | Z791 | Z853 | Z915 |
| AV | Z48 | Z110 | Z172 | Z234 | Z296 | Z358 | Z420 | Z482 | Z544 | Z606 | Z668 | Z730 | Z792 | Z854 | Z916 |
| AW | Z49 | Z111 | Z173 | Z235 | Z297 | Z359 | Z421 | Z483 | Z545 | Z607 | Z669 | Z731 | Z793 | Z855 | Z917 |
| AX | Z50 | Z112 | Z174 | Z236 | Z298 | Z360 | Z422 | Z484 | Z546 | Z608 | Z670 | Z732 | Z794 | Z856 | Z918 |
| AY | Z51 | Z113 | Z175 | Z237 | Z299 | Z361 | Z423 | Z485 | Z547 | Z609 | Z671 | Z733 | Z795 | Z857 | Z919 |
| AZ | Z52 | Z114 | Z176 | Z238 | Z300 | Z362 | Z424 | Z486 | Z548 | Z610 | Z672 | Z734 | Z796 | Z858 | Z920 |
| BA | Z53 | Z115 | Z177 | Z239 | Z301 | Z363 | Z425 | Z487 | Z549 | Z611 | Z673 | Z735 | Z797 | Z859 | Z921 |
| BB | Z54 | Z116 | Z178 | Z240 | Z302 | Z364 | Z426 | Z488 | Z550 | Z612 | Z674 | Z736 | Z798 | Z860 | Z922 |
| BC | Z55 | Z117 | Z179 | Z241 | Z303 | Z365 | Z427 | Z489 | Z551 | Z613 | Z675 | Z737 | Z799 | Z861 | Z923 |
| BD | Z56 | Z118 | Z180 | Z242 | Z304 | Z366 | Z428 | Z490 | Z552 | Z614 | Z676 | Z738 | Z800 | Z862 | Z924 |
| BE | Z57 | Z119 | Z181 | Z243 | Z305 | Z367 | Z429 | Z491 | Z553 | Z615 | Z677 | Z739 | Z801 | Z863 | Z925 |
| BF | Z58 | Z120 | Z182 | Z244 | Z306 | Z368 | Z430 | Z492 | Z554 | Z616 | Z678 | Z740 | Z802 | Z864 | Z926 |
| BG | Z59 | Z121 | Z183 | Z245 | Z307 | Z369 | Z431 | Z493 | Z555 | Z617 | Z679 | Z741 | Z803 | Z865 | Z927 |
| BH | Z60 | Z122 | Z184 | Z246 | Z308 | Z370 | Z432 | Z494 | Z556 | Z618 | Z680 | Z742 | Z804 | Z866 | Z928 |
| BI | Z61 | Z123 | Z185 | Z247 | Z309 | Z371 | Z433 | Z495 | Z557 | Z619 | Z681 | Z743 | Z805 | Z867 | Z929 |
| BJ | Z62 | Z124 | Z186 | Z248 | Z310 | Z372 | Z434 | Z496 | Z558 | Z620 | Z682 | Z744 | Z806 | Z868 | Z930 |

In each of the above-listed aspects, the compounds include optical isomers, diastereomers, enantiomers and pharmaceutically acceptable salts thereof in isolation or mixture, where, independently at each location, the substituents $R^1$, $R^2$ etc. are as defined herein.

Thus, for example, in one embodiment, the present invention provides a compound, or a mixture including a compound, wherein the stereochemistry of the $R^1$ and $C(=O)R^2$ groups are as shown in formula Ia, with $R^1$ and $C(=O)R^2$ in a cis arrangement, both over the benzo ring substituted with —$OR^6$

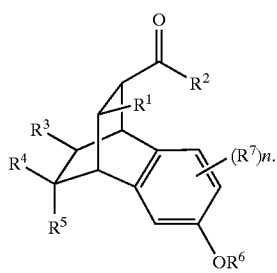

(Ia)

In another exemplary embodiment, the present invention provides a compounds, or a mixture including a compound, wherein the stereochemistry of the $R^1$ and $C(=O)R^2$ groups are as shown in formula Ib, with $R^1$ and $C(=O)R^2$ in a trans arrangement, with only $C(=O)R^2$ over the benzo ring substituted with —$OR^6$

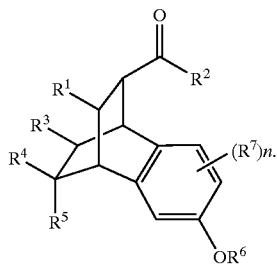

(Ib)

In yet another exemplary embodiment, the present invention provides a compound, or a mixture including a compound, having the stereochemistry of the $R^1$ and $C(=O)$ $R^2$ groups as shown in formula Ic, with $R^1$ and $C(=O)R^2$ in a trans arrangement, with only $R^1$ over the benzo ring substituted with —$OR^6$

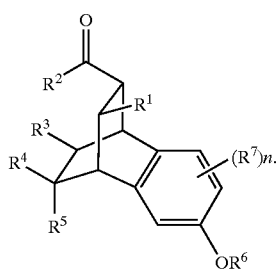

(Ic)

Another exemplary embodiment of the present invention provides a benzobicyclooctane compound, or a mixture containing a benzobicyclooctane compound, wherein the stereochemistry of the $R^1$ and $C(=O)R^2$ groups are as shown in formula Id, with $R^1$ and $C(=O)R^2$ in a cis arrangement, with neither of the $R^1$ nor $C(=O)R^2$ groups being over the benzo ring substituted with —$OR^6$

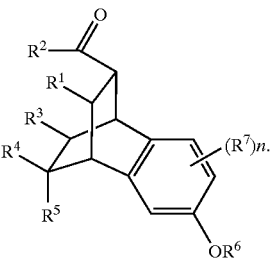

(Id)

In one embodiment, the present invention provides a compound of formula (I) wherein $R^1$ is selected from the following four formulae, i.e., $R^1$ is R1AX:

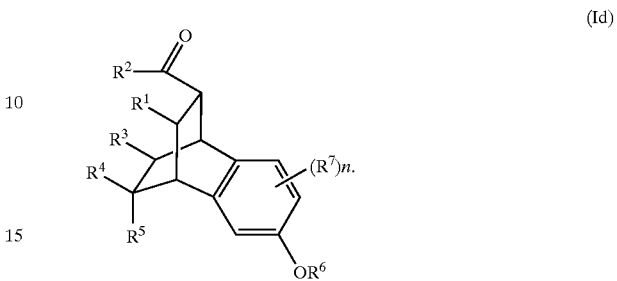

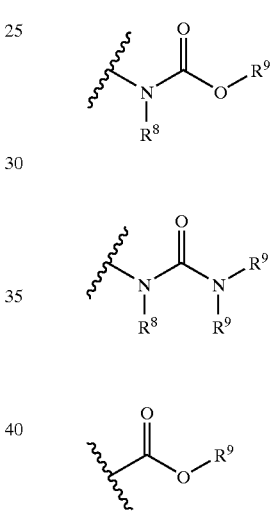

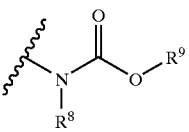

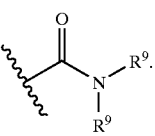

In one embodiment, the present invention provides a compound of formula (I) wherein $R^1$ is R1AX; $R^8$ is selected from hydrogen and $C_1$–$C_{15}$alkyl; and $R^9$ is selected from hydrogen, heteroalkyl, $C_1$–$C_{15}$alkyl, (heteroaryl) $C_1$–$C_{15}$alkylene, ($C_6$–$C_{10}$aryl)$C_1$–$C_{15}$alkylene, $C_6$–$C_{10}$aryl fused to $C_1$–$C_{15}$alkylene, (alkyl)$_p$($C_6$–$C_{10}$arylene) $C_1$–$C_{15}$alkylene, ($C_6$–$C_{10}$aryl)($C_6$–$C_{10}$arylene) $C_1$–$C_{15}$alkylene, ($C_1$–$C_{15}$alkyl)$_p$(heteroarylene) $C_1$–$C_{15}$alkylene, and (heteroalkyl)$_p$($C_6$–$C_{10}$arylene) $C_1$–$C_{15}$alkylene, or two $R^9$ groups bonded to a common nitrogen of $R^1$ may be joined together to form a 5–8 membered heterocycle including the common nitrogen, where this 5–8 membered heterocycle may be substituted with 0–5 groups selected from alkyl and heteralkyl, where p is selected from 1, 2, 3, 4 and 5.

In one embodiment, the present invention provides a compound of formula I wherein $R^1$ is R1A and $R^8$ and $R^9$ are each independently selected from $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^9$ is selected from heteroalkyl, $C_1$–$C_{15}$alkyl, $(C_6$–$C_{10}$aryl$)C_1$–$C_{15}$alkylene, $(C_6$–$C_{10}$aryl) $(C_6$–$C_{10}$arylene$)C_1$–$C_{15}$alkylene, $(C_1$–$C_{15}$alkyl$)_p$ (heteroarylene)$C_1$–$C_{15}$alkylene, and $C_6$–$C_{10}$aryl fused to $C_1$–$C_{15}$alkylene.

In one embodiment, the present invention provides a compound of formula (I) wherein $R^1$ is R1C and $R^8$ and $R^9$ are each independently selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^8$ is selected from hydrogen and $C_1$–$C_{15}$alkyl; and $R^9$ is selected from hydrogen, heteroalkyl, $C_1$–$C_{15}$alkyl, $(C_6$–$C_{10}$aryl$)C_1$–$C_{15}$alkylene, (heteroaryl) $C_1$–$C_{15}$alkylene, and (heteroalkyl)$_p$($C_6$–$C_{10}$arylene) $C_1$–$C_{15}$alkylene, or the two $R^9$ groups joined to a common nitrogen of $R^1$ may be joined together to form a 5–8 membered heterocycle including the common nitrogen.

In one embodiment, the present invention provides a compound of formula (I) wherein $R^1$ is R1E and $R^9$ is selected from hydrogen, $RK^1$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^9$ is selected from hydrogen, heteroalkyl, $C_1$–$C_{15}$alkyl, (heteroaryl)$C_1$–$C_{15}$alkylene, and (heteroalkyl)$_p$($C_6$–$C_{10}$arylene)$C_1$–$C_{15}$alkylene.

In one embodiment, the present invention provides a compound of formula (I) wherein $R^1$ is R1F and $R^9$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^9$ is selected from hydrogen, heteroalkyl, $C_1$–$C_{15}$alkyl, (heteroaryl)$C_1$–$C_{15}$alkylene, $(C_6$–$C_{10}$aryl) $C_1$–$C_{15}$alkylene, (alkyl)$_p$($C_6$–$C_{10}$arylene)$C_1$–$C_{15}$alkylene, or the two $R^9$ groups of $R^1$ may be joined together to form a 5–8 membered heterocycle including the common nitrogen, where this 5–8 membered heterocycle may be substituted with 0–5 groups selected from alkyl and heteralkyl.

In one embodiment, the present invention provides a compound of formula (I) wherein $R^2$ is —$OR^9$, i.e., aspects Y1 through Y937. Optionally, $R^9$ of —$OR^9$ of $R^2$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{12})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene; $(R^{14})_p$-arylene, and $(R^{14})_p$-heteroarylene, and p is selected from 0, 1, 2, 3, 4 and 5. In a further optional embodiment, $R^9$ of —$OR^9$ of $R^2$ is selected from hydrogen, heteroalkyl, $C_1$–$C_{15}$alkyl, $(C_6$–$C_{10}$aryl$)(C_6$–$C_{10}$arylene$)C_1$–$C_{15}$alkylene, $(C_1$–$C_{15}$alkyl$)_p$(heteroarylene)$C_1$–$C_{15}$alkylene, $(C_1$–$C_{15}$alkyl$)_p$(heteroarylene)heteroalkylene, (heteroalkyl)$_p$($C_6$–$C_{10}$arylene)$C_1$–$C_{15}$alkylene, and $(C_1$–$C_{15}$alkyl$)_p$ ($C_6$–$C_{10}$arylene)heteroalkylene. In a further embodiment, $R^9$ of —$OR^9$ of $R^2$ is selected from a heteroalkyl group having 1–10 carbons and 1–4 heteroatoms selected from nitrogen, oxygen, silicon and sulfur, where —$CH_2CH_2Si$ $(CH_3)_3$ is a preferred heteroaklyl within this group.

In one embodiment, the present invention provides a compound of formula (I) wherein $R^2$ is —$NR^9R^9$. Optionally, $R^9$ of —$NR^9R^9$ of $R^2$ is independently selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. In a further optional embodiment, $R^9$ of —$NR^9R^9$ of $R^2$ is selected from hydrogen, heteroalkyl, $C_1$–$C_{15}$alkyl, (heteroaryl)$C_1$–$C_{15}$alkylene, (heteroalkyl)$_p$(aryl) heteroalkylene, (heteroalkyl)$_p$(aryl)$C_1$–$C_{15}$alkylene, and $(C_1$–$C_{15}$alkyl$)_p$($C_6$–$C_{10}$arylene)$C_1$–$C_{15}$alkylene.

In one embodiment, the present invention provides a compound of formula (I) wherein $R^3$ is hydrogen.

In two embodiments, the present invention provides a compound of formula (I) wherein $R^4$ and $R^5$ are independently selected from: hydrogen, —$R^9$, —$OR^9$, and —$NR^9R^9$, or $R^4$ and $R^5$ may together with the carbon to which they are both attached form a spiro carbocyclic or heterocyclic ring; and wherein $R^4$ and $R^5$ are each hydrogen.

In one embodiment, the present invention provides a compound of formula (I) wherein at least one of $R^4$ and $R^5$ is selected from $C_1$–$C_{15}$alkyl, heteroalkyl, and $C_6$–$C_{10}$aryl. In one embodiment, the present invention provides a compound of formula (I) wherein one of $R^4$ and $R^5$ is hydrogen and the other of $R^4$ and $R^5$ is selected from hydrogen, —$OR^9$, —$NR^9R^9$ and —N=N—$R^9$ where the $R^9$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R)_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})$-heteroalkylene, $(R^{12})_p$-arylene, and $(R^{12})_p$-heteroarylene; $R^{14}$ is selected from $(R^{13})_p$alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^9$ of —$OR^9$, —$NR^9R^9$ and —N=N—$R^9$ from $R^4$ and $R^5$ is selected from hydrogen, $C_6$–$C_{10}$aryl, heteroalkyl, $C_1$–$C_{15}$alkyl, and $(C_1$–$C_{15}$alkyl$)_p(C_6$–$C_{10}$arylene) $C_1$–$C_{15}$alkylene. In one embodiment, the present invention provides a compound of formula (I) wherein $R^4$ and $R^5$ together with the carbon to which they are both attached form a 3–6-membered spiro carbocyclic or heterocyclic ring. In one embodiment, the present invention provides a compound of formula (I) wherein $R^4$ and $R^5$ together form =O. In one embodiment, the present invention provides a compound of formula (I) wherein $R^4$ and $R^5$ together form =$NR^{10}$ and $R^{10}$ is —$OR^9$ where $R^9$ is selected from hydrogen, $C_6$–$C_{10}$aryl, $C_1$–$C_8$alkyl, heteroalkyl, $(C_6$–$C_{10}$aryl)heteroalkyl, $(C_6$–$C_{10}$aryl)$C_1$–$C_{15}$alkylene, (heteroalkyl)$_p$(heteroarylene)$C_1$–$C_{15}$alkylene, (heteroalkyl)$_p$($C_6$–$C_{10}$arylene)$C_1$–$C_{15}$alkylene, and $(C_1$–$C_{15}$alkyl)$_p$($C_6$–$C_{10}$arylene)heteroalkylene. In one embodiment, the present invention provides a compound of formula (I) wherein $R^4$ and $R^5$ together form =$NR^{10}$ and $R^{10}$ is —$N(R^9)(R^9)$ where $R^9$ is selected from hydrogen, $C_1$–$C_8$alkyl, heteroalkyl, $C_6$–$C_{10}$aryl, $(C_6$–$C_{10}$aryl)heteroalkylene, (heteroalkyl)$_p C_6$–$C_{10}$arylene, $(C_1$–$C_{15}$alkyl)$_p C_6$–$C_{10}$arylene, (heteroalkyl)$_p(C_6$–$C_{10}$arylene)heteroalkylene, $(C_1$–$C_{15}$alkyl)$_p(C_6$–$C_{10}$arylene) $C_1$–$C_{15}$alkylene, and $(C_1$–C15alkyl)$_p(C_6$–$C_{10}$arylene) $C_1$–$C_{15}$heteroalkylene. In one embodiment, the present invention provides a compound of formula (I) wherein $R^4$ and $R^5$ together form =$CR^8R^8$, and one of $R^8$ is hydrogen while the other $R^8$ is selected from hydrogen, $C_1$–$C_8$alkyl and heteroalkyl.

In one embodiment, the present invention provides a compound of formula (I) wherein $R^6$ is hydrogen. In another embodiment, the present invention provides a compound of formula (I) wherein $R^6$ is selected from $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. In another embodiment, $R^6$ is selected from $C_1$–$C_{15}$alkyl, $C_1$–$C_{15}$heteroalkyl, $(C_6$–$C_{10}$aryl) $C_1$–$C_{15}$alkylene, $(C_6$aryl)$(C_6$aryl)$C_1$–$C_{15}$alkylene, $(C_2$–$C_6$heteroaryl)$C_1$–$C_{15}$alkylene, $(C_6$–$C_{10}$aryl) $C_1$–$C_{15}$heteroalkylene, (heteroalkyl)$_p(C_6$–$C_{10}$arylene) $C_1$–$C_{15}$alkylene, (heteroalkyl)$_p(C_2$–$C_6$heteroarylene) $C_1$–$C_{15}$alkylene, and (heteroalkyl)$_p(C_6$arylene) heteroalkylene)$(C_6$arylene)$C_1$–$C_{15}$alkylene. In one embodiment of the present invention, $R^6$ is as defined above with the proviso that $R^6$ is not lower alkyl, e.g., is not $C_1$–$C_6$ so that —$OR^6$ is not $C_1$–$C_6$alkoxy.

In one embodiment, the present invention provides a compound of formula (I) wherein $R^8$ is hydrogen.

In one embodiment, the present invention provides a compound of formula (1) wherein n is 0. In another embodiment, the present invention provides a compound of formula (I) wherein n is 1. In another embodiment, the present invention provides a compound of formula (I) wherein n is 0 or 1.

In one embodiment, the present invention provides a compound of formula (I) wherein —$R^1$ is trans to —C(O)$R^2$, ie., compounds of formula (Ib) and (Ic), also referred to herein as compounds of formula (Ih).

In one embodiment, the present invention provides a compound of formula (I) wherein —$R^1$ is cis to —C(O)$R^2$, i.e., compounds of formula (Ia) and (Id), also referred to herein as compounds of formula (Ig).

In one embodiment, the present invention provides a compound of formula (I) wherein $R^3$ is hydrogen; $R^4$ and $R^5$ are selected from (a) $R^4$ is hydrogen and $R^5$ is hydroxyl or protected hydroxyl and (b) $R^4$ and $R^5$ together form carbonyl; $R^6$ is hydrogen; and n is 0. In one embodiment $R^2$ is —$OR^9$ where a preferred $R^2$ group is —$OCH_2CH_2Si(CH_3)_3$.

In one embodiment $R^1$ is

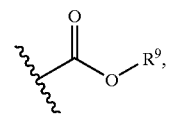

where optionally $R^9$ is a $C_1$–$C_6$ hydrocarbyl, such as, in one embodiment, n-propyl and —$CH_2$—CH=$CH_2$.

In one embodiment $R^1$ is

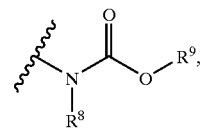

where optionally $R^8$ is hydrogen and $R^9$ is $C_1$–$C_6$ hydrocarbyl, such as, in one embodiment, $R^9$ is —$CH_2$—CH=$CH_2$.

B. Preparation of Benzobicyclooctane Compounds

The benzobicyclooctanes of this invention may be prepared according to Schemes 1–4. In these Schemes, "PG" denotes a protecting group. Suitable protecting groups are set forth in, for example, Greene and Wuts, Protective Groups in Organic Synthesis, 2d Edition, John Wiley & Sons, New York, 1991.

Scheme 1

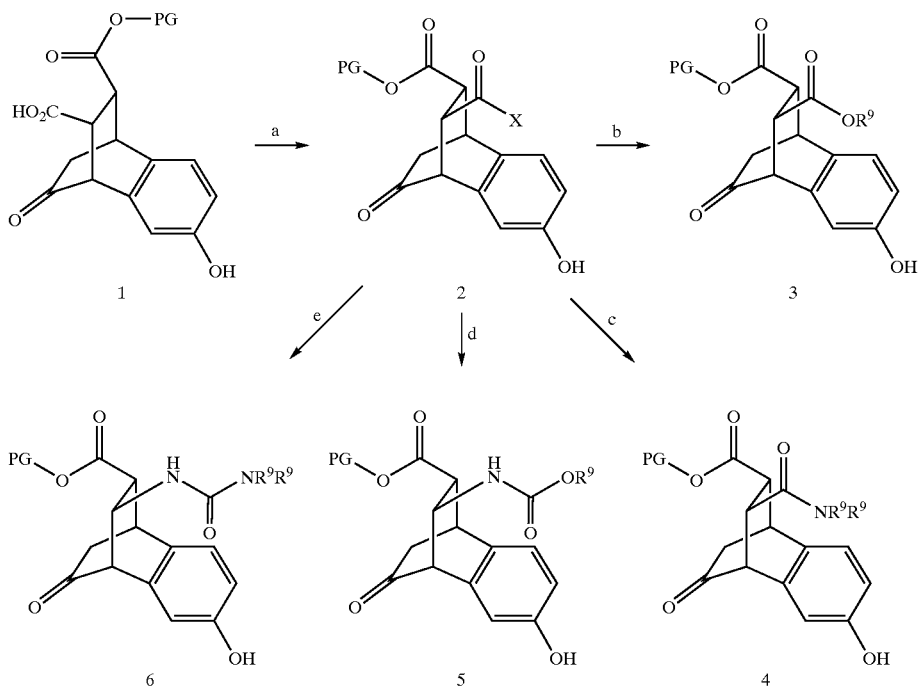

In Scheme 1, the starting material (not shown) for 1 may be prepared by the Diels-Alder reaction of 2,7-dihydroxynaphthalene with maleic anhydride (see, e.g., Singh, A. K.; Yadar, S.; Bhattacharjee, G., *J. Indian Chemical Soc.* 1990, 67, 818; and Takeda, K.; Hagishita, S.; Sugiura, M.; Kitahonoki, K.; Ban, I.; Miyazaki, S.; Kuriyama, K., *Tetrahdedron* 1970, 26, p. 1435). The resulting anhydride may be opened with a suitable alcohol, e.g., trimethylsilylethanol, to give the 9-protected and the 10-protected benzobicyclooctane, 1 (only the 9-ester is depicted).

In Scheme 1, chemical steps a, b, c, d, and e represent the following reaction conditions.

(a) is a chemical reaction wherein the free acid of 1 is transformed into the reactive intermediate 2. Suitable conditions for this type of reaction involve treating 1 with a suitable activating agent, e.g. diphenylphosphoryl azide, in the presence of a suitable base, e.g., an organoamine such as diisopropylethylamine (DIEA), in an appropriate solvent, e.g., tetrahydrofuran (THF), at a suitable reaction temperature, e.g., at ambient temperature. Alternatively, formation of an active ester via a suitable coupling agent and hydroxy compound, e.g., 1-(3-dimethylaminopropyl)-3-ethylcarbodiimide hydrochloride (EDCI) and 1-hydroxybenzotriazole (HOBt), under the same conditions produce 2, suitable for use in steps b or c. In either process, X is a leaving group that activates the adjoining carbonyl group.

(b) is a chemical reaction in which the activated acid 2 forms the ester 3. Suitable conditions for this type of reaction involve treating 2 with a suitable alcohol ($R^9OH$), e.g., n-propanol, in the presence of a suitable catalyst, e.g., 4-dimethylaminopyridine (DMAP), in an appropriate solvent, e.g., THF, at an appropriate temperature, e.g., ambient temperature. In alcohols of formula $R^9OH$, $R^9$ is an organic group having 1–30 carbons and optionally containing 1–4 heteroatoms selected from nitrogen, oxygen, silicon and sulfur, with the provision that two $R^9$ groups both joined to a common atom may be joined together so as to form a ring with the common atom. In one embodiment, $R^9$ is selected from $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^9$ is selected from heteroalkyl, $C_1$–$C_{15}$alkyl, $(C_6$–$C_{10}$aryl$)C_1$–$C_{15}$alkylene, $(C_6$–$C_{10}$aryl$)(C_6$–$C_{10}$arylene$)C_1$–$C_{15}$alkylene, $(C_1$–$C_{15}$alkyl$)_p$(heteroarylene$)C_1$–$C_{15}$alkylene, and $C_6$–$C_{10}$aryl fused to $C_1$–$C_{15}$alkylene. Numerous suitable alcohols of formula $R^9OH$ are either commercially available chemicals or are compounds described in the chemical literature.

(c) is a chemical reaction in which 2 is coupled with an amine to give the amide 4. Suitable conditions for this type of reaction involve treating 2 with a suitable amine ($R^9R^9NH$), e.g., di(n-pentyl)amine, and a suitable base (if required), e.g., DIEA, in the presence of a suitable catalyst, e.g., DMAP, in an appropriate solvent, e.g., THF, at ambient temperature. In amines of formula $R^9R^9NH$, $R^9$ is selected from hydrogen and organic groups having 1–30 carbons and optionally containing 1–4 heteroatoms selected from nitrogen, oxygen, silicon and sulfur, with the proviso that the two $R^9$ groups may be joined together so as to form a ring with the nitrogen to which they are both attached. In one embodiment, $R^9$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5. Optionally, $R^9$ is selected from hydrogen, heteroalkyl, $C_1$–$C_{15}$alkyl, (heteroaryl)$C_1$–$C_{15}$alkylene, and (heteroalkyl)$_p$($C_6$–$C_{10}$arylene)$C_1$–$C_{15}$alkylene. Numerous suitable amines of formula $R^9R^9NH$ are either commercially available chemicals or are compounds described in the chemical literature.

(d) is a chemical reaction in which 2 is an acyl azide and is converted to the corresponding isocyanate prior to reaction with an alcohol ($R^9OH$ as defined above) to yield carbamate 5. Suitable conditions for this type of reaction involve first heating 2 in suitable solvent, e.g., refluxing dioxane, and then treating the resulting isocyanate with a suitable alcohol $R^9OH$, e.g., n-propanol, in the absence or presence of a suitable catalyst, e.g., DMAP.

(e) is a chemical reaction in which 2 is an acyl azide and is converted to the isocyanate prior to reacting with an amine ($R^9R^9NH$ as defined above), to yield urea 6. Suitable conditions for this type of reaction involve first heating 2 in a suitable solvent, e.g., refluxing dioxane, and then treating the resulting isocyanate with a suitable amine ($R^9R^9NH$), e.g., morpholine or tyramine.

In Scheme 2, chemical steps f, g and h represent the following reaction conditions.

(f) is a chemical reaction in which the protecting group of 3 is removed to give 7. When, for example, PG is trimethylsilylethyl, it may be removed by exposure to a suitable fluoride source, e.g., tetrabutylammonium fluoride (TBAF), in a suitable solvent, e.g., anhydrous THF. Alternatively, suitable deprotection conditions involve performing an acidolysis in, e.g., TFA/$H_2O$, 9/1 (v/v). Other conditions for removing protecting groups are set forth in Greene and Wuts, Protective Groups in Organic Synthesis, 2d Edition, John Wiley & Sons, New York, 1991.

(g) is a chemical reaction in which 7 is coupled to an alcohol to give 8. Suitable conditions for this type of reaction involve treating 7 with a suitable alcohol, e.g., dimethylbutanol, a coupling reagent such as O—(N-Succinimidyl)-1,1,3,3-tetramethyluronium tetrafluoroborate (TSTU), a suitable base, e.g., an organoamine such as N-methylmorpholine (NMM), in the presence of a suitable catalyst, e.g., DMAP, in an appropriate solvent, e.g., 5% dimethylformamide (DMF) in THF.

(h) is a chemical reaction in which 7 is coupled with an amine $HNR^9R^9$ to give 9. Suitable conditions for this type of reaction involve treating 7 with a suitable coupling reagent such as O-(7-azabenzotriazol-1-yl)-N,N,N',N'-tetramethyluronium hexafluorophosphate (HATU), a suitable base, e.g., an organoamine such as NMM, in the presence of a suitable catalyst, e.g., DMAP, in an appropriate solvent, e.g., THF.

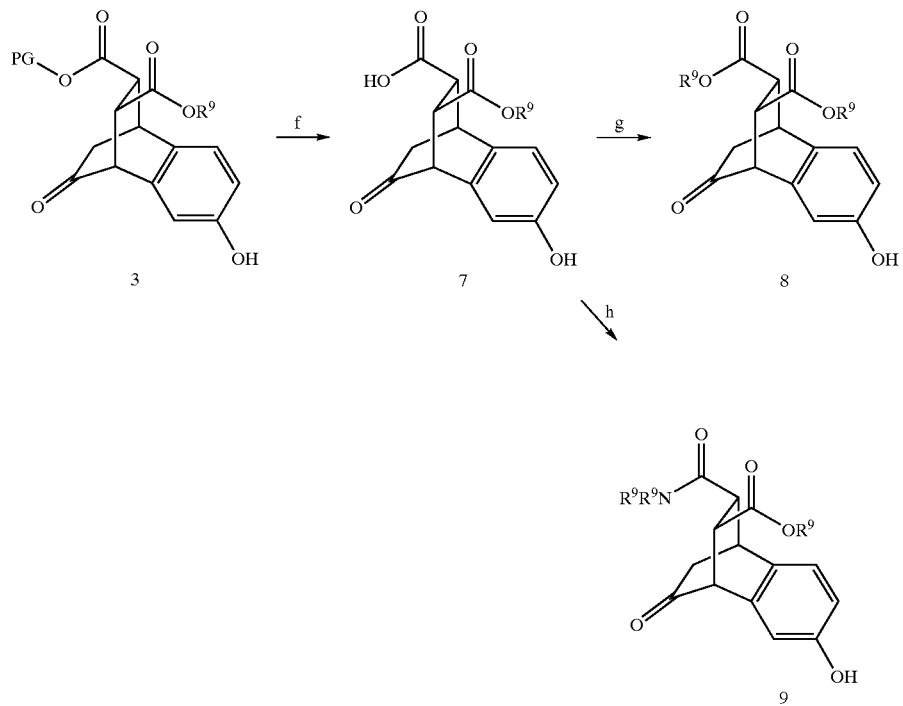

Scheme 3

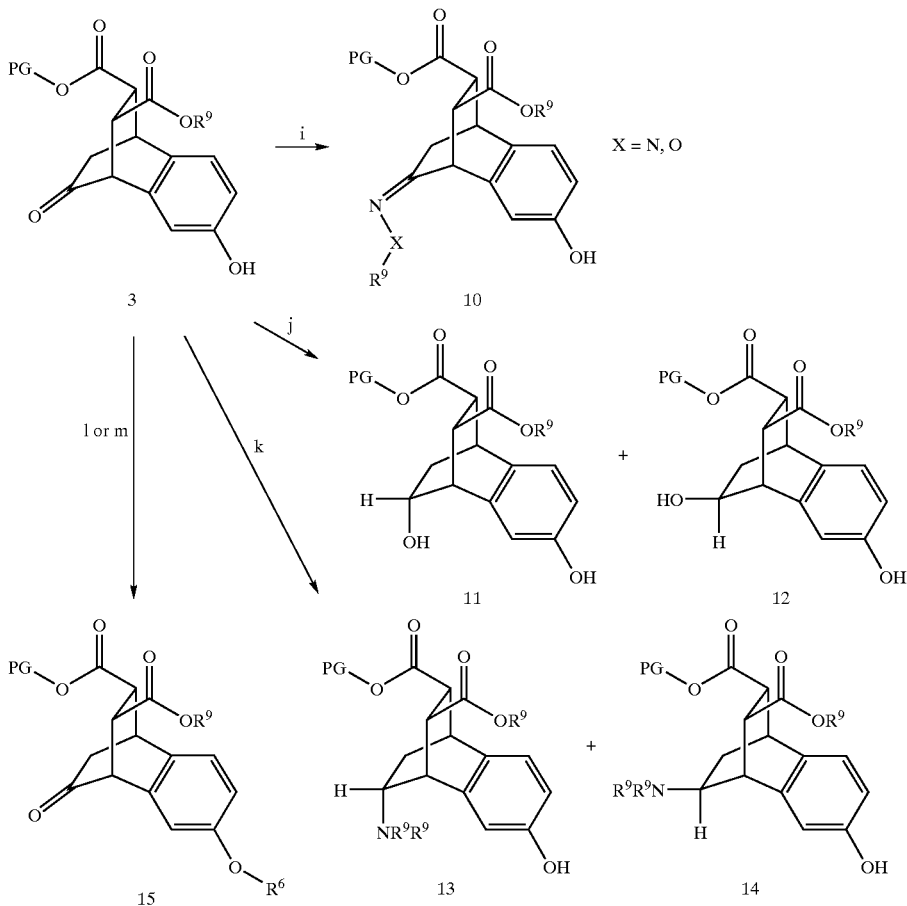

In Scheme 3, chemical steps i, j, k, l and m represent the following reaction conditions.

(i) is a chemical reaction in which the ketone group of 3 is derivatized with an organohydrazine or organohydroxylamine to give 10. Suitable conditions for performing this type of reaction involve treating the ketone with a suitable hydrazine or hydroxylamine, e.g., methyl hydrazine or O-phenyl-hydroxylamine, in a suitable solvent, e.g., methanol.

(j) is a chemical reaction in which the ketone group of 3 is reduced to give alcohols 11 and 12. Suitable conditions for performing this type of reaction involve treating the ketone with a suitable reducing agent, e.g., $NaBH_4$, in a suitable solvent, e.g., methanol. Other suitable reducing conditions are set forth in well known books and treatises. The resulting stereoisomers 11 and 12 may be separated from one another by, e.g., column chromatography.

(k) is a chemical reaction in which the ketone of group of 3 undergoes reductive amination to give amines 13 and 14. Suitable conditions for performing this type of reaction involve treating the ketone with a suitable amine ($HNR^9R^9$), e.g., dimethylamine, a suitable reducing agent, e.g., $NaBH_3CN$, in the presence of a mild acid, e.g., acetic acid, in a suitable solvent, e.g., methanol. Other suitable reductive amination conditions are set forth in well known books and treatises. The resulting stereoisomers 13 and 14 may be separated from one another by, e.g., column chromatography.

(l) is a chemical reaction in which the phenolic group of 3 is alkylated to give 15. Suitable conditions for performing this type of reaction involve treating 3 with a suitable alkyl halide, e.g., N,N-diethyl-2-chloroacetamide, in the presence of a suitable inorganic base, e.g., $CS_2CO_3$, in a suitable solvent, e.g., dimethoxyethane (DME) or DMF. Other suitable alkyl halides of formula $R^6$-X are well known in the art, where X is halide, and $R^6$ is selected from $R^{11}, R^{12}, R^{13}, R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5, and optionally is selected from $C_1-C_{15}$alkyl, $C_1-C_{15}$heteroalkyl, $(C_6-C_{10}$aryl$)C_1-C_{15}$alkylene, $(C_6$aryl$)$ $(C_6$aryl$)C_1-C_{15}$alkylene, $(C_2-C_6$heteroaryl$)$ $C_1-C_{15}$alkylene, $(C_6-C_{10}$aryl$)C_1-C_{15}$heteroalkylene, (heteroalkyl)$_p$($C_6-C_{10}$arylene)$C_1-C_{15}$alkylene, (heteroalkyl)$_p$($C_2-C_6$heteroarylene)$C_1-C_{15}$alkylene, and (heteroalkyl)$_p$($C_6$arylene)(heteroalkylene)($C_6$arylene) $C_1-C_{15}$alkylene. Numerous suitable alkyl halides are either commercially available chemicals or are compounds described in the chemical literature.

(m) is a chemical reaction in which the phenolic group of 3 is alkylated to give 15. Suitable conditions for performing this type of reaction involve treating 3 with an organic compound having a suitably activated hydroxyl group in a suitable solvent, such as THF. For example, allyl 4-hydroxymethylbenzoate may be activated by exposure to a phosphine, e.g., triphenylphosphine, and a suitable azo compound, e.g., diethylazodicarboxylate (DEAD). Other suitable compounds having an activated hydroxyl group may be readily prepared from the corresponding alcohol of the formula $R^6$-OH where $R^6$ is an organic group. Alcohols of the formula $R^6$-OH are well known in the art, including alcohols wherein $R^6$ is selected from $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5, and optionally is selected from $C_1$–$C_{15}$alkyl, $C_1$–$C_{15}$heteroalkyl, $(C_6$–$C_{10}$aryl)$C_1$–$C_{15}$alkylene, $(C_6$aryl) $(C_6$aryl)$C_1$–$C_{15}$alkylene, $(C_2$–$C_6$heteroaryl) $C_1$–$C_{15}$alkylene, $(C_6$–$C_{10}$aryl)$C_1$–$C_{15}$heteroalkylene, (heteroalkyl)$_p$($C_6$–$C_{10}$arylene)$C_1$–$C_{15}$alkylene, (heteroaklyl)$_p$($C_2$–$C_6$heteroarylene)$C_1$–$C_{15}$alkylene, and (heteroalkyl)$_p$($C_6$arylene)(heteroalkylene)($C_6$arylene) $C_1$–$C_{15}$alkylene. Numerous suitable alcohols are either commercially available chemicals or are compounds described in the chemical literature.

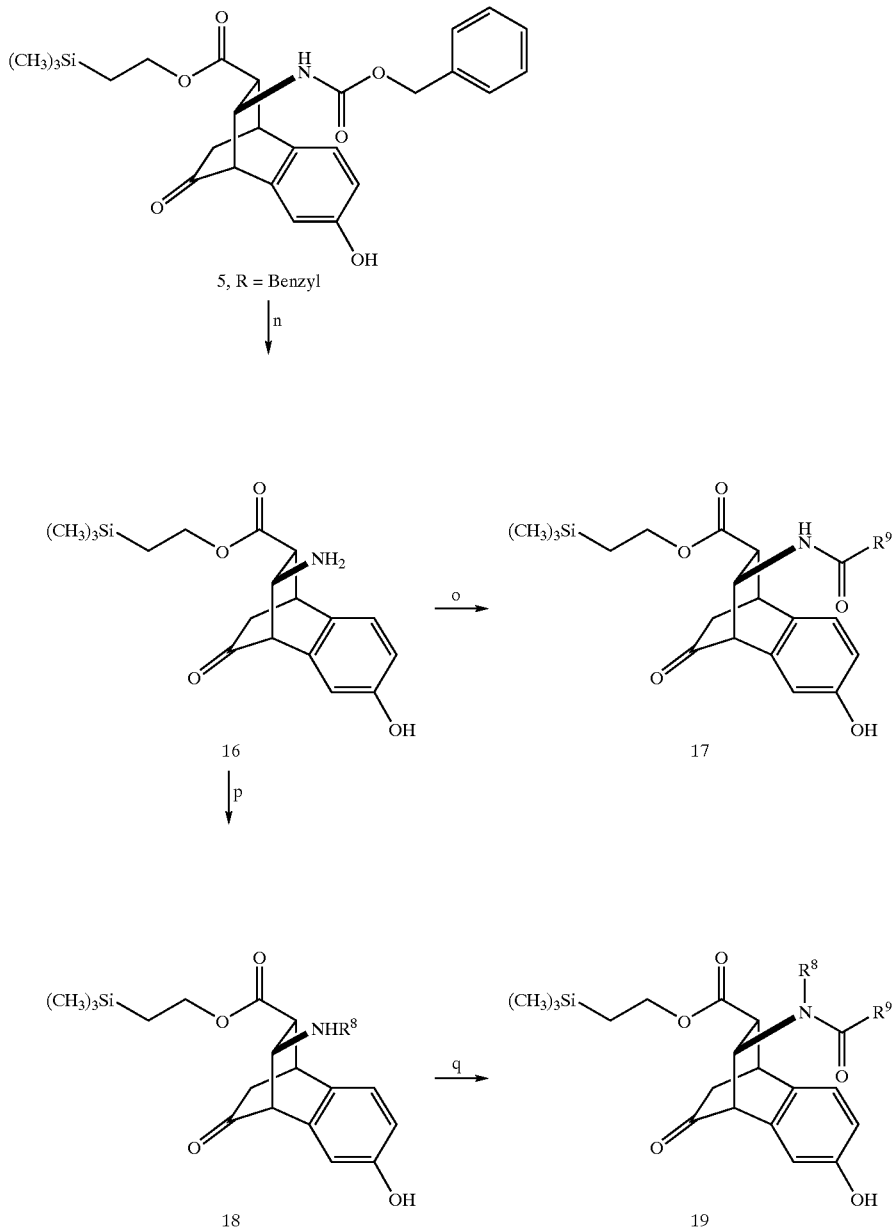

Scheme 4

5, R = Benzyl

16

17

18

19

In Scheme 4, chemical steps n, o, p and q represent the following reaction conditions.

(n) is a chemical reaction wherein the ester-carbamate 5 (prepared in, e.g., Scheme 1) is transformed into the corresponding ester-amine 16. Suitable conditions for this type of reaction involve treating 5 under reducing conditions, e.g., $H_2$, on a suitable catalyst or solid support, e.g., palladium, in the presence of a suitable solvent, e.g. ethanol.

(o) is a chemical reaction wherein the ester-amine 16 is acylated to form the corresponding ester-amide 17. Suitable conditions for this type of reaction involve treating 16 with an acylating agent, generally denoted as $R^9$—C(=O)—X where $R^9$ represents $R^9$ as set forth in compounds of formula R1a, and X is a leaving group, e.g., chloride. The acylation reaction is suitably conducted in the presence of an amine, such as a secondary or tertiary amine, e.g., diisopropylethylamine (DIEA).

(p) is a chemical reaction wherein the ester-1°amine 16 is transformed into an ester-2°amine 18. Suitable conditions for this type of reaction involve treating 16 with an aldehyde of the formula $R^8$—CHO, in the presence of a reducing agent, e.g., $NaCNBH_3$. In Scheme 4, the designation "$R^{8"}$" is used to denote the "$R^{8"}$" group as found in, for example, compound of formula R1a. Compounds of formula $R^8$—CHO wherein $R^8$ is selected from alkyl, aryl and heteroalkyl are well known in the chemical literature, and are available from commercial suppliers of chemicals. The ester-2°amine 18 is a suitable intermediate in the preparation of compounds of formula 19, which are also compounds of formula R1a.

(q) is a chemical reaction wherein the ester-2°amine 18 is transformed into an ester-amide 19. Suitable conditions for this type of reaction involve treating 18 with an acylating agent, generally denoted as $R^9$—C(=O)—X, where $R^9$ is used in Scheme 4 to denote "$R^{9"}$" in, for example, compounds of formula R1a, and X is a leaving group, e.g., chloride. The acylation reaction is suitably conducted in the presence of an amine, such as a secondary or tertiary amine, e.g., diisopropylethylamine (DIEA). Compounds of the formula $R^9$—C(=O)—X are readily prepared from the corresponding carboxylic acid of the formula $R^9$—C(=O)—OH by treatment with, e.g., thionyl chloride.

Numerous compounds of the formula $R^9$—C(=O)—OH wherein $R^9$ is an organic group having 1–30 carbons and optionally containing 1–4 heteroatoms selected from nitrogen, oxygen and silicon are well known in the chemical literature, and/or may be obtained from many commercial suppliers of chemicals. Furthermore, many compounds of formula $R^9$—C(=O)—OH wherein $R^9$ is selected from $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5, are well known in the chemical literature and/or may be obtained from commercial suppliers of chemicals. Furthermore, many compounds of formula $R^9$—C(=O)—OH wherein $R^9$ is selected from heteroalkyl, $C_1$–$C_{15}$alkyl, (heteroaryl)$C_1$–$C_{15}$alkylene, ($C_6$–$C_{10}$aryl)$C_1$–$C_{15}$alkylene, $C_6$–$C_{10}$aryl fused to $C_1$–$C_{15}$alkylene, (alkyl)$_p$($C_6$–$C_{10}$arylene)$C_1$–$C_{15}$alkylene, ($C_6$–$C_{10}$aryl)($C_6$–$C_{10}$arylene)$C_1$–$C_{15}$alkylene, ($C_1$–$C_{15}$alkyl)$_p$(heteroarylene)$C_1$–$C_{15}$alkylene, and (heteroalkyl)$_p$($C_6$–$C_{10}$arylene)$C_1$–$C_{15}$alkylene, are well known in the chemical literature and/or may be obtained from commercial suppliers of chemicals. Furthermore, many compounds of formula $R^9$—C(=O)—OH wherein $R^9$ is selected from heteroalkyl, $C_1$–$C_{15}$alkyl, ($C_6$–$C_{10}$aryl)$C_1$–$C_{15}$alkylene, (heteroaryl)$C_1$–$C_{15}$alkylene, and (heteroalkyl)$_p$($C_6$–$C_{10}$arylene)$C_1$–$C_{15}$alkylene, are well known in the chemical literature and/or may be obtained from commercial suppliers of chemicals. Furthermore, many compounds of formula $R^9$—C(=O)—OH wherein $R^9$ is selected from heteroalkyl, $C_1$–$C_{15}$alkyl, ($C_6$–$C_{10}$aryl)$C_1$–$C_{15}$alkylene, ($C_6$–$C_{10}$aryl)($C_6$–$C_{10}$arylene)$C_1$–$C_{15}$alkylene, ($C_1$–$C_{15}$alkyl)$_p$(heteroarylene)$C_1$–$C_{15}$alkylene, and $C_6$–$C_{10}$aryl fused to $C_1$–$C_{15}$alkylene are well known in the chemical literature and/or may be obtained from commercial suppliers of chemicals. Furthermore, many compounds of formula $R^9$—C(=O)—OH wherein $R^9$ is selected from heteroalkyl, $C_1$–$C_{15}$alkyl, ($C_6$–$C_{10}$aryl)$C_1$–$C_{15}$alkylene, ($C_6$–$C_{10}$aryl)($C_6$–$C_{10}$arylene)$C_1$–$C_{15}$alkylene, ($C_1$–$C_{15}$alkyl)$_p$-(heteroarylene)$C_1$–$C_{15}$alkylene, and $C_6$–$C_{10}$aryl fused to $C_1$–$C_{15}$alkylene are well known in the chemical literature and/or may be obtained from commercial suppliers of chemicals. Furthermore, many compounds of formula $R^9$—C(=O)—OH wherein $R^9$ is selected from heteroalkyl, $C_1$–$C_{15}$alkyl, (heteroaryl)$C_1$–$C_{15}$alkylene, and (heteroalkyl)$_p$($C_6$–$C_{10}$arylene)$C_1$–$C_{15}$alkylene are well known in the chemical literature and/or may be obtained from commercial suppliers of chemicals. Furthermore, many compounds of formula $R^9$—C(=O)—OH wherein $R^9$ is selected from heteroalkyl, $C_1$–$C_{15}$alkyl, (heteroaryl)$C_1$–$C_{15}$alkylene, ($C_6$–$C_{10}$aryl)$C_1$–$C_{15}$alkylene, (alkyl)$_p$($C_6$–$C_{10}$arylene)$C_1$–$C_{15}$alkylene, are well known in the chemical literature and/or may be obtained from commercial suppliers of chemicals. These carboxylic acids may be used in the preparation of compounds of the present invention.

One skilled in the art of organic synthesis would readily understand that the chemical steps disclosed above may be performed in a variety of sequences to produce bicyclooctanes of this invention. For instance, the compound of Example 2 undergoes step (h) to give the compound of Example 4. This compound in turn undergoes step (m) to give the bicyclooctane of Example 5.

The present invention provides benzobicyclooctane compounds wherein $R^3$ may or may not be hydrogen, and independently, $R^7$ may replace a hydrogen either 0, 1, 2 or 3 times on the "benzo" portion of the benzobicyclooctane compound. Compounds wherein $R^3$ is hydrogen and n is 0 are readily prepared from (unsubstituted) 2,7-dihydroxynaphthalene, as shown in Schemes 1, 2, 3 and 4. Compounds wherein $R^3$ is not hydrogen, and/or n is not 0, are readily prepared from the corresponding substituted 2,7-dihydroxynaphthalene. For example, a benzobicyclooctane compound of the invention wherein $R^3$ is methyl and n is 1 with $R^7$ being a methyl group may be prepared from a dimethyl substituted 2,7-dihydroxynaphthalene, e.g., 2,7-dihydroxy-3,6-dimethylnaphthalene as shown in Scheme 5. Commercial supply houses, custom chemical supply houses, and published synthetic methods provide access to a large number of substituted 2,7-dihydroxynaphthalene compounds that may be used in preparing compounds of the present invention.

Furthermore, benzobicyclooctane compounds wherein $R^3$ is not equal to hydrogen and/or n is 1, 2 or 3 may be used in the synthetic transformations shown in Schemes 1, 2, 3 and/or 4, in lieu of the hydrogen-substituted benzobicyclooctane depicted in those Schemes, to provide compounds of the present invention. For instance, the benzobicyclooctane produced by the Diels-Alder reaction of maleic anhydride and 2,7-dihydroxy-3,6-dimethylnaphthalene as shown in Scheme 5 may be treated to open up the anhydride and form the corresponding acid/ester. Exemplary treatment conditions are DMAP with trimethylsilylethanol (see, e.g., Example 1 as described herein), which provides the corresponding carboxylic acid/trimethylsilylethylene ester as shown in Scheme 5, where this acid/ester is a representative compound of formula 1 as shown in Schemes 1, 2, 3 and 4.

Scheme 5

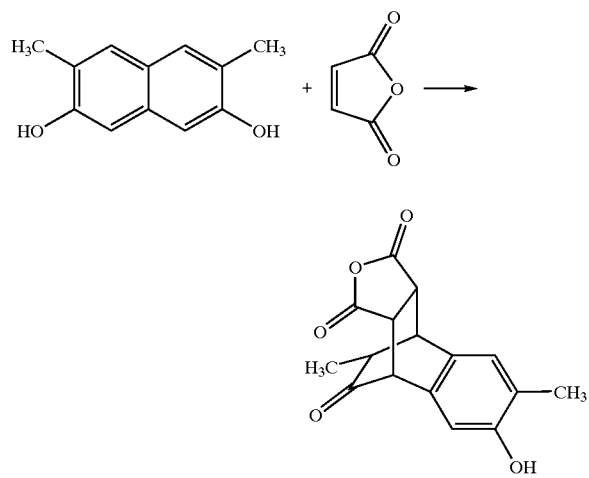

In one aspect, the present invention provides benzobicyclooctane compounds wherein $R^6$ is hydrogen or an organic group having 1–20 carbons, wherein the organic group may optionally include 1–4 heteroatoms selected from nitrogen, oxygen, silicon and sulfur. Schemes 1, 2, 3 and 4 illustrate synthetic methodology using a benzobicyclooctane compound wherein $R^6$ is hydrogen. However, the same methodology may be employed with benzobicyclooctane compounds wherein $R^6$ is an organic group.

Alternatively, a compound of the invention may be prepared according to Schemes 1, 2, 3 and 4, having desired $R^1$, $R^2$, $R^3$, $R^4$, $R^5$ and $R^7$ groups, with $R^6$ being hydrogen. The $R^6$ hydrogen may be replaced with an organic group having 1–20 carbons and optionally having 1–4 heteroatoms selected from nitrogen, oxygen, silicon and sulfur, as shown in steps 1 or m of Scheme 3. This later approach is illustrated in several Examples as set forth herein (see, e.g., Examples 5, 10, 33 (describing General Procedure F for converting $R^6$=H to $R^6$=organic group), 35 (describing General Procedure G) 36–43 and 45 (employing General Procedure F), and 44, 46–52 (employing General Procedure G) and 87–88. See also Examples 7, 8 and 34 wherein the $R^6$ group is replaced with a different $R_6$ group). Accordingly, in view of the present disclosure, those of ordinary skill in the art can prepare compounds of the present invention wherein $R^6$ is hydrogen or an organic group.

Benzobicyclooctane compounds of the invention wherein $R^6$ is an inorganic group having 1–8 atoms exclusively selected from boron, sulfur, phosphorous, silicon and hydrogen, may readily be prepared from the corresponding phenolic compound, i.e., compounds wherein $R^6$ is H. Methodology to convert alcohols to, e.g., sulfates, sulfonates, phosphates, phosphonates, borates, and boronates, where these groups are exemplary inorganic $R^6$ groups, are well known in the art, and may be employed in the preparation of compounds of the present invention. For clarification, it will be noted that groups including heteroatoms as well as carbon atoms, e.g., —O—B(OR)$_2$ and —S(O)$_2$R where R is an organic group, are included within the scope of heteroalkyls as defined herein.

The present invention provides various stereoisomers of benzobicyclooctanes, in isolated form or as mixtures of stereoisomers, and in particular provides the diastereomers shown as Formulae Ia, Ib, Ic and Id. Any of these four diastereomers can be prepared according to the present invention. The Diels-Alder reaction of 2,7-dihydroxynaphthalene and maleic acid typically forms two diastereomers, shown as structures A and B in Scheme 6.

Scheme 6

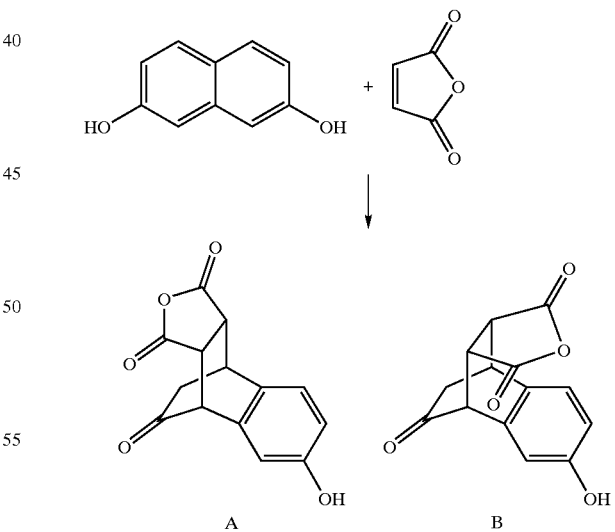

The diastereomers A and B can be separated from one another by, for example, chromatography, and then each can be reacted individually with trimethylsilyl ethanol to provide a mixture of the corresponding two cis acid-esters (C and D), as shown in Scheme 7a starting from diastereomer A, or the corresponding two trans acid-esters (E and F), as shown in Scheme 7b starting from diastereomer B.

Scheme 7a

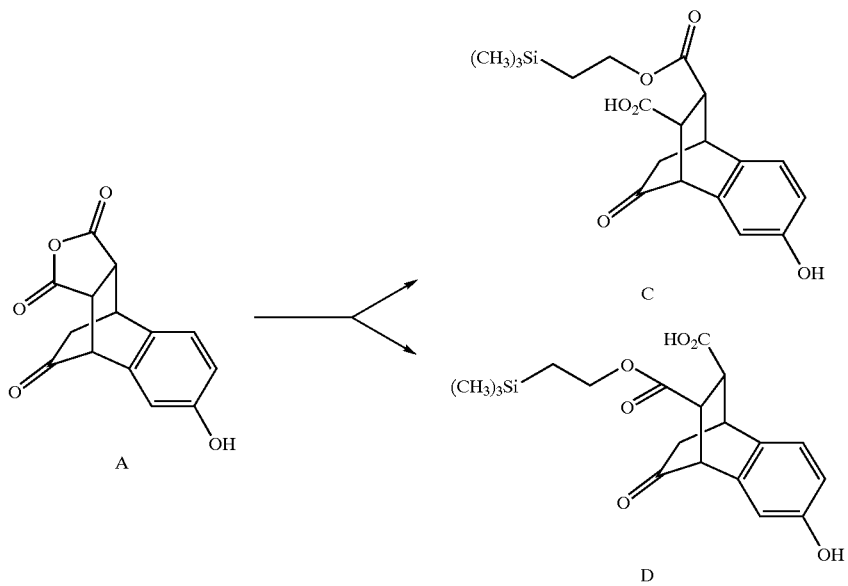

Scheme 7b

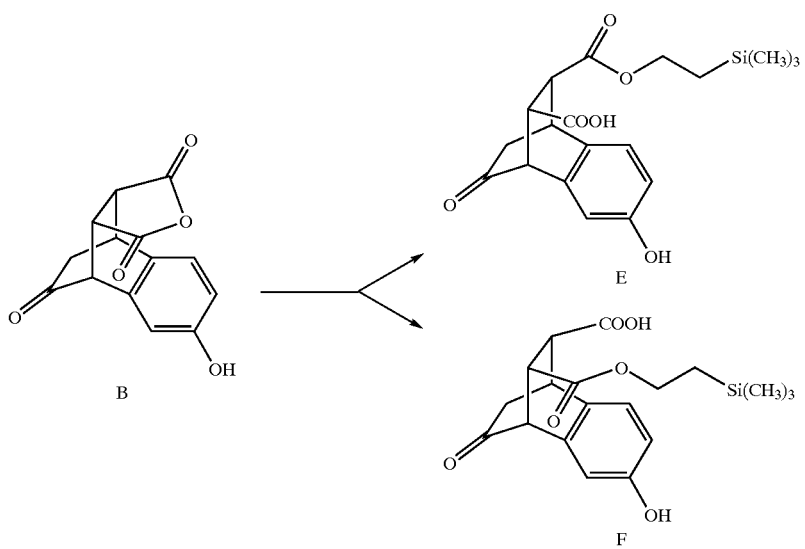

The diastereomers C and D may be separated from one another by, for example, chromatography. Likewise, the diastereomers E and F can be separated from one another by, for example, chromatography. Each of the diastereomers C, D, E and F may be reacted under conditions to give either the trans or cis products. For example, as shown in Scheme 8a, diastereomer C may be reacted to form the trans diastereomer G or the cis diastereomer H where X is —OR (diester) or —NRR (ester amide). Likewise, diastereomer D may be reacted to form cis and trans products as shown in Scheme 8b.

Scheme 8a
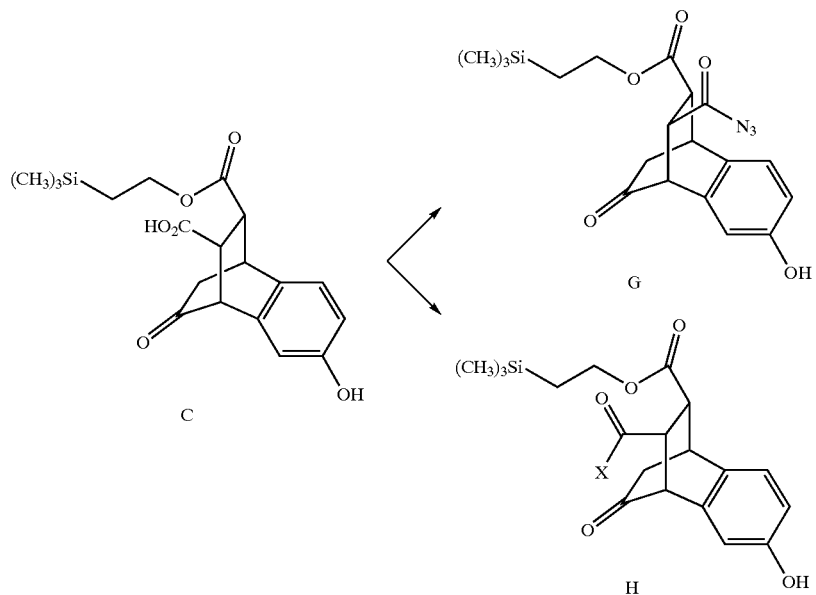
Scheme 8b
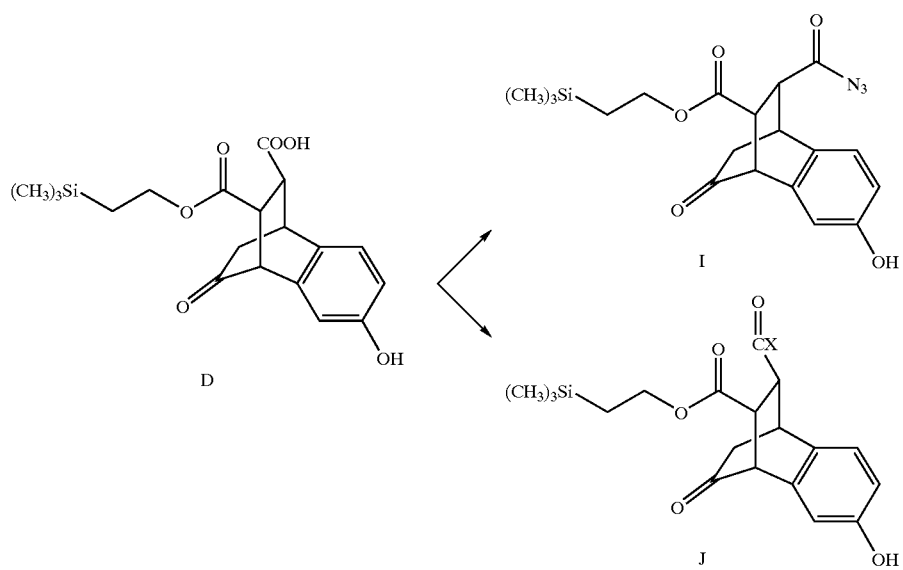
C. Libraries
In one aspect, the present invention provides a library of benzobicyclooctane compounds. In one aspect the library includes, i.e., comprises, a plurality of compounds each having a structure of formula (I), while in another aspect the library consists of a plurality of compounds each having a structure of formula (I)
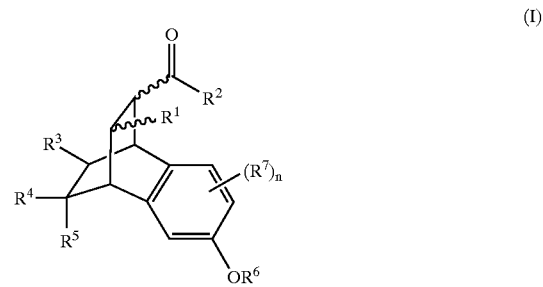

where each of $R^1$, $R^2$, $R^3$, $R^4$, $R^5$, $R^6$, and $R^7$ have been defined above, including narrower embodiments thereof and set forth above, and diversity is present among the $R^1$, $R^2$, $R^3$, $R^4$, $R^5$, $R^6$, and $R^7$ groups.

A library according to the present invention may be prepared by combinatorial synthetic techniques, where such a library is referred to herein as a combinatorial library. An exemplary combinatorial approach to preparing a library of the present invention is a solid-phase technique, where the benzobicyclooctane scaffold is covalently attached to a solid support. An exemplary solid-phase combinatorial technique includes the following steps:

(a) providing a compound bound to a solid support according to formula

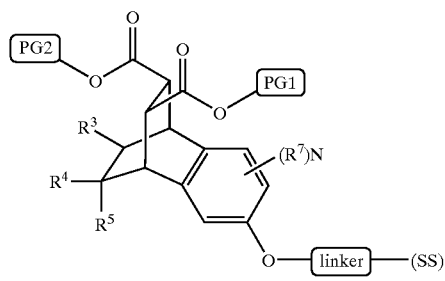

(II)

wherein PG1 and PG2 refer to first and second protecting groups, respectively, where the first protecting group can be removed in the continued presence of the second protecting group, and the second protecting group can be removed in the continued presence of the linker, and (SS) refers to a solid support;

(b) removing the first protecting group but not the second protecting group, to provide a first deprotected product;

(c) reacting the first deprotected product with a plurality of amines of the formula HNRR' to provide a plurality of compounds bound to a solid support, each according to formula (IIa)

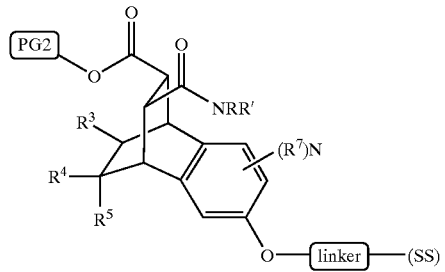

(IIa)

where R and R' are each independently selected from $R^9$;

(d) removing the second protecting group from (IIa) to provide a second deprotected product;

(e) reacting the second deprotected product with a plurality of amines of the formula HNR"R'" to provide a plurality of compounds bound to a solid support, each according to formula (IIb)

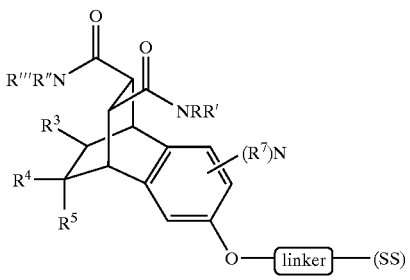

(IIb)

where R" and R'" are each independently selected from $R^9$; and (f) removing the benzobicyclooctane compounds from the linker to provide a library of compounds according to formula (IIc)

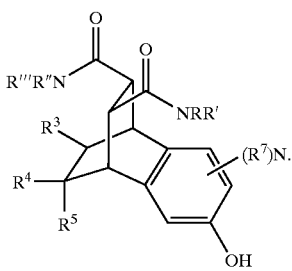

(IIc)

In various embodiments of this method: PG1 is —CH$_2$—CH=CH$_2$; and/or wherein PG2 is —CH$_2$CH$_2$—Si(CH$_3$)$_3$; and/or linker is

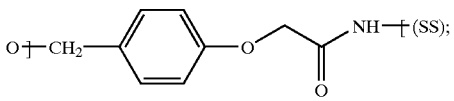

or PG1 is —CH2—CH=CH2 while PG2 is —CH$_2$CH$_2$—Si(CH$_3$)$_3$ and while linker is

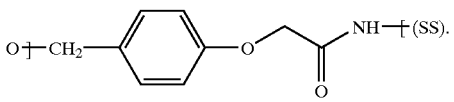

In various embodiments, additionally or alternatively: removing the first protecting group but not the second protecting group, to provide a first deprotected product according to step (b), is accomplished by reacting (II) with Pd(PPh$_3$)$_4$ and N-methylaniline; and/or removing the second protecting group from (IIa) to provide a second deprotected product according to step (d) is accomplished by treating (IIa) with tetrabutylammonium fluoride solution; and/or removing the linker to provide a library of compounds according to formula (IIc) is accomplished by treating (IIb) with aqueous trifluoroacetic acid.

In various embodiments, additionally or alternatively, the library prepares compounds wherein $R^3$ is H, $R^4$ and $R^5$ collectively form =O, and n is zero.

C. Pharmaceutical Compositions

In another aspect, the present invention provides a composition containing a benzobicyclooctane compound of formula (I) in admixture with a pharmaceutically acceptable adjuvant, carrier, diluent or excipient, i.e., the present invention provides a pharmaceutical composition containing a compound of formula (I). In other aspects, the present invention provides a composition containing a benzobicyclooctane compound according to each of embodiments, X1–X930, Y1–Y930 and Z1–Z930 in admixture with a pharmaceutically acceptable adjuvant, carrier, diluent or excipient. The pharmaceutical composition may contain optional ingredient(s) if desired.

The pharmaceutical compositions of the present invention may be in any form which allows for the composition to be administered to a patient. Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of benzobicyclooctane in aerosol form may hold a plurality of dosage units.

The composition may be in the form of a solid, liquid or gas (aerosol). In one aspect, the carrier(s) are particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active vanadium(V) complex. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the benzobicyclooctane compounds of the invention and thereby assists in the delivery of the active compound. Suitable agents which may act in this capacity include a monoclonal or polyclonal antibody, a protein or a liposome.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation.

The pharmaceutical compositions may be prepared by methodology well known in the pharmaceutical art. For example, a composition intended to be administered by injection can be prepared by combining a benzobicyclooctane compounds of formula (I) with water so as to form a solution. A surfactant may be added to facilitate the formation of a homogeneous solution or suspension. Surfactants are compounds that non-covalently interact with the benzobicyclooctane compound so as to facilitate dissolution or homogeneous suspension of the compound in the aqueous delivery system.

D. Biological Applications

The present invention provides benzobicyclooctanes, compositions containing a benzobicyclooctane, and methods of using benzobicyclooctane compounds to inhibit cellular events involving TNF-α or IL-8. Thus, in one aspect, the present invention provides a method to modulate binding of TNF-α to cell receptors, and/or modulate the consequential intracellular events comprising administering to a subject in a need thereof an effective amount of a benzobicyclooctane compounds of formula (I). The inhibition of TNF-α induced apoptosis and of NFκB activation is one means of preventing and/or treating autoimmune and inflammatory diseases including, but not limited to, rheumatoid arthritis, inflammatory bowel disease, psoriasis, atherosclerosis, asthma, reperfusion injury, ischemia, sepsis, graft vs. host disease, adult respiratory distress syndrome, multiple sclerosis, and a host of severe invasive infections such as fulminant hepatitis, AIDS and bacterial meningitis, and allergic inflammation-of the lungs and airways.

Thus, in one aspect, the present invention provides a method of inhibiting TNF-α induced apoptosis comprising administering to a subject in a need thereof an effective amount of a benzobicyclooctane compounds of formula (I). In another aspect, the present invention provides a method of inhibiting NFκB activation comprising administering to a subject in a need thereof an effective amount of a benzobicyclooctane compounds of formula (I). In another aspect, the present invention provides a method of inhibiting, preventing, treating, or preventing and/or treating autoimmune and inflammatory diseases including, but not limited to, rheumatoid arthritis, Inflammatory Bowel Disease (IBD), psoriasis, atherosclerosis, asthma, reperfusion injury, ischemia, sepsis, graft vs. host disease, Adult Respiratory Distress Syndrome (ARDS), and multiple sclerosis, comprising administering to a subject in a need thereof an effective amount of a benzobicyclooctane compounds of formula (I). In another aspect, the present invention provides a method of inhibiting, preventing, treating, or preventing and/or treating severe invasive infections such as fulminant hepatitis comprising administering to a subject in a need thereof an effective amount of a benzobicyclooctane compounds of formula (I).

In another aspect, the present invention provides a method for the inhibition of IL-8 or other CXC chemokines binding to CXCR1 and/or CXCR2 receptors comprising administering an effective amount of a compound of formula (I) to a subject in need thereof. In another aspect, the present invention provides a method for reducing the levels of IL-8 within a subject comprising administering to a subject in need thereof an effective amount of a compound of formula (I). In another aspect, the present invention provides a method for treating, preventing, or treating and/or preventing one or more of inflammatory and autoimmune diseases such as Inflammatory Bowel Disease (IBD), psoriasis, rheumatoid arthritis, Acute Respiratory Distress Syndrome (ARDS), cancer, atherosclerosis, reperfusion injury, and graft vs. host disease, comprising administering to a subject in need thereof an effective amount of a compound of formula (I).

The present invention provides a method for inhibiting TNF-α mediated processes, comprising administering to a patient in need thereof, through a therapeutically or prophylactically acceptable manner, a therapeutically or pharmaceutically effective amount of a composition comprising a compound of formula (I). Administering may be by, for example, transdermal, oral, intravenous, intramuscular, vaginal, rectal, pulmonary, subcutaneous, sublingual and transmucosal administration.

The present invention provides a method for treating an inflammation event, comprising administering to a patient in need thereof, through a therapeutically or prophylactically acceptable manner, a therapeutically or pharmaceutically effective amount of the compound of formula (I). Administering may be selected from transdermal, oral, intravenous, intramuscular, vaginal, rectal, pulmonary, subcutaneous, sublingual and transmucosal administration.

The "effective amount" or "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In addition, this invention provides a method for identifying a binding partner to a compound of formula (I), wherein the method comprises immoblizing proteins known to be involved in the TNF-a signaling pathway onto a suitable carrier; and passing a solution of said compounds in isolation or mixture over said proteins and analyzing for compound:protein complex formation using surface plasmon resonance (SPR) in a manner similar to that reported by Karlsson, R et al. Biosensor Analysis of Drug-Target Interactions: Direct and Competitive Binding Assays for Investigation of Interactions Between Thrombin and Thrombin Inhibitors. *Anal. Biochem.* 2000, 278(1), 1–13. For other examples of identifying small molecule-protein interactions using SPR see the Biacore website: http://www.biacore.com In addition, this invention provides a method for identifying a binding partner to a compound of formula (I), wherein the method comprises (in a manner similar to that reported by Shimizu, N et al. High Performance Affinity Beads for Identifying Drug Receptors. *Nature Biotechnology*, 2000, 18(8), 877–881) providing said compound(s) bound to a solid support to provide solid phase compounds; contacting a cell or cell components with said solid phase compounds in isolation or mixture; removing uncomplexed cellular material, for example by gentle washing with aqueous buffer, from said solid phase compounds; and recovering said binding partner from the solid phase compounds.

As to each publication or patent referenced herein, that publication or patent is incorporated herein by reference in its entirety for all purposes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The following examples are offered by way of illustration, and not by way of limitation.

EXAMPLES

Abbreviations and acronyms used in the examples include: AcOH, acetic acid; APCI-MS, atmospheric pressure chemical ionization mass spectroscopy; DBU, 1,8-diazabicyclo[5.4.0]undec-7-ene; DEAD, diethylazodicarboxylate; DIEA, diisopropylethylamine;-DMAP, 4-N,N-dimethylaminopyridine; DME, 1,2-dimethoxyethane; DMF, dimethylformamide; DMSO, dimethyl sulfoxide; DPPA, diphenylphosphorylazide; ESI-MS, electrospray ionization mass spectroscopy; FAB-MS, fast atom bombardment mass spectroscopy; FTIR, Fourier transform infrared spectroscopy; HATU, O-(7-azabenzotriazol-1-yl)-N,N,N',N'-tetramethyluronium hexafluorophosphate; HPLC, high pressure liquid chromatography; HRMS, high resolution mass spectroscopy; LC-MS, liquid chromatography-mass spectroscopy; NMA, N-methylaniline; NMM, N-methylmorpholine; NMP, N-methylpyrrolidinone; NMR, nuclear magnetic resonance spectroscopy; TBAF, tetrabutylammonium fluoride; TFA, trifluoroacetic acid; THF, tetrahydrofuran; TSTU, O-(N-Succinimidyl)-1,1,3,3,-tetramethyluronium tetrafluoroborate; rt, room temperature; h, hour; min, minute; eq, equivalents.

Example 1

Synthesis of 4-Hydroxy-11-oxo-tricyclo[6.2.2.0$^{2,7}$]dodeca-2(7),3,5-triene-9,10-dicarboxylic acid 9-(2-trimethylsilylethyl) ester

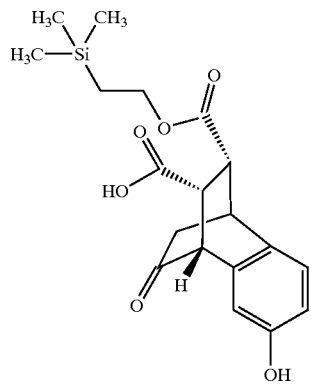

A. 4-Hydroxy-11-oxo-tricyclo[6.2.2.0$^{2,7}$]dodeca-2(7),3,5-triene-9,10-dicarboxylic acid anhydride A solution of dihydroxynaphthalene (500 g, 3.125 mol) and maleic anhydride (765 g, 7.815 mol, 2.5 eq) in 1 L 1:1 1,2-dichlorobenzene:toluene were heated at 110° C. for 3 days. The reaction mixture was then cooled to 90° C., 1.5 L ethyl acetate added, and then further cooled to room temperature overnight. The mixture was then cooled over ice after another 0.5 L ethyl acetate was added and left stirring for 2 hours. The resultant solid was isolated by filtration, washed with 2×200 mL cold ethyl acetate and dried in oven at 40° C. to provide 130 g of the anhydride as a beige solid (16% yield). $^1$H NMR (acetone-d$_6$) 7.33 (d, J=8.2 Hz, 1H), 6.97 (d, J=2.3 Hz, 1H), 6.85 (dd, J=8.1, 2.4 Hz, 4.05 (d, J=3.9 Hz, 1H), 3.98 (dd, J=6.0, 2.9 Hz, 1H), 3.88 (dd, J=10.2, 3.9 Hz, 1H), 3.70 (dd, J=10.2, 2.7 Hz, 1H), 2.39 (br s, 2H). HRMS for MH$^+$259.0600 (theoretical 259.0606).

B. 4-Hydroxy-11-oxo-tricyclo[6.2.2.0$^{2,7}$]dodeca-2(7),3,5-triene-9,10-dicarboxylic acid 9-(2-trimethylsilanylethyl) ester, 1

DMAP (0.96 g, 7.9 mmol, 10 mol %) and trimethylsilylethanol (12.43 mL, 0.087 mol, 1.1 eq) were added to a stirred suspension of the anhydride from step A (20.5 g, 0.079 mol) in 200 mL acetonitrile and heated to reflux for 7 hours. By HPLC there was some starting material present and the two regioisomers of the opened anhydride were present in a 1:1 ratio. The reaction mixture was cooled and dicyclohexylamine (15.71 mL, 0.079 mol) was added dropwise. A precipitate formed instantaneously but was left overnight. The resulting white salt (40.73 g, 93%) was filtered, suspended in water, acidified with 2 M HCl and extracted with ethyl acetate. An emulsion formed, but was removed by filtration before the layers could be separated, and the organic layer was dried and evaporated in vacuo to give a mixture of the regioisomeric acid-esters as a beige foam (25.59 g, 93%). A hazy solution of the solids (25.59 g, 0.068 mol) in 150 mL isopropanol was treated with isopropylamine (5.79 mL, 0.068 mol) and left stirring overnight. The precipitate was isolated by filtration yielding a white solid (12.44 g, 42% yield) as a 86/17 mixture of diastereomers. This solid was slurried in 48 mL isopropanol for 1.5 hours giving a second white solid (10.69 g) as a 93/7 mixture of diasteroemers. This salt was cracked as described above to give a white foam (6.76 g) which was then triturated in 33 mL 20% diethyl ether/toluene at −20° C. The resulting white solid was collected by filtration and washed with 10 mL cold solvent. This afforded 1 as a white solid (4.59 g, 300% overall yield from the anhydride) of 98.2% purity by HPLC. $^1$H NMR (acetonitrile-d$_3$) 7.12 (d, J=8.0 Hz, 1H), 6.76 (d, J=2.5 Hz, 1H), 6.72 (dd, J=8.0, 2.5 Hz, 1H), 4.20–4.06 (m, 2H), 3.65 (d, J=3 Hz, 1H), 3.61 (br s, 1H), 3.22 (br d, J=11.0 Hz, 1H), 2.93 (br s, 1H), 2.85 (dd, J=18.3, 2.3 Hz, 1H), 2.04 (br d, 1H), 0.99–0.93 (m, 2H), 0.03 (s, 9H). MS for MNa$^+$ 399.4. Elemental analysis for C$_{19}$H$_{24}$O$_6$Si, Theoretical: C, 60.62; H, 6.43. Found: C, 60.61; H, 6.58.

Example 2

Synthesis of (4-Hydroxy-11-oxo-tricyclo[6.2.2.0$^{2,7}$]dodeca-2(7),3,5-triene-9,10-dicarboxylic acid 10-(2-trimethylsilanyl-ethyl) ester)

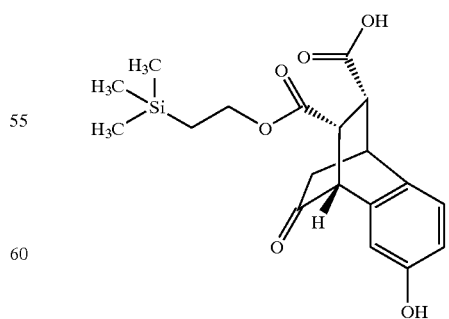

DMAP (0.5 g, 4 mmol, 10 mol %) and trimethylsilylethanol (6.6 mL, 5.45 g, 46 mmol) were added to a stirred suspension of the anhydride (10.83 g, 42 mmol) from Example 1.A in 400 mL acetonitrile and heated to reflux for 6 h. The volatiles were evaporated, and the resulting foam was chromatographed on silica gel (20% acetonitrile/dichloromethane with 2% AcOH). Appropriate fractions were combined and dichloromethane and toluene were used to remove residual AcOH. Repeated trituration of the less polar product with ethyl ether provided 4.9 g (31%) of the title compound. $^1$H NMR (acetonitrile-$d_3$) 7.13 (d, J=8.0 Hz, 1H), 6.75 (d, J=2.2 Hz, 1H), 6.72 (dd, J=8.0, 2.5 Hz, 1H), 4.17–4.11 (m, 2H), 3.64–3.62 (m, 1H), 3.60 (d, J=3.0 Hz, 1H), 3.22 (dd, J=11.8, 3.0 Hz, 1H), 2.97 (dt, J=11.8, 2.2 Hz, 1H), 2.87 (dd, J=18.7, 2.2 Hz, 1H), 2.08 (ddd, J=18.4, 3.3, 2.5 Hz, 1H), 1.00–0.95 (m, 2H), 0.04 (s, 9H). MS 399.4 (MNa$^+$). Elemental for $C_{19}H_{24}O_6Si$: Theoretical, C, 60.62; H, 6.43. Found: C, 60.58; H, 6.57. In addition, repeated trituration of the more polar product provided 5.0 g (32%) of acid 1.

Example 3

Synthesis of (9,10 cis)-10-Allyloxycarbonylamino-4-hydroxy-11-oxo-tricyclo[6.2.2.0$^{2,7}$]dodeca-2(7),3,5-triene-9-(2-Trimethylsilanyl-ethyl) ester

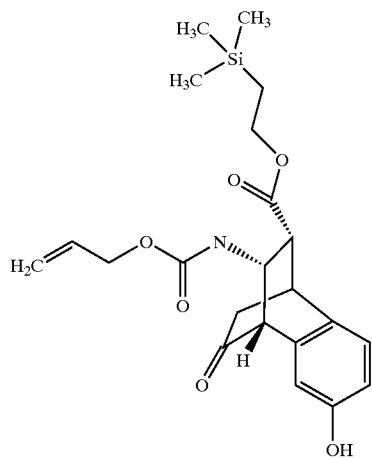

To a solution of acid 1 (196 mg, 0.52 mmol) in THF (25 mL) was added DPPA (230 μL, 1.05 mmol), triethylamine (150 μL, 1.08 mmol), and allyl alcohol (360 μL, 5.3 mmol). The mixture was heated to reflux and held for 15 h. Upon cooling, the mixture was concentrated in vacuo, and the residue chromatographed, initially with 30% ethyl acetate/hexane followed by a second chromatography using 15% ethyl acetate/dichloromethane to afford a total of 65.8 mg (30%) of the title compound. ESI-MS m/z 454 (MNa$^+$).

Example 4

Synthesis of 5-Hydroxy-10-{methyl-[(2,4,6-trimethoxy-benzylcarbamoyl)-methyl]-carbamoyl}-12-oxo-tricyclo[6.2.2.0$^{2,7}$]dodeca-2(7),3,5-triene-9-(2-trimethylsilanyl-ethyl) ester

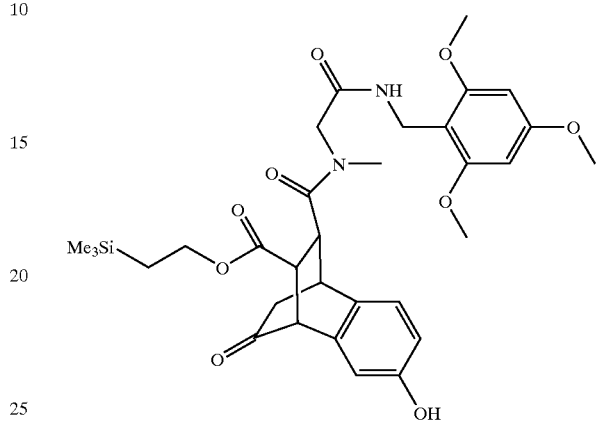

A. Sarcosine-2,4,6-trimethoxybenzylamide

To a solution of N-Fmoc-sarcosine (5 g, 16 mmol) in dichloromethane (160 mL) containing 3A molecular sieves was added NMM (6 mL, 5.52 g, 55 mmol), HATU (7.33 g, 19 mmol) and 2,4,6-trimethoxybenzylamine hydrochloride (4.5 g, 19.2 mmol). The resulting reaction mixture was allowed to stir at rt overnight. The sieves were filtered, the volatiles evaporated and ethyl acetate was added. Acid wash (0.1 N HCl, 3×300 mL) followed by sodium bicarbonate (5% solution, 1×300 mL) provided a solid precipitate, which was collected, washed with ethyl acetate, collected and air dried. The organic layer was concentrated to dryness to give a residue which was triturated with ethyl acetate to provide an additional amount of the Fmoc derivative of 101: amount recovered 7.5 g (95%). $^1$H NMR (CDCl$_3$) 7.77–7.27 (m, 8H), 6.35 (br s, 1H), 6.05 (br s, 2H), 4.49–4.05 (m, 5H), 3.93 (s, 2H), 3.74 (s, 9H), 2.99 (s, 3H). FAB-MS m/z 513 (MNa$^+$), 491 (MH$^+$).

The isolated N-Fmoc-sarcosine-2,4,6-trimethoxybenzylamide (6.5 g, 13 mmol) was suspended in 25% pyrrolidine/chloroform (100 mL) and allowed to stir at rt for 50 min. The volatiles were then evaporated to give a pale yellow solid. Column chromatography (10% methanol/dichloromethane) provided the desired product 101 upon trituration with ethyl ether, wt. 3.1 g (88%). $^1$H NMR (CDCl$_3$) 6.13 (d, 2H), 4.48 (d, J=5.5 Hz, 2H), 3.82 (s, 9H), 3.24 (s, 2H), 2.40 (s, 3H). Elemental for $C_{13}H_{20}N_2O_4$: Theoretical, C, 58.19; H, 7.51; N, 10.44. Found: C, 58.09; H, 7.66; N, 10.18.

B. 5-Hydroxy-10-{methyl-[(2,4,6-trimethoxy-benzylcarbamoyl)-methyl]-carbamoyl}-12-oxo-tricyclo[6.2.2.0$^{2,7}$]dodeca-2(7),3,5-triene-9-(2-trimethylsilanyl-ethyl) ester To a solution of the carboxylic acid from Example 2 (4.5 g, 11.8 mmol) in dichloromethane (25 mL) was added NMM (3.2 mL, 2.9 g, 29 mmol), HATU (5.3 g, 13.9 mmol), 3A molecular sieves and sarcosine-2,4,6-trimethoxybenzylamide (3.1 g). The resulting solution was allowed to stir at rt under nitrogen overnight. The volatiles were then evaporated, ethyl acetate (300 mL) was added and the organic layer was washed with 0.1 N HCl (2×150 mL), 5% $NaHCO_3$ solution (1×100 mL) and brine (1×100 mL). The organic layer was dried ($MgSO_4$), filtered and the volatiles were evaporated to give a yellow foam. Column chromatography (90% ethyl acetate/hexane) provided the desired product, wt. 3.5 g (49%). $^1$H NMR ($CDCl_3$) 7.05–6.70 (m, 3H), 6.48 (t, 1H), 6.12, 6.05 (2s, 2H), 4.56–4.40 (m, 2H), 4.20–2.71 (m, 21H), 2.20–2.07 (m, 1H), 1.00–0.90 (m, 2H), 0.02 (s, 9H). Elemental for $C_{32}H_{42}N_2O_9Si$: Theoretical, C, 60.16; H, 7.04; N, 4.25. Found: C, 60.29; H, 6.93; N, 4.18.

Example 5

Synthesis of 2,4,6-trimethoxy-benzylcarbamoyl)-methyl]-carbamoyl}-11-oxo-tricyclo[6.2.2.0$^{2,7}$]dodeca-2(7),3,5-trien-4-yloxymethyl)-benzoic acid allyl ester

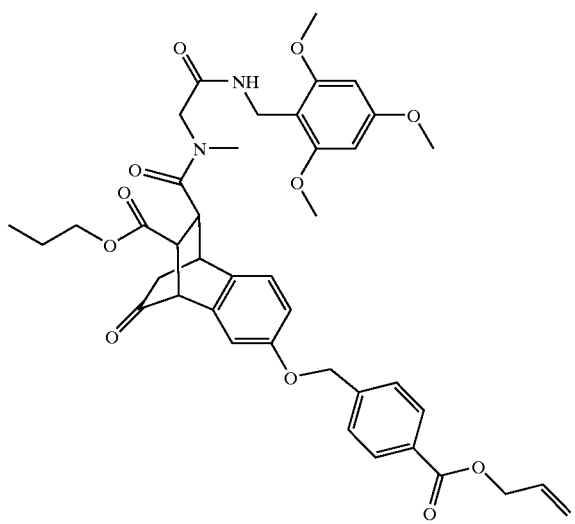

A. Allyl 4-Hydroxymethylbenzoate

To a solution of 4-hydroxymethylbenzoic acid (0.5 g, 3.3 mmol) in $CHCl_3$ (10 mL) was added allyl bromide (0.6 mL, 0.84 g, 6.9 mmol) and diisopropylethylamine (1.3 mL, 0.96 g, 7.5 mmol). The resulting reaction mixture was allowed to reflux under nitrogen for 2.5 h. Upon cooling to rt, dichloromethane (50 mL) was added and the organic layer was washed with 0.1 N HCl (3×30 mL), 5% $NaHCO_3$ solution (1×30 mL) and brine (1×30 mL). Upon drying ($MgSO_4$), filtration of the drying agent and concentration, the resulting oily residue was chromatographed on silica gel (30% ethyl acetate/hexane) to give 440 mg (70%) of a colorless oil. $_1$H NMR ($CDCl_3$) 8.06 (d, J=8.2 Hz, 2H), 7.44 (d, J=8.2 Hz, 2H), 6.11–5.98 (m, 11H), 5.42 (dd, J=17.2, 1.5 Hz, 11H), 5.30 (dd, J=10.4, 1.2 Hz, 1H), 4.83 (dd, J=5.6, 1.2 Hz, 2H), 4.78 (s, 2H), 1.80 (br s, 1H). MS 192 (M$^+$).

B. 5-(4-Allyloxycarbonyl-benzyloxy)-10-{methyl-[(2,4,6-trimethoxy-benzylcarbamoyl)-methyl]-carbamoyl}-11-oxo-tricyclo [6.2.2.0$^{2,7}$]dodeca-2(7),3,5-triene-9-carboxylic acid-(2-trimethylsilanyl-ethyl) ester To a cooled solution (ice bath) of allyl 4-hydroxymethylbenzoate (0.62 g, 3.2 mmol) and the compound prepared in Example 4 (1.33 g, 2 mmol) in anhydrous THF (40 mL) was added $PPh_3$ (1.34 g, 5.1 mmol) and DEAD (0.8 mL, 0.88 g, 5.1 mmol). The resulting reaction mixture was allowed to warm to room temperature and then allowed to reflux under $N_2$ for 0.5 h. Column chromatography of the concentrated residue (90% ethyl acetate/hexane) provided the title compound as a white foamy material, wt. 0.98 g (58%). $^1$H NMR ($CDCl_3$) 8.09 (d, J=8.2 Hz, 2H), 7.49 (d, J=8.0 Hz, 2H), 7.16–6.46 (m, 4H), 6.11–5.98 (m, 3H), 5.42 (d, J=17.2 Hz, 1H), 5.30 (d, J=10.4 Hz, 1H), 5.11 (s, 2H), 5.83 (d, J=5.6 Hz, 2H), 4.56–4.37 (m, 2H), 4.17–3.9 (m, 2H), 3.81–3.70 (m, 12H), 3.55–2.05 (m, 8H), 0.97–0.89 (m, 2H), 0.02 (s, 9H). Elemental for $C_{43}H_{52}N_2O^{11}Si$: Theoretical, C, 64.48; H, 6.54; N, 3.50. Found: C, 64.18; H. 6.67; N, 3.28.

Example 6

Synthesis of 4-(10-Dipentylcarbamoyl-9-{methyl-[(2,4,6-trimethoxy-benzylcarbamoyl)-methyl]-carbamoyl}-11-oxo-tricyclo[6.2.2.0$^{2,7}$]dodeca-2(7),3,5-trien-4-yloxymethyl)-benzoic acid allyl ester

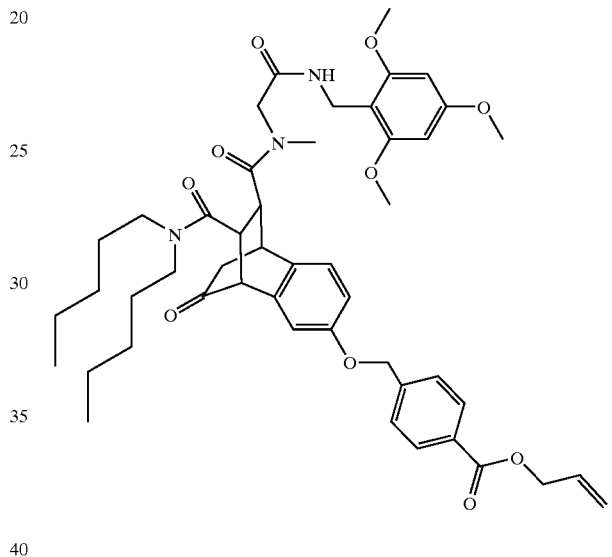

To a solution of the diester prepared in Example 5 (0.5 g, 0.62 mmol) in anhydrous THF (14 mL) was added a 1.0 M solution of TBAF (1.0 mL, 1 mmol). The reaction mixture was allowed to stir at rt for 1.75 h, after which ethyl acetate (200 mL) was added. The organic layer was then washed with 0.1 N HCl (2×50 mL), brine (2×50 mL), dried ($MgSO_4$), filtered and concentrated to give a colorless oil. The free acid was dissolved in dichloromethane (12 mL) and HATU (0.29 g, 0.76 mmol); NMM (0.17 mL, 0.16 g, 1.55 mmol) and dipentylamine (.15 mL, 0.12 g, 0.7 mmol) were added. The resulting reaction mixture was then allowed to stir at rt under $N_2$ for 3 days, after which dichloromethane (300 mL) was added. The organic layer was then washed with 0.1 N HCl (2×100 mL), 55 solution of $NaHCO_3$ (2×50 mL), water (2×50 mL), brine (1×50 mL), dried ($MgSO_4$), filtered and the volatiles were evaporated to give a colorless oil. Column chromatography (5% methanol/dichloromethane) provided the desired product, wt. 303 mg (58%). $^1$H NMR ($CDCl_3$) 8.08 (d, J=8.2 Hz, 2H), 7.50 (d, J=8.3 Hz, 2H), 7.18–6.72 (m, 3H), 6.11–5.98 (m, 3H), 5.41 (dd, J=17.2, 1.3 Hz, 1H), 5.30 (apt t, J=6.0, 4.4 Hz, 1H), 5.11 (s, 2H), 4.83 (d, J=5.6 Hz, 2H), 4.53–4.35 (m, 2H), 4.02 (d, J=15.4 Hz, 1H), 3.85–2.80 (m, 23H), 2.16 (d, J=18.5 Hz, 1H), 1.60–1.10 (m, 12H), 0.94–0.86 (m, 6H). Elemental for $C_{48}H_{61}N_3O_{10}$.methanol: Theoretical, C, 67.49; H, 7.51; N, 4.82. Found: C, 67.68; H, 7.45; N, 4.63.

Example 7

Synthesis of 4-(10-Dipentylcarbamoyl-9-{methyl-[(2,4,6-trimethoxy-benzylcarbamoyl)-methyl]-carbamoyl}-11-oxo-tricyclo[6.2.2.0$^{2,7}$]dodeca-2(7),3,5-trien-4-yloxymethyl)-benzoic acid

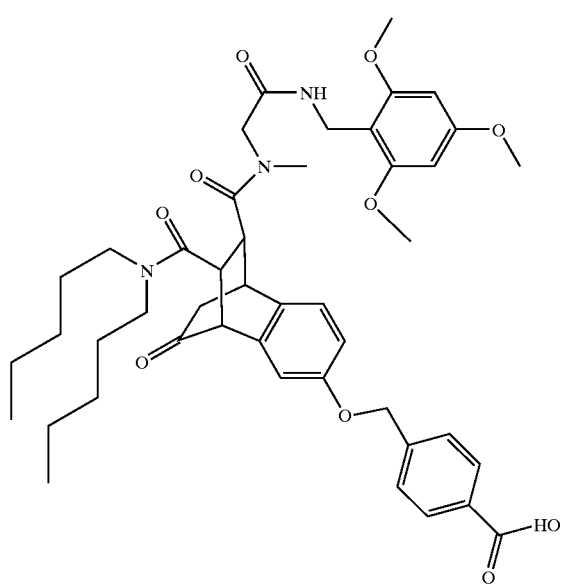

A solution of allyl ester prepared in Example 6 (0.28 g, 0.33 mmol), tetrakis(triphenylphosphine) palladium (0) (27 mg, 23 μmol) and N-methylaniline (75 μL, 74 mg, 0.69 mmol) in dichloromethane (3.5 mL) was allowed to stir at rt for 1 h. The reaction mixture was then diluted with dichloromethane (50 mL) and washed with 0.1 N HCl solution (2×20 mL) and brine (2×20 mL). Upon drying (MgSO$_4$), filtration of the drying agent and concentration, the resulting oily residue was chromatographed on silica gel (5% methanol/dichloromethane) to provide the desired product as a white solid, wt. 160 mg (60%). $^1$H NMR (CDCl$_3$) 8.14, 7.92 (2 d, J=8.0, 7.8 Hz, 2H), 7.54 (d, J=7.9 Hz, 2H), 7.31–6.89 (m, 4H), 6.12 (s, 2H), 5.15, 5.06 (2 br s, 2H), 4.57–4.39 (m, 2H), (m, 2H), 4.08 (J=15.5 Hz, 1H), 3.91–3.52 (m, 13H), 3.30–2.86 (m, 7H), 2.38 (s, 2H), 2.20 (d, J=18.4 Hz, 1H), 159–0.80 (m, 18H). MS (ESI +ve) 800 (MH$^+$), 822 (MNa$^+$). Elemental for C$_{45}$H$_{57}$N$_3$O$_{10}$. methanol: Theoretical, C, 66.41; H, 7.39; N, 5.05. Found: C, 66.28; H, 7.22; N, 4.83.

Example 8

Synthesis of 4-[4-(2-Dimethylcarbamoyl-pyrrolidine-1-carbonyl)-benzyloxy]-11-oxo-tricyclo[6.2.2.0$^{2,7}$]dodeca-2(7),3,5-triene-9,10-dicarboxylic acid 10-dipentylamide 10-{methyl-[(2,4,6-trimethoxy-benzylcarbamoyl)-methyl]-amide}

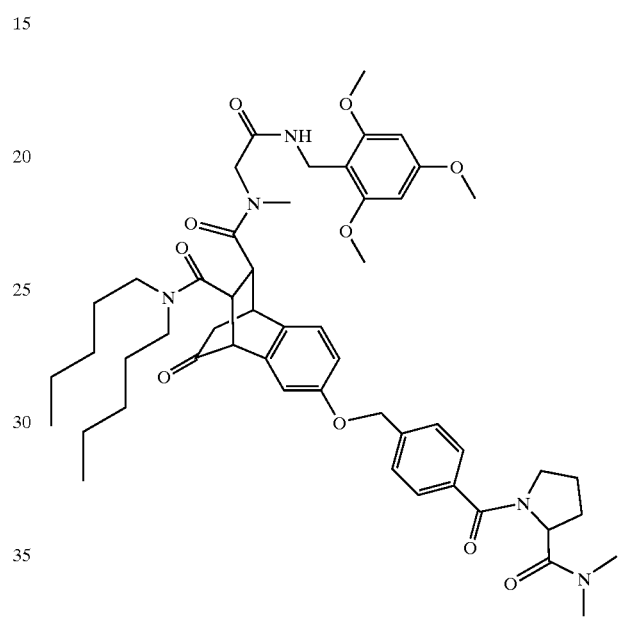

A solution of the acid prepared in Example 7 (67 mg, 84 μmol), HATU (38 mg, 100 μmol), NMM (22 μL, 20 mg, 0.2 mmol) and H-prolinedimethylamide (15 mg, 0.1 mmol) in dichloromethane (1.0 mL) was allowed to stir at rt overnight. The reaction mixture was then diluted with dichloromethane (30 mL) and washed with 0.1 N HCl solution (2×20 mL), 5% NaHCO$_3$ solution (1×25 mL) and brine (1×25 mL). Upon drying (MgSO$_4$), filtration of the drying agent and concentration, the resulting oily residue was chromatographed on silica gel (5% methanol/dichloromethane) to provide the diastereomeric mixture as a white solid, wt. 54 mg (70%). $^1$H NMR (CDCl$_3$) 7.61 (d, J=8.0 Hz), 7.43 (d, J=8.0 Hz), 7.38 (s), 7.15(d, J=8.0 Hz), 7.02–6.78 (m), 6.11 (s), 6.09 (s), 5.06 (s), 5.02 (s), 4.52–4.33 (m), 4.04–3.88 (m), 3.86–3.67 (m), 3.57–3.49 (m), 3.27–3.06 (m), 2.99 (s), 2.85 (s), 2.82 (s), 2.76 (d, J=10.6 Hz), 2.53 (d, J=9.1 Hz), 2.31–1.80 (m), 1.60–1.10 (m), 0.91 (t, J=5.8 Hz), 0.87 (t, J=6.0 Hz). ESI-MS m/z 925 (MH$^+$), 947 (MNa$^+$).

Example 9

Synthesis of 4-Hydroxy-11-oxo-tricyclo [6.2.2.0$^{2,7}$] dodeca-2(7),3,5-triene-9,10-dicarboxylic acid 10-(2, 4-dimethyoxy-benzyl) ester 9-(2-trimethylsilanyl-ethyl) ester

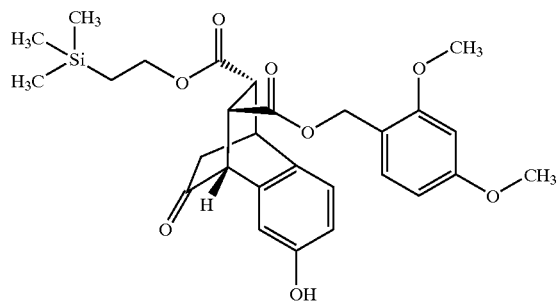

To a solution of acid 1 (2.83 g, 7.5 mmol), prepared in Example 1, 2,4-dimethoxybenzylalcohol (1.65 g, 9.8 mmol) and DMAP (0.1 g, 0.8 mmol) in dichloromethane (50 mL) was added DIEA (2.8 mL, 2.1 g, 16 mmol) and 1-(3-dimethylaminopropyl)-3-ethylcarbodiimide hydrochloride (2.2 g, 11.5 mmol). The resulting reaction mixture was allowed to stir at rt for 24 h, after which time it was concentrated to dryness, redissolved in ethyl acetate (300 mL) and washed with 0.1 N HCl solution (2×100 mL), 5% NaHCO$_3$ solution (1×100 mL) and brine (1×100 mL). Upon drying (MgSO$_4$), filtration of the drying agent and concentration, the resulting oily residue was chromatographed on silica gel (35% ethyl acetate/hexane) to provide 370 mg (10%) of the trans bis-ester. $^1$H NMR (CDCl$_3$) 7.10 (dd, J=8.1, 2.9 Hz, 2H), 6.69 (dd, J=8.0, 2.4 Hz, 1H), 6.48–6.42 (m, 2H), 6.33 (d, J=2.4 Hz, 1H), 5.30–5.22 (br s, 1H), 5.03 (dd, J=37.1, 11.8 Hz, 2H), 4.27–4.21 (m, 2H), 3.91 (d, J=2.2 Hz, 1H), 3.83 (s, 3H), 3.80 (s, 3H), 3.76–3.73 (m, 1H), 3.69 (dd, J=5.8, 2.2 Hz, 1H), 3.28–3.22 (m, 1H), 2.40 (dd, J=18.9, 2.0 Hz, 1H), 2.10 (dm, 1H), 1.04–0.99 (m, 2H), 0.01 (s, 9H). FAB-MS m/z 526 (M$^+$).

Example 10

Synthesis of 4-Methoxy-11-oxo-tricyclo[6.2.2.0$^{2,7}$] dodeca-2(7),3,5-triene-9,10-dicarboxylic acid 10-(2, 4-dimethoxy-benzyl) ester 9-(2-trimethylsilanyl-ethyl) ester

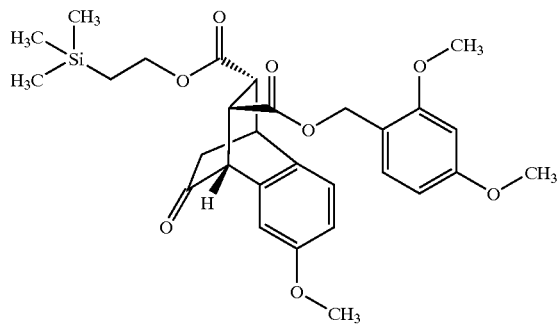

To a solution of the phenol prepared in Example 9 (70 mg, 0.13 mmol) in anhydrous THF (5 mL) was added cesium carbonate (48 mg, 0.14 mmol) and methyl iodide (45 µL, 103 mg, 0.7 mmol). The resulting reaction mixture was allowed to stir at rt under N$_2$ for 22 h. The reaction mixture was then diluted with ethyl acetate (20 mL) and washed with 0.1 N HCl solution (2×10 mL), 5% NaHCO$_3$ solution (1×10 mL) and brine (1×10 mL). Upon drying (MgSO$_4$), filtration of the drying agent and concentration, the resulting oily residue was chromatographed on silica gel (1% methanol/dichloromethane) to provide 35 mg (49%) of the methyl ether. $^1$H NMR (CDCl$_3$) 7.18 (d, J=8.2 Hz, 1H), 7.11 (d, J=8.2 Hz, 1H), 6.77 (dd, J=8.2, 2.5 Hz, 1H), 6.58 (d, J=2.4 Hz, 1H), 6.49–6.41 (m, 2H), 5.02 (dd, J=24.7, 11.8 Hz, 2H), 4.28–4.22 (m, 2H), 3.98 (d, J=2.2 Hz, 1H), 3.83 (s, 3H), 3.80 (s, 3H), 3.78–3.75 (m, 1H), 3.72 (s, 3H), 3.71–3.69 (m, 1H), 3.28–3.26 (m, 1H), 2.41 (dd, J=19.0, 2.1 Hz, 1H), 2.11 (dm, 1H), 1.05–0.99 (m, 2H), 0.06 (s, 9H). FAB-MS m/z 540 (M$^+$).

Example 11

Synthesis of 10-(2,4-Dimethoxy-benzylcarbamoyl)-4-hydroxy-11-oxo-tricyclo[6.2.2.0$^{2,7}$]dodeca-2(7),3, 5-triene-9-(2-trimethylsilanyl-ethyl) ester

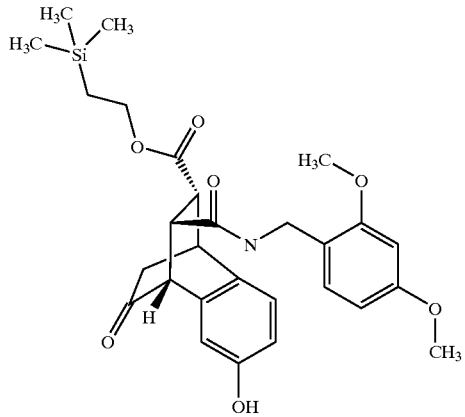

General Procedure A for the Synthesis of 4-Hydroxy-10-amido Derivatives

To a solution of the cis acid ester 1 (0.5 mmol) and molecular sieves (3A) in THF (2 mL) was added diisopropylethylamine (2.8 mmol) and diphenylphosphoryl azide (0.7 mmol). The solution was allowed to stir at rt under nitrogen for 3–4 h, after which time a selected amine (1.5–2 mol equivalents) and DMAP (2 mol equivalents) were added and the resulting reaction mixture was allowed to stir overnight. Dilution with ethyl acetate (25 mL), followed by washes with 1 N HCl (2×25 mL), 5% NaHCO$_3$ solution (2×25 mL) and brine (1×25 mL) provided a pale yellow solution, which was dried (MgSO$_4$), filtered and concentrated to dryness. Column chromatography provided the desired product.

The title compound was prepared as in general procedure A, above. Column chromatography (10% acetonitrile/dichloromethane) provided 35% of the title compound. $^1$H NMR (acetonitrile-d$_3$) 7.14 (br s, 1H), 7.11 (d, J=8.2 Hz, 1H), 7.05 (br s, 1H), 7.02 (d, J=8.2 Hz, 1H), 6.65 (dd, J=8.0, 2.5 Hz, 1H), 6.53 (dd, J=8.4, 2.3 Hz, 2H), 6.44 (dd, J=8.4 2.3 Hz, 1H), 4.25–4.16 (m, 4H), 3.81, 3.77 (2 s, 6H), 3.74 (app. q, J=2.4 Hz, 1H), 3.69 (d, J=1.9 Hz, 1H), 3.39 (dd, J=6.3, 1.9 Hz, 1H), 3.20 (dt, J=6.3, 2.2 Hz, 1H), 2.37 (dd, J=19.0, 2.2 Hz, 1H), 2.03 (dq, J=19.0, 3.0, 2.2 Hz, 1H), 1.01–0.96 (m, 2H), 0.04 (s, 9H). $^{13}$C NMR (acetonitrile-d$_3$) 209.20, 174.55, 171.38, 161.73, 159.66, 157.60, 135.53, 134.32, 130.69, 126.08, 120.02, 115.50, 114.98, 105.26, 99.43, 64.48, 57.56, 56.30, 56.10, 46.27, 43.91, 39.42, 39.01, 38.41, 17.96, −1.43. FAB-MS m/z 540 (MH⁺). Elemental for $C_{28}H_{35}NO_7Si$: Theoretical, C, 63.98; H, 6.71; N, 2.66. Found: C, 63.77; H, 6.86; N, 2.63.

Example 12

Synthesis of 10-Dipentylcarbamoyl-4-hydroxy-11-oxo-tricyclo[6.2.2.0$^{2,7}$]dodeca-2(7),3,5-triene-9-(2-trimethylsilanyl-ethyl) ester

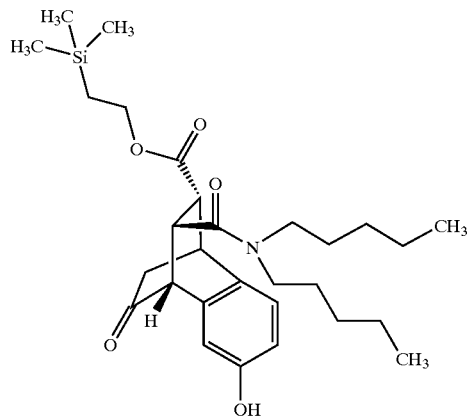

The title compound was prepared as in general procedure A in Example 11. Column chromatography (5% acetonitrile/dichloromethane) provided 23% of the title compound. $^1H$ NMR (acetonitrile-d$_3$) 7.12 (d, J=8.0 Hz, 1H), 6.98 (br s, 1H), 6.67 (dd, J=8.0, 2.5 Hz, 1H), 6.53 (d, J=2.5 Hz, 1H), 4.62–4.23 (m, 2H), 3.76–3.73 (m, 1H), 3.36 (dd, J=6.6, 1.7 Hz, 1H), 3.56–3.19 (m, 5H), 2.97–2.88 (m, 1H), 2.47 (dd, J=18.8, 2.1 Hz, 1H), 2.04 (dt, J=19.0, 2.6 Hz, 1H), 1.69–1.15 (m, 12H), 1.02–0.97 (m, 2H), 0.92, 0.88 (2 t, J=5.9, 5.6 Hz, 6H), 0.03 (s, 9H). $^{13}C$ NMR (acetonitrile-d$_3$) 208.83, 174.55, 170.74, 157.60, 135.21, 134.56, 125.88, 115.47, 114.94, 64.27, 57.27, 48.65, 46.87, 46.77, 40.21, 38.98, 38.25, 29.94, 29.86, 29.75, 28.34, 23.30, 23.26, 18.10, 14.44, −1.46. FAB-MS m/z 516 (MH⁺). Elemental for $C_{29}H_{45}NO_5Si$: Theoretical, C, 67.53; H, 8.79; N, 2.72. Found: C, 67.36; H, 9.00; N, 2.73.

Example 13

Synthesis of 4-Hydroxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

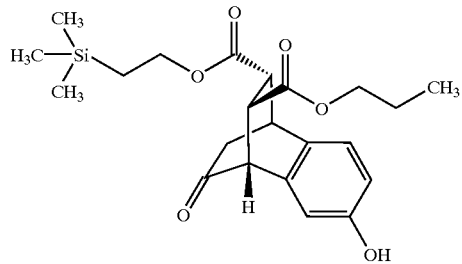

A mixture of the product from Example 1 (1.46 g, 3.88 mmol), TSTU (1.40 g 4.65 mmol), DIEA (3.2 mL, 18.4 mmol) were dissolved in THF (15 mL) and stirred under N₂ for 5 h. The solution was then treated with DMAP (0.58 g, 4.7 mmol) and n-propanol (7.5 mL) and stirred an additional 19 h. The reaction was quenched with 0.2 M HCl (aq) and diluted with 150 mL ethyl acetate. The phases were separated and the organic was washed with 5% NaHCO₃ (aq) and brine. The organic layer was separated, dried (Na₂SO₄) and concentrated to 2.0 g of light yellow oil. Silica chromatography (ethyl acetate/hexanes) afforded 1.0 g (62%) of the title compound. $^1H$ NMR (CDCl₃) 7.12 (d, J=8 Hz, 1H), 6.70 (dd, J=2.5, 8 Hz, 1H), 6.64 (d, J=2.5 Hz, 1H), 5.26 (s, 1H), 4.25 (dd, J=7, 9 Hz, 2H), 3.98–3.93 (m, 3H), 3.74 (d, J=2.5 Hz, 1H), 3.65 (dd, J=2.2, 5.8 Hz, 1H), 3.2 (dd, J=2, 5 Hz, 1H), 2.41 (dd, J=2, 19 Hz, 1H), 2.16 (dd, J=2, 21 Hz, 1H), 1.57 (dd, J=7, 14 Hz, 2H), 1.05 (ddd, J=7, 7, <1 Hz, 2H), 0.87 (t, J=7, 7 Hz, 3H), 0.04 (s, 9H); ESI-MS m/z 417 (M-H)⁻.

Example 14

Synthesis of 4-Hydroxy-11-oxo-tricyclo[6.2.2.0$^{2,7}$] dodeca-2(7),3,5-triene-9,10-dicarboxylic acid 10-(2-cyclohexyloxy-ethyl) ester 9-(2-trimethylsilanyl-ethyl) ester

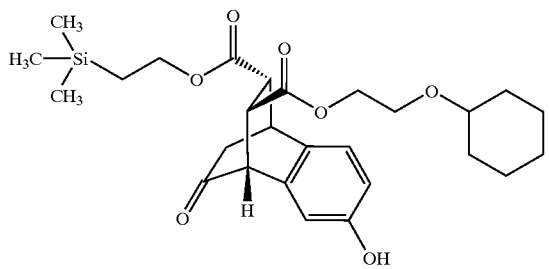

General Procedure B for the Synthesis of Trans Bis-esters 3

To a solution of the cis acid ester 1 (0.27 mmol) and molecular sieves (3A) in THF (1.0 mL) was added DIEA (1.4 mmol) and DPPA (0.37 mmol). The solution was allowed to stir at rt under nitrogen for 3–4 h, after which time a selected alcohol (2.5 mol equivalents) and DMAP (2 mol equivalents) were added and the resulting reaction mixture was allowed to stir overnight. Dilution with ethyl acetate (25 mL), followed by washes with 1 N HCl (2×25 mL), 5% NaHCO₃ solution (2×25 mL) and brine (1×25 mL) provided a pale yellow solution, which was dried (MgSO₄), filtered and concentrated to dryness. Column chromatography provided the desired product.

The title compound was prepared as described in general procedure B using 2-cyclohexyloxyethanol. Column chromatography (7% acetonitrile/dichloromethane) provided a 30% yield of the title compound. $^1H$ NMR (acetonitrile-d$_3$) 7.15 (d, J=8.0 Hz, 1H), 7.01 (br s, 1H), 6.74–6.69 (m, 2H), 4.32–4.19 (m, 2H), 4.14–4.05 (m, 2H), 3.84 (d, J=2.2 Hz, 1H), 3.73 (app. q, J=2.7 Hz, 1H), 3.60 (dd, J=6.0, 2.2 Hz, 1H), 3.56–3.53 (m, 2H), 3.27–3.20 (m, 1H), 3.09 (dt, J=6.0, 2.3 Hz, 1H), 2.36 (dd, J=19.0, 2.5 Hz, 1H), 2.06 (ddd, J=19.0, 3.2, 2.1 Hz, 1H), 1.87–1.75 (m, 2H), 1.74–1.64 (m, 2H), 1.56–1.46 (m, 1H), 1.34–1.12 (m, 5H), 1.06–1.00 (m, 2H), 0.05 (s, 9H). $^{13}C$ NMR (acetonitrile-d$_3$) 208.86, 173.97, 172.62, 157.71, 135.64, 134.36, 126.38, 115.77, 115.03, 78.49, 66.37, 65.95, 64.74, 55.95, 47.07, 43.78, 39.32, 38.30, 33.03, 26.63, 24.84, 18.01, −1.42. FAB-MS m/z 502 (M⁺). Elemental for $C_{27}H_{38}O_7Si$: Theoretical, C, 64.51; H, 7.62. Found: C, 64.47; H, 7.76.

Example 15

Synthesis of 4-Hydroxy-11-oxo-tricyclo[6.2.2.0$^{2,7}$] dodeca-2(7),3,5-triene-9,10-dicarboxylic acid 10-(2-pyridin-2-yl-ethyl) ester 9-(2-trimethylsilanyl-ethyl) ester

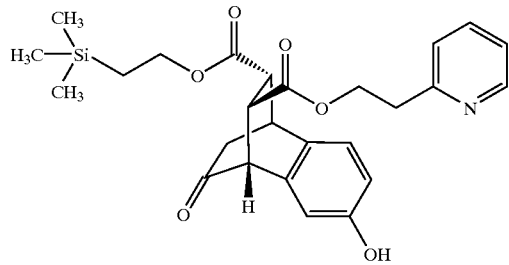

The title compound was prepared as described in general procedure B using 2-(2-hydroxyethyl)-pyridine. Column chromatography (neat ethyl acetate) provided 48% of the title compound. $^1$H NMR (acetonitrile-d3) 8.49 (ddd, J=4.7, 1.7, 1.1 Hz, 1H), 7.68 (td, J=7.7, 1.9 Hz, 1H), 7.23–7.18 (m, 2H), 7.14 (d, J=8.2 Hz, 1H), 6.72 (dd, J=8.0, 2.5 Hz, 1H), 6.57 (d, J=2.5 Hz, 1H), 4.42–4.15 (2 m, 4H), 3.72–3.68 (m, 2H), 3.53 (dd, J=6.0, 2.2 Hz, 1H), 3.04–2.99 (m, 3H), 2.33 (dd, J=19.0, 2.2 Hz, 1H), 2.03 (ddd, J=19.0, 3.2, 2.1 Hz, 1H), 1.03–0.97 (m, 2H), 0.04 (s, 9H). $^{13}$C NMR (acetonitrile-d$_3$) 208.85, 173.90, 172.50, 159.30, 157.78, 150.50, 137.92, 135.53, 134.23, 126.38, 124.73, 123.06, 115.82, 114.95, 65.40, 64.68, 55.86, 46.87, 43.75, 39.22, 38.30, 37.71, 17.95, −1.42. FAB-MS m/z 482 (MH$^+$). Elemental for C$_{26}$H$_{31}$NO$_6$Si: Theoretical, C, 64.84; H, 6.49; N, 2.91. Found: C, 64.63; H, 6.43; N, 2.70.

Example 16

Synthesis of 4-Hydroxy-11-oxo-tricyclo[6.2.2.0$^{2,7}$] dodeca-2(7),3,5-triene-9,10-dicarboxylic acid 10-(3-fluoro-benzyl) ester 9-(2-trimethylsilanyl-ethyl) ester

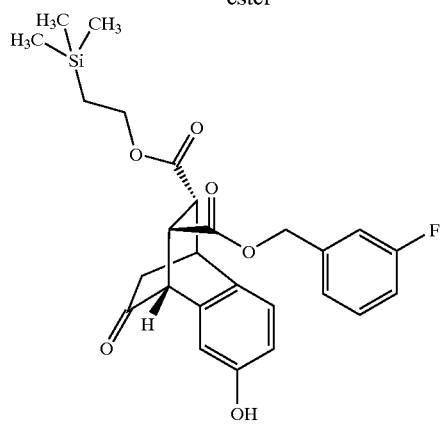

The title compound was prepared as described in general procedure B using 3-fluorobenzyl alcohol. Column chromatography (1% methanol/dichloromethane) provided a 56% yield of the title compound. $^1$H NMR (acetonitrile-d$_3$) 7.41–7.34 (m, 1H), 7.16 (d, J=8.2 Hz, 1H), 7.11–7.02 (m, 3H), 6.98 (br s, 1H), 6.72 (dd, J=8.2, 2.5 Hz, 1H), 6.61 (d, J=2.5 Hz, 1H), 5.03 (s, 2H), 4.27–4.22 (m, 2H), 3.86 (d, J=2.2 Hz, 1H), 3.74 (dd, J=5.2, 2.5 Hz, 1H), 3.67 (dd, J=6.0, 2.2 Hz, 1H), 3.12 (dt, J=6.0, 2.3 Hz, 1H), 2.38 (dd, J=19.0, 2.2 Hz, 1H), 2.06 (ddd, J=19.1, 3.3, 2.2 Hz, 1H), 1.03–0.97 (m, 2H), 0.04 (S, 9H). $^{13}$C NMR (acetonitrile-d$_3$) 208.68, 173.91, 172.49, 165.58, 162.35, 157.72, 140.06, 139.95, 135.46, 134.36, 131.72, 131.62, 126.43, 124.97, 124.94, 116.26, 115.99, 115.91, 115.82, 115.61, 114.97, 67.07, 64.74, 55.81, 47.06, 43.81, 39.19, 38.27, 17.96, −1.45. FAB-MS m/z 484 (M$^+$). Elemental for C$_{26}$H$_{29}$FO$_6$Si: Theoretical, C, 64.44; H, 6.03. Found: C, 64.47; H, 6.13.

Example 17

Synthesis of 4-Hydroxy-11-oxo-tricyclo[6.2.2.0$^{2,7}$] dodeca-2(7),3,5-triene-9,10-dicarboxylic acid 10-(2-pyrrolidin-1-yl-ethyl) ester 9-(2-trimethylsilanyl-ethyl) ester

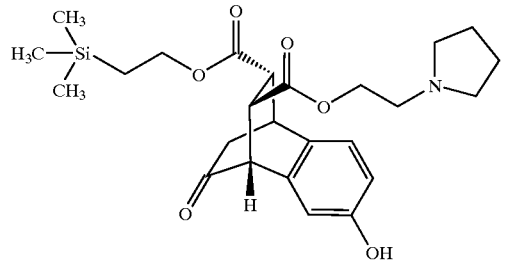

The title compound was prepared as described in general procedure B using 1-(2-hydroxyethyl)-pyrrolidine. Column chromatography (10% methanol/dichloromethane) provided 39% of the title compound. $^1$H NMR (acetonitrile-d$_3$) 7.17–7.13 (m, 1H), 6.73–6.68 (m, 2H), 4.29–4.21 (m, 2H), 4.08 (t, J=5.8 Hz, 2H), 3.83 (d, J=2.2 Hz, 1H), 3.72 (dd, J=5.5, 2.8 Hz, 1H), 3.57 (dd, J=6.0, 2.2 Hz, 1H), 3.11 (dt, J=6.0, 2.3 Hz, 1H), 2.63 (td, J=5.6, 2.5 Hz, 2H), 2.51–2.45 (m, 4H), 2.35 (dd, J=19.0, 2.2 Hz, 1H), 2.05 (ddd, J=19.0, 3.2, 2.1 Hz, 1H), 1.73–1.68 (m, 4H), 1.05–1.00 (m, 2H), 0.05 (s, 9H). $^{13}$C NMR (acetonitrile-d$_3$) 208.89, 174.00, 172.59, 157.89, 135.58, 134.18, 126.41, 126.34, 115.83, 115.09, 114.94, 65.13, 64.69, 55.92, 55.10, 55.04, 54.93, 46.99, 43.79, 43.72, 39.27, 38.33, 24.31, 24.11, 17.99, −1.42. FAB-MS m/z 474 (MH$^+$).

Example 18

Synthesis of 4-Hydroxy-11-oxo-tricyclo[6.2.2.0$^{2,7}$] dodeca-2(7),3,5-triene-9,10-dicarboxylic acid 10-dodecyl ester 9-(2-trimethylsilanyl-ethyl) ester

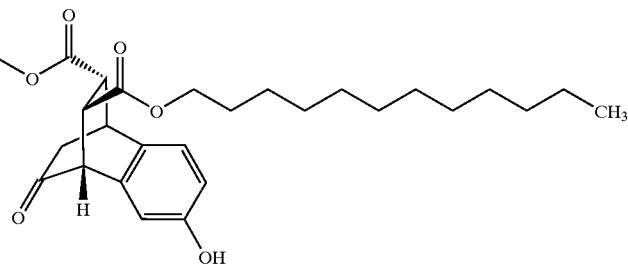

The title compound was prepared as described in general procedure B using n-dodecanol. Column chromatography (1% methanol/dichloromethane) provided 50% of the title compound. $^1$H NMR (acetonitrile-d3) 7.15 (d, J=8.0 Hz, 1H), 7.00 (br s, 1H), 6.71 (dd, J=8.0, 2.5 Hz, 1H), 6.67 (d, J=2.5 Hz, 1H), 4.28–4.22 (m, 2H), 4.04–3.91 (m, 2H), 3.83 (d, J=2.2 Hz, 1H), 3.72 (dd, J=5.4, 2.6 Hz, 1H), 3.57 (dd, J=5.9, 2.3 Hz, 1H), 3.09 (dt, J=6.0, 2.4 Hz, 1H), 2.37 (dd, J=19.0, 2.5 Hz, 1H), 2.05 (ddd, J=19.0, 3.1, 2.1 Hz, 1H), 1.56–1.44 (m, 2H), 1.28 (br s, 18H), 1.05–1.00 (m, 2H), 0.88 (t, J=6.6 Hz, 3H), 0.05 (s, 9H). $^{13}$C NMR (acetonitrile-d$_3$) 208.88, 174.01, 172.64, 157.75, 135.65, 134.36, 126.39, 115.75, 114.92, 66.38, 64.68, 55.98, 47.05, 43.87, 39.27, 38.32, 32.78, 30.52, 30.49, 30.44, 30.35, 30.21, 30.03, 29.41, 26.69, 23.50, 18.01, 14.50, −1.40. ESI-MS m/z 567.3 (MNa$^+$). Elemental for C$_{31}$H$_{48}$O$_6$Si: Theoretical, C, 68.34; H, 8.88. Found: C, 68.22; H, 8.98.

Example 19

Synthesis of 4-Hydroxy-11-oxo-tricyclo[6.2.2.0$^{2,7}$]dodeca-2(7),3,5-triene-9,10-dicarboxylic acid 10-allyl ester 9-(2-trimethylsilanyl-ethyl) ester

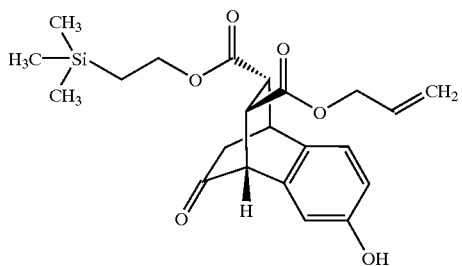

The title compound was prepared as described in general procedure B using allyl alcohol. Column chromatography (7% acetonitrile/dichloromethane) provided 39% of the title compound. $^1$H NMR (acetonitrile-d$_3$) 7.16 (d, J=8.0 Hz, 1H), 7.02 (br s, 1H), 6.72 (dd, J=8.0, 2.5 Hz, 1H), 6.69 (d, J=2.5 Hz, 1H), 5.92–5.81 (m, 1H), 5.28–5.17 (m, 2H), 4.56–4.43 (m, 2H), 4.33–4.19 (m, 2H), 3.87 (d, J=2.2 Hz, 1H), 3.74 (dd, J=5.4, 2.6 Hz, 1H), 3.64 (dd, J=5.9, 2.3 Hz, 1H), 3.12 (dt, J=5.9, 2.5 Hz, 1H), 2.37 (dd, J=19.0, 2.2 Hz, 1H), 2.06 (ddd, J=19.0, 3.3, 2.2 Hz, 1H), 1.06–1.00 (m, 2H), 0.05 (s, 9H). $^{13}$C NMR (acetonitrile-d$_3$) 208.79, 173.96, 172.37, 157.71, 135.58, 134.36, 133.51, 126.44, 118.75, 115.79, 114.95, 66.75, 64.72, 55.92, 47.01, 43.81, 39.22, 38.31, 17.98, −1.43. FAB-MS m/z 416 (M$^+$). Elemental for C$_{22}$H$_{28}$O$_6$Si: Theoretical, C, 63.44; H, 6.78. Found: C, 63.19; H, 6.97.

Example 20

Synthesis of 10-Azidocarbonyl-4-hydroxy-11-oxo-tricyclo[6.2.2.0$^{2,7}$]dodeca-2(7),3,5-triene-9-(2-trimethylsilanyl-ethyl) ester

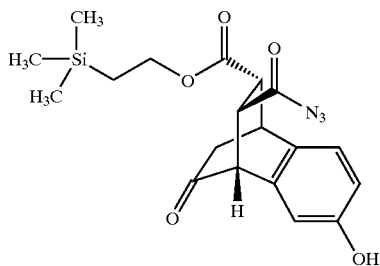

To a solution of 1 (584 mg, 1.51 mmol) in THF (15.6 mL) was added triethylamine (0.864 mL, 6.14 mmol) and DPPA (0.384 mL, 1.79 mmol). After 6.5 h the reaction was diluted with ethyl acetate and 1% HCl. The layers were separated and the organic layer washed with 5% NaHCO$_3$, H$_2$O, and brine, then dried (Na$_2$SO$_4$) and concentrated. Flash chromatography (25% ethyl acetate/hexane) afforded the trans acyl azide 2 (218 mg, 36%). FTIR (NaCl, cm$^{-1}$): 3435, 2960, 2907, 2152, 2129, 1803, 1735, 1728. $^1$H NMR (CDCl$_3$): 7.15 (d) 1H), 6.7 (m, 2H), 4.23 (m, 2H), 3.94 (d, 1H), 3.77 (dd, 1H), 3.68 (dd, 1H), 3.20 (ddd, 1H), 2.40 (dd, 1H), 2.15 (ddd, 1H), 0.10 (s, 9H).

Example 21

Synthesis of 4-Hydroxy-11-oxo-10-propoxycarbonylamino-tricyclo[6.2.2.0$^{2,7}$]dodeca-2(7),3,5-triene-9-(2-trimethylsilanyl-ethyl) ester

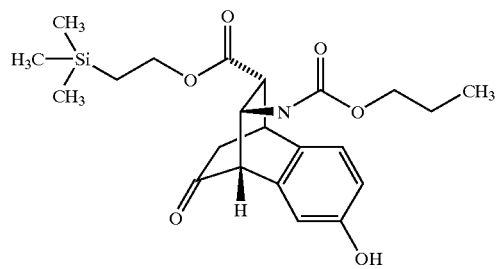

General Procedure C for Synthesis of 10-Alkoxycarbonylamino Derivatives

A 0.1 M solution of the acyl azide 2 in dioxane was refluxed for 1 h to generate the isocyanate. A selected alcohol was added in large excess and the solution heated for 4–20 h. The solution was cooled, and the crude product isolated by concentration in vacuo or by extraction. Chromatography on SiO$_2$ afforded the product.

The title compound was prepared as described in general procedure C employing propyl alcohol. Chromatography with 10% to 30% ethyl acetate/hexane afforded the title compound in 11% overall yield. FAB-MS m/z 434 (MH$^+$).

Example 22

Synthesis of 4-Hydroxy-10-(5-methyl-isoxazol-3-yl-methoxycarbonylamino)-11-oxo-tricyclo[.6.2.2.0$^{2,7}$]dodeca-2(7),3,5-triene-9-(2-trimethylsilanyl-ethyl) ester

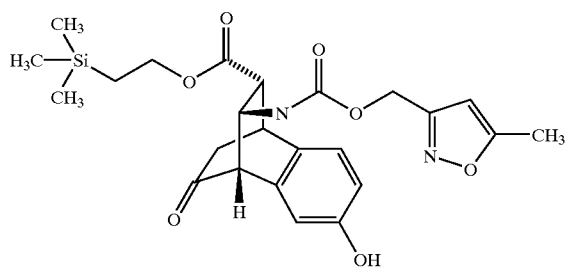

General Procedure D for Synthesis of 10-Alkoxycarbonylamino Derivatives

A 0.1 M solution of the acyl azide 2 in dioxane was refluxed for 1 h to generate the isocyanate. The alcohol (1.2–2 eq) was added followed by DMAP and the solution refluxed until complete, typically 12–20 h. The crude product was isolated by extraction.

The title compound was prepared as described in general procedure D employing 5-methylisoxazole-3-methanol, and with the following modifications. A solution of the acyl azide (200 mg, ~0.36 mol) in dioxane (3.6 mL) was heated to reflux for 30 min. The reaction was cooled to rt and 171 mg of 5-methylisoxazole-3-methanol was added. The reaction was returned to reflux for 15 h, then cooled to rt. The reaction was quenched with aqueous ammonium chloride and diluted with ethyl acetate. The phases were partitioned, and the organic layer was separated and washed with 5% aqueous $NaHCO_3$, then brine. The solution was dried ($Na_2SO_4$) and concentrated to dryness. Chromatography with 5% to 40% ethyl acetate/hexane afforded the title compound in 4% overall yield. $^1H$ NMR ($CDCl_3$) 7.12 (d, 1H), 6.71 (dd, 1H), 6.56 (d, 1H), 5.81 (s, 1H), 5.49 (s, 1H), 4.97 (dd, 2H), 4.25 (dd, 2H), 3.95 (d, 1H), 3.75 (m, 2H), 3.48 (s, 1H), 3.25–3.23 (m, 1H), 2.41 (s, 3H), 2.38 (dd, 1H), 2.25 (dd, 1H), 1.03 (dd, 2H), 0.05 (s, 9H).

Example 23

Synthesis of 4-Hydroxy-10-isopropoxycarbonylamino-11-oxo-tricyclo[6.2.2.0$^{2,7}$]dodeca-2(7),3,5-triene-9-(2-trimethylsilanyl-ethyl) ester

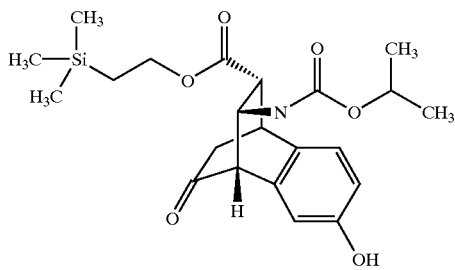

The title compound was prepared as described in general procedure C employing isopropyl alcohol. Chromatography with 30% ethyl acetate/hexane afforded a 53% yield of product. ESI-MS m/z 456 (MNa$^+$).

Example 24

Synthesis of 10-Cyclopentyloxycarbonylamino-4-hydroxy-11-oxo-tricyclo[6.2.2.0$^{2,7}$]dodeca-2(7),3,5-triene-9-(2-trimethylsilanyl-ethyl) ester

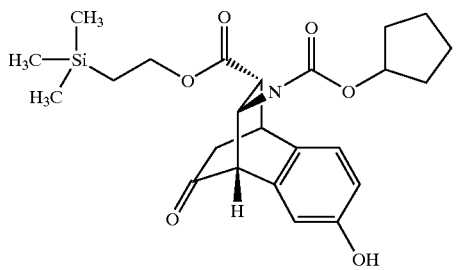

The title compound was prepared as in general procedure C employing cyclopentanol. Chromatography with 30% ethyl acetate/hexane afforded a 64% yield of product. ESI-MS m/z 482 (MNa$^+$).

Example 25

Synthesis of (9, 10 trans)-10-Allyloxycarbonylamino-4-hydroxy-11-oxo-tricyclo [6.2.2.0$^{2,7}$]dodeca-2(7),3,5-triene-9-(2-trimethylsilanyl-ethyl) ester

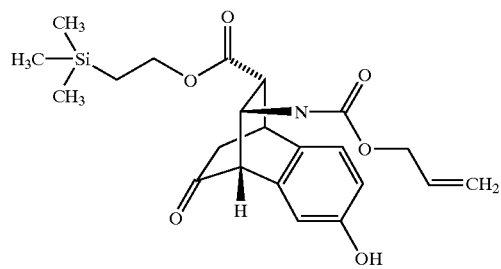

The title compound was prepared as in general procedure C employing allyl alcohol. Chromatography with 40% ethyl acetate/hexane afforded a 44% yield of product. ESI-MS m/z 454 (MNa$^+$).

Example 26

Synthesis of 4-Hydroxy-10-(indan-2-yloxycarbonylamino)-11-oxo-tricyclo[6.2.2.0$^{2,7}$] dodeca-2(7),3,5-triene-9-(2-trimethylsilanyl-ethyl) ester

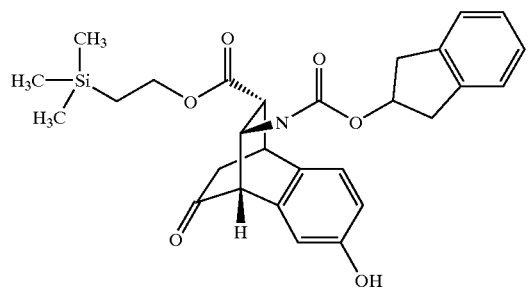

The title compound was prepared as in general procedure D employing 2-indanol. Chromatography with 30% ethyl acetate/hexane afforded 17% yield of product. ESI-MS m/Z 530 (MNa$^+$).

Example 27

Synthesis of 10-(3-Allyl-ureido)-4-hydroxy-11-oxo-tricyclo [6.2.2.0$^{2,7}$]dodeca-2(7),3,5-triene-9-(2-trimethylsilanyl-ethyl) ester

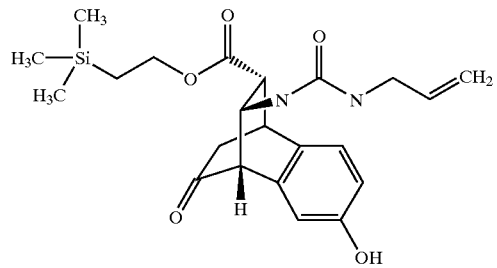

General Procedure E for The Synthesis of 10-Ureido Derivatives

A 0.1 M solution of the acyl azide 2 in dioxane was refluxed for 0.5 h. Upon cooling the appropriate amine was added and the solution stirred at ambient temperature for 1–4 h. Ethyl acetate and 1% HCl were added and the layers separated. The organic layer was washed with 5% NaHCO$_3$, H$_2$O, brine, dried (Na$_2$SO$_4$) and concentrated in vacuo. Flash chromatography afforded the urea.

The title compound was prepared as described in general procedure E employing 3.6 eq of allylamine. The crude product was chromatographed on SiO$_2$ to afford a 27% yield of the urea. ESI-MS m/z 453 (MNa$^+$).

Example 28

Synthesis of 4-Hydroxy-10-{3-[2-(4-hydroxy-phenyl)-ethyl]-ureido}-11-oxo-tricyclo[6.2.2.0$^{2,7}$]dodeca-2(7),3,5-triene-9-(2-trimethylsilanyl-ethyl) ester

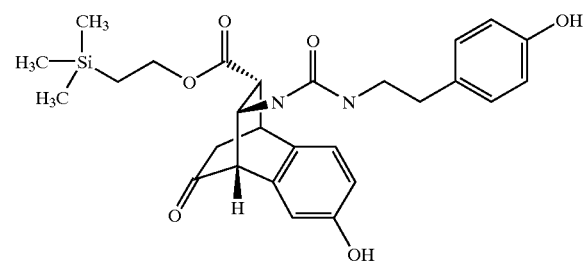

The title compound was prepared as described in general procedure E employing 2.2 eq of tyramine. The crude product was chromatographed with 50% ethyl acetate/hexane to 65% ethyl acetate/hexane gradient to afford an 18% yield of the urea. ESI-MS m/z 533 (MNa$^+$).

Example 29

Synthesis of 4-Hydroxy-10-[(morpholine-4-carbonyl)-amino]-11-oxo-tricyclo[6.2.2.0$^{2,7}$]dodeca-2(7),3,5-triene-9-(2-trimethylsilanyl-ethyl) ester

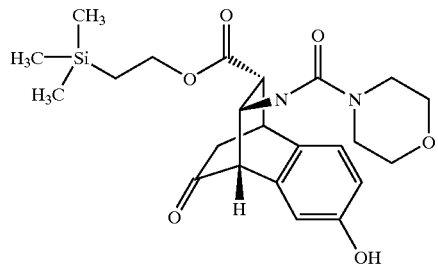

The title compound was prepared as described in general procedure E employing 3.3 eq of morpholine. The crude product was chromatographed with 70% ethyl acetate/methylene chloride to afford a 50% yield of the urea. ESI-MS m/z 483 (MNa$^+$).

Example 30

Synthesis of 10-(3-tert-Butyl-ureido)-4-hydroxy-11-oxo-tricyclo[6.2.2.0$^{2,7}$]dodeca-2(7),3,5-triene-9-(2-trimethylsilanyl-ethyl) ester

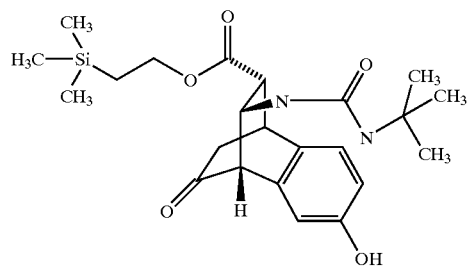

The title compound was prepared as described in general procedure E employing 3 eq of tert-butylamine. The crude product was chromatographed with 35% ethyl acetate/hexane to 45% ethyl acetate/hexane gradient to afford a 57% yield of the urea. ESI-MS m/z 469 (MNa$^+$).

Example 31

Synthesis of 10-[3-(2,4-Dimethoxy-benzyl)-ureido]-4-hydroxy-11-oxo-tricyclo[6.2.2.0$^{2,7}$]dodeca-2(7),3,5-triene-9-(2-trimethylsilanyl-ethyl) ester

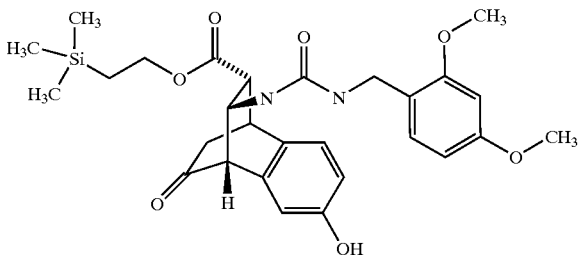

The title compound was prepared as described in general procedure E employing 1.5 eq of 2,4-dimethoxybenzylamine. The crude product was chromatographed with 60% ethyl acetate/hexane to afford a 16% yield of the urea. ESI-MS m/z 563 (MNa$^+$).

Example 32

Synthesis of 4-Hydroxy-10-(3-naphthalen-1-ylmethyl-ureido)-11-oxo-tricyclo[6.2.2.0$^{2,7}$]dodeca-2(7)3,5-triene-9-(2-trimethylsilanyl-ethyl) ester

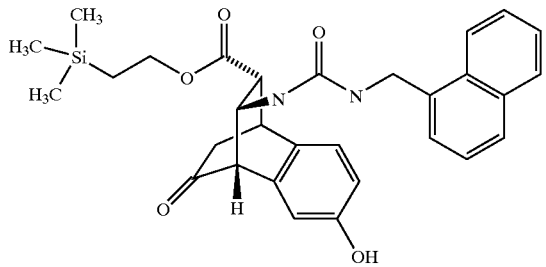

The title compound was prepared as described in general procedure E employing 2 eq of 1-naphthalene methylamine.

The crude product was chromatographed with 50% ethyl acetate/hexane to afford a 47% yield of the urea. ESI-MS m/z 531 (MH⁺).

Example 33

Synthesis of 4-(4-Allyloxycarbonyl-benzyloxy)-11-oxo-tricyclo[6.2.2.0$^{2,7}$]dodeca-2(7),3,5-triene-9, 10-dicarboxylic acid 10-propyl ester 9-(2-trimethylsilanyl-ethyl) ester

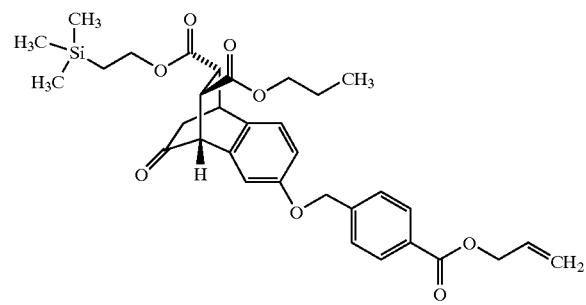

General Procedure F for the Synthesis of 4-Alkoxy Derivatives

To a 0.1 M solution of the benzobicyclooctane phenol (1 eq), prepared in Example 13, in tetrahydrofuran was added triphenylphosphine and the appropriate alcohol. The solution was cooled to 0° C. and DEAD was added. The cooling bath was removed, the solution stirred at ambient temp for 5 min then heated at reflux until reaction was complete, typically 20–30 min. After cooling, the solution was diluted with ethyl acetate, water was added and the layers separated. The organic layer was washed with brine, dried (Na$_2$SO4), and concentrated in vacuo. Chromatography on SiO$_2$ afforded the aryl ether.

The title compound was prepared as described in general procedure F employing 2.5 eq triphenyphosphine, 1.9 eq of allyl-4-(hydroxymethyl)-benzoate, and 2.5 eq of DEAD. Chromatography with 15% ethyl acetate/hexane followed by a second chromatography with 25% ethyl acetate/hexane afforded a 54% yield of aryl ether. ESI-MS m/z 615 (MNa⁺).

Example 34

Synthesis of 4-[4-(2-Dimethylcarbamoyl-pyrrolidine-1-carbonyl)-benzyloxy]-11-oxo-tricyclo[6.2.2.02,7]dodeca-2(7),3,5-triene-9,10-dicarboxylic acid 10-propyl ester 9-(2-trimethylsilanyl-ethyl) ester

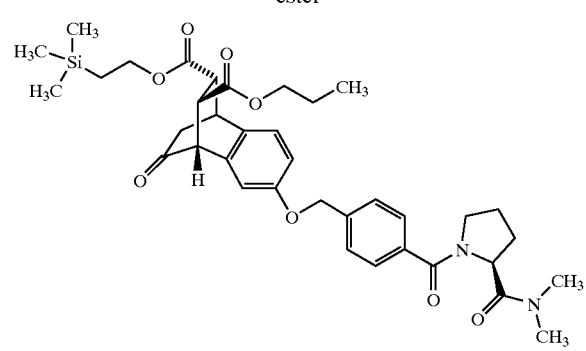

A. 4-(4-Carboxy-benzyloxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester To a solution of the allyl ester prepared in Example 33 in methylene chloride was added N-methylaniline (40 μL, 0.37 mmol) followed by tetrakis(triphenylphosphine)palladium (0) (21 mg, 0.02 mmol). The reaction was stirred for 20 min, diluted with ethyl acetate, and 2% HCl added. The layers were separated and the organic layer was washed with 1% HCl, H$_2$O, brine, dried (Na$_2$SO$_4$), and concentrated in vacuo. Chromatography with 65% ethyl acetate/methylene chloride to 95% ethyl acetate/dichloromethane afforded a 60% yield of product. ESI-MS m/z 551 (M-H)[31].

B. 4-[4-(2-Dimethylcarbamoyl-pyrrolidine-1-carbonyl)-benzyloxy]-11-oxo-tricyclo[6.2.2.0$^{2,7}$]dodeca-2(7),3,5-triene-9,10-dicarboxylic acid 10-propyl ester 9-(2-trimethylsilanyl-ethyl) ester To a solution of the acid (51.1 mg), N-methylmorpholine (30 μL), and proline dimethylamide (17.5 mg, 0.12 mmol) in methylene chloride (0.7 mL) was added HATU (46 mg, 0.12 mmol). The solution was stirred for 6 h, diluted with ethyl acetate, and quenched with 3% HCl. The layers were separated and the organic layer washed with 1% HCl, 5% NaHCO$_3$, H$_2$O, brine, dried (Na$_2$SO$_4$), and concentrated in vacuo. Chromatography with 100% ethyl acetate—5% methanol/methylene chloride gradient afforded the product contaminated with tetramethyl urea. An ethereal solution of the mixture was washed with H$_2$O (10×), dried (Na$_2$SO$_4$) and concentrated to afford 29.6 mg (46%) of the titled product as a 1/1 mixture of diasteroemers. ESI-MS m/z 677 (MH⁺).

Example 35

Synthesis of 4-Diethylcarbamoylmethoxy-11-oxo-tricyclo[6.2.2.0$^{2,7}$]dodeca-2(7),3,5-triene-9,10-dicarboxylic acid 10-propyl ester 9-(2-Trimethylsilanylethyl) ester

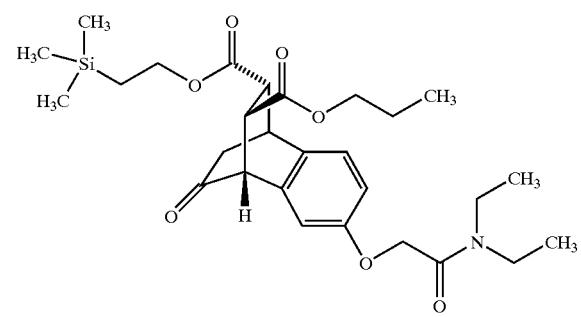

General Procedure G for the Synthesis of 4-Alkoxy Derivatives

To a 0.2 M solution of the phenol prepared as in Example 13 (1 eq) in DME or DMF was added alkyl halide and cesium carbonate (Cs$_2$CO$_3$). The solution was stirred at ambient temperature until complete, normally 1–12 h. The reaction was diluted with ethyl acetate, 1% HCl was added and the layers separated. The organic layer was washed with 5% NaHCO$_3$, brine, dried (Na$_2$SO$_4$) and concentrated in vacuo. Chromatography on SiO$_2$ afforded the aryl ether.

The title compound was prepared as described in general procedure G employing DME, 1.5 eq of N,N-diethyl-2-chloroacetamide and 2.0 eq of cesium carbonate. Chromatography with 3% ethyl acetate/methylene chloride to 10% ethyl acetate/methylene chloride gradient afforded a 26% yield of product. ESI-MS m/z 554 (MNa⁺).

Example 36

Synthesis of 4-(4-Nitro-benzyloxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

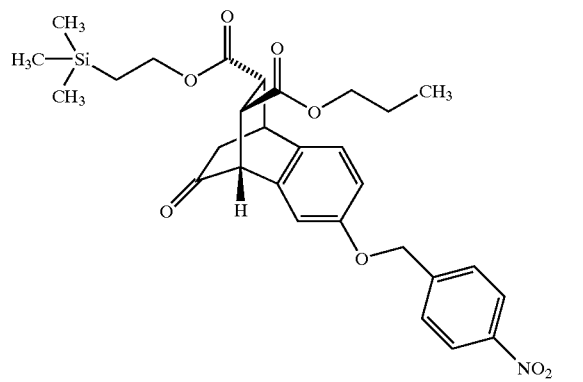

The title compound was prepared as described in general procedure F employing 2.3 eq PPh$_3$, 2.0 eq. nitrobenzyl alcohol and 2.3 eq DEAD. Chromatography with 10% ethyl acetate/hexane afforded the title compound in 30% yield. ESI-MS m/z 576 (MNa$^+$).

Example 37

Synthesis of 4-(Biphenyl-4-ylmethoxy)-11-oxo-tricyclo[6.2.2.0$^{2,7}$]dodeca-2(7), 3,5-triene-9,10-dicarboxylic acid 10-propyl ester 9-(2-trimethylsilanyl-ethyl) ester

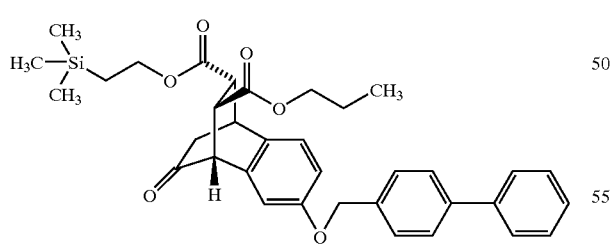

The title compound was prepared as described in general procedure F employing 1.7 eq PPh$_3$, 1.7 eq. biphenylmethanol and 1.7 eq DEAD. Chromatography with 10% ethyl acetate/hexane afforded the title compound in 47% yield. ESI-MS m/Z 607 (MNa$^+$).

Example 38

Synthesis of 4-(2-Naphthalen-2-yl-ethoxy)-11-oxo-tricyclo[6.2.2.0$^{2,7}$]dodeca-2(7),3,5-triene-9,10-dicarboxylic acid 10-propyl ester 9-(2-trimethylsilanyl-ethyl)

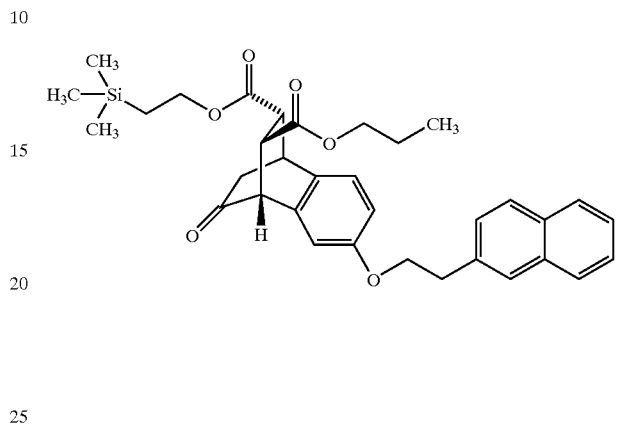

The title compound was prepared as described in general procedure F employing 2.3 eq PPh$_3$, 2.0 eq. naphthaleneethanol and 2.3 eq DEAD. Chromatography with 5% ethyl acetate/hexane afforded the title compound in 46% yield. ESI-MS m/z 595 (MNa$^+$).

Example 39

Synthesis of 4-(3-Fluoro-benzyloxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

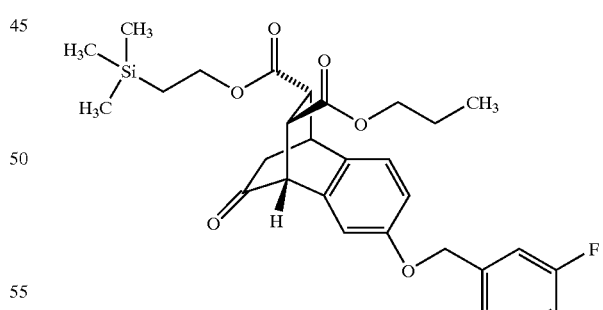

The title compound was prepared as described in general procedure F employing 2.3 eq PPh$_3$, 2.0 eq. 3-fluorobenzyl alcohol and 2.3 eq DEAD. Chromatography with 5% ethyl acetate/hexane afforded the title compound in 50% yield. ESI-MS m/z 549 (MNa$^+$).

Example 40

Synthesis of 11-Oxo-4-(3-phenyl-propoxy)-tricyclo[6.2.2.0$^{2,7}$]dodeca-2(7),3,5-triene-9,10-dicarboxylic acid 10-propyl ester 9-(2-trimethylsilanyl-ethyl) ester

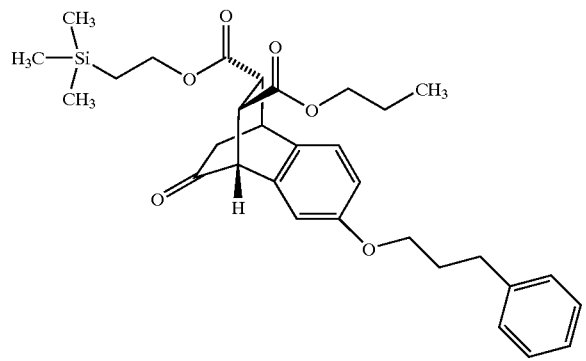

The title compound was prepared as described in general procedure F employing 2.3 eq PPh$_3$, 2.0 eq. 3-phenyl-1-propanol and 2.3 eq DEAD. Chromatography with 5% ethyl acetate/hexane afforded the title compound in 40% yield. ESI-MS m/z 559 (MNa$^+$).

Example 41

Synthesis of 11-Oxo-4-(2-pyridin-2-yl-ethoxy)-tricyclo[6.2.2.0$^{2,7}$]dodeca-2(7),3,5-triene-9,10-dicarboxylic acid 10-propyl ester 9-(2-trimethylsilanyl-ethyl) ester

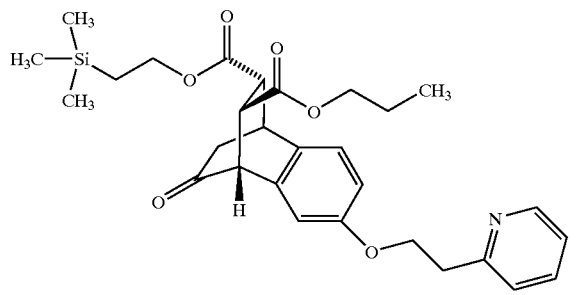

The title compound was prepared as described in general procedure F employing 2.3 eq PPh$_3$, 2.0 eq. 2-(2-hydroxyethyl) pyridine and 2.3 eq DEAD. Chromatography with 20% ethyl acetate/dichloromethane afforded the title compound in 36% yield. ESI-MS m/z 546 (MNa$^+$).

Example 42

Synthesis of 4-(2-Methoxy-ethoxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

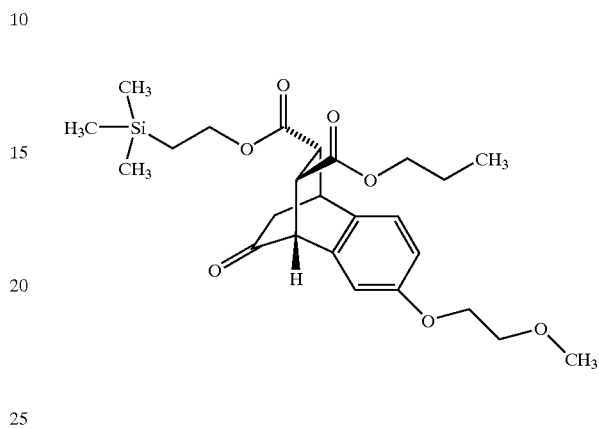

The title compound was prepared as described in general procedure F employing 2.3 eq PPh$_3$, 2.0 eq. 2-methoxyethanol and 2.3 eq DEAD. Chromatography with 18% ethyl acetate/hexane, then 15% acetone/hexane afforded the title compound in 50% yield. ESI-MS m/z 499 (MNa$^+$), 515 (MK$^+$).

Example 43

Synthesis of 4-Cyclopentyloxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

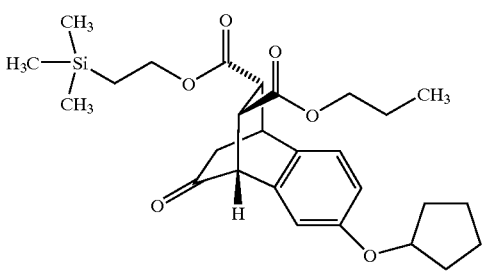

The title compound was prepared as described in general procedure F employing 2.3 eq PPh$_3$, 2.0 eq. cyclopentanol and 2.3 eq DEAD. Chromatography with 10% ethyl acetate/hexane afforded the title compound in 36% yield. ESI-MS m/z 509 (MNa$^+$).

Example 44

Synthesis of 4-(3-Cyano-propoxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

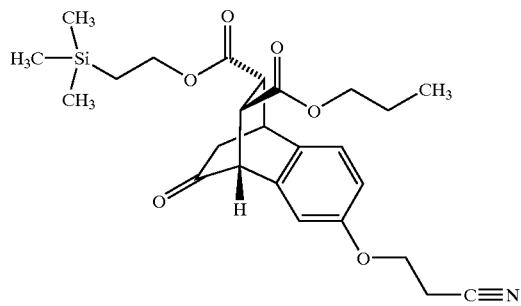

The title compound was prepared as described in general procedure G employing DMF, 1.5 eq 4-bromobutyronitrile and 2.0 eq Cs$_2$CO$_3$. Chromatography with 20% ethyl acetate/hexane afforded the title compound in 82% yield. ESI-MS m/z 508 (MNa$^+$).

Example 45

Synthesis of 4-(5-Methyl-isoxazol-3-ylmethoxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

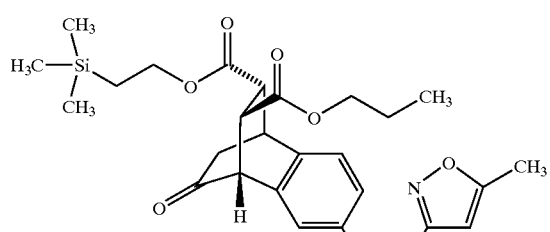

The title compound was prepared as described in general procedure F employing 2.3 eq PPh$_3$, 2.0 eq. 5-methylisoxazole-3-methanol and 2.3 eq DEAD. Chromatography with 20% ethyl acetate/dichloromethane afforded the title compound in 36% yield. ESI-MS m/z 536 (MNa$^+$).

Example 46

Synthesis of 4-Ethoxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

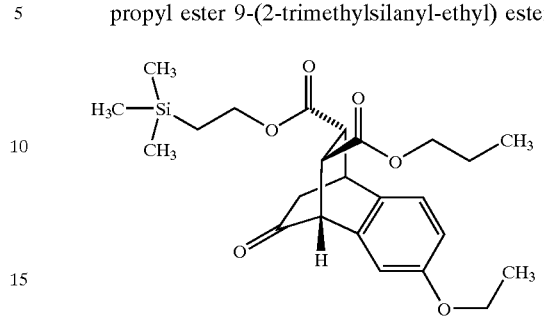

The title compound was prepared as described in general procedure G employing DMF, 1.5 eq iodoethane and 2.0 eq Cs$_2$CO$_3$. Chromatography with 10% ethyl acetate/hexane afforded the title compound in 40% yield. ESI-MS m/z 469 (MNa$^+$).

Example 47

Synthesis of 4-Methoxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

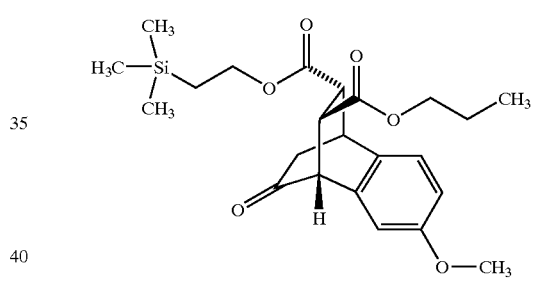

The title compound was prepared as described in general procedure G employing DMF, 3.0 eq iodomethane and 2.0 eq Cs$_2$CO$_3$. Chromatography with 15% ethyl acetate/hexane afforded the title compound in 54% yield. ESI-MS m/z 455 (MNa$^+$).

Example 48

Synthesis of 4-Allyloxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

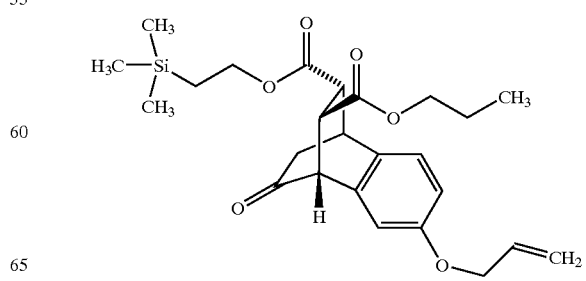

The title compound was prepared as described in general procedure G employing DMF, 3.0 eq 1,3-diiodopropane and 1.0 eq Cs₂CO₃. Chromatography with 10% ethyl acetate/hexane afforded the title compound in 8% yield. ESI-MS m/z 481 (MNa⁺).

Example 49

Synthesis of 11-Oxo-4-(pyridin-3-ylmethoxy)-tricyclo[6.2.2.0$^{2,7}$]dodeca-2(7),3,5-triene-9,10-dicarboxylic acid 10-propyl ester 9-(2-trimethylsilanyl-ethyl) ester

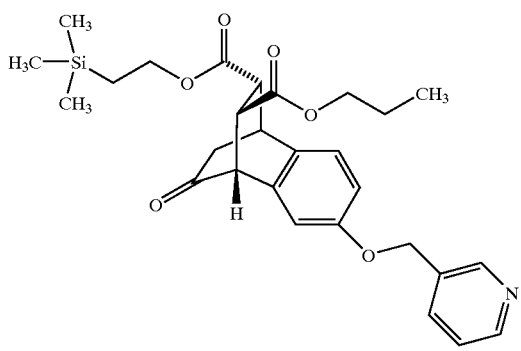

The title compound was prepared as described in general procedure G employing DMF, 2.0 eq 3-picolylchloride hydrochloride and 4.0 eq Cs₂CO₃. Chromatography with 40% ethyl acetate/hexane afforded the title compound in 75% yield. ESI-MS m/z 532 (MNa⁺).

Example 50

Synthesis of 11-Oxo-4-(pyridin-2-ylmethoxy)-tricyclo[6.2.2.0$^{2,7}$]dodeca-2(7),3,5-triene-9,10-dicarboxylic acid 10-propyl ester 9-(2-trimethylsilanyl-ethyl) ester

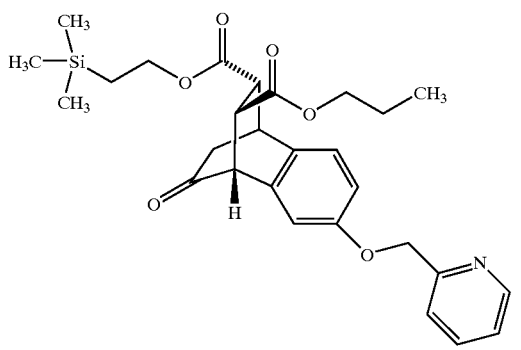

The title compound was prepared as described in general procedure G employing DMF, 2.0 eq 2-picolylchloride·HCl and 4.0 eq Cs₂CO₃. Chromatography with 15% ethyl acetate/hexane afforded the title compound in 72% yield. ESI-MS m/z 532 (MNa⁺).

Example 51

Synthesis of 4-tert-Butoxycarbonylmethoxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

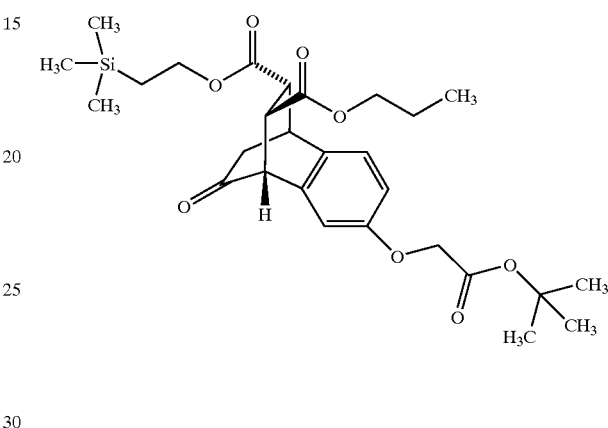

The title compound was prepared as described in general procedure G employing DMF, 1.1 eq oftert-butylbromo acetate, and 1.5 eq of Cs₂CO₃. Chromatography with 20% ethyl acetate/hexane afforded the title compound in 89% yield. ESI-MS m/z 555 (MNa⁺).

Example 52

Synthesis of 4-(Dimethoxy-phosphoryloxy)-11-oxo-tricyclo[6.2.2.0$^{2,7}$]dodeca-2(7),3,5-triene-9,10-dicarboxylic acid 10-propyl ester 9-(2-trimethylsilanyl-ethyl) ester

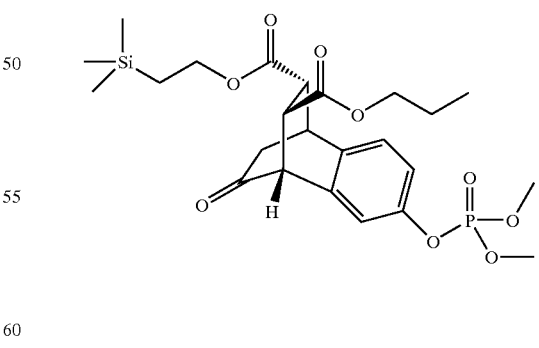

The title compound was prepared as described in general procedure G employing DMF, 1.5 eq dimethylchlorophosphate and 2.0 eq Cs₂CO₃. Chromatography with 40% ethyl acetate/hexane afforded the title compound in 19% yield. ESI-MS m/z 549 (MNa⁺).

Example 53

Synthesis of 11-Oxo-tricyclo[6.2.2.0$^{2,7}$]dodeca-2(7), 3,5-triene-9,10-dicarboxylic acid 10-propyl ester 9-(2-trimethylsilanyl-ethyl) ester

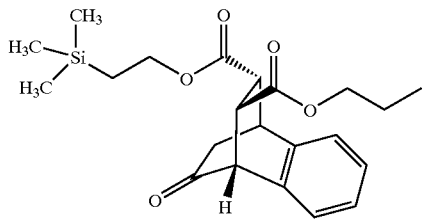

A. 11-Oxo-4-trifluoromethanesulfonyloxy-tricyclo[6.2.2.0$^{2,7}$]dodeca-2(7),3,5-triene-9,10-dicarboxylic acid 10-propyl ester 9-(2-trimethylsilanyl-ethyl) ester To a 0.3 M solution of the propyl ester of Example 13 in dichloromethane was added DIEA (2 eq) and N-phenyltrifluoromethanesulfonimide (1.1 eq). The reaction was stirred for 18 h at rt, then diluted with dichloromethane, quenched with aqueous ammonium chloride. The phases were partitioned, and the organic layer was separated and washed with 5% aqueous NaHCO$_3$. The solution was dried (Na$_2$SO$_4$), concentrated to dryness and chromatographed with 20% to 30% ethyl acetate/hexane.

B. 11-Oxo-tricyclo[6.2.2.0$^{2,7}$]dodeca-2(7),3,5-triene-9,10-dicarboxylic acid 10-propyl ester 9-(2-trimethylsilanyl-ethyl) ester A 0.155 M solution of the purified triflate in DMF was treated with Pd(OAc)$_2$ (0.048 eq), 1,1'-Bis(diphenylphosphino)ferrocene (0.054 eq), triethylamine (7.7 eq) and formic acid (8.5 eq). The reaction was heated to 90° C. for 2 days, then diluted with dichloromethane and quenched with aqueous ammonium chloride. The phases were partitioned, and the organic layer was separated, washed with brine, then dried (Na$_2$SO$_4$). Chromatography with 30% ethyl acetate/hexane afforded the title compound in 59% yield. $^1$H NMR (CDCl$_3$) 7.27 (dd, 2H), 7.23–7.15 (m, 2H), 4.26 (ddd, 2H), 4.04 (d, 1H), 3.96 (ddd, 2H), 3.80 (dd, 1H), 3.69 (dd, 1H), 3.23 (ddd, 1H), 2.43 (dd, 1H), 2.13 (ddd, 1H), 1.57 (dd, 2H), 1.61–1.54 (m, 4H), 1.03 (ddd, 2H), 0.88 (t, 3H), 0.04 (s, 9H).

Example 54

Synthesis of 4-Hydroxy-11-(methyl-hydrazono)-tricyclo[6.2.2.0$^{2,7}$]dodeca-2(7),3,5-triene-9,10-dicarboxylic acid 10-propyl ester 9-(2-trimethylsilanyl-ethyl) ester

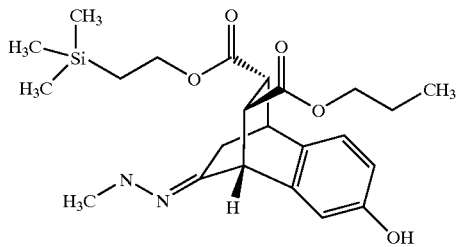

General Procedure H for the Synthesis of 11-Imino Derivatives

To a solution of the product of Example 13 (1 eq, 0.12–0.3 M) in methanol is added a selected amino derivative. Sodium acetate may be used as acid scavenger in the case where the nucleophile is added as an acid salt. The reaction is stirred until complete, normally 1–18 h. The crude material is isolated either by concentration in vacuo or by extraction using ethyl acetate or diethyl ether.

The title compound was prepared as described in general procedure H using 4 eq. of methylhydrazine. The crude product was isolated by adding diethyl ether and concentrating in vacuo Trituration with diethyl ether afforded a 69% yield of hydrazone as predominately the E isomer. ESI-MS m/z 447 (MH$^+$), 469 (MNa$^+$).

Example 55

Synthesis of 4-Hydroxy-11-(phenyl-hydrazono)-tricyclo[6.2.2.0$^{2,7}$]dodeca-2(7),3,5-triene-9,10-dicarboxylic acid 10-propyl ester 9-(2-trimethylsilanyl-ethyl) ester

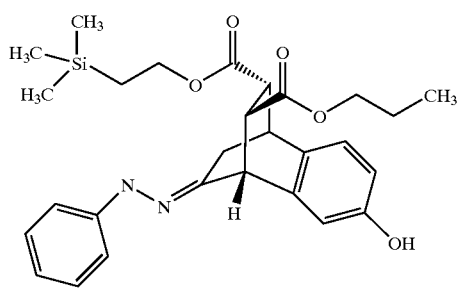

The title compound was prepared as described in general procedure H using 3 eq. of phenylhydrazine. The, crude product was isolated by extraction with ethyl acetate. Trituration with CHCl$_3$/hexane afforded a 62% yield of the hydrazone. ESI-MS m/z 509 (MH$^+$).

Example 56

Synthesis of 11-[(2-Bromo-phenyl)-hydrazono]-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

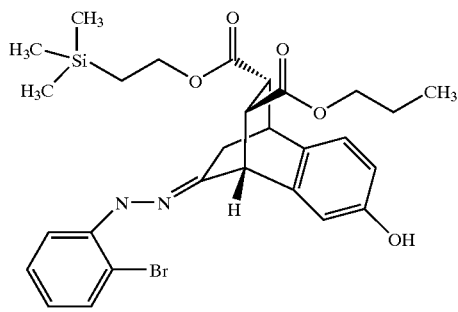

The title compound was prepared as described in general procedure H using 2 eq of 2-bromophenylhydrazine hydrochloride and 2 eq. of sodium acetate. The crude product was isolated by extraction with ethyl acetate. Chromatography on SiO$_2$ using 20% ethyl acetate/hexane afforded a 61% yield of the hydrazone. $^1$H NMR (CDCl$_3$): 7.48 (dd 1H), 7.38 (dd, 1H), 7.2 (m, 2H), 7.10 (d, 1H), 6.65 (m, 3H), 5.7 (br. S, 1H), 4.25 (m, 3H), 3.97 (m, 2H), 3.80 (m, 1H), 3.63 (m, 1H), 3.20 (m, 1H), 2.50 (dd, 1H), 2.20 (m, 1H), 1.59 (hex, 2H), 1.07 (m, 2H), 0.89 (t, 3H), 0.02 (s, 9H).

Example 57

Synthesis of 11-(Dimethyl-hydrazono)-4-hydroxy-tricyclo[6.2.2.0²,⁷]dodeca-2(7),3,5-triene-9,10-dicarboxylic acid 10-propyl ester 9-(2-trimethylsilanyl-ethyl) ester

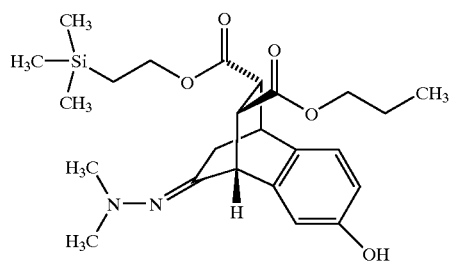

The title compound was prepared as described in general procedure H employing 1,1-dimethylhydrazine (1.4 eq). Chromatography using 40%–50% ethyl acetate/hexane afforded the title compound in 38% yield. ESI-MS m/z 461 (MH⁺).

Example 58

Synthesis of 4-Hydroxy-11-[(2-hydroxy-ethyl)-hydrazono]-tricyclo[6.2.2.0²,⁷]dodeca-2(7),3,5-triene-9,10-dicarboxylic acid 10-propyl ester 9-(2-trimethylsilanyl-ethyl) ester

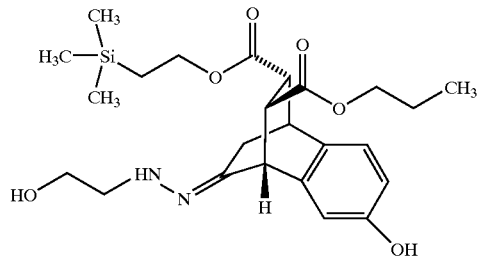

The title compound was prepared as described in general procedure H employing 2-hydroxyethyl hydrazine (1.4 eq) as the reagent. Chromatography using 50%–80% ethyl acetate/hexane afforded the title compound in 46% yield. ¹H NMR (CDCl₃) 7.25 (d, 1H), 6.70 (dd, 1H), 6.65 (d, 1H), 5.3–5.1 (br s, 1H), 4.25 (dd, 2H) 4.25–4.15 (m, 2H), 3.98–3.91 (m, 4H), 3.74 (d, 1H), 3.68 (dd, 1H), 3.21–3.19 (m, 1H), 2.41 (dd, 1H), 2.12 (ddd, 1H), 1.58 (dd, 2H), 1.24 (s, 1H), 1.04 (dd, 2H), 0.91 (t, 3H), 0.05 (s, 9H).

Example 59

Synthesis of 11-(Thiosemicarbazono)-4-hydroxy-tricyclo[6.2.2.0²,⁷]dodeca-2(7),3,5-triene-9,10-dicarboxylic acid 10-propyl ester 9-(2-trimethylsilanyl-ethyl) ester

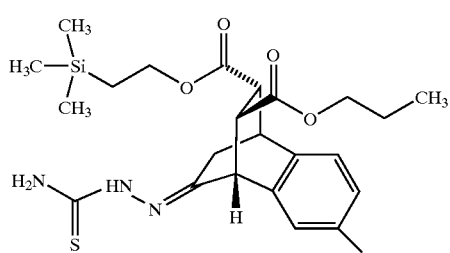

The title compound was prepared as described in general procedure H employing thiosemicarbazide as the reagent. Chromatography using 50% ethyl acetate/hexane afforded the title compound in 42% yield. ESI-MS m/z 492 (MH⁺), 514 (MNa⁺).

Example 60

Synthesis of 1-(4-Methyl-3-thiosemicarbazono)-4-hydroxy-tricyclo[6.2.2.0²,⁷]dodeca-2(7),3,5-triene-9,10-dicarboxylic acid 10-propyl ester 9-(2-trimethylsilanyl-ethyl) ester

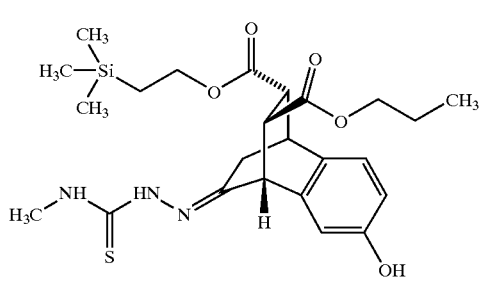

The title compound was prepared as described in general procedure H employing 4-methyl-3-thiosemicarbazide (1.4 eq) as the reagent. Chromatography using 35% ethyl acetate/hexane afforded the title compound in 35% yield. APC₁-MS m/z 506 (MH⁺), 505 (M⁻).

Example 61

Synthesis of 4-Hydroxy-11-(methyl-phenyl-hydrazono)-tricyclo[6.2.2.0$^{2,7}$]dodeca-2(7),3,5-triene-9,10-dicarboxylic acid 10-propyl ester 9-(2-trimethylsilanyl-ethyl) ester

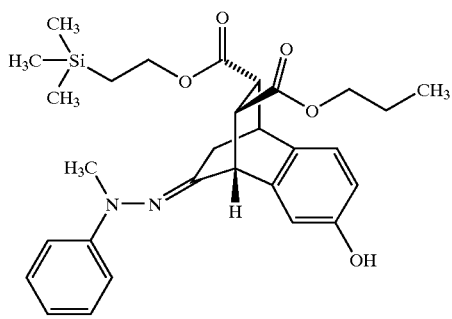

The title compound was prepared as in general procedure H using 1.2 eq. of N-methyl-N-phenylhydrazine. The crude product was isolated by concentration in vacuo. Chromatography on SiO$_2$ using 5% ethyl acetate/methylene chloride afforded a 57% yield of the hydrazone. ESI-MS m/z 523 (MH$^+$), 521 (M-H)$^-$.

Example 62

Synthesis of 11-(Methanesulfonyl-hydrazono)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

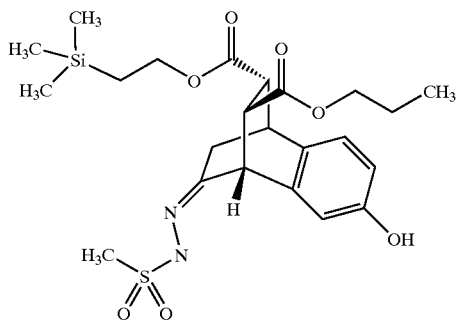

The title compound was prepared as in general procedure H using 2.4 eq. of methanesulfonyl hydrazine. The crude product was isolated by extraction with ethyl acetate. Chromatography on SiO$_2$ using 35% ethyl acetate/hexane afforded a 10% yield of the Z-isomer and 50% of the E-isomer. ESI-MS 533.1 (MNa$^+$).

Example 63

Synthesis of 11-(Benzenesulfonyl-hydrazono)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

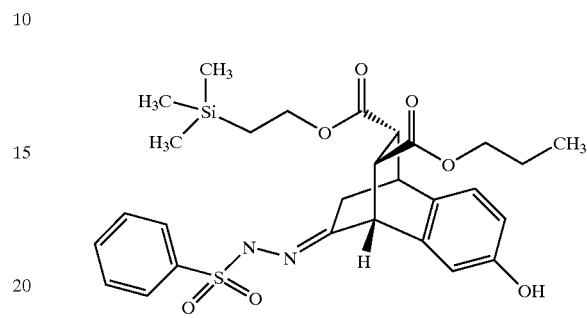

The title compound was prepared as in general procedure H using 2.4 eq. of benzenesulfonyl hydrazine. The crude product was isolated by extraction with ethyl acetate. Chromatography on SiO$_2$ using 30% ethyl acetate/hexane afforded a 62% yield of product. ESI-MS m/z 595 (MNa$^+$).

Example 64

Synthesis of 11-(4-Methoxybenzenesulfonyl-hydrazono)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

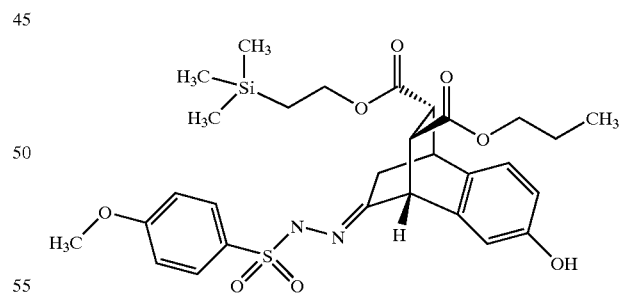

The title compound was prepared as described in general procedure H using 2 eq. of 4-methoxybenzenesulfonyl hydrazine. The crude product was isolated by extraction with ethyl acetate. Chromatography on SiO$_2$ using 40% ethyl acetate/hexane afforded an 82% yield of product. ESI-MS m/z 603 (MH$^+$).

Example 65

Synthesis of 11-(Acetyl-hydrazono)-4-hydroxy-tricyclo[6.2.2.0²,⁷]dodeca-2(7),3,5-triene-9,10-dicarboxylic acid 10-propyl ester 9-(2-trimethylsilanyl-ethyl) ester

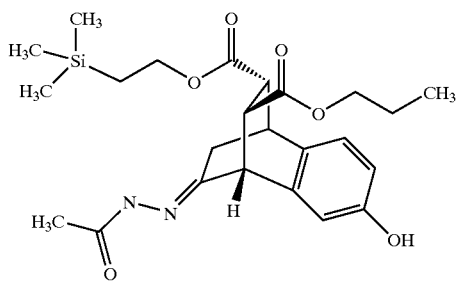

The title compound was prepared as described in general procedure H using 2.6 eq. of acetyl hydrazine. The crude product was isolated by extraction. Chromatography on SiO₂ using 50% ethyl acetate/hexane afforded a 34% yield of a 4/1 mix of E/Z isomers. ESI-MS m/z 475 (MH⁺).

Example 66

Synthesis of 4-Hydroxy-11-hydroxyimino-tricyclo[6.2.2.0²,⁷]dodeca-2(7),3,5-triene-9,10-dicarboxylic acid 10-propyl ester 9-(2-trimethylsilanyl-ethyl) ester

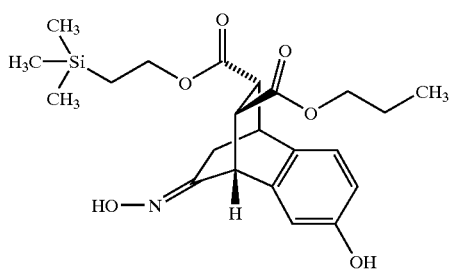

The title compound was prepared as described in general procedure H employing hydroxylamine (1.1 eq) and sodium acetate (2.3 eq). The crude product was isolated by extraction. Chromatography with 5% Acetone/1% acetic acid/94% dichloromethane followed by recrystallization in dichloromethane/hexane afforded the title compound in 58% yield. ESI-MS m/z 456 (MNa⁺).

Example 67

Synthesis of 4-Hydroxy-11-methoxyimino-tricyclo[6.2.2.0²,⁷]dodeca-2(7),3,5-triene-9,10-dicarboxylic acid 10-propyl ester 9-(2-trimethylsilanyl-ethyl) ester

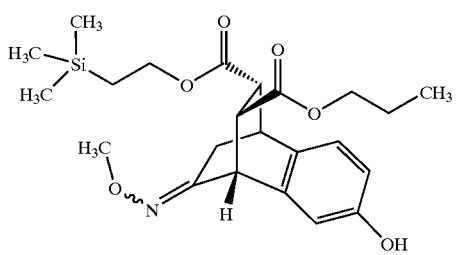

The title compound was prepared as described in general procedure H employing methoxylamine (1.1 eq) and sodium acetate (2.3 eq). The crude product was isolated by extraction. Chromatography with 10% ethyl acetate/dichloromethane resulted in a 34% yield of the less polar isomer: ESI-MS m/z 448 (MNa⁺), 470 (MNa⁺) and a 34% yield of the more polar isomer: ESI-MS m/z 448 (MH⁺), 470 (MNa⁺).

Example 68

Synthesis of 4-Hydroxy-11-phenoxyimino-tricyclo[6.2.2.0²,⁷]dodeca-2(7),3,5-triene-9,10-dicarboxylic acid 10-propyl ester 9-(2-trimethylsilanyl-ethyl) ester

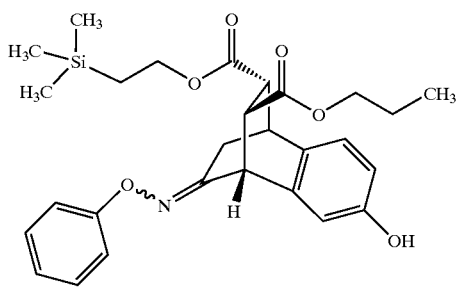

The title compound was prepared as described in the general procedure H employing 1.1 eq of O-phenylhydroxylamine and 2.3 eq of sodium acetate. The crude product was isolated by extraction. Chromatography with 30% ethyl acetate/dichloromethane afforded the title compounds as a 1:1 mixture in 63% combined yield. ESI-MS m/z 510 (MH⁺), 532 (MNa⁺).

Example 69

Synthesis of 11-Benzyloxyimino-4-hydroxy-tricyclo[6.2.20^{2,7}]dodeca-2(7),3,5-triene-9,10-dicarboxylic acid 10-propyl ester 9-(2-trimethylsilanyl-ethyl) ester

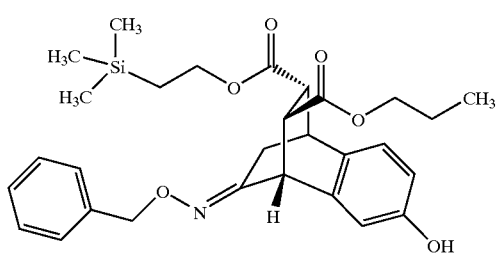

The title compound was prepared as described in general procedure H employing 1.1 eq of benzylhydroxylamine and 2.3 eq of sodium acetate. The crude product was isolated by extraction. Chromatography with 30% ethyl acetate/dichloromethane afforded the title compounds as a 2:1 mixture of Z and E isomers in 47% combined yield. ESI-MS m/z 524 (MH$^{30}$).

Example 70

Synthesis of 4-Hydroxy-11-(4-nitro-benzyloxyimino)-tricyclo[6.2.2.0$^{2,7}$]dodeca-2(7),3,5-triene-9,10-dicarboxylic acid 10-propyl ester 9-(2-trimethylsilanyl-ethyl) ester

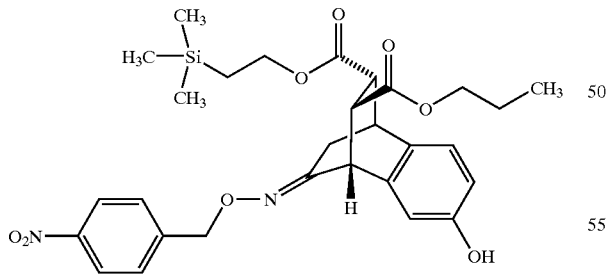

The title compound was prepared as described in general procedure H employing 1.1 eq of (4-nitrobenzyl)hydroxylamine and 2.3 eq of sodium acetate. The crude product was isolated by extraction. Chromatography with 20–30% ethyl acetate/dichloromethane afforded the title compound in 28% yield. ESI-MS m/z 569 (MH$^+$).

Example 71

Synthesis of 11-(5-Chloro-[1,2,3]thiadiazol-4-ylmethoxyimino)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

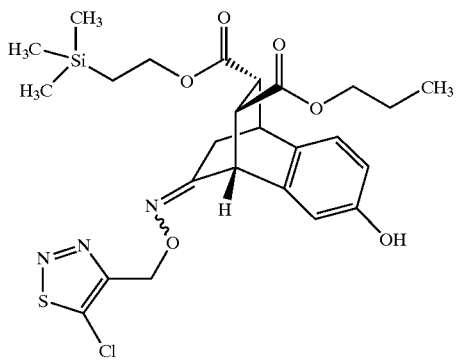

The title compound was prepared as described in general procedure H employing 1.1 eq of (4-chloro)thiadiazolyl-5-methoxyhydroxylamine and 2.3 eq of sodium acetate. The crude product was isolated by extraction. Chromatography with 30%–40% ethyl acetate/dichloromethane afforded the title compounds as a 1:1 mixture of E and Z isomers in 92% yield. ESI-MS m/z 566 (MNa$^+$).

Example 72

Synthesis of 11-(3-Fluoro-benzyloxyimino)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

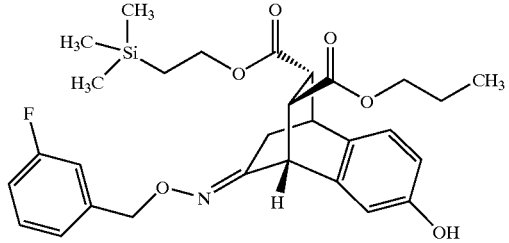

The title compound was prepared as described in general procedure H employing 1.1 eq of (3-fluoro)benzylhydroxylamine and 2.3 eq of sodium acetate. The crude product was isolated by extraction. Chromatography with 30% ethyl acetate/dichloromethane afforded the title compounds as a 1:1.3 mixture of E and Z isomers in 89% yield. ESI-MS m/z 542 (MNa$^+$).

Example 73

Synthesis of 4-Hydroxy-11-[2-oxo-2-(4-phenyl-piperazin-1-yl)-ethoxyimino]-tricyclo[6.2.2.0$^{2,7}$]dodeca-2(7),3,5-triene-9,10-dicarboxylic acid 10-propyl ester 9-(2-trimethylsilanyl-ethyl) ester

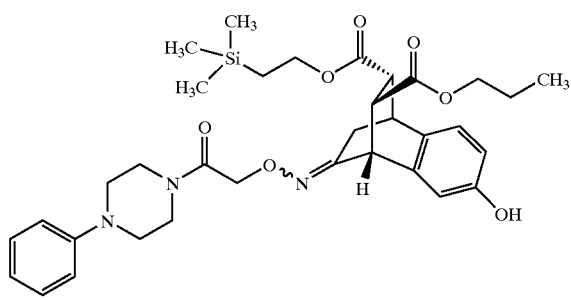

The title compound was prepared as described in general procedure H employing 2-aminooxy-1-(4-phenyl-piperazin-1-yl)-ethanone (1.1 eq) and sodium acetate (2.3 eq). The crude product was isolated by extraction. Chromatography with 40%–60% ethyl acetate/dichloromethane afforded the less polar E isomer in 8% yield and the more polar Z isomer in 18% yield. ESI-MS m/z 636 (MH$^+$), 658 (MNa$^+$).

Example 74

Synthesis of 11-(4-Fluoro-benzyloxyimino)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

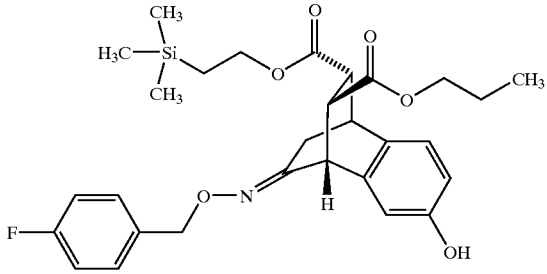

The title compound was prepared as described in general procedure H employing (4-fluoro)benzylhydroxylamine (1.1 eq) and sodium acetate (2.3 eq). The crude product was isolated by extraction. Chromatography with 0%–10% ethyl acetate/dichloromethane afforded the title compound in 25% yield. $^1$H NMR (CDCl$_3$) 7.32 (dd, 2H), 7.09–6.99 (m, 3H), 6.69–6.64 (m, 2H), 5.05–5.03 (m, 3H), 4.95 (s, 1H), 4.24 (dd, 2H), 3.95 (ddd, 2H), 3.64 (d, 1H), 3.50 (dd, 1H), 3.08–3.06 (m, 1H), 2.50 (dd, 1H), 2.12 (ddd, 1H), 1.58 (dd, 2H), 1.02 (dd, 2H), 0.87 (t, 3H), 0.04 (s, 9H).

Example 75

Synthesis of 4-Hydroxy-11-(2-phenoxy-ethoxyimino)-tricyclo [6.2.2.0$^{2,7}$]dodeca-2(7),3,5-triene-9,10-dicarboxylic acid 10-propyl ester 9-(2-trimethylsilanyl-ethyl) ester

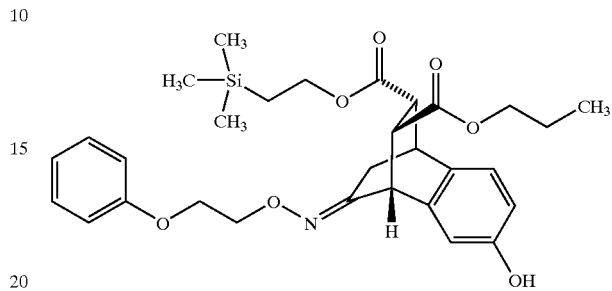

The title compound was prepared as described in general procedure H employing (3-phenoxy)ethyllhydroxylamine (1.1 eq) and sodium acetate (2.3 eq). The crude product was isolated by extraction. Chromatography with 0%–10% ethyl acetate/dichloromethane afforded the title compound in 22% yield. $^1$H NMR (CDCl$_3$) 7.31–7.30 (m, 2H), 7.06 (d, 1H), 6.97–6.92 (m, 3H), 6.64 (dd, 1H), 6.57 (d, 1H), 5.03 (d, 1H), 4.87 (s, 1H), 4.41–4.37 (m, 2H), 4.25 (ddd, 2H), 4.16 (dd, 2H), 3.94 (ddd, 2H), 3.63 (dd, 1H), 3.51 (dd, 1H), 3.09–3.06 (m, 1H), 2.52 (dd, 1H), 2.13 (ddd, 1H), 1.57 (ddd, 2H), 1.03 (dd, 2H), 0.86 (t, 3H), 0.05 (s, 9H).

Example 76 synthesis of 11-Allyloxyimino-4-hydroxy-tricyclo [6.2.2.0$^{2,7}$]dodeca-2(7),3,5-triene-9,10-dicarboxylic acid 10-propyl ester 9-(2-trimethylsilanyl-ethyl) ester

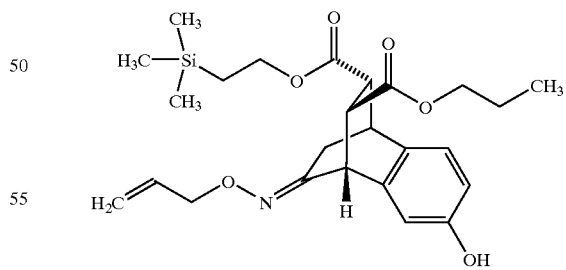

The title compound was prepared as described in general procedure H employing O-allylhydroxylamine (1.1 eq) and sodium acetate (2.3 eq). The crude product was isolated by extraction. Chromatography with 25%–40% ethyl acetate/hexane afforded the title compound in 45% yield. ESI-MS m/z 496 (MNa$^+$).

Example 77

Synthesis of 11-(2,4-Dichlorobenzyl-oximo)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

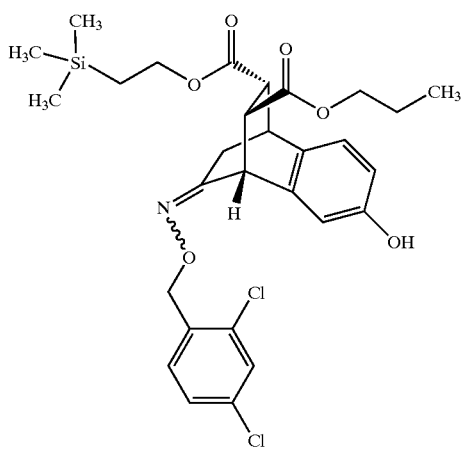

The title compound was prepared as described in general procedure H using 1.1 eq of O-2,4-dichlorobenzyl hydroxyl amine hydrochloride and 1.1 eq of sodium acetate. The crude product was isolated by concentrating in vacuo. Chromatography on SiO$_2$ using 25% ethyl acetate/hexane followed by 3% ethyl acetate/methylene chloride afforded a 28% yield of Z-isomer, the less polar compound, and 33% yield of the E-isomer, the more polar compound. ESI-MS m/z, Z-isomer 592 (MH$^+$), 594 ((M+2)H$^+$); E-isomer 592 (MH$^+$), 594 ((M+2)H$^+$).

Example 78

Synthesis of 11-(Semicarbazono)-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

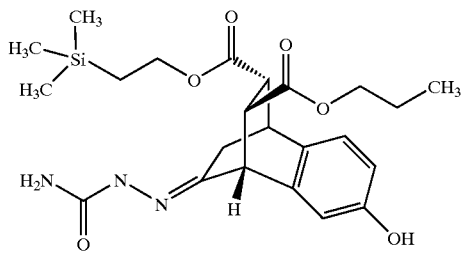

The title compound was prepared as described in general procedure H using 1.3 eq of semicarbazide hydrochloride and 1.3 eq of sodium acetate. The crude product was isolated by extraction with ethyl acetate. Chromatography on SiO$_2$ using 70% ethyl acetate/hexane afforded a 48% yield of product. ESI-MS m/z 498 (MNa$^+$).

Example 79

Synthesis of (9,10 trans)-10-Allyloxycarbonylamino-4,11-dihydroxy-tricyclo[6.2.2.0$^{2,7}$]dodeca-2(7),3,5-triene-9-(2-trimethylsilanyl-ethyl) ester

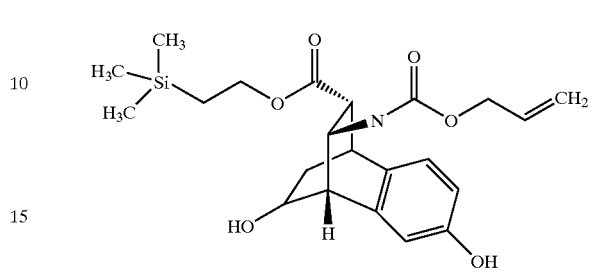

To a solution of the ketone prepared in Example 25 (12.4 mg, 0.029 mmol) in 0.5 mL methanol was added sodium borohydride (21.1 mg, 0.56 mmol). After 20 min H$_2$O was added, the solution acidified to pH 1 with 1% HCl, and the product extracted with ethyl acetate. The organic layer was washed with H$_2$O, brine, dried (Na$_2$SO$_4$) and concentrated. Flash chromatography (SiO$_2$, 45% ethyl acetate/dichloromethane) afforded 3.7 mg (30%) of the less polar alcohol and 4.1 mg (33%) of the more polar alcohol. ESI-MS m/z: less polar product 456 (MNa$^+$), more polar product 456 (MNa$^+$).

Example 80

Synthesis of (9,10 cis)-10-Allyloxycarbonylamino-4,11-dihydroxy-tricyclo[6.2.2.0$^{2,7}$]dodeca-2(7),3,5-triene-9-(2-trimethylsilanyl-ethyl) ester

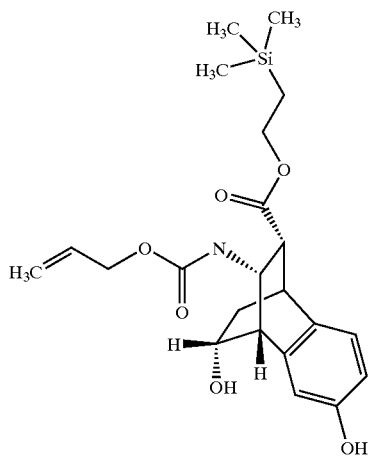

To a solution of the ketone from Example 3 (25.9 mg, 0.06 mmol) in methanol (1.1 mL) held at 20° C. with a water bath was added sodium borohydride (44.7 mg, 1.2 mmol). The reaction was stirred for 20 min, diluted with ethyl acetate and quenched with water followed by 1% HCl. The layers were separated, and the organic layer washed with 5% NaHCO$_3$, water, brine, dried (Na$_2$SO$_4$), and concentrated in vacuo. Chromatography on SiO$_2$ using 40% ethyl acetate/hexane afforded 13.2 mg (50%) of product as the less polar diastereomer. ESI-MS m/z 456 (MNa$^+$).

Example 81

Synthesis of 4,11-Dihydroxy-11-phenyl-tricyclo[[6.2.2.0$^{2,7}$]dodeca-2(7),3,5-triene-9,10-dicarboxylic acid 10-propyl ester 9-(2-trimethylsilanyl-ethyl) ester

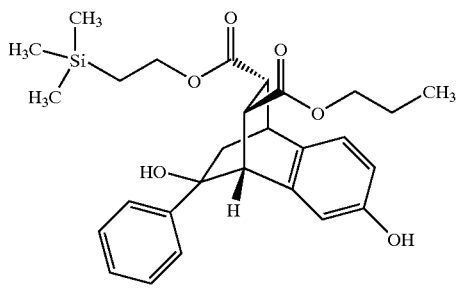

To a solution of the compound of Example 13 (61 mg, 0.146 mmol) in tetrahydrofuran (2.9 mL) at −10° was added phenylmagnesium bromide (360 µL, 1 M). Additional aliquots (720 µL) of phenylmagnesium bromide were added at 30 min intervals until the reaction was complete by TLC. The cooling bath was removed, the reaction diluted with ethyl acetate, then quenched with 3% HCl. The layers were separated and the organic layer washed with 1% HCl, 5% NaHCO$_3$, H$_2$O, brine, and dried (Na$_2$SO$_4$). Concentration in vacuo followed by chromatography afforded 26 mg (36%) of the tertiary alcohol. ESI-MS m/z 519 (MNa$^+$).

Example 82

Synthesis of 4-Hydroxy-11-propylamino-tricyclo[[6.2.2.0$^{2,7}$]dodeca-2(7),3,5-triene-9,10-dicarboxylic acid 10-Propyl ester 9-(2-trimethylsilanyl-ethyl) ester

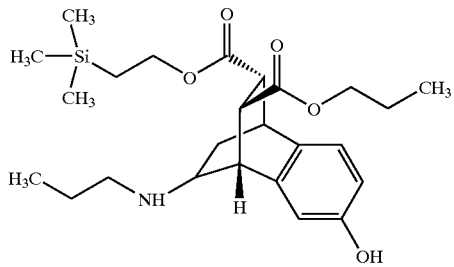

To a solution of the compound of Example 13 (75 mg, 0.18 mmol) in methanol (1 mL) was added n-propylamine (75 µL, 1.8 mmol) and acetic acid (52 µL, 1.8 mmol). After 10 min sodium triacetoxy borohydride (380 mg, 1.8 mmol) was added and the solution stirred overnight. Additional aliquots of n-propylamine (600 EL), acetic acid (500 µL) and sodium triacetoxy borohydride (400 mg) were added and the reaction allowed to proceed for 1.5 h. The reaction was diluted with ethyl acetate and 5% NaHCO$_3$. The layers were separated, and the organic layer washed with 5% NaHCO$_3$, H$_2$0, brine, dried (Na$_2$SO$_4$), and concentrated in vacuo. Chromatography on SiO$_2$ using a gradient of 45% ethyl acetate/methylene chloride—2% methanol/methylene chloride—8% methanol/methylene chloride afforded a 34% yield of the less polar amine and 37% yield of the more polar amine. ESI-MS m/z 462 (MH$^+$).

Example 83

Synthesis of 4-Hydroxy-11-(4-methyl-Benzylamino)-tricyclo[[6.2.2.0$^{2,7}$]dodeca-2(7),3,5-triene-9,10-dicarboxylic acid 10-propyl ester 9-(2-trimethylsilanyl-ethyl) ester

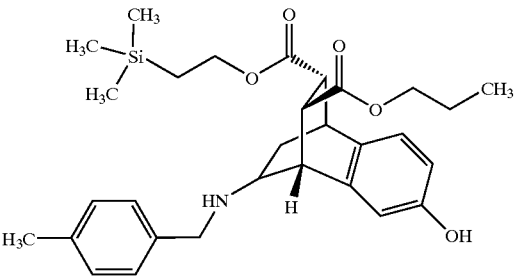

To a solution of the compound of Example 13 (50 mg, 0.12 mmol) in methanol (0.5 mL) was added acetic acid (14 µL, 0.24 mmol), 4-methylbenzyl amine (31 µL, 2.1 eq.) and sodium cyanoborohydride (38 mg, 0.60 mmol). After 2 h an additional aliquot of sodium cyanoborohydride (10 mg) was added and the reaction allowed to stir for 30 more min. The reaction was then quenched with 3% HCl and diluted with ethyl acetate. The biphasic mixture was then basified to pH 8 with 5% NaHCO$_3$. The layers were separated, and the organic layer washed with H$_2$O, brine, dried (Na$_2$SO$_4$) and concentrated in vacuo. Chromatography on SiO$_2$ using first a gradient of 15% ethyl acetate/hexane—25% ethyl acetate/hexane followed by a second chromatography using a gradient 10% ethyl acetate/methylene chloride—17% ethyl acetate/methylene chloride afforded a 19% yield of the less polar amine and 16% of the more polar amine. ESI-MS m/z 524 (MH$^+$).

Example 84

Synthesis of 4-Hydroxy-11-methylamino-tricyclo[[6.2.2.0$^{2,7}$]dodeca-2(7),3,5-triene-9,10-dicarboxylic acid 10-propyl ester 9-(2-trimethylsilanyl-ethyl) ester

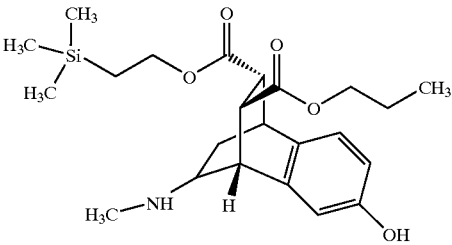

To a solution of the compound of Example 13 (75 mg, 0.18 mmol) in methanol (1.8 mL) was added acetic acid (260 µL, 25 eq), methylamine (40% in H$_2$O, 310 µL) and sodium triacetoxy borohydride (760 mg, 20 eq). After stirring overnight additional aliquots of acetic acid (200 µL), methylamine (200 µL) and reducing agent (300 mg) were added. The reaction was allowed to stir for an additional 3 h, then it was diluted with ethyl acetate and 5% NaHCO$_3$. The layers were separated and the organic layer was washed with 5% NaHCO$_3$, H$_2$O, brine, dried (Na$_2$SO$_4$) and concentrated in vacuo. Chromatography on SiO$_2$ using a gradient of 65% ethyl acetate/hexane Π 8% methanol/methylene chloride afforded a 28% yield of less polar amine and 43% of the more polar product. ESI-MS m/z: less polar compound 434 (MH⁺), more polar compound 434 (MH⁺).

Example 85

Synthesis of 4-Hydroxy-11-phenylamino-tricyclo[[6.2.2.0$^{2,7}$]dodeca-2(7),3,5-triene-9,10-dicarboxylic acid 10-propyl ester 9-(2-trimethylsilanyl-ethyl) ester

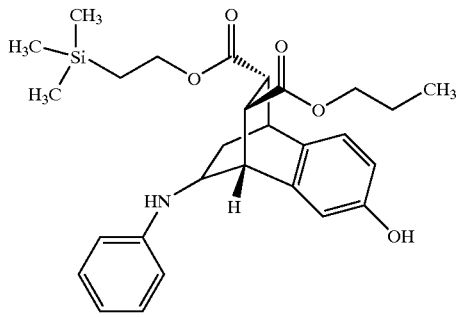

To a solution of the compound of Example 13 (76.5 mg, 0.18 mmol) in methanol (1.5 mL) was added acetic acid (104 μL, 1.7 mmol) and aniline (82 μL, 0.9 mmol). Additional aliquots were added at 3 h and 5.5 h and the reaction allowed to proceed to completion overnight. The solution was concentrated to dryness and the residue partitioned between ethyl acetate/hexane (3/1) and 5% NaHCO₃. The layers were separated and the organic layer washed with 5% NaHCO₃, H₂O, dried (Na₂SO₄), and concentrated in vacuo. Flash chromatography on SiO₂ afforded 30.5 mg (34%) of the less polar diastereomer and 14.7 mg (16%) of the more polar diastereomer. ESI-MS ml/z 496 (MH⁺).

Example 86

Synthesis of 11-Dimethylamino-4-hydroxy-tricyclo[[6.2.2.0$^{2,7}$]dodeca-2(7),3,5-triene-9,10-dicarboxylic acid 10-propyl ester 9-(2-trimethylsilanyl-ethyl) ester

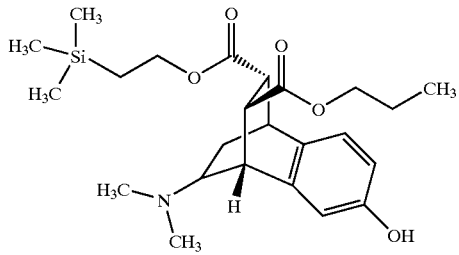

To a solution of the compound of Example 13 (79.5 mg, 0.19 mmol) in methanol (0.5 mL) was added dimethylamine (40 wt % in H₂O, 600 μL, 4.8 mmol) and acetic acid (330 μL, 5.7 mmol). After 10 min sodium triacetoxy borohydride (1.0 g, 4.8 mmol) was added. Additional aliquots of reagents were added at 3 h and 4.5 h, and the reaction allowed to proceed for 2 h after the final addition of reagents. The reaction was quenched with H₂O and diluted with ethyl acetate. The layers were separated and the organic layer washed with 5% NaHCO₃, H₂O, brine, dried (Na₂SO₄) and concentrated in vacuo. Flash chromatography on SiO₂ with 5% methanol/methylene chloride afforded 9.4 mg of a single diastereomer.

Example 87

Synthesis of 11-[Acetyl-(4-methyl-benzyl)-amino]-4-acetoxy-tricyclo[[6.2.2.0$^{2,7}$]dodeca-2(7),3,5-triene-9,10-dicarboxylic acid 10-propyl ester 9-(2-trimethylsilanyl-ethyl) ester

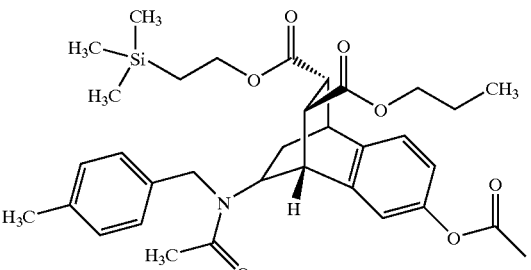

To a solution of the more polar amine from Example 83 (16.5 mg, 0.03 mmol) in methylene chloride (0.4 mL) was added N-methylmorpholine (12 μL, 0.10 mmol) followed by acetic anhydride (10 μL, 0.10 mmol). The reaction was stirred for 16 h at room temp, diluted with ethyl acetate, and quenched with 5% NaHCO3. The layers were separated, and the organic layer was washed with H₂O, brine, dried (Na₂SO₄), and concentrated in vacuo. Flash chromatography on SiO₂ with 40% ethyl acetate/hexanes afforded the amide. ESI-MS m/z 608 (MH⁺), 630 (MNa⁺).

Example 88

Synthesis of 11-[Acetyl-methylamino]-4-acetoxy-tricyclo[[6.2.2.0$^{2,7}$]dodeca-2(7),3,5-triene-9,10-dicarboxylic acid 10-propyl ester 9-(2-trimethylsilanyl-ethyl) ester

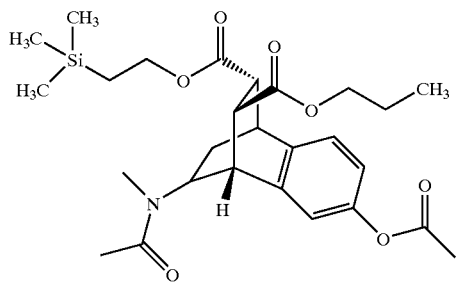

A. Diastereomer 1.

To a solution of the less polar amine from Example 84 (35 mg, 0.08 mmol) in dichloromethane (1.1 mL) was added NMM (27 μL, 0.24 mmol) and acetic anhydride (15.3 μL, 0.16 mmol). The reaction was stirred for 18 h at ambient temperature, diluted with ethyl acetate and quenched with 1% HCl. The layers were separated, and the organic layer washed with 1% HCl, 5% NaHCO₃, H₂O, brine, dried (Na₂SO₄) and concentrated in vacuo. Chromatography on SiO₂ using a gradient of 45% ethyl acetate/hexane—55% ethyl acetate/hexane afforded 9.3 mg (22%) of the bis-acylated product, which by TLC is slightly less polar than the free phenol product. ¹H NMR (CDCl₃, 53° C.): 7.19 (d, 1H), 6.95 (m, 2H), 4.30 (m, 2H), 3.89 (t, 2H), 3.54 (m, 3H), 3.20 (s 3H), 2.96 (d, 1H), 2.26 (s, 3H), 2.13 (s, 3H), 1.80 (m, 2H), 1.59 (m, 2H), 1.06 (sextet, 2H), 0.91 (t, 2H), 0.07 (s, 9H).

B. Diastereomer 2.

To a solution of the more polar amine from Example 84 (58 mg, 0.13 mmol) in methylene chloride (2 mL) was added N-methylmorpholine (43 µL, 0.39 mmol) and acetic anhydride (15 µL, 0.16 mmol). The reaction was stirred at room temp for 21 h, diluted with ethyl acetate, and quenched with 1% HCl. The layers were separated, and the organic layer washed with 1% HCl, 5% NaHCO$_3$, H$_2$O, brine, dried (Na$_2$SO$_4$), and concentrated in vacuo. Multiple flash chromatographies on SiO$_2$ using 2% methanol/methylene chloride afforded 34 mg (53%) of the phenol as the more polar product and 14.7 mg (21%) of the phenol acetate as the less polar product. $^1$H NMR (CDCl$_3$, 21° C., ca. 3:1 mix of rotamers): 7.24 (d, 1H), 6.90 (m, 2H), 5.21 (m, 0.75H), 4.23 (m, 2.25H), 3.90 (t, 2H), 3.52 (m, 3H), 2.99 (m, 1H), 2.30–1.96 (m, 10H), 1.56 (sextet, 2H), 1.30 (m, 1H), 1.03 (m, 2H), 0.93 (t, 2H), 0.05 (s, 9H).

Example 89

Synthesis of 11-[Acetyl-methylamino]-4-hydroxy-tricyclo[[6.2.2.0$^{2,7}$]dodeca-2(7),3,5-triene-9,10-dicarboxylic acid 10-propyl ester 9-(2-trimethylsilanyl-ethyl) ester

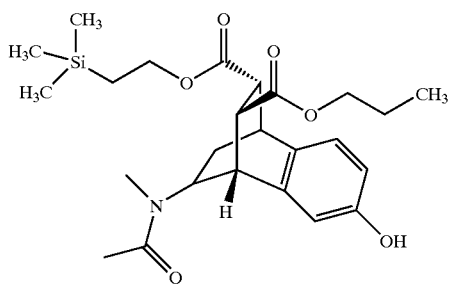

The title compound was isolated from the preparation of Diastereomer 2 of Example 88. By TLC it is more polar than the corresponding phenol acetate. ESI-MS m/z 476 (MH$^+$), 498 (MNa$^+$), 474 (M-H)$^-$.

Example 90

Synthesis of 4,11-Dihydroxy-tricyclo[[6.2.2.0$^{2,7}$]dodeca-2(7),3,5-triene-9,10-dicarboxylic acid 10-(2,4-dimethoxy-benzyl) ester 9-(2-trimethylsilanyl-ethyl) ester

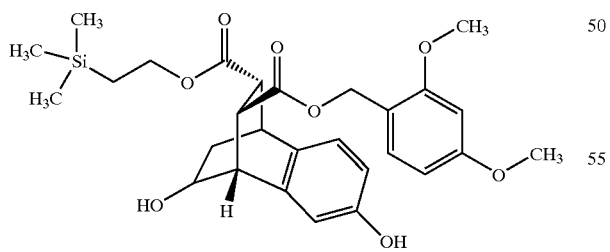

To a solution of the ketone of Example 9 (31.1 mg, 0.06 mmol) in methanol (1 mL) at 15° C. was added NaBH$_4$ (44.0 mg, 1.16 mmol). The reaction was stirred for 45 min, diluted with ethyl acetate, and quenched with 1% HCl. The layers were separated, and the organic layer washed with 5% NaHCO$_3$, H$_2$O, brine, dried (Na$_2$SO$_4$), and concentrated in vacuo. Flash chromatography on SiO$_2$ using 30% ethyl acetate/methylene chloride afforded 6.5 mg (21%) of the less polar alcohol and 13.8 mg (44%) of the more polar alcohol. ESI-MS m/z, less polar product 551 (MNa$^+$), more polar product 551 (MNa$^+$).

Example 91

Synthesis of 11-Spiro-(1,4-dioxacyclopentyl)-4-hydroxy-tricyclo[[6.2.2.0$^{2,7}$]dodeca-2(7),3,5-triene-9,10-dicarboxylic acid 10-propyl ester 9-(2-trimethylsilanyl-ethyl) ester

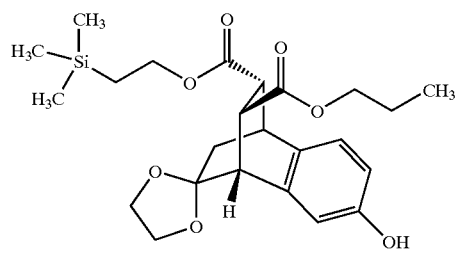

To a solution of the ketone of Example 13 (56.0 mg, 0.133 mmol) in benzene (1.3 mL) was added ethylene glycol (45 µL) and p-touenesulfonic acid monohydrate (4.5 mg). The solution was refluxed for 1 h, using a Dean-Stark trap to collect the water. Upon cooling the reaction was diluted with ethyl acetate and 5% NaHCO$_3$ was added. The layers were separated, and the organic layer washed with 5% NaHCO$_3$, H$_2$O, brine, dried (Na$_2$SO$_4$), and concentrated in vacuo. Flash chromatography on SiO$_2$ using 25% ethyl acetate/hexane afforded 14.1 mg (23%) of the ketal. ESI-MS In/z 485 (MNa$^+$).

Example 92

Synthesis of 11-Ethoxycarbonylmethylene-4-hydroxy-tricyclo[[6.2.2.0$^{2,7}$]dodeca-2(7),3,5-triene-9,10-dicarboxylic acid 10-propyl ester 9-(2-trimethylsilanyl-ethyl) ester

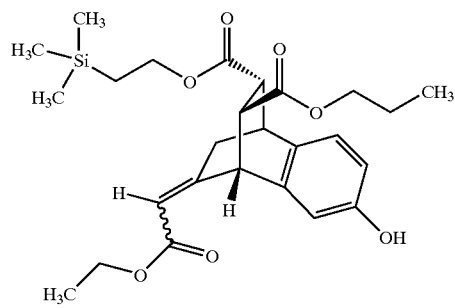

To a solution of triethylphosphonoacetate (59 µL, 0.30 mmol) in tetrahydrofuran (0.5 mL) at 0° C. was added a solution of potassium hexamethyldisilazide (0.45 M in toluene, 0.685 mL, 0.31 mmol). After stirring for 15 min at 0° C. a solution of the ketone from Example 13 (59.6 mg, 0.14 mmol) in tetrahydrofuran (0.9 mL) was added. The reaction was stirred for 30 min at 0° C., 3 h at ambient, then placed in a refrigerator without stirring for 66 h. Upon removal, the reaction was stirred at ambient temperature for 6 h, diluted with ethyl acetate, and quenched with 1% HCl. The layers were separated, and the organic layer washed with 1% HCl, 5% NaHCO$_3$, H$_2$O, brine, dried (Na$_2$SO$_4$), and concentrated in vacuo. Flash chromatography on SiO$_2$ using 17% ethyl acetate/hexane afforded 32.2 mg (46%) of product as a 1/1 mixture of E/Z isomers. ESI-MS m/z 511 (MNa$^+$).

Example 93

Synthesis of 4-Hydroxy-11-methylene-tricyclo[[6.2.2.0$^{2,7}$]dodeca-2(7),3,5-triene-9,10-dicarboxylic acid 10-propyl ester 9-(2-trimethylsilanyl-ethyl) ester

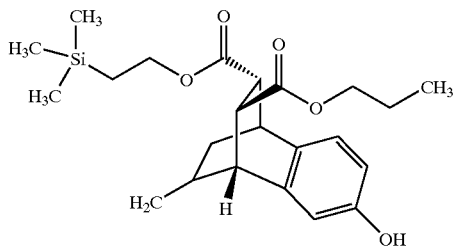

To a solution of methyl triphenylphosphonium bromide (236 mg, 0.66 mmol) in tetrahydrofuran (0.5 mL) was added potassium hexamethyldisilazide (0.5 M in toluene, 1.3 mL, 0.65 mmol). The yellow-orange solution was stirred for 15 min at ambient temp, then a solution of the ketone from example 13 (63.5 mg, 0.15 mmol) in tetrahydrofuran (0.3 mL) was added. After 30 min at room temp the reaction was diluted with ethyl acetate and quenched with H$_2$O. The layers were separated, and the organic layer washed with 1% HCl, 5% NaHCO$_3$, H$_2$O, brine, dried (Na$_2$SO$_4$), and concentrated in vacuo. Flash chromatography on SiO$_2$ using 15% ethyl acetate/hexane afforded 34.2 mg (54%) of the olefin. $^1$H NMR (CDCl$_3$), 7.05 (2H), 6.63 (2H), 5.10 (1H), 4.96 (1H), 4.73 (11H), 4.25 (2H), 3.95 (3H), 3.55 (2H), 3.07 (1H), 2.49 (1H), 2.08 (2H), 1.60 (2H), 1.06 (2H), 0.88 (3H), 0.09 (9H).

Example 94

Synthesis of 4,11-Dihydroxy-tricyclo[6.2.2.0$^{2,7}$]dodeca-2(7),3,5-triene-9,10-dicarboxylic acid 10-propyl ester 9-(2-trimethylsilanyl-ethyl) ester

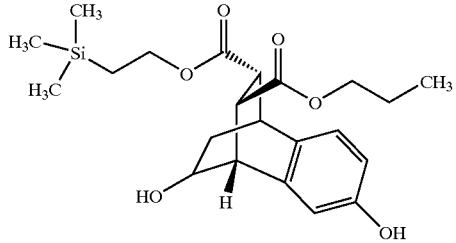

To a 0.1 M solution of ketone from Example 13 in methanol was added NaBH$_4$ (10 eq). After stirring at rt for 20 min, the reaction was quenched with saturated aqueous ammonium chloride and diluted with dichloromethane. The aqueous phase was acidified with 1 M HCl, the phases were partitioned, and the aqueous phase extracted 3× with dichloromethane. Organic extracts were combined, dried (Na$_2$SO$_4$) and concentrated. Chromatography with 40% ethyl acetate/hexane afforded the less polar isomer in 40% yield ESI-MS m/z 419 (M-H)$^-$, and the more polar isomer in 20% yield ESI-MS m/z 419 (M-H)$^-$.

Example 95

Synthesis of 11-Amino-4-hydroxy-tricyclo[6.2.2.0$^{2,7}$]dodeca-2(7),3,5-triene-9,10-dicarboxylic acid 10-propyl ester 9-(2-trimethylsilanyl-ethyl) ester

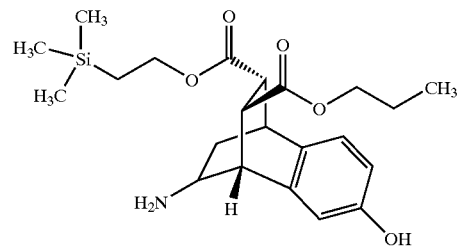

To a 0.1 M solution of ketone from Example 13 in methanol was added 4-methylbenzylamine (3 eq), Na(OAc)$_3$BH (3 eq), acetic acid (3 eq) and 3A mol. sieves (300 mg/mL methanol). The reaction was stirred overnight, then quenched with aqueous NaHCO$_3$, and extracted with ethyl acetate. The organic extracts were combined, dried (Na$_2$SO$_4$) and concentrated. Chromatography with 5%–30% ethyl acetate/hexane afforded the less polar isomer in 29% yield.

The product from the preceding reaction was dissolved in enough ethanol to give a 0.07 M solution, which was treated with 20% palladium hydroxide on carbon (135 mg/mmol st. mat) and acetic acid (24 eq.). The reaction was stirred at rt under an atmosphere (balloon) of hydrogen gas. After 1.5 h, the reaction was filtered over Celite with dichloromethane and concentrated. Chromatography using 10%–20% methanol/dichloromethane afforded a single isomer in 45% yield. ESI-MS m/z 420 (MH$^+$), 418 (M-H)$^-$.

Example 96

Synthesis of 4,11-Dihydroxy-11-methyl-tricyclo[6.2.2.0$^{2,7}$]dodeca-2(7),3,5-triene-9,10-dicarboxylic acid 10-propyl ester 9-(2-trimethylsilanyl-ethyl) ester

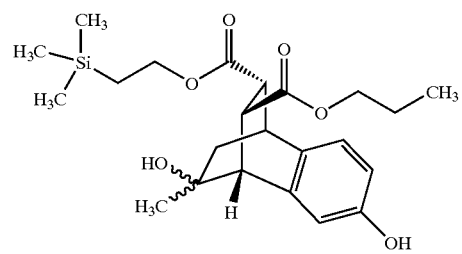

To a 0° C. solution of ketone from Example 13 in THF (0.12 M) was added methylmagnesium bromide (1.4 M in THF/toluene, 6.7 eq). After complete reaction and aqueous workup, the crude product was purified by column chromatography using 25%–40% ethyl acetate/hexane. The less polar isomer was isolated in 12% yield. $^1$H NMR (CDCl$_3$) 7.26 (d, 1H), 6.99 (s, 1H), 6.82 (dd, 1H), 4.94 (s, 1H), 4.27 (ddd, 2H), 3.90 (dd, 2H), 3.90–3.85 (m, 1H), 3.35 (d, 1H), 3.28 (d, 1H), 3.18–3.15 (m, 1H), 1.77 (dd, 1H), 1.57 (dd, 2H), 1.44–1.39 (m, 1H), 1.25 (s, 2H), 1.06 (ddd, 2H), 1.01 (s, 3H), 0.89 (dd, 3H). 0.06 (s, 9H).

Example 97

Synthesis of 4,11-Dihydroxy-11-methyl-tricyclo[6.2.2.0$^{2,7}$]dodeca-2(7),3,5-triene-9,10-dicarboxylic acid 10-propyl ester 9-(2-trimethylsilanyl-ethyl) ester

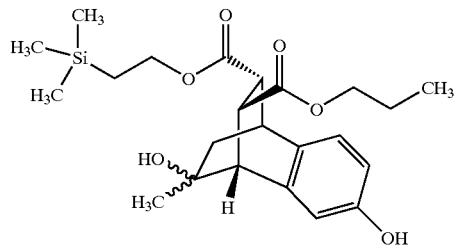

Cerium chloride (2.0 eq) was heated under vacuum, cooled and suspended in THF. The 0.3 M solution was cooled to −75° C. and treated with methylmagnesium bromide (1.4 M in THF/toluene, 4 eq) in a dropwise fashion. The slurry was stirred for 1.5 h, at which point the ketone from Example 13 was added as a 0.3 M solution in THF. The reaction was stirred at −75° C. for 2 h, then warmed to rt. After 1.5 h, reaction quenched with saturated aqueous ammonium chloride and extracted with ethyl acetate. Chromatography using 30%–40% ethyl acetate/hexane afforded the more polar isomer in 13% yield. $^1$H NMR (CDCl$_3$) 7.26 (d, 1H), 6.70 (s, 1H), 6.68 (dd, 1H), 5.26 (s, 1H), 4.25 (ddd, 2H), 3.93 (ddd, 2H), 3.57 (dd, 1H), 3.42–3.40 (s, 1H), 3.31–3.29 (s, 1H), 2.92–2.91 (s, 1H), 1.72 (dd, 1H), 1.57 (dd, 2H), 1.56 (s, 3H), 1.40 (dm, 1H), 1.26 (s, 1H), 1.04 (dd, 2H), 0.87 (t, 3H), 0.06 (s, 9H).

Example 98

Synthesis of 4,11-Dihydroxy-11-hydroxymethyl-tricyclo[6.2.2.0$^{2,7}$]dodeca-2(7),3,5-triene-9,10-dicarboxylic acid 10-propyl ester 9-(2-trimethylsilanyl-ethyl) ester

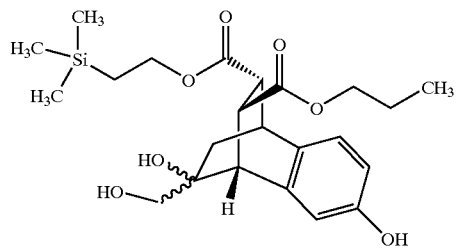

The olefin of Example 93 (61077) was dissolved in enough 1:1 tert-butanol:water to give a 0.06 M solution. The solution was treated with OsO$_4$ (4 wt. % soln. in water, 0.03 eq) and 4-methyl morpholine-N-oxide (3 eq) and heated to 50° C. After stirring overnight, the reaction was quenched with sodium bisulfite. Celite was added, and the solution allowed to stir an additional 3 hours. The solution was then diluted 20 fold with THF and filtered over a short plug of silica. The crude solids were purified by column chromatography (50%–60% ethyl acetate/hexane) to afford the less polar isomer in 36% yield. APCI-MS m/z 449 (M-H)$^-$.

Example 99

Synthesis of 10-(Benzyl-methyl-carbamoyl)-5-hydroxy-12-oxo-tricyclo[6.2.2.0$^{2,7}$]dodeca-2(7),3,5-triene-9-carboxylic acid allyl ester

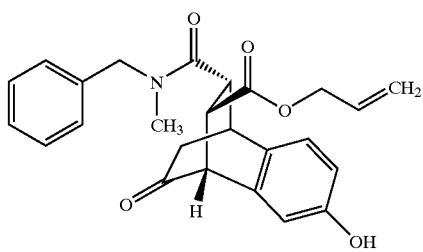

General Procedure I for the Synthesis of 5-Hydroxy-10-amido Derivatives

A solution of the trans allyl TMS-ethyl ester prepared in Example 19 (1 equivalent) in 2 mL of TFA/H$_2$O (95%) was allowed to stir at rt for 30 min. The volatiles were evaporated, acetonitrile (2 mL) and toluene (5 mL) were added and the resulting solution was concentrated to dryness (2×) to afford the crude carboxylic acid. The white residue was dissolved in DMF (0.6 mL) and a selected amine (1.5 equivalents), HATU (1.2 equivalents) and NMM (2.7 equivalents) were added and the reaction mixture was allowed to stir at rt under nitrogen overnight. The solution was concentrated to dryness and dichloromethane or ethyl acetate was added (10 mL) and the organic layer was washed with HCl (1 N, 3×10 mL), NaHCO$_3$ solution (5%, 2×10 mL) and brine (1×10 mL). Upon drying (MgSO$_4$) the organic layer, the filtered solution was concentrated to dryness and column chromatography provided the desired product.

The title compound was prepared as described in general procedure I using N-methylbenzylamine, resulting in a yield of 19% (10 mg). ESI-MS m/z 442 (MNa$^+$), 418 (M-H)$^-$.

Example 100

Synthesis of 5-Hydroxy-12-oxo-10-propylcarbamoyl-tricyclo[6.2.2.0$^{2,7}$]dodeca-2(7),3,5-triene-9-carboxylic acid allyl ester

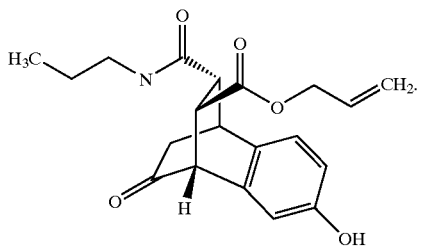

The title compound was prepared as described in general procedure I using propylamine, resulting in a yield of 55% (24 mg). ESI 380 (MNa$^+$), 356 (M-H)$^-$.

Example 101

Synthesis of 4-Hydroxy-11-oxo-tricyclo[6.2.2.0$^{2,7}$]dodeca-2(7),3,5-triene-9,10-dicarboxylic acid 10-propyl ester 9-[2-(toluene-4-sulfonyl)-ethyl]ester

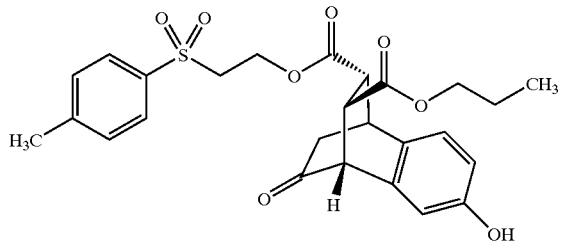

General Procedure J for the Synthesis of 9-Esters

To a 0.5 M solution of the corresponding 9-carboxylic acid prepared as described in General Procedure I in 5% DMF/THF was added TSTU (2 eq), 4-methylmorpholine (4 eq), DMAP (2 eq) and a selected alcohol (2 eq). The reaction was allowed to proceed overnight at ambient temperature, after which the reaction was quenched with saturated aqueous ammonium. chloride and diluted with 1:1 ethyl acetate-:hexane. Aqueous further acidified (pH ~2) with 1 M HCl (aq). The phases were partitioned, and the organic layer separated and washed with brine. Solution dried (Na$_2$SO$_4$) and concentrated. The products were purified by column chromatography.

Reaction run as in general procedure J using 2-(p-Tosyl)ethanol. Chromatography (ethyl acetate/hexane) affords the title compound in 61% yield. ESI-MS m/z 523 (MNa$^+$), 499 (M-H)$^-$.

Example 102

Synthesis of 4-Hydroxy-11-oxo-tricyclo[6.2.2.0$^{2,7}$]dodeca-2(7),3,5-triene-9,10-dicarboxylic acid 9-(3,3-dimethyl-butyl) ester 10-propyl ester

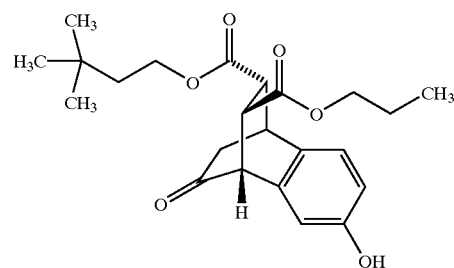

Reaction run as in general procedure J using 3,3 dimethylbutanol. Chromatography (30% ethyl acetate/hexane) affords the title compound in 55% yield. ESI-MS m/z 425 (MNa$^+$).

Example 103

Synthesis of 4-Hydroxy-11-oxo-tricyclo[6.2.2.0$^{2,7}$]dodeca-2(7),3,5-triene-9,10-dicarboxylic acid 9-(2-adamantan-1-yl-ethyl) ester 10-propyl ester

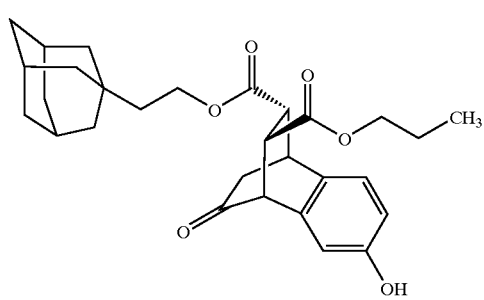

Reaction run as in general procedure J using 1-adamantaneethanol. Chromatography (ethyl acetate/hexane) affords the title compound in 87% yield. ESI-MS m/z 479 (M-H)$^-$.

Example 104

Synthesis of 4-Hydroxy-11-oxo-tricyclo[6.2.2.0$^{2,7}$]dodeca-2(7),3,5-triene-9,10-dicarboxylic acid 10-propyl ester 9-(3-trimethylsilanyl-propyl) ester

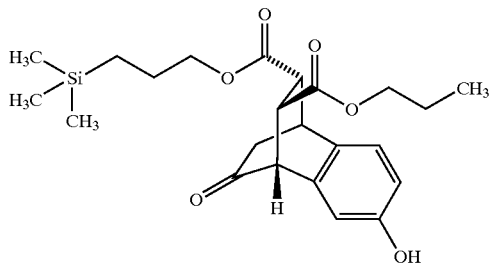

Reaction run as in general procedure J using 1-(trimethylsilyl)-3-propanol. Chromatography (25%–30% ethyl acetate/hexane) affords the title compound in 38% yield. APCI-MS m/z 433 (MH$^+$), 431 (M-H)$^-$.

Example 105

Synthesis of 4-(4-Carboxymethoxy-benzyloxy)-11-oxo-tricyclo[6.2.2.0$^{2,7}$]dodeca-2,4,2-triene-9,10-dicarboxylic acid 10-allyl ester 9-(2-trimethylsilanyl-ethyl) ester

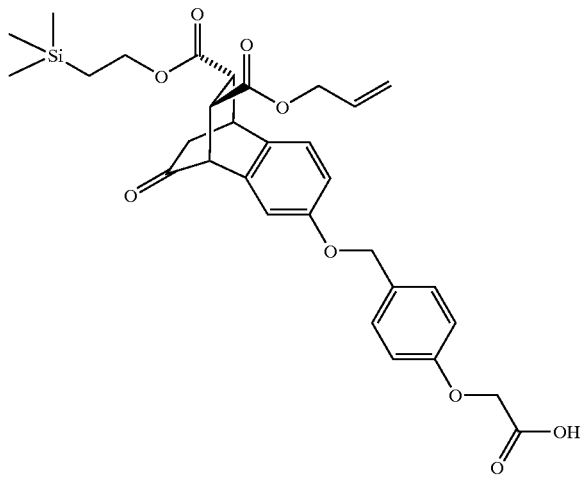

A. Butyldimethylsilanyl [4-(tert-butyl-dimethyl-silanyloxymethyl)-phnoxy]-acetate:

To a solution of (4-hydroxymethylphenoxy)acetic acid (10 g, 55 mmol) in dichloromethane (200 mL) was added t-butyldimethylsilyl chloride (18.2 g, 121 mmol), diisopropylethylamine (24 mL, 17.8 g, 138 mmol) and dimethylaminopyridine (2.7 g, 22 mmol). The resulting reaction mixture was allowed to stir at rt for 1.5 h, after which time it was diluted with an additional 300 ml, of dichloromethane and washed with 0.1 M citric acid (2×300 mL) and brine (3×300 mL). The resulting yellow organic layer was dried (MgSO$_4$), filtered and concentrated to dryness to give a white solid, wt. 22.5 g (quantitative). $^1$H NMR (CDCl$_3$) 7.23 (d, J=8.8 Hz, 2H), 6.85 (d, J=8.8 Hz, 2H), 4.67 (s, 2H), 4.58 (s, 2H), 0.92 (s, 9H), 0.89 (s, 9H), 0.28 (s, 6H), 0.08 (s, 6H).

B. Synthesis of 2-(Toluene-4-sulfonyl)-ethyl (4-hydroxymethyl-phenoxy)-acetate:

a) To a solution of the product from Step A (22.5 g, 55 mmol) in dichloromethane (200 mL) was added 2-toluenesulfonylethanol (26.4 g, 132 mmol), HATU (25 g, 65.8 mmol) and diisopropylethylamine (23 mL, 17.1 g, 132 mmol). The resulting reaction mixture was allowed to stir at rt overnight under nitrogen atmosphere, after which time it was concentrated to dryness, diluted with ethyl acetate (400 mL), washed with 0.1 M citric acid (3×330 mL), 5% NaHCO$_3$ solution (2×100 mL) and brine (2×100 mL). The resulting organic layer was dried (MgSO$_4$), filtered and concentrated to dryness to give a brown solid, wt. 49.41 g (185%). Used as is without further purification.

b) The brown residue obtained above was suspended in 80% acetic acid/water solution (500 mL) and allowed to stir at rt for 3 h. The resulting cloudy solution was then concentrated to dryness and used dichloromethane/toluene mixture to get rid of residual acetic acid. Column chromatography (45% acetone/hexane) provided the desired product, which upon trituration with methanol provided the desired product as a white solid, wt. 15.6 g (78% for the three steps). $^1$H NMR (CDCl$_3$) 7.78 (dt, J=8.4, 1.9 Hz, 2H), 7.36 (d, J=8.0 Hz, 2H), 7.27 (dt, J=9.2, 2.5 Hz, 2H), 6.80 (dt, J=9.2, 2.5 Hz, 2H), 4.60 (s, 2H), 4.51 (t, J=6.1 Hz, 2H), 4.39 (s, 2H), 3.45 (t, J=6 0 Hz, 2H), 2.41 (s, 31H). ESI-MS m/z 387 (MNa$^+$).

C. 4-(4-Carboxymethoxy-benzyloxy)-11-oxo-tricyclo[6.2.2.0$^{2,7}$]dodeca-2,4,6-triene-9,10-dicarboxylic acid 10-allyl ester 9-(2-trimethylsilanyl-ethyl) ester a) To a solution of the phenol of Example 19 (17.4 g, 42 mmol), 2-(toluene-4-sulfonyl)ethyl (4-hydroxymethyl-phenoxy)acetate (18.2 g, 50 mmol) and triphenylphosphine (13.1 g, 50 mmol) in anhydrous tetrahydrofuran (175 mL) was added DEAD (8.0 mL, 8.85 g, 51 mmol). The resulting reaction mixture was allowed to stir at rt for 5 h, after which time it was concentrated to dryness. The residue was then dissolved in ethyl acetate (1.0 L) and washed with 0.1 M citric acid (2×100 mL), 5% NaHCO$_3$ solution (2×100 mL) and brine (2×100 mL). The resulting organic layer was dried (MgSO$_4$), filtered and concentrated to dryness to give a yellow oil. Column chromatography (4% acetonitrile/dichloromethane) provided the desired tosylethyl ester, wt. 23.9 g (75%).

b) To a solution of the above ester (23.9 g, 31 mmol) in acetonitrile (200 mL) was added piperidine (7.5 mL, 6.5 g, 76 mmol) and DBU (5.6 mL, 5.7 g, 37.4 mmol). The resulting mixture was allowed to stir at rt for 45 min, after which the solution was concentrated to dryness and redissolved in ethyl acetate (1 L). The organic layer was washed with 0.1 N HCl solution (850/150/150 mL) and brine (2×150 mL), dried (MgSO$_4$), filtered and the solvent was evaporated to give a yellow oil. Column chromatography (2% methanol/dichloromethane, 2 L, followed by 2% methanol/dichloromethane with 2% AcOH, 3 L) provided the desired product as a foamy off-white solid, wt. 15.2 g (63% over two steps). $^1$H NMR (CDCl$_3$) 7.35 (d, J=8.5 Hz, 2H), 7.19 (d, J=8.2 Hz, 1H), 6.94 (d, J=8.8 Hz, 2H), 6.85 (dd, J=8.1, 2.6 Hz, 1H), 6.80 (d, J=2.5 Hz, 1H), 5.88–5.75 (m, 1H), 5.28–5.19 (m, 2H), 4.94 (s, 2H), 4.69 (s, 2H), 4.49 (dq, J=5.6, 1.3 Hz, 2H), 4.30–4.27 (m, 2H), 4.01 (d, J=2.5 Hz, 1H), 3.77 (q, J=2.7 Hz, 1H), 3.73 (dd, J=5.9, 2.3 Hz, 1 Hz), 3.23 (dt, J=5.8, 2.3 Hz, 1H), 2.42 (dd, J=19.0, 2.2 Hz, 1H), 2.13 (dt, J=18.7, 2.6 Hz, 1H), 1.07–1.01 (m, 2H), 0.06 (s, 9H). APCI-MS 603.3 (MNa$^+$), 579.2 (M-H)$^-$.

Example 106

Procedure for the Synthesis of a Library of Representative Benzobicyclooctanes

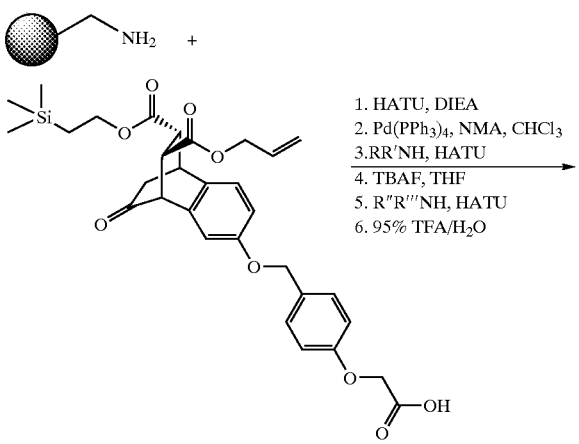

1. HATU, DIEA
2. Pd(PPh$_3$)$_4$, NMA, CHCl$_3$
3. RR'NH, HATU
4. TBAF, THF
5. R"R'"NH, HATU
6. 95% TFA/H$_2$O

-continued

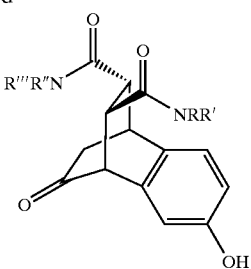

A. Loading Scaffold onto TentaGel Amine Resin (Novabiochem A18764)
 1. Place dry resin (5 g, 0.43 mmol/g loading) in Schlenk ware
 2. Swell resin with dichloromethane (2×30 mL, 2 min)
 3. Add NMP, bubble $N_2$ through frit and drain (4×30 mL, 5 min)
 4. Add the following solutions to swelled resin: NMP solution of Scaffold (0.5 M, 6 mL), NMP solution of DIEA (1.25 M, 7 mL) and NMP solution of HATU (0.5 M, 6.5 mL)
 5. Bubble $N_2$ through frit for 1.5 h; drain
 6. Wash resin with NMP (3×30 mL, 5 min)
 7. Kaiser test of resin proved negative (Kaiser, E. et al, Anal. Biochem., 1970, 34, 595)
 8. Add the following solutions to swelled resin: NMP solution of Scaffold (0.5 M, 4 mL), NMP solution of DIEA (1.25 M, 4 mL) and NMP solution of HATU (0.5 M, 4 mL)
 9. Repeat steps 5–7
 10. Wash resin with 1:1 NMP/dichloromethane (2×30 mL, 3 min)
 11. Wash resin with 1:4 NMP/dichloromethane (2×30 mL, 3 min)
 12. Wash resin with neat dichloromethane (3×30 mL, 3 min)
 13. Dry under vacuum overnight
 14. Distribute resin into 96-well plate (50 mg/well); store at about −15/−20° C. in a ziplock bag
B. Allyl Ester Deprotection/$1^{st}$ Amide Formation
 1. Swell resin (in each well) with $CHCl_3$ (3×0.5 mL, 3 min); drain
 2. Add $CHCl_3$ solution of N-methylaniline (0.5 M, 0.5 mL)
 3. Add $CHCl_3$ solution of $Pd(PPh_3)_4$ (0.05 M, 0.5 mL)
 4. Bubble $N_2$ & vortex for 45 min; drain
 5. Wash with $CHCl_3$ (3×0.5 mL, 3 min)
 6. Repeat steps 2–5
 7. Wash resin with DMF solution of diethyldithiocarbamic acid, sodium salt trihydrate (0.03 M) and DIEA (0.06 M) (3×0.75 mL, 3 min)
 8. Wash resin with DMF (3×0.5 mL, 3 min)
 9. Wash resin with NMP (3×0.5 mL, 3 min)
 10. Add the following: NMP solution of DIEA (1.25 M, 0.15 mL), NMP solution of HATU (0.5 M, 0.1 5 mL) and NMP solution of amine (0.5 M, 0.15 mL) respectively (amine $(HCl)_z$ were treated with an excess of an NMP solution of DIEA (1.25 M, (z)×0.15 mL)
 11. Bubble $N_2$ & vortex for 2 h; drain
 12. Wash with NMP (3×0.5 mL, 3 min)
 13. Repeat steps 10–12
 14. Wash resin with 1:1 NMP/dichloromethane (2×0.5 mL, 3 min)
 15. Wash resin with neat dichloromethane (3×0.5 mL, 3 min)
 16. Keep 96-well plate in the reaction block at rt overnight
C. TMSE Ester Deprotection/$2^{nd}$ Amide Formation
 1. Swell resin with THF (3×0.5 mL, 3 min); drain
 2. Add THF solution of TBAF (1 M, 0.5 mL)
 3. Bubble $N_2$ & vortex for 45 min; drain
 4. Wash resin with THF (3×0.5 mL, 3 min)
 5. Repeat steps 2–4
 6. Wash with 1:1 THF/NMP (2×0.5 mL, 3 min)
 7. Wash with NMP (3×0.5 mL, 3 min)
 8. Add the following: NMP solution of DIEA (1.25 M, 0.15 mL), NMP solution of HATU (0.5 M, 0.15 mL) and NMP solution of amine (0.5 M, 0.15 mL) respectively (amine $(HCl)_z$ were treated with an excess of an NMP solution of DIEA (1.25 M, (z)×0.15 mL))
 9. Bubble $N_2$ & vortex for 1.5 h; drain
 10. Wash with NMP (3×0.5 mL, 3 min)
 11. Repeat steps 8–10
 12. Wash with 1:1 NMP/dichloromethane (2×0.5 mL, 3 min)
 13. Wash with neat dichloromethane (3×0.5 mL, 3 min)
 14. Store at about −15/−20° C. in a ziplock bag
D. TFA Cleavage of Compound from Resin
 1. Swell resin with dichloromethane (2×0.5 mL, 2 min); drain
 2. Add 95:5 $TFA/H_2O$ solution to each well (0.5 mL)
 3. Bubble $N_2$ & vortex for 2 h; drain into cube tubes
 4. Wash wells with $TFA/H_2O$ (3×0.25 mL, 2 min)
 5. Add AcOH (0.5 mL) to each cube tube
 6. Concentrate under reduced pressure with heat (Savant) for about 1 h
 7. Add AcOH (0.75 mL) to each cube tube
 8. Concentrate under reduced pressure with heat (Savant) for 45 min
 9. Add AcOH (0.25 mL) and toluene (0.75 mL) to each cube tube
 10. Concentrate under reduced pressure with heat (Savant) for 2 h
 11. Add methanol (0.25 mL), vortex then add toluene (0.75 mL)
 12. Concentrate under reduced pressure with heat (Savant) overnight A 1152-member bicyclic library was produced using TentaGel™ as the solid support and the procedure described in steps A–D above. The library was made using 36 (3*12) by 32 (4*8) sets of diverse amines (see Table 2). The acid-labile protecting groups tert-butoxycarbonyl, tert-butyl ethers, and tert-butyl esters were utilized for the protection of amines alcohols and carboxylic acids, respectively. On average, each well provided 6.5 micromoles of desired product [17.2 micromoles (of starting resin)*0.76 (% yield) *0.5 (assuming 50% purity on average)]. Each well was analyzed by MS (loop injection). In addition, 15% wells from plate 4 and 12 wells from plate 12 were analyzed by LC-MS to confirms that MS-loop injection analysis was consistent with the LC-MS data. Each compound of the 1152-member library was then placed into one of three relative purity categories: high purity, lower purity and failures. The data is summarized in Table 1.

TABLE 1

| Plate # | # of High Purity wells | % | # of Lower Purity wells | % | # of Failures | % |
|---|---|---|---|---|---|---|
| 1 | 69 | 72 | 18 | 19 | 9 | 9 |
| 2 | 77 | 79 | 18 | 19 | 1 | 2 |
| 3 | 74 | 77 | 22 | 23 | 0 | 0 |
| 4 | 74 | 77 | 11 | 11 | 11 | 11 |
| 5 | 72 | 75 | 21 | 22 | 3 | 3 |
| 6 | 68 | 71 | 28 | 29 | 0 | 0 |

TABLE 1-continued

| Plate # | # of High Purity wells | % | # of Lower Purity wells | % | # of Failures | % |
|---|---|---|---|---|---|---|
| 7 | 76 | 79 | 20 | 21 | 0 | 0 |
| 8 | 77 | 80 | 19 | 20 | 0 | 0 |
| 9 | 78 | 81 | 18 | 19 | 0 | 0 |
| 10 | 67 | 70 | 29 | 30 | 0 | 0 |
| 11 | 49 | 51 | 47 | 49 | 0 | 0 |
| 12 | 62 | 65 | 34 | 35 | 0 | 0 |
| Totals | 843 | 73 | 285 | 25 | 24 | 2 |

High purity indicates that the molecular ion and/or fragments resulting from the desired ion were the only/major peaks in the MS spectra. Lower purity refers to wells when the molecular ion and/or fragment were present in addition to a number of other peaks. Although a significant number of wells were of lower purity, the major impurity in these wells (about 90% of the wells) was the carboxylic acid resulting from incomplete coupling with the second amine. A failure indicates very little or no molecular ion or identifiable fragment was detected.

TABLE 2

Structures of Combinatorial Library Compounds

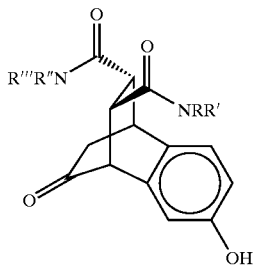

TABLE 2-continued
Structures of Combinatorial Library Compounds
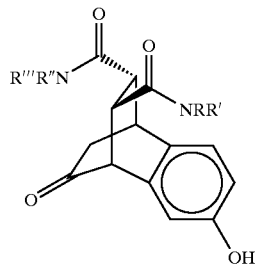
| | NRR' | NR"R''' |
|---|---|---|
| 8 |  | 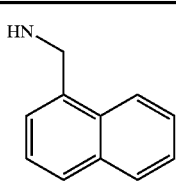 |
| 9 | 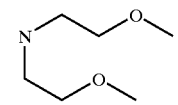 | 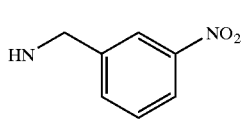 |
| 10 | 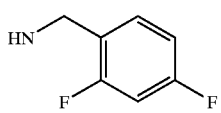 | 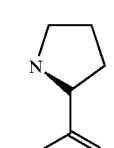 |
| 11 | 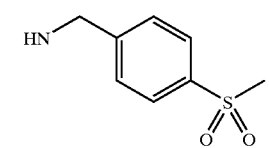 | 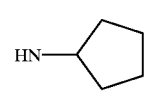 |
| 12 | | |
| 13 | | |
| 14 | | |
| 15 | | |

TABLE 2-continued
Structures of Combinatorial Library Compounds
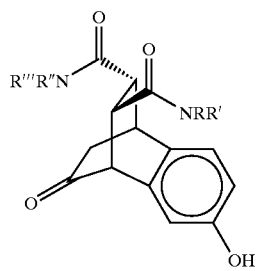
| | NRR' | NR"R"' |
|---|---|---|
| 16 | 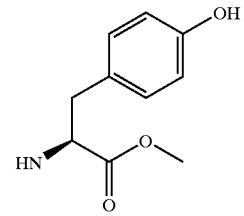 | 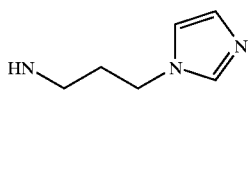 |
| 17 | 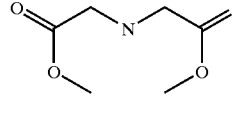 | 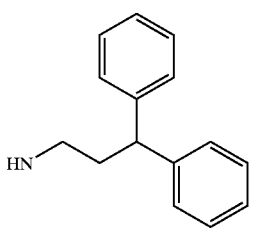 |
| 18 | 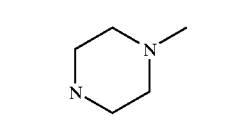 | 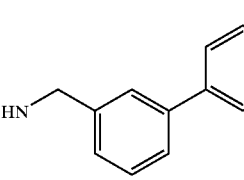 |
| 19 | | |
| 20 | | |
| 21 | | |

TABLE 2-continued

Structures of Combinatorial Library Compounds

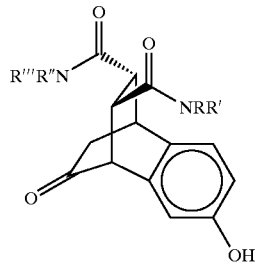

| NRR' | NR"R''' |
|---|---|
| 22 | |

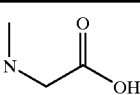

| 23 | |

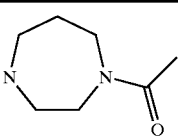

| 24 | |

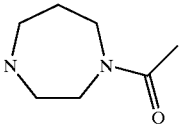

Example 107

Biological Activities of Representative Bicyclooctanes

Apoptosis:

The protocol used for determining inhibition of apoptosis in A549 cells was adopted from a system previously described (K. Last-Barney et al., *J. of Immunology* 141:527–530, 1988). Briefly, $10^5$ cells in 200 μL 10% FBS/RPMI antibiotic containing culture medium were plated into 96 well round bottom culture plates and allowed to adhere for 6 hours at 37° C. in a 5% $CO_2$ atmosphere. The media was removed and 100 μL of RPMI+1 μg/mL actinomycin-D was added to each well, followed by 90 μL of test compound solution in 1% DMSO. This was incubated for 1 hour 10 AL TNF-α was added at its $EC_{50}$ (normally 1 ng/mL FAC) and the plates incubated for 18 hours. The media was aspirated from the plates and 100 μL of 0.5% crystal violet in 20% methanol was added. After 10 minutes the plates were rinsed with water to remove excess stain, air dried, and read on a Spectramax at a wavelength of 590 nm. The data obtained from the Spectramax was converted into percent inhibition data at a concentration of 20 μM or $IC_{50}$ measured in μM. Data is presented for representative compounds under the column titled "Apopt inh" in Table 3 as follows: "*" refers to percent inhibition from 6% to 64%; "" refers to an $IC_{50}$ from 10 μM to 50 μM; "*" refers to an $IC_{50}$ below 10 μM.

NFκB:

A549 cells were stably transfected with an E-selectin promoter containing three NFκB binding sites driving luciferase expression. For the assay, $5 \times 10^4$ cells were incubated in 96 well round bottom plates overnight in 100 μL of 10% FBS/RPMI medium at 37° C. in a 5% $CO_2$ atmosphere. The following morning the medium was removed and 90 μL of a 1% DMSO solution of test compound solution was added and the plates incubated for 1 hour. 10 μL of TNF-α was added at its $EC_{50}$ (normally 6 ng/mL FAC) to each well and the plate incubated for 5 hours. 100 μL of luciferase buffer was added, and after 10 minutes luminescence was read on a Wallac Victor 1420 Multilabel Counter. The data obtained from the Wallac Victor was converted into % inhibition data or $IC_{50}$ measured in μM. Data is presented for representative compounds under the column titled "NFκB inh" in Table 3 as follows: "*" refers to percent inhibition from 6% to 64%; "" refers to an $IC_{50}$ from 10 μM to 50 μM; "*" refers to an $IC_{50}$ below 10 μM.

The compounds of Table 3 were synthesized according to disclosed methods of Examples 1–106, and tested for activity according to the above assays. In Table 3, each compound is provided with a unique compound number, as set forth in the column "No."

TABLE 3

| STRUCTURE | No. | Apopt inh | NFκB inh |
|---|---|---|---|
| 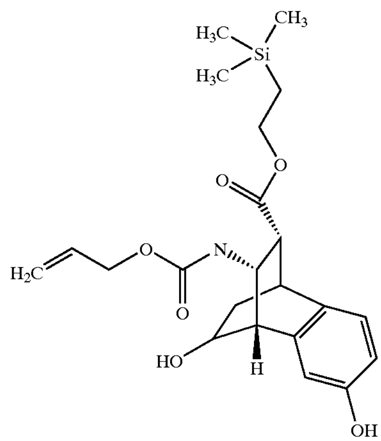 | 1 | ** | * |
| 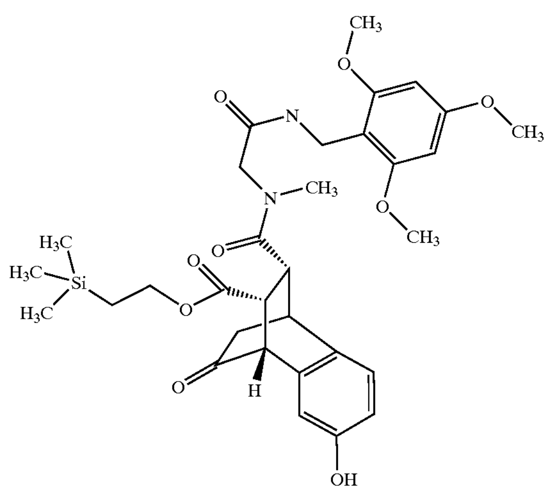 | 2 | * | * |
| 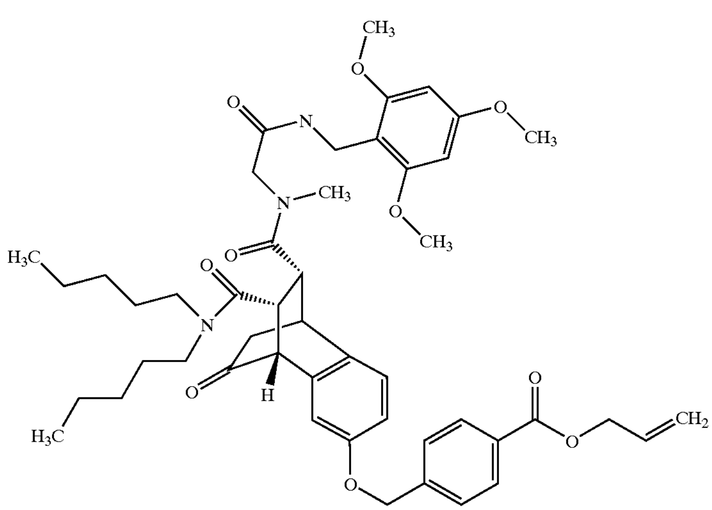 | 3 | * | * |

TABLE 3-continued
| STRUCTURE | No. | Apopt inh | NFκB inh |
|---|---|---|---|
| 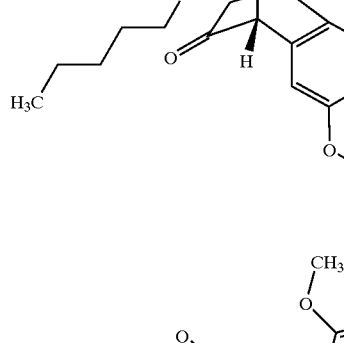 | 4 | * | * |
| 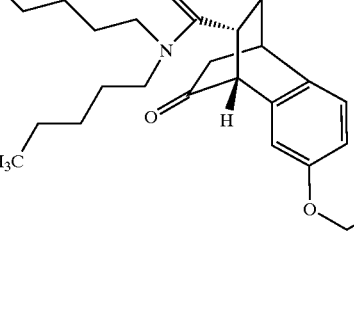 | 5 | ** | * |
| 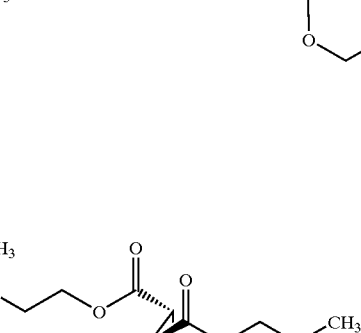 | 6 | * | * |

TABLE 3-continued
| STRUCTURE | No. | Apopt inh | NFκB inh |
|---|---|---|---|
| 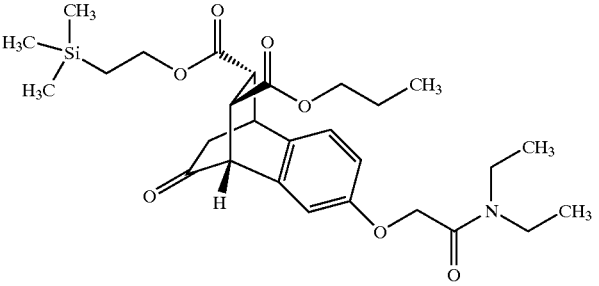 | 7 | * | * |
| 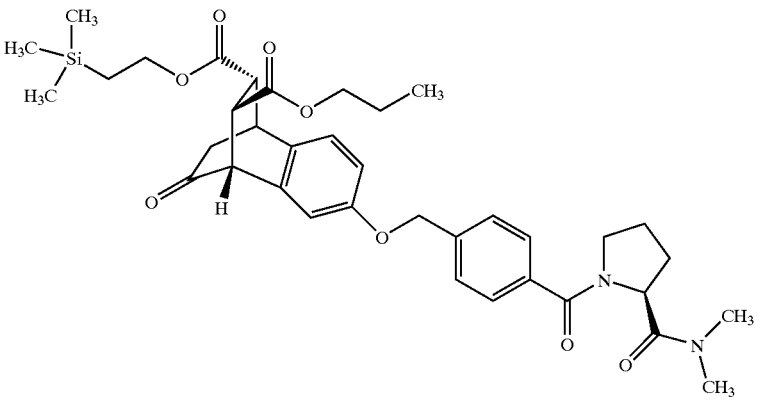 | 8 | * | ** |
| 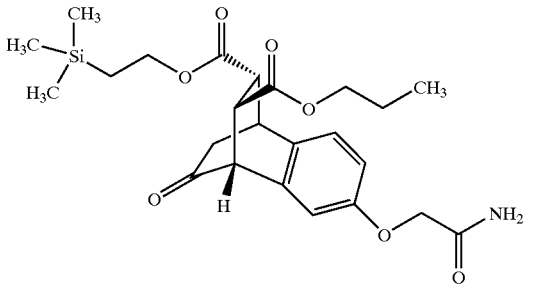 | 9 | * | * |
| 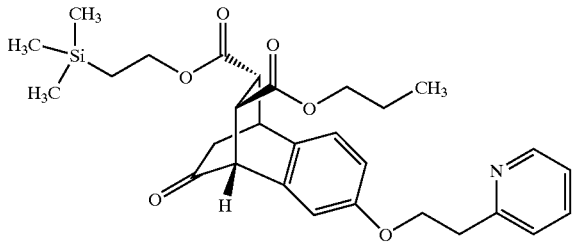 | 10 | * |  |
| 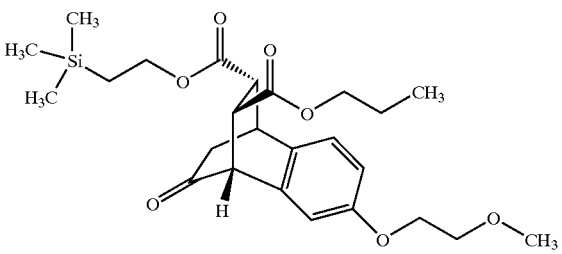 | 11 | ** | * |

TABLE 3-continued

| STRUCTURE | No. | Apopt inh | NFκB inh |
|---|---|---|---|
| 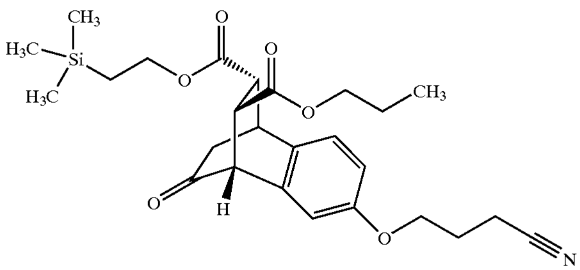 | 12 |  |  |
| 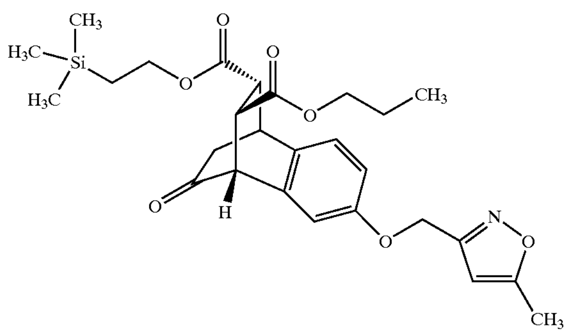 | 13 | ** | * |
| 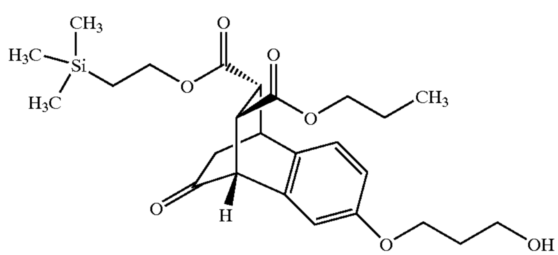 | 14 |  |  |
| 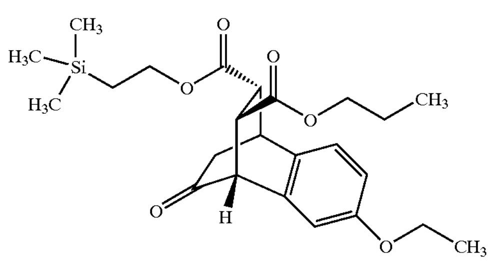 | 15 | ** | * |
| 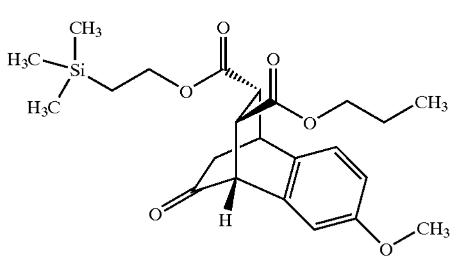 | 16 |  |  |

TABLE 3-continued
| STRUCTURE | No. | Apopt inh | NFκB inh |
|---|---|---|---|
| 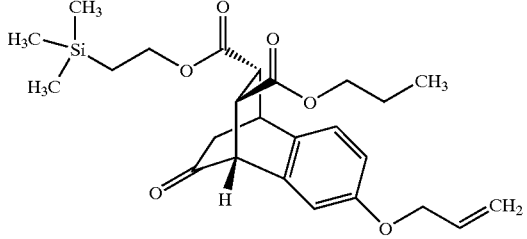 | 17 | * | * |
| 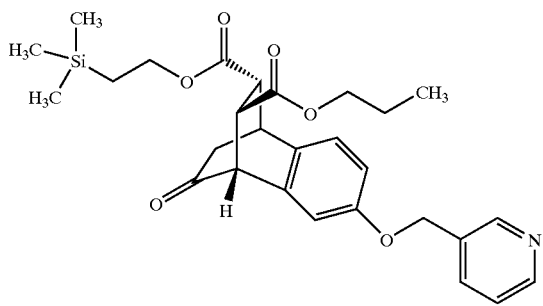 | 18 | ** | — |
| 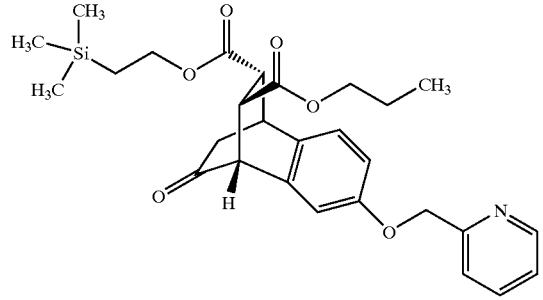 | 19 | * | * |
| 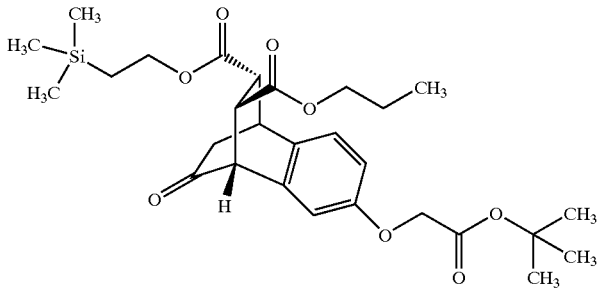 | 20 | * | * |
| 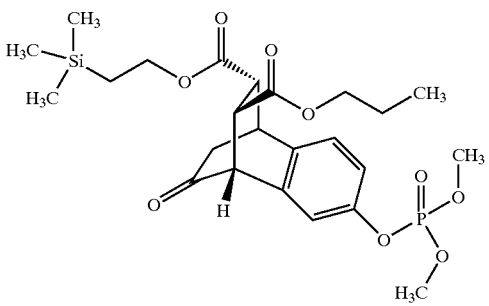 | 21 | * | * |

TABLE 3-continued

| STRUCTURE | No. | Apopt inh | NFκB inh |
|---|---|---|---|
| 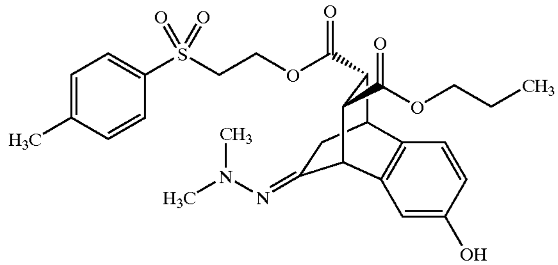 | 22 | — | * |
| 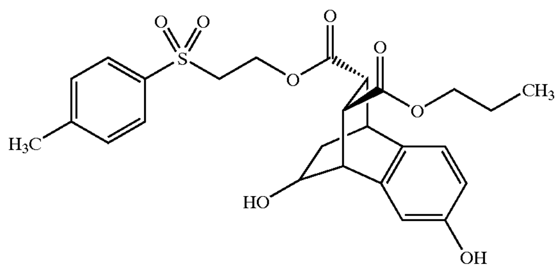 | 23 | — | ** |
| 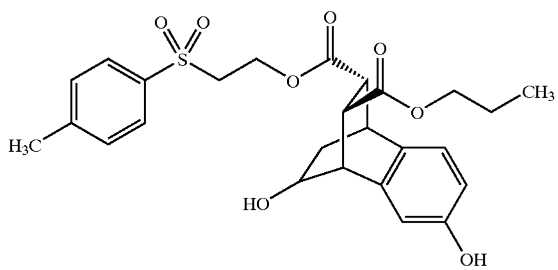 | 24 | — | ** |
| 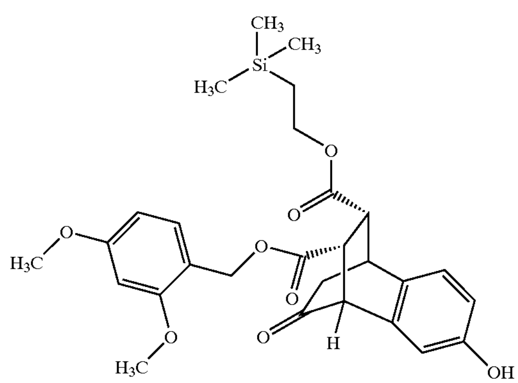 | 25 | ** | * |
| 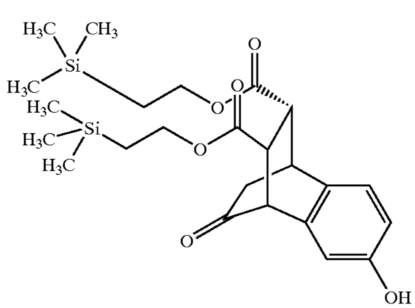 | 26 | — | * |

TABLE 3-continued

| STRUCTURE | No. | Apopt inh | NFκB inh |
|---|---|---|---|
| 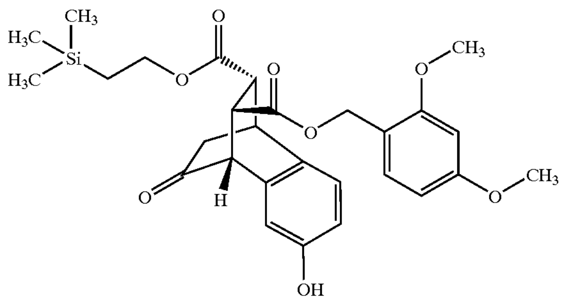 | 27 | ** | * |
| 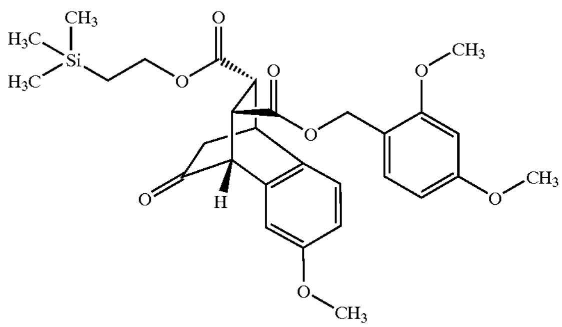 | 28 | ** | * |
| 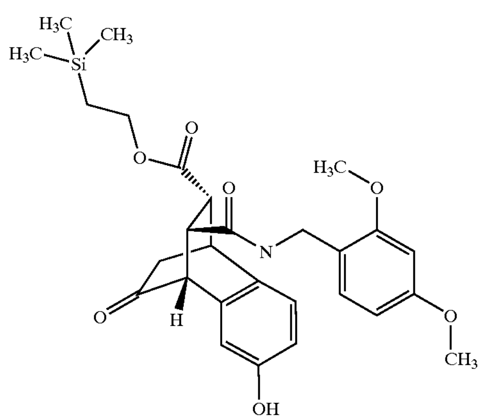 | 29 | ** | * |
| 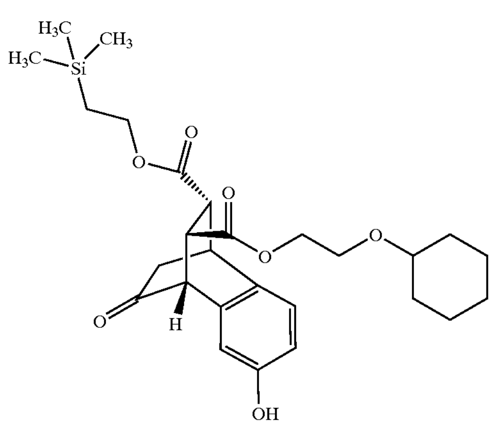 | 30 | *** | — |

TABLE 3-continued
| STRUCTURE | No. | Apopt inh | NFκB inh |
|---|---|---|---|
| 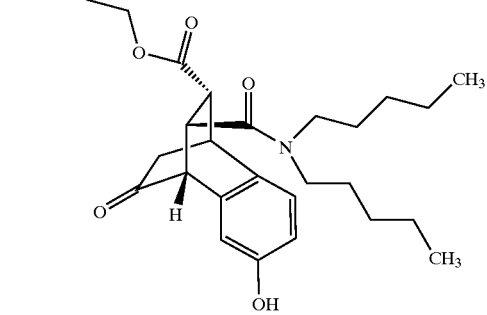 | 31 | * | * |
| 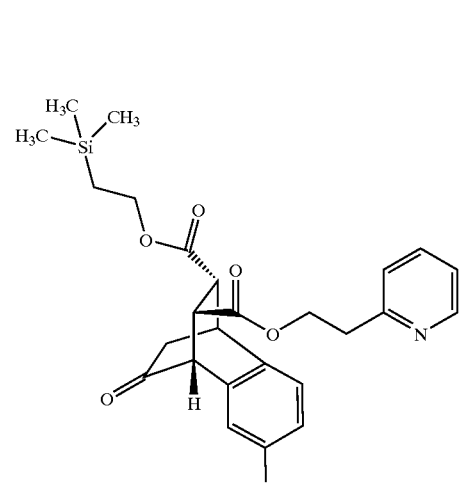 | 32 | ** | * |
| 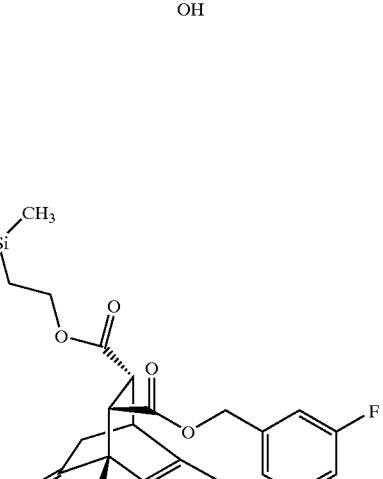 | 33 | ** | * |

TABLE 3-continued
| STRUCTURE | No. | Apopt inh | NFκB inh |
|---|---|---|---|
| 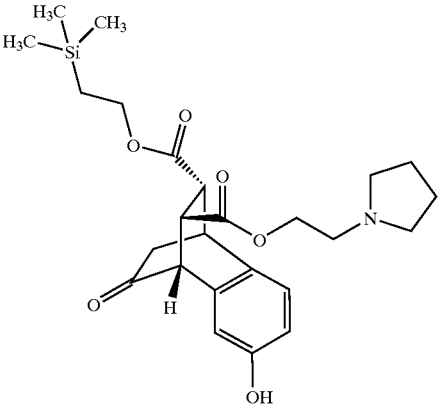 | 34 | * |  |
| 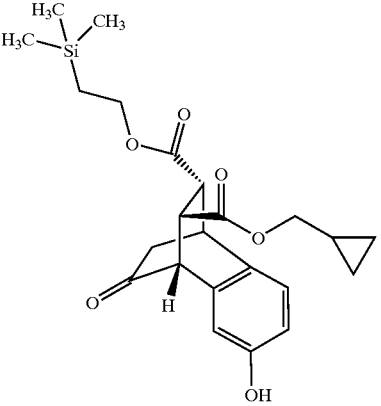 | 35 | *** | * |
| 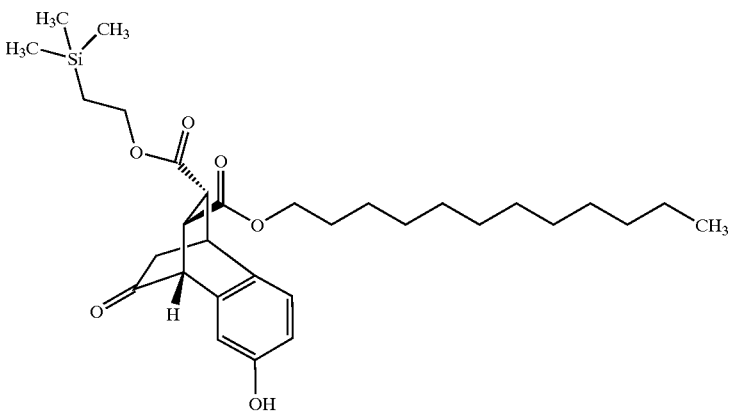 | 36 | * | * |

TABLE 3-continued

| STRUCTURE | No. | Apopt inh | NFκB inh |
|---|---|---|---|
| 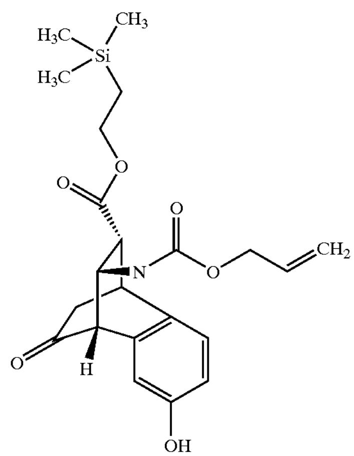 | 37 | ** | * |
| 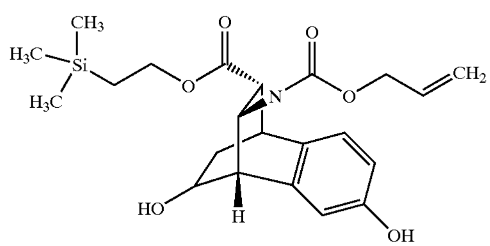 | 38 | * |  |
| 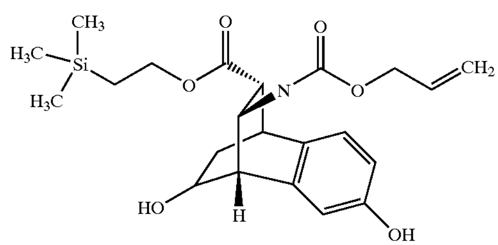 | 39 | * | ** |
| 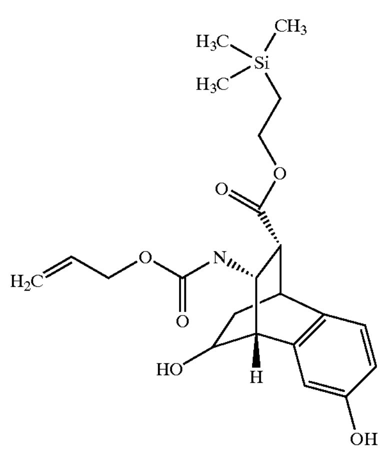 | 40 | ** | * |

TABLE 3-continued
| STRUCTURE | No. | Apopt inh | NFκB inh |
|---|---|---|---|
| 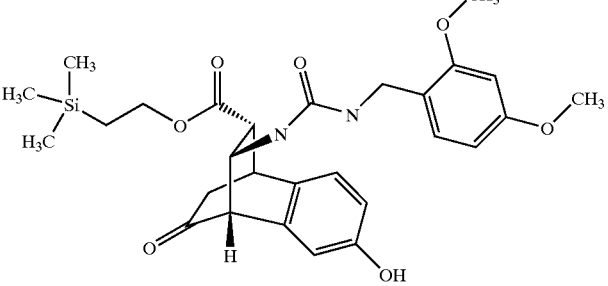 | 41 | * | ** |
| 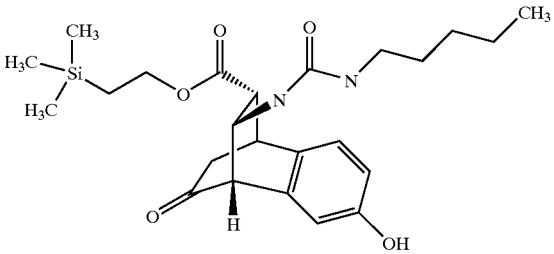 | 42 | * | * |
| 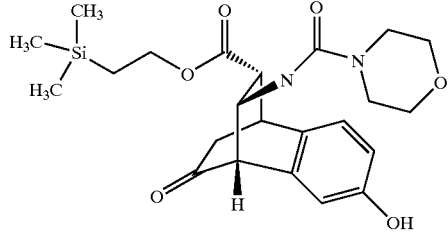 | 43 | * | * |
| 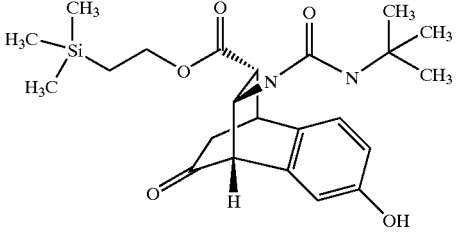 | 44 | * | * |
| 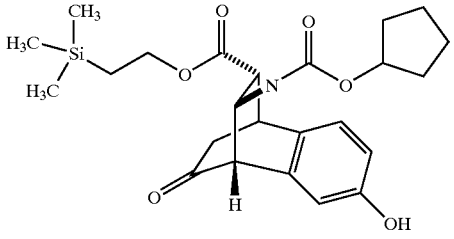 | 45 | *** | * |
| 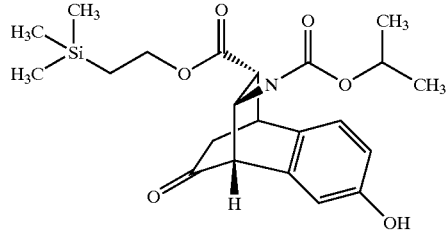 | 46 | * | * |

TABLE 3-continued
| STRUCTURE | No. | Apopt inh | NFκB inh |
|---|---|---|---|
| 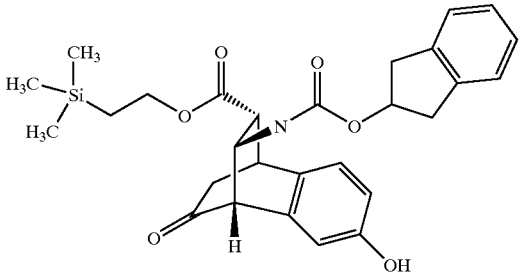 | 47 | * | * |
| 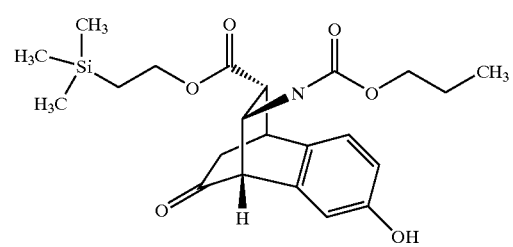 | 48 | ** | * |
| 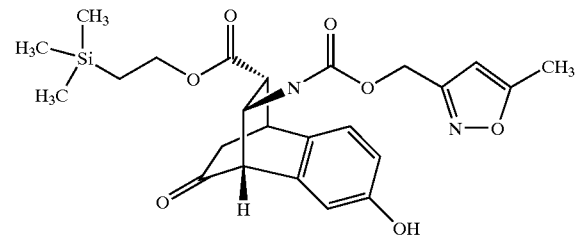 | 49 | * | * |
| 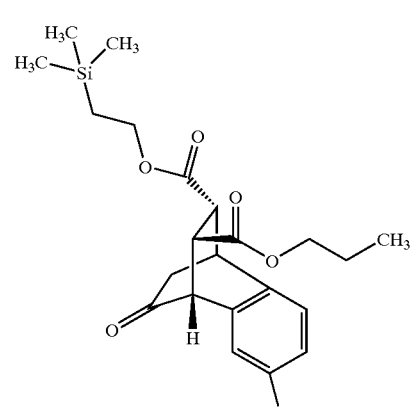 | 50 | * |  |

TABLE 3-continued

| STRUCTURE | No. | Apopt inh | NFκB inh |
|---|---|---|---|
| 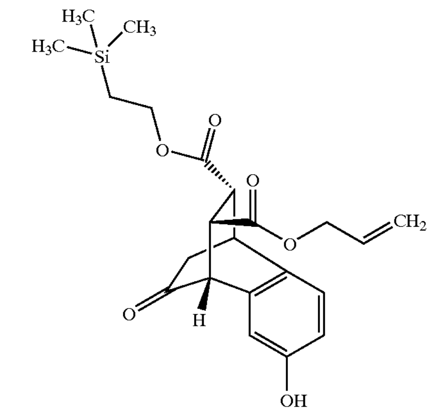 | 51 | * |  |
| 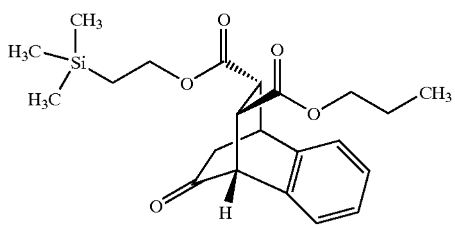 | 52 | * | ** |
| 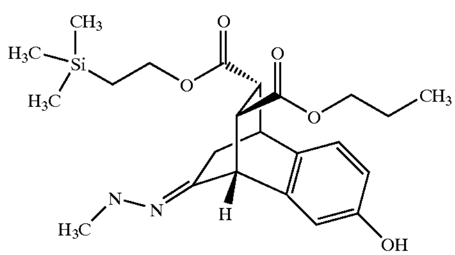 | 53 | * |  |
| 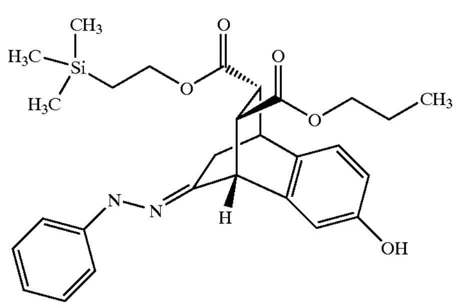 | 54 | * |  |
| 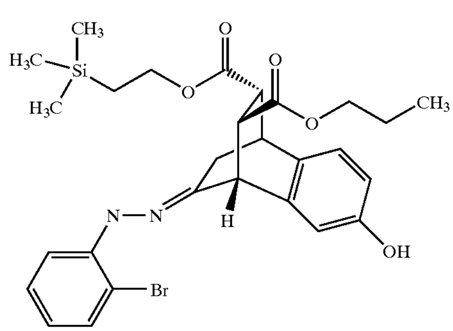 | 55 | — | * |

TABLE 3-continued

| STRUCTURE | No. | Apopt inh | NFκB inh |
|---|---|---|---|
| 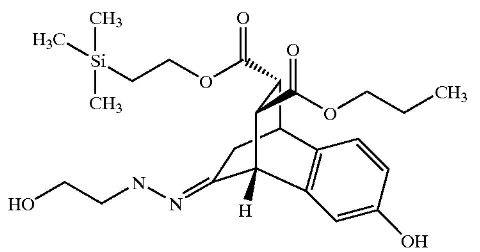 | 56 | *** | * |
| 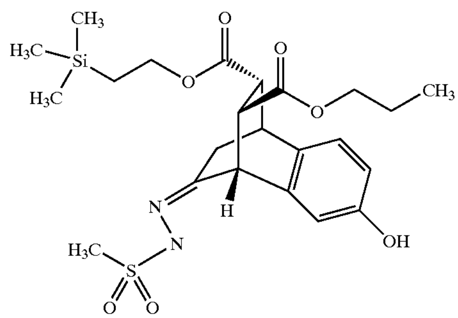 | 57 | ** | * |
| 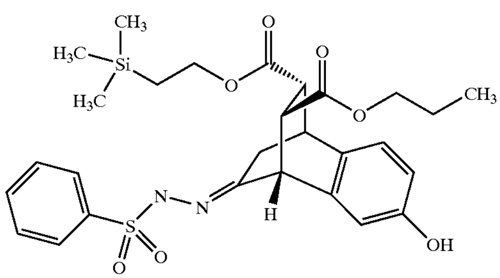 | 58 | ** | * |
| 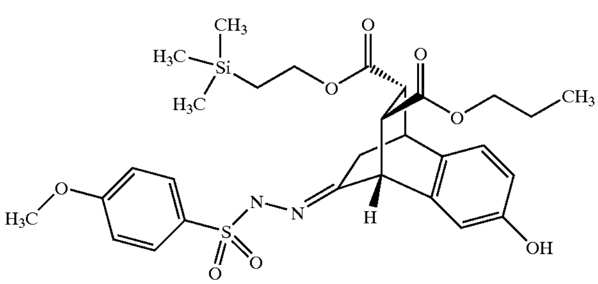 | 59 | * |  |
| 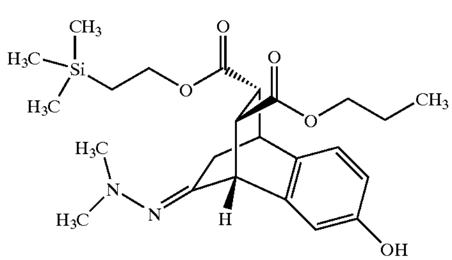 | 60 |  |  |

TABLE 3-continued

| STRUCTURE | No. | Apopt inh | NFκB inh |
|---|---|---|---|
| 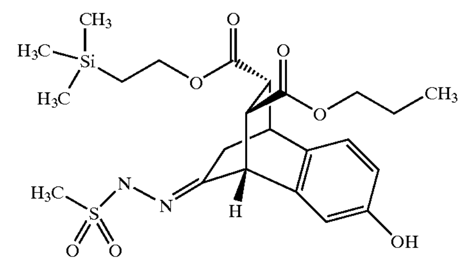 | 61 | ** | * |
| 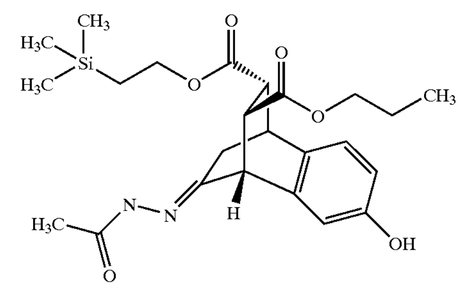 | 62 | ** | * |
| 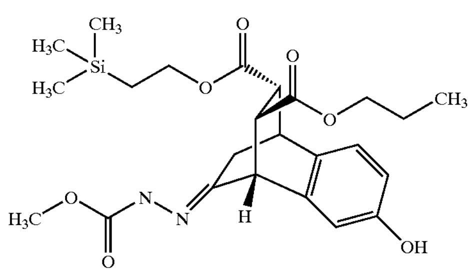 | 63 | * | * |
| 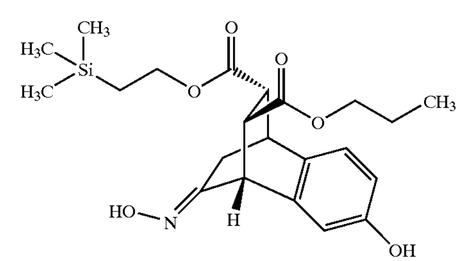 | 64 | *** | * |
| 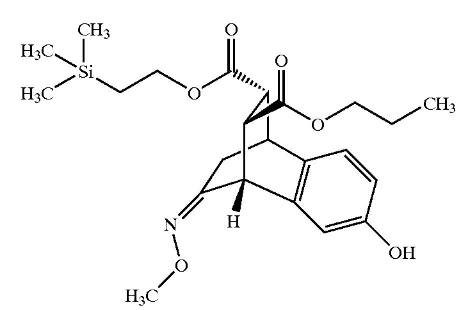 | 65 | * |  |

TABLE 3-continued

| STRUCTURE | No. | Apopt inh | NFκB inh |
|---|---|---|---|
| 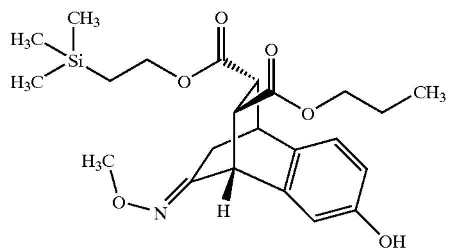 | 66 | * | ** |
| 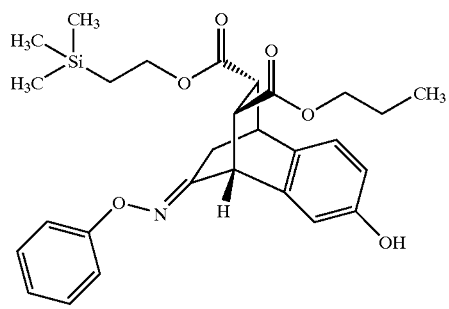 | 67 | * |  |
| 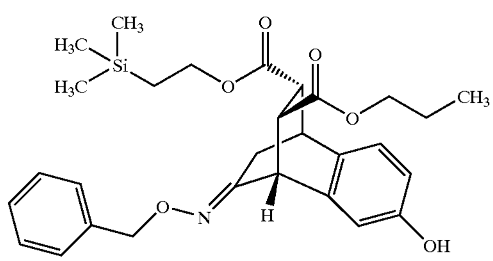 | 68 | * |  |
| 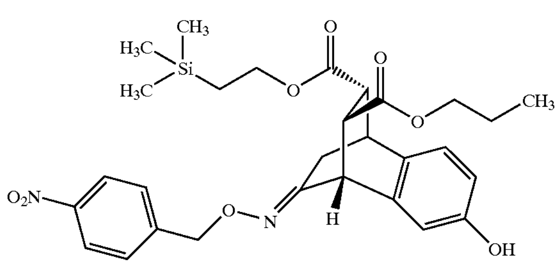 | 69 | *** | * |
| 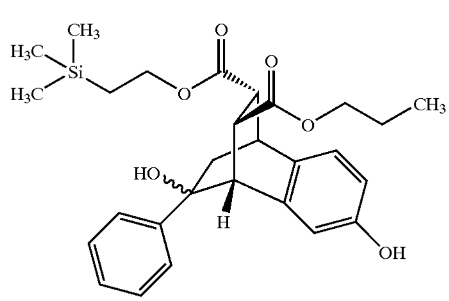 | 70 | * | * |

TABLE 3-continued

| STRUCTURE | No. | Apopt inh | NFκB inh |
|---|---|---|---|
| 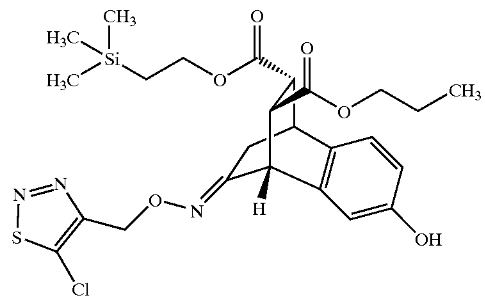 | 71 | * |  |
| 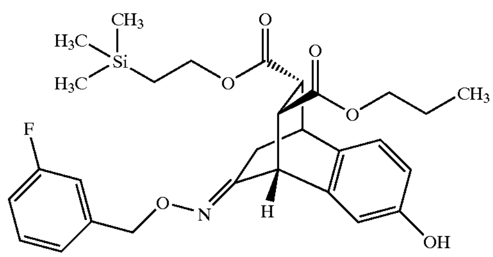 | 72 | *** | * |
| 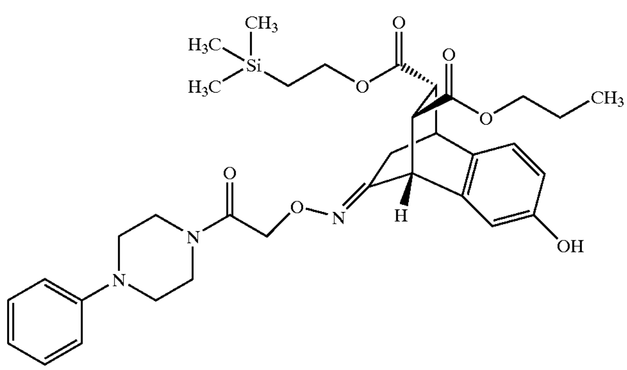 | 73 | — | ** |
| 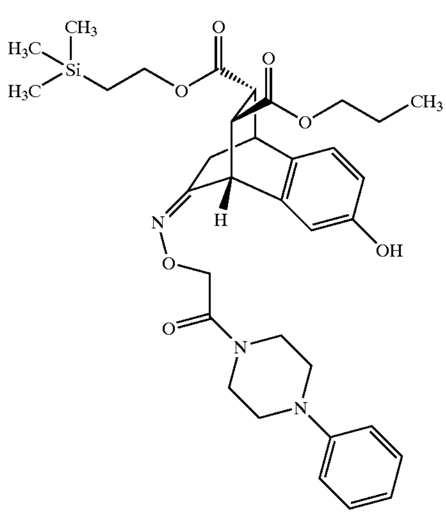 | 74 | — | ** |

TABLE 3-continued
| STRUCTURE | No. | Apopt inh | NFκB inh |
|---|---|---|---|
| 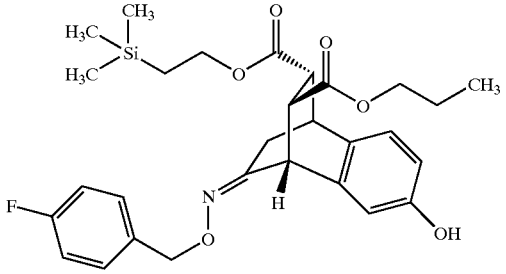 | 75 | — | * |
| 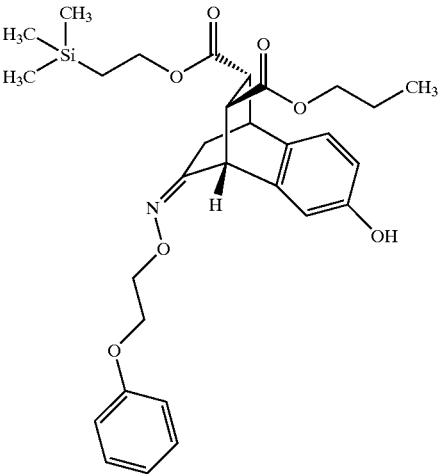 | 76 | — | ** |
| 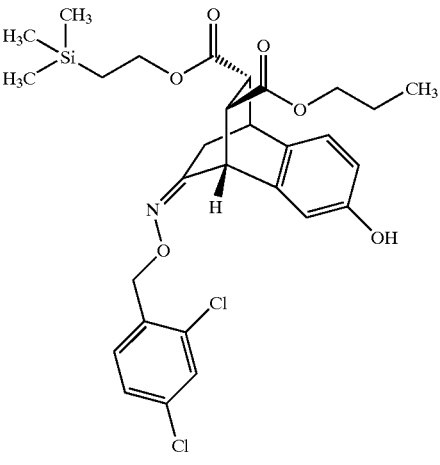 | 77 | — | ** |
| 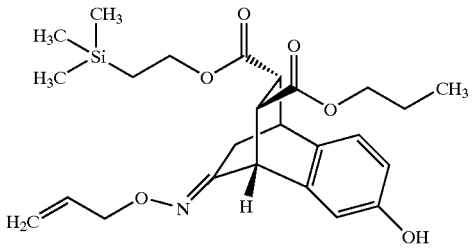 | 78 | *** | — |

TABLE 3-continued

| STRUCTURE | No. | Apopt inh | NFκB inh |
|---|---|---|---|
| 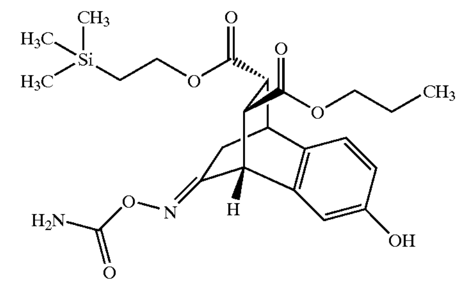 | 79 | * |  |
| 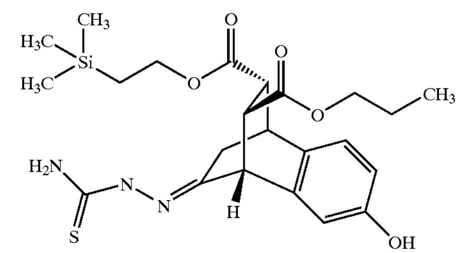 | 80 | * |  |
| 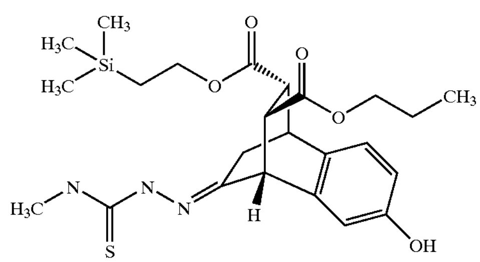 | 81 | *** | * |
| 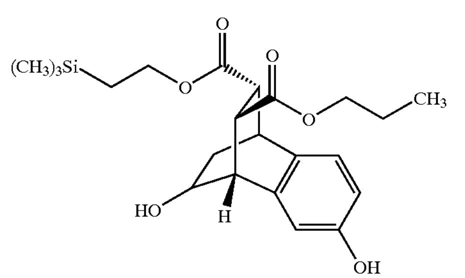 | 82 | * |  |
| 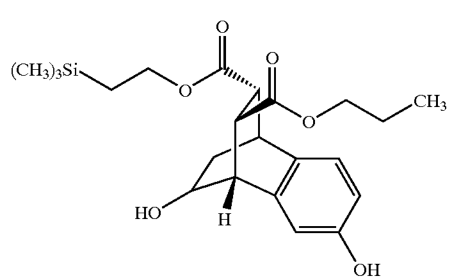 | 83 | * |  |

TABLE 3-continued
| STRUCTURE | No. | Apopt inh | NFκB inh |
|---|---|---|---|
| 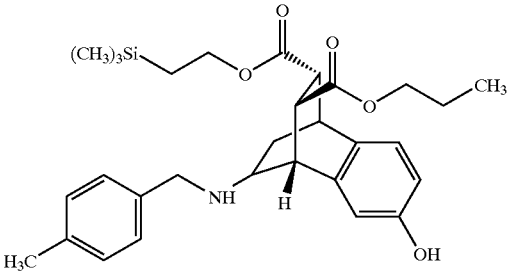 | 84 | * |  |
| 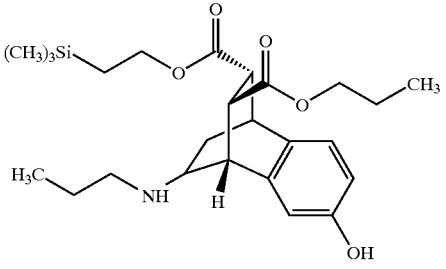 | 85 | — | ** |
| 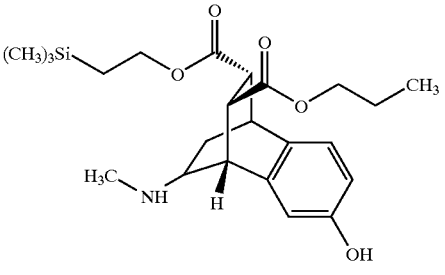 | 86 | — | ** |
| 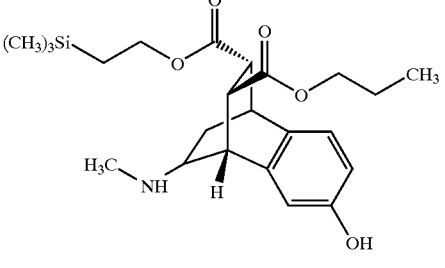 | 87 | — | ** |
| 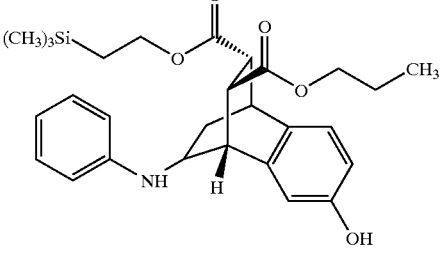 | 88 | — | * |

TABLE 3-continued
| STRUCTURE | No. | Apopt inh | NFκB inh |
|---|---|---|---|
| 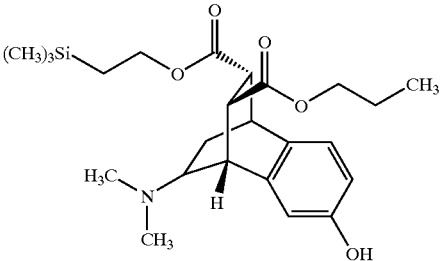 | 89 | — | * |
| 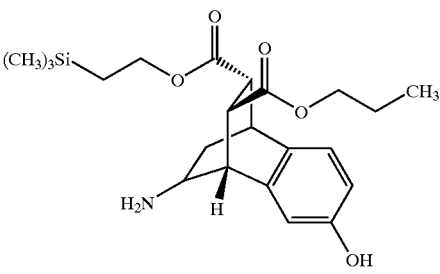 | 90 | — | * |
| 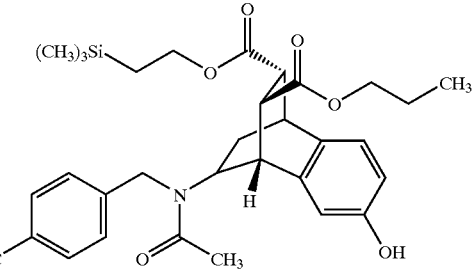 | 91 | — | ** |
| 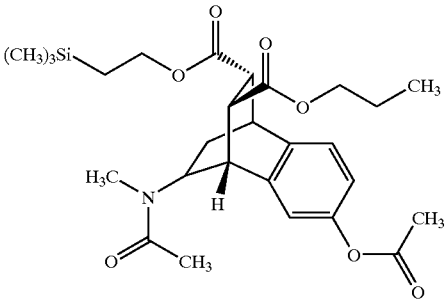 | 92 | — | ** |
| 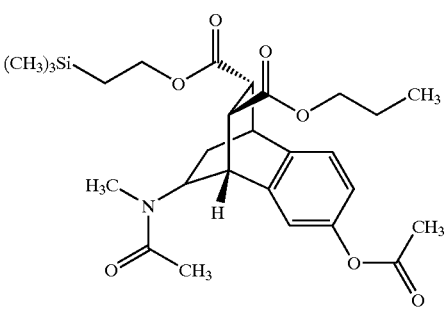 | 93 | — | ** |

TABLE 3-continued

| STRUCTURE | No. | Apopt inh | NFκB inh |
|---|---|---|---|
| 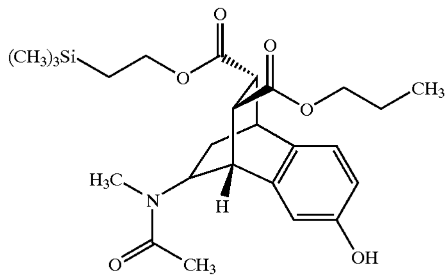 | 94 | — | ** |
| 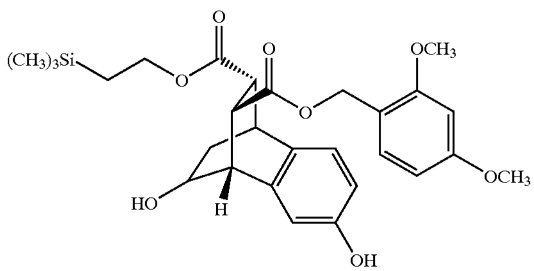 | 95 | * | * |
| 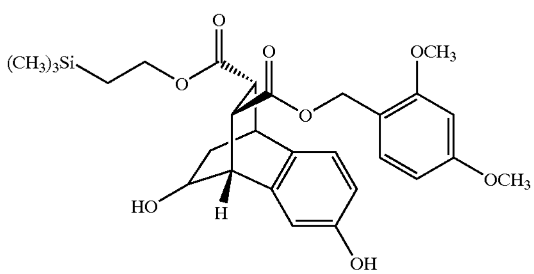 | 96 | *** | * |
| 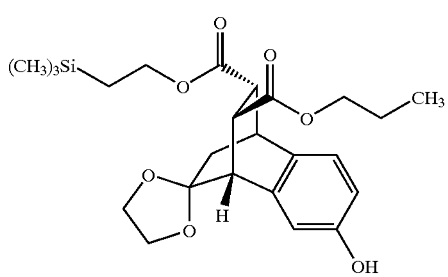 | 97 | * | ** |
| 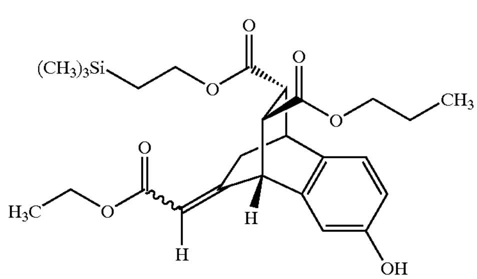 | 98 | * | * |

TABLE 3-continued

| STRUCTURE | No. | Apopt inh | NFκB inh |
|---|---|---|---|
| 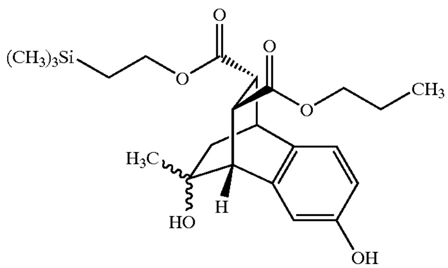 | 99 | — | ** |
| 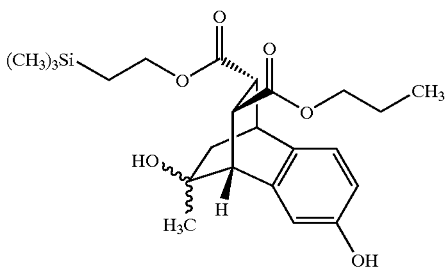 | 100 | — | ** |
| 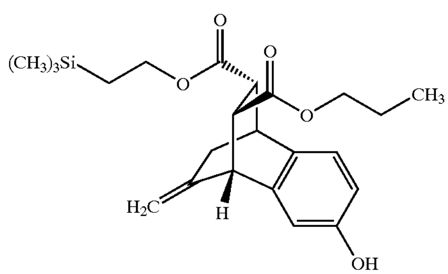 | 101 | *** | * |
| 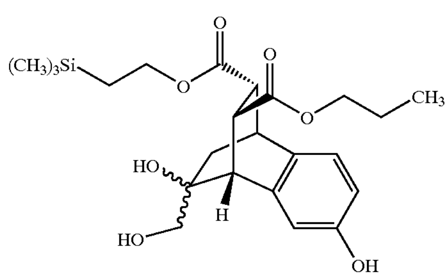 | 102 | * | * |
| 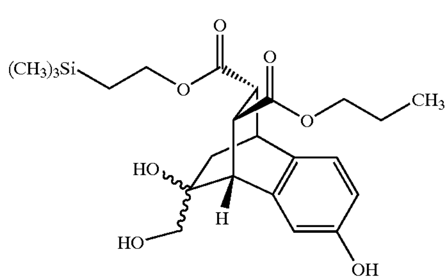 | 103 | * | * |

TABLE 3-continued
| STRUCTURE | No. | Apopt inh | NFκB inh |
|---|---|---|---|
| 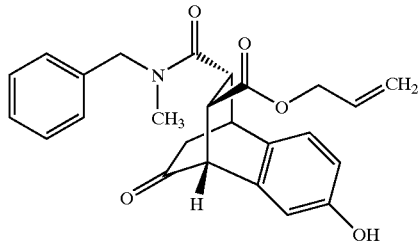 | 104 | — | * |
| 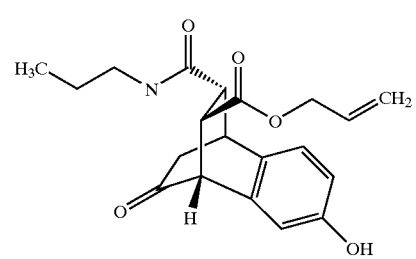 | 105 | — | * |
| 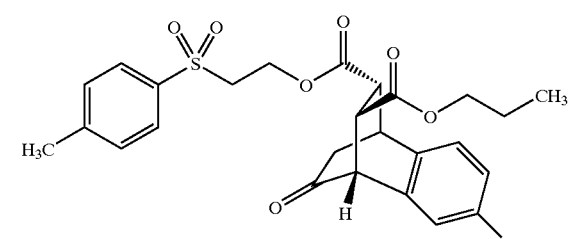 | 106 | — | ** |
| 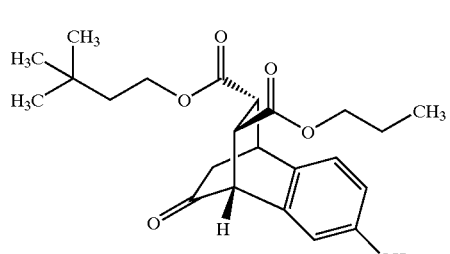 | 107 | — | ** |
| 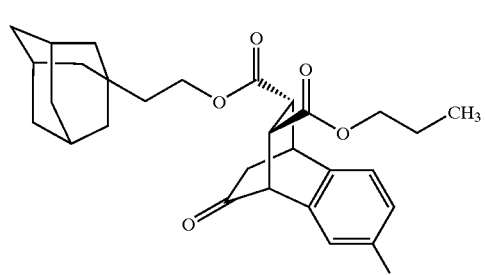 | 108 | — | ** |
| 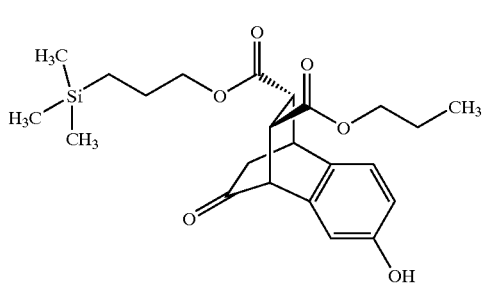 | 109 | — | ** |

TABLE 3-continued

| STRUCTURE | No. | Apopt inh | NFκB inh |
|---|---|---|---|
| 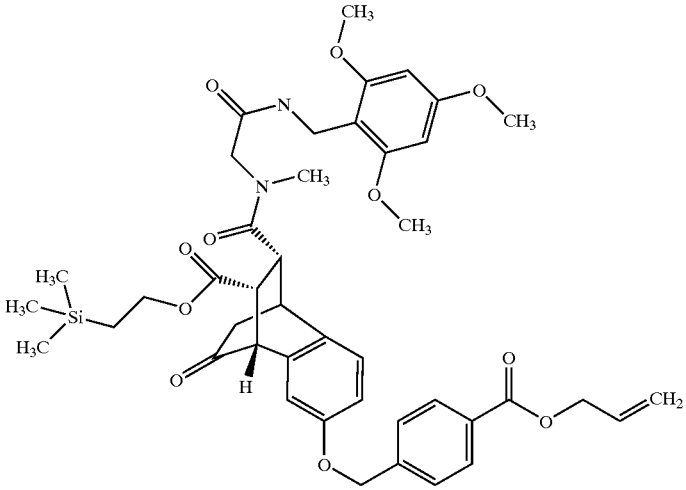 | 110 | * | * |

Example 108

Biological Activities of Representative Bicyclooctanes

Compounds of the present invention were synthesized according to methods disclosed in Examples 1–106, and tested for activity according to the apoptosis and NFκB assays described in Example 107, and the CXCR1 and CXCR2 assays described below. The results from these biological testings are set forth in Table 4, where each compound is provided with a unique compound number, as set forth in the column "No."

CXCR1

This assay is a radioligand binding assay in human recombinant CHO cells with $^{125}$I labeled IL-8 as the ligand. The assay procedure is described in Ahuja, S. K.; Murphy, P. M;. *J. Biol. Chem.* 1996, 271, 20545, and was performed by Panlabs Taiwan, Ltd. Data is presented for representative compounds under the column titled "CXCR1 inh" in Table 4 as follows: "*" refers to percent inhibition from 10–36%; "*" refers to an $IC_{50}$ from 10 μM to 50 μM; "**" refers to an $IC_{50}$ below 10μM.

CXCR2

This assay is a radioligand binding assay in human recombinant CHO cells with $^{125}$I labeled IL-8 as the ligand. The assay procedure is described in Ahuja, S. K.; Murphy, P. M;. *J. Biol. Chem.* 1996, 271, 20545, and was performed by Panlabs Taiwan, Ltd. Data is presented for representative compounds under the column titled "CXCR2 inh" in Table 4 as follows: "*" refers to percent inhibition from 10–36%; "*" refers to an $IC_{50}$ from 10 μM to 50 μM; "**" refers to an $IC_{50}$ below 10 μM.

TABLE 4

| STRUCTURE | No. | Apopt. Inh. | NFkB inh. | CXCR1 inh. | CXCR2 2 inh. |
|---|---|---|---|---|---|
| 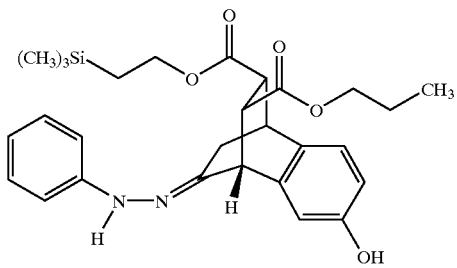 | 111 | * |  | * | * |

TABLE 4-continued
| STRUCTURE | No. | Apopt. Inh. | NFkB inh. | CXCR1 inh. | CXCR2 inh. |
|---|---|---|---|---|---|
| 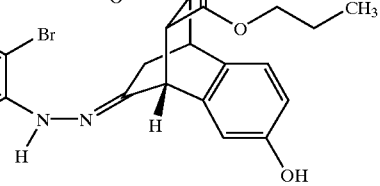 | 112 | N.D. | * |  | * |
| 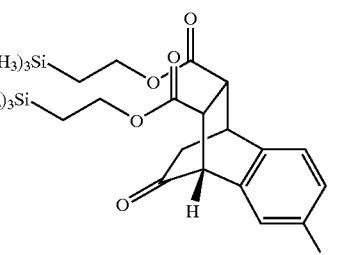 | 113 | N.D. | * |  |  |
| 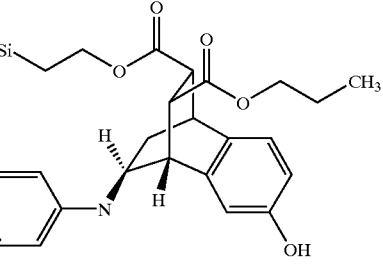 | 114 | N.D. | * | N.D. | * |
| 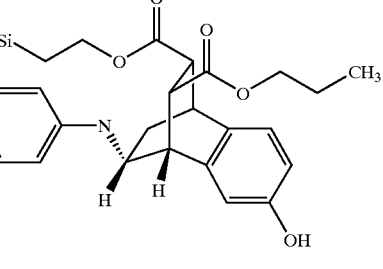 | 115 | — | * | * | * |
| 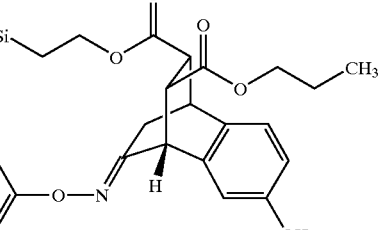 | 116 | * |  | * | * |

All other acronyms and abbreviations have the corresponding meaning as published in journals relative to the art of organic chemistry. From the foregoing it will be appreciated that, although specific embodiments of the invention have been described herein for purposes of illustration, various modifications may be made without deviating from the spirit and scope of the invention. Accordingly, the invention is not limited except as by the appended claims.

All references cited herein are incorporated by reference.

What is claimed is:

1. A compound of formula (I)

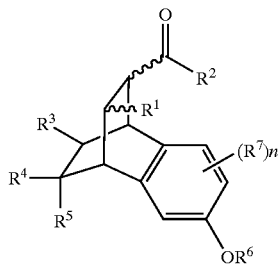
(I)

and optical isomers, diastereomers, enantiomers and pharmaceutically acceptable salts thereof in isolation or mixture, where, independently at each location:

$R^1$ is selected from the following six formulae:

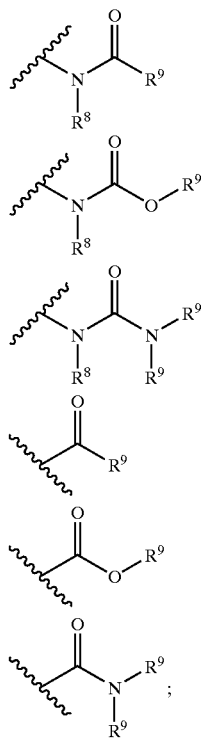

$R^2$ is —$OR^9$ or —$NR^9R^9$;

$R^3$ is selected from hydrogen, halogen, hydroxyl or protected hydroxyl, amino or protected amino, and $C_1$–$C_8$alkyl or $C_1$–$C_8$haloalkyl;

$R^4$ and $R^5$ are independently selected from $R^9$, —$OR^9$, —$NR^9R^9$ and —N=N—$R^9$, or $R^4$ and $R^5$ may together form a group selected from =O, =$CR^8R^8$ and =$NR^{10}$, or $R^4$ and $R^5$ may together with the carbon to which they are both attached form a spiro carbocyclic or heterocyclic ring;

$R^6$ is selected from hydrogen, inorganic groups having 1–8 atoms selected from boron, sulfur, phosphorous, silicon and hydrogen, and organic groups having 1–20 carbons and optionally containing 1–4 heteroatoms selected from nitrogen, oxygen and silicon;

$R^7$ is selected from halogen, hydroxyl or protected hydroxyl, amino or protected amino, and $C_1$–$C_8$alkyl or $C_1$–$C_8$haloalkyl;

$R^8$ is selected from hydrogen, alkyl, aryl and heteroalkyl;

$R^9$ is selected from hydrogen and organic groups having 1–30 carbons and optionally containing 1–4 heteroatoms selected from nitrogen, oxygen and silicon, with the provision that two $R^9$ groups both joined to a common atom may be joined together so as to form a ring with the common atom;

$R^{10}$ is selected from —$R^9$, —$OR^9$, —$NR^9R^9$, —NH—C(O)$R^9$; —NH—C(O)$OR^9$ and —NH—C(S)$NHR^9$; and n is 0, 1, 2 or 3;

with the proviso that when $R^6$ is hydrogen, methyl, or ethyl and $R^4$ and $R^5$ together form =O or $R^4$ is hydrogen and $R^5$ is hydroxy, $R^1$ is —C(O)$OR^9$, then $R^2$ is not —OH, —$OCH_3$, OR —$OCH_2CH_3$.

2. A compound of claim 1 wherein $R^1$ is

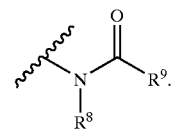

3. A compound of claim 1 wherein $R^1$ is

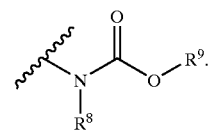

4. A compound of claim 1 wherein $R^1$ is

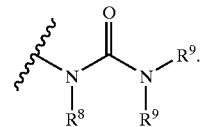

5. A compound of claim 1 wherein $R^8$ is selected from hydrogen and $C_1$–$C_8$ alkyl.

6. A compound of claim 5 where $R^8$ is hydrogen.

7. A compound of claim 1 wherein $R^1$ is

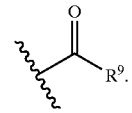

8. A compound of claim 1 wherein $R^1$ is

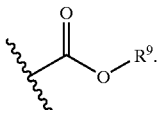

9. A compound of claim 1 wherein $R^1$ is

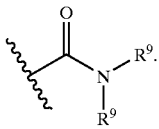

10. A compound of claim 1 wherein $R^1$ is selected from the following four formulae:

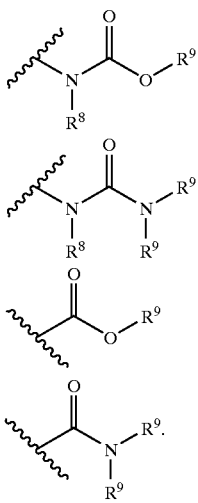

11. A compound of claim 1 wherein $R^9$ is independently selected at each occurrence from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5, with the provision that two $R^9$ groups both joined to a common atom may be joined together so as to form a ring with the common atom.

12. A compound of claim 1 wherein $R^9$ is independently selected at each occurrence from $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14}p$-heteroarylene, and p is selected from 0, 1, 2, 3, 4 and 5.

13. A compound of claim 11 wherein $R^9$ is selected from hydrogen, heteroalkyl, $C_1$–$C_{15}$alkyl, (heteroaryl) $C_1$–$C_{15}$alkylene, $(C_6$–$C_{10}$aryl)$C_1$–$C_{15}$alkylene, $C_6$–$C_{10}$aryl fused to $C_1$–$C_{15}$alkylene, (alkyl)$_p$($C_6$–$C_{10}$arylene) $C_1$–$C_{15}$alkylene, $(C_6$–$C_{10}$aryl)($C_6$–$C_{10}$arylene) $C_1$–$C_{15}$alkylene, $(C_1$–$C_{15}$alkyl)$_p$(heteroarylene) $C_1$–$C_{15}$alkylene, and (heteroalkyl)$_p$($C_6$–$C_{10}$arylene) $C_1$–$C_{15}$alkylene, or two $R^9$ groups bonded to a common nitrogen of $R^1$ may be joined together to form a 5–8 membered heterocycle including the common nitrogen, where this 5–8 membered heterocycle may be substituted with 0–5 groups selected from alkyl and heteralkyl, where p is selected from 1, 2, 3, 4 and 5.

14. A compound of claim 11 wherein $R^9$ is selected from hydrogen, heteroalkyl, $C_1$–$C_{15}$alkyl, $(C_6$–$C_{10}$aryl) $C_1$–$C_{15}$alkylene, (heteroaryl)$C_1$–$C_{15}$alkylene, and (heteroalkyl)$_p$($C_6$–$C_{10}$arylene)$C_1$–$C_{15}$alkylene, or the two $R^9$ groups joined to a common nitrogen of $R^1$ may be joined together to form a 5–8 membered heterocycle including the common nitrogen.

15. A compound of claim 11 wherein $R^9$ is selected from heteroalkyl, $C_1$–$C_{15}$alkyl, $(C_6$–$C_{10}$aryl)$C_1$–$C_{15}$alkylene, $(C_6$–$C_{10}$aryl)($C_6$–$C_{10}$arylene)$C_1$–$C_{15}$alkylene, $C_1$–$C_{15}$alkyl)$_p$(heteroarylene)$C_1$–$C_{15}$alkylene, and $C_6$–$C_{10}$aryl fused to $C_1$–$C_{15}$alkylene.

16. A compound of claim 11 wherein $R^1$ is selected from hydrogen, heteroalkyl, $C_1$–$C_{15}$alkyl, $(C_6$–$C_{10}$aryl) $C_1$–$C_{15}$alkylene, $(C_6$–$C_{10}$aryl)($C_6$–$C_{10}$arylene) $C_1$–$C_{15}$alkylene, $(C_1$–$C_{15}$alkyl)$_p$(heteroarylene) $C_1$–$C_{15}$alkylene, and $C_6$–$C_{10}$aryl fused to $C_1$–$C_{15}$alkylene.

17. A compound of claim 11 wherein $R^9$ is selected from hydrogen, heteroalkyl, $C_1$–$C_{15}$alkyl, (heteroaryl) $C_1$–$C_{15}$alkylene, and (heteroalkyl)$_p$($C_6$–$C_{10}$arylene) $C_1$–$C_{15}$alkylene.

18. A compound of claim 11 wherein $R^9$ is selected from hydrogen, heteroalkyl, $C_1$–$C_{15}$alkyl, (heteroaryl) $C_1$–$C_{15}$alkylene, $(C_6$–$C_{10}$aryl)$C_1$–$C_{15}$alkylene, (alkyl)$_p$ ($C_6$–$C_{10}$arylene)$C_1$–$C_{15}$alkylene, or the two $R^9$ groups of $R^1$ may be joined together to form a 5–8 membered heterocycle including the common nitrogen, where this 5–8 membered heterocycle may be substituted with 0–5 groups selected from alkyl and heteralkyl.

19. A compound of claim 1 wherein $R^2$ is —$OR^9$.

20. A compound of claim 1 wherein $R^2$ is —$NR^9R^9$.

21. A compound of claim 1 wherein $R^9$ of $R^2$ is selected from hydrogen, $R^{11}$, $R^{12}$, $R^{13}$, $R^{14}$ and $R^{15}$ where $R^{11}$ is selected from alkyl, heteroalkyl, aryl and heteroaryl; $R^{12}$ is selected from $(R^{11})_p$-alkylene, $(R^{11})_p$-heteroalkylene, $(R^{11})_p$-arylene and $(R^{11})_p$-heteroarylene; $R^{13}$ is selected from $(R^{12})_p$-alkylene, $(R^{12})_p$-heteroalkylene, $(R^{12})_p$-arylene, and $(R^{12})_p$-heteroarylene; $R^{14}$ is selected from $(R^{13})_p$-alkylene, $(R^{13})_p$-heteroalkylene, $(R^{13})_p$-arylene, and $(R^{13})_p$-heteroarylene, $R^{15}$ is selected from $(R^{14})_p$-alkylene, $(R^{14})_p$-heteroalkylene, $(R^{14})_p$-arylene, and $(R^{14})_p$-heteroarylene, and p is selected from 0, 1, 2, 3, 4 and 5.

22. A compound of claim 1 wherein $R^9$ of $R^2$ is selected from hydrogen, heteroalkyl, $C_1$–$C_{15}$alkyl, $(C_6$–$C_{10}$aryl) $(C_6$–$C_{10}$arylene)$C_1$–$C_{15}$alkylene, $(C_1$–$C_{15}$alkyl)$_p$-(heteroarylene)$C_1$–$C_{15}$alkylene, $(C_1$–$C_{15}$alkyl)$_p$ (heteroarylene)heteroalkylene, (heteroalkyl)$_p$ $(C_6$–$C_{10}$arylene)$C_1$–$C_{15}$alkylene,land($C_1$–$C_{15}$alkyl)$_p$ $(C_6$–$C_{10}$arylene)heteroalkylene.

23. A compound of claim 1 wherein $R^2$ is —$OR^9$ where $R^9$ is selected from a heteroalkyl group having 1–10 carbons and 1–4 heteroatoms selected from nitrogen, oxygen, silicon and sulfur.

24. A compound of claim 1 wherein $R^2$ is —$NR^9R^9$ and $R^9$ is selected from hydrogen, heteroalkyl, $C_1$–$C_{15}$alkyl, (heteroaryl)$C_1$–$C_{15}$alkylene, (heteroalkyl)$_p$(aryl)- heteroalkylene, (heteroalkyl)$_p$(aryl)C$_1$–C$_{15}$alkylene, and (C$_1$–C$_{15}$alkyl)$_p$(C$_6$–C$_{10}$arylene)C$_1$–C$_{15}$alkylene.

25. A compound of claim 1 wherein R$^3$ is selected from hydrogen and alkyl.

26. A compound of claim 25 wherein R$^3$ is hydrogen.

27. A compound of claim 1 wherein R$^4$ and R$^5$ are independently selected from R$^9$, —OR$^9$, —NR$^9$R$^9$ and —N=N—R$^9$.

28. A compound of claim 27 wherein R$^9$ of R$^4$ and R$^5$ is selected from hydrogen, R$^{11}$, R$^{12}$, R$^{13}$, R$^{14}$ and R$^{15}$ where R$^{11}$ is selected from alkyl, heteroalkyl, aryl and heteroaryl; R$^{12}$ is selected from (R$^{11}$)$_p$-alkylene, (R$^{11}$)$_p$-heteroalkylene, (R$^{11}$)$_p$-arylene and (R$^{11}$)$_p$-heteroarylene; R$^{13}$ is selected from (R$^{12}$)$_p$-alkylene, (R$^{12}$)$_p$-heteroalkylene, (R$^{12}$)$_p$-arylene, and (R$^{12}$)$_p$-heteroarylene; R$^{14}$ is selected from (R$^{13}$)$_p$-alkylene, (R$^{13}$)$_p$-heteroalkylene, (R$^{13}$)$_p$-arylene, and (R$^{13}$)$_p$-heteroarylene, R$^{15}$ is selected from (R$^{14}$)$_p$-alkylene, (R$^{14}$)$_p$-heteroalkylene, (R$^{14}$)$_p$-arylene, and (R$^{14}$)$_p$-heteroarylene, and p is selected from 0, 1, 2, 3, 4 and 5.

29. A compound of claim 27 wherein each of R$^4$ and R$^5$ is hydrogen.

30. A compound of claim 27 wherein at least one of R$^4$ and R$^5$ is selected from C$_1$–C$_{15}$alkyl, heteroalkyl, and C$_6$–C$_{10}$aryl.

31. A compound of claim 27 wherein one of R$^4$ and R$^5$ is hydrogen and the other of R$^4$ and R$^5$ is selected from hydrogen, —OR$^9$, —NR$^9$R$^9$ and —N=N—R$^9$ where the R$^9$ is selected from hydrogen, R$^{11}$, R$^{12}$, R$^{13}$, R$^{14}$ and R$^{15}$ where R$^{11}$ is selected from alkyl, heteroalkyl, aryl and heteroaryl; R$^{12}$ is selected from (R$^{11}$)$_p$-alkylene, (R$^{11}$)$_p$-heteroalkylene, (R$^{11}$)$_p$-arylene and (R$^{11}$)$_p$-heteroarylene; R$^{13}$ is selected from (R$^{12}$)$_p$-alkylene, (R$^{12}$)$_p$-heteroalkylene, (R$^{12}$)$_p$-arylene, and (R$^{12}$)$_p$-heteroarylene; R$^{14}$ is selected from (R$^{13}$)$_p$-alkylene, (R$^{13}$)$_p$-heteroalkylene, (R$^{13}$)$_p$-arylene, and (R$^{13}$)$_p$-heteroarylene, R$^{15}$ is selected from (R$^{14}$)$_p$-alkylene, (R$^{14}$)$_p$-heteroalkylene, (R$^{14}$)$_p$-arylene, and (R$^{14}$)$_p$-heteroarylene, and p is selected from 0, 1, 2, 3, 4 and 5.

32. A compound of claim 1 wherein R$^4$ and R$^5$ together form a group selected from =O, =CR$^8$R$^8$ and =NR$^{10}$.

33. A compound of claim 32 wherein R$^4$ and R$^5$ together form =O.

34. A compound of claim 32 wherein R$^4$ and R$^5$ together form =NR$^{10}$ and R$^{10}$ is —OR$^9$ where R$^9$ is selected from hydrogen, C$_6$–C$_{10}$aryl, C$_1$–C$_8$alkyl, heteroalkyl, (C$_6$–C$_{10}$aryl)heteroalkyl, (C$_6$–C$_{10}$aryl)C$_1$–C$_{15}$alkylene, (heteroalkyl)$_p$(heteroarylene)C$_1$–C$_{15}$alkylene, (heteroalkyl)$_p$(C$_6$–C$_{10}$arylene)C$_1$–C$_{15}$alkylene, and (C$_1$–C$_{15}$alkyl)$_p$(C$_6$–C$_{10}$arylene)heteroalkylene.

35. A compound of claim 32 wherein R$^4$ and R$^5$ together form =NR$^{10}$ and R$^{10}$ is —N(R$^9$)(R$^9$) where R$^9$ is selected from hydrogen, C$_1$–C$_8$alkyl, heteroalkyl, C$_6$–C$_{10}$aryl, (C$_6$–C$_{10}$aryl)heteroalkylene, (heteroalkyl)$_p$C$_6$–C$_{10}$arylene, (C$_1$–C$_{15}$alkyl)$_p$C$_6$–C$_{10}$arylene, (heteroalkyl)$_p$(C$_6$–C$_{10}$arylene)heteroalkylene, (C$_1$–C$_{15}$alkyl)$_p$(C$_6$–C$_{10}$arylene)C$_1$–C$_{15}$alkylene, and (C$_1$–C$_{15}$alkyl)$_p$(C$_6$–C$_{10}$arylene)C$_1$–C$_{15}$heteroalkylene.

36. A compound of claim 32 wherein R$^4$ and R$^5$ together form =CR$^8$R$^8$, and one of R$^8$ is hydrogen while the other R$^8$ is selected from hydrogen, C$_1$–C$_8$alkyl and heteroalkyl.

37. A compound of claim 32 wherein R$^8$ is selected from hydrogen and C$_1$–C$_8$alkyl, and R$^{10}$ is selected from hydrogen, R$^{11}$, R$^{12}$, R$^{13}$, R$^{14}$ and R$^{15}$ where R$^{11}$ is selected from alkyl, heteroalkyl, aryl and heteroaryl; R$^{12}$ is selected from (R$^{11}$)$_p$-alkylene, (R$^{11}$)$_p$-heteroalkylene, (R$^{11}$)$_p$-arylene and (R$^{11}$)$_p$-heteroarylene; R$^{13}$ is selected from (R$^{12}$)$_p$-alkylene, (R$^{12}$)$_p$-heteroalkylene, (R$^{12}$)$_p$-arylene, and (R$^{12}$)$_p$-heteroarylene; R$^{14}$ is selected from (R$^{13}$)$_p$-alkylene, (R$^{13}$)$_p$-heteroalkylene, (R$^{13}$)$_p$-arylene, and (R$^{13}$)$_p$-heteroarylene, R$^{15}$ is selected from (R$^{14}$)$_p$-alkylene, (R$^{14}$)$_p$-heteroalkylene, (R$^{14}$)$_p$-arylene, and (R$^{14}$)$_p$-heteroarylene, and p is selected from 0, 1, 2, 3, 4 and 5.

38. A compound of claim 30 wherein R$^8$ is hydrogen.

39. A compound of claim 28 wherein R$^{10}$ is R$^{11}$.

40. A compound of claim 1 wherein R$^4$ and R$^5$ together with the carbon to which they are both attached form a spiro carbocyclic or heterocyclic ring.

41. A compound of claim 1 wherein R$^6$ is selected from hydrogen, R$^{11}$, R$^{12}$ R$^{13}$, R$^{14}$ and R$^{15}$ where R$^{11}$ is selected from alkyl, heteroalkyl, aryl and heteroaryl; R$^{12}$ is selected from (R$^{11}$)$_p$-alkylene, (R$^{11}$)$_p$-heteroalkylene, (R$^{11}$)$_p$-arylene and (R$^{11}$)$_p$-heteroarylene; R$^{13}$ is selected from (R$^{12}$)$_p$-alkylene, (R$^{12}$)$_p$-heteroalkylene, (R$^{12}$)$_p$-arylene, and (R$^{12}$)$_p$-heteroarylene; R$^{14}$ is selected from (R$^{13}$)$_p$-alkylene, (R$^{13}$)$_p$-heteroalkylene, (R$^{13}$)$_p$-arylene, and (R$^{13}$)$_p$-heteroarylene, R$^{15}$ is selected from (R$^{14}$)$_p$-alkylene, (R$^{14}$)$_p$-heteroalkylene, (R$^{14}$)$_p$-arylene, and (R$^{14}$)$_p$-heteroarylene, and p is selected from 0, 1, 2, 3, 4 and 5.

42. A compound of claim 41 wherein R$^6$ is selected from C$_1$–C$_{15}$alkyl, C$_1$–C$_{15}$heteroalkyl, (C$_6$–C$_{10}$aryl)C$_1$–C$_{15}$alkylene, (C$_6$aryl)(C$_6$aryl)C$_1$–C$_{15}$alkylene, (C$_2$–C$_6$heteroaryl)C$_1$–C$_{15}$alkylene, (C$_6$–C$_{10}$aryl)C$_1$–C$_{15}$heteroalkylene, (heteroalkyl)$_p$(C$_6$–C$_{10}$arylene)C$_1$–C$_{15}$alkylene, (heteroalkyl)$_p$(C$_2$–C$_6$heteroarylene)C$_1$–C$_{15}$alkylene, and (heteroalkyl)$_p$(C$_6$arylene)(heteroalkylene)(C$_6$arylene)C$_1$–C$_{15}$alkylene.

43. A compound of claim 41 wherein R$^1$ is hydrogen.

44. A compound of claim 1 wherein n is 0.

45. A compound of claim 1 wherein n is 1.

46. A compound of claim 1 wherein R$^3$ is hydrogen; R$^4$ and R$^5$ are selected from (a) R$^4$ is hydrogen and R$^5$ is hydroxyl or protected hydroxyl and (b) R$^4$ and R$^5$ together form carbonyl; R$^6$ is hydrogen; and n is 0.

47. A compound of claim 46 wherein R$^2$ is —OR$^9$.

48. A compound of claim 47 wherein R$^2$ is —OCH$_2$CH$_2$Si(CH$_3$)$_3$.

49. A compound of claim 46 wherein R$^1$ is

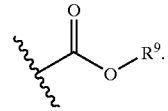

50. A compound of claim 49 wherein R$^9$ is a C$_1$–C$_6$ hydrocarbyl.

51. A compound of claim 50 wherein R$^9$ is selected from n-propyl and —CH$_2$—CH=CH$_2$.

52. A compound of claim 46 wherein R$^1$ is

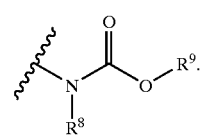

53. A compound of claim 52 wherein R$^8$ is hydrogen and R$^9$ is C$_1$–C$_6$ hydrocarbyl.

54. A compound of claim 53 wherein R$^9$ is —CH$_2$—CH=CH$_2$.

55. 4-Hydroxy-11-oxo-tricyclo[6.2.2.0$^{2,7}$]dodeca-2(7),3,5-triene-9,10-dicarboxylic acid 10-propyl ester 9-(2-trimethylsilanyl-ethyl) ester, and optical isomers, enantiomers and pharmaceutically acceptable salts thereof in isolation or mixture.

56. 4-Hydroxy-11-oxo-tricyclo[6.2.2.0$^{2,7}$]dodeca-2(7),3,5-triene-9,10-dicarboxylic acid 10-allyl ester 9-(2-trimethylsilanyl-ethyl) ester, and optical isomers, enantiomers and pharmaceutically acceptable salts thereof in isolation or mixture.

57. 4,11-Dihydroxy-tricyclo[6.2.2.0$^{2,7}$]dodeca-2(7),3,5-triene-9,10-dicarboxylic acid 10-propyl ester 9-(2-trimethylsilanyl-ethyl) ester and optical isomers, diastereomers, enantiomers and pharmaceutically acceptable salts thereof in isolation or mixture.

58. A compound of claim 1 wherein the stereochemistry of the R$^1$ and C(=O)R$^2$ groups being as shown in formula Ia, with R$^1$ and C(=O)R$^2$ in a cis arrangement, both over the benzo ring substituted with —OR$^6$

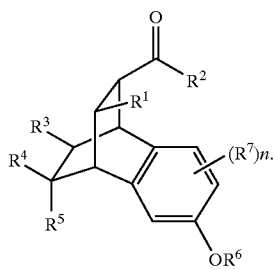

(Ia)

59. A compound of claim 1 wherein the stereochemistry of the R$^1$ and C(=O)R$^2$ groups being as shown in formula Ib, with R$^1$ and C(=O)R$^2$ in a trans arrangement, with only C(=O)R$^2$ over the benzo ring substituted with —OR$^6$

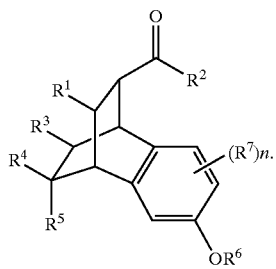

(Ib)

60. A compound of claim 1 with the stereochemistry of the R$^1$ and C(=O)R$^2$ groups being as shown in formula Ic, with R$^1$ and C(=O)R$^2$ in a trans arrangement, with only R$^1$ over the benzo ring substituted with —OR$^6$

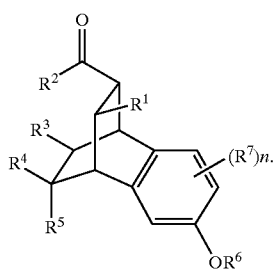

(Ic)

61. A compound of claim 1 with the stereochemistry of the R$^1$ and C(=O)R$^2$ groups being as shown in formula Id, with R$^1$ and C(=O)R$^2$ in a cis arrangement, with neither of the R$^1$ nor C(=O)R$^2$ groups being over the benzo ring substituted with —OR$^6$

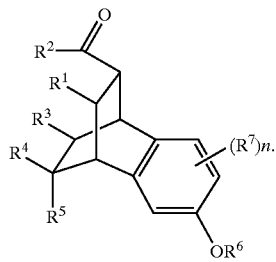

(Id)

62. A composition comprising a compound according to claim 1 and a pharmaceutically acceptable carrier, adjuvant or incipient.

63. A method for inhibiting a TNF-α mediated processes, comprising administering to a patient in need thereof, through a therapeutically or prophylactically acceptable manner, a therapeutically or pharmaceutically effective amount of a composition comprising a compound of claim 1.

64. The method according to claim 63 wherein the administering is selected from transdermal, oral, intravenous, intramuscular, vaginal, rectal, pulmonary, subcutaneous, sublingual and transmucosal administration.

65. A method for inhibiting a CXCR1 and/or CXCR2 mediated processes, comprising administering to a patient in need thereof, through a therapeutically or prophylactically acceptable manner, a therapeutically or pharmaceutically effective amount of a composition comprising a compound of claim 1.

66. The method of claim 65 wherein the method inhibits a CXCR1 mediated processes.

67. The method of claim 65 wherein the method inhibits a CXCR2 mediated processes.

68. The method according to claim 65 wherein the administering is selected from transdermal, oral, intravenous, intramuscular, vaginal, rectal, pulmonary, subcutaneous, sublingual and transmucosal administration.

69. A method for treating an inflammation event, comprising administering to a patient in need thereof, through a therapeutically or prophylactically acceptable manner, a therapeutically or pharmaceutically effective amount of a composition comprising a compound of claim 1.

70. The method according to claim 65 wherein the administering is selected from transdermal, oral, intravenous, intramuscular, vaginal, rectal, pulmonary, subcutaneous, sublingual and transmucosal administration.

71. A library of benzobicyclooctanes where said library comprises a plurality of compounds each having a structure of formula (I)

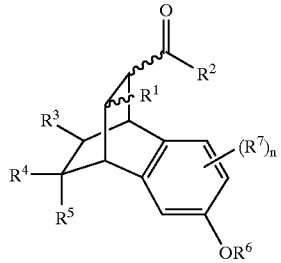

(I)

and optical isomers, diastereomers, enantiomers and pharmaceutically acceptable salts thereof in isolation or mixture, where, independently at each location:

$R^1$ is selected from the following six formulae:

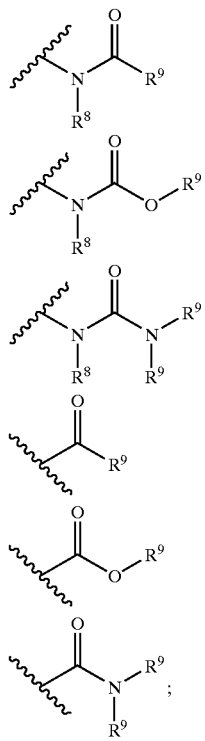

$R^2$ is —$OR^9$ or —$NR^9R^9$;

$R^3$ is selected from hydrogen, halogen, hydroxyl or protected hydroxyl, amino or protected amino, and $C_1$–$C_8$alkyl or $C_1$–$C_8$haloalkyl;

$R^4$ and $R^5$ are independently selected from $R^9$, —$OR^9$, —$NR^9R^9$ and —N=N—$R^9$, or $R^4$ and $R^5$ may together form a group selected from =O, =$CR^8R^8$ and =$NR^{10}$, or $R^4$ and $R^5$ may together with the carbon to which they are both attached form a spiro carbocyclic or heterocyclic ring;

$R^6$ is selected from hydrogen, inorganic groups having 1–8 atoms selected from boron, sulfur, phosphorous, silicon and hydrogen, and organic groups having 1–20 carbons and optionally containing 1–4 heteroatoms selected from nitrogen, oxygen and silicon;

$R^7$ is selected from halogen, hydroxyl or protected hydroxyl, amino or protected amino, and $C_1$–$C_8$alkyl or $C^1$–$C^8$haloalkyl;

$R^8$ is selected from hydrogen, alkyl, aryl and heteroalkyl;

$R^9$ is selected from hydrogen and organic groups having 1–30 carbons and optionally containing 1–4 heteroatoms selected from nitrogen, oxygen and silicon, with the provision that two $R^9$ groups both joined to a common atom may be joined together so as to form a nng with the common atom;

$R^{10}$ is selected from —$R^9$, —$OR^9$, —$NR^9R^9$, —NH—C(O)$R^9$; —NH—C(O)$OR^9$ and —NH—C(S)$NHR^9$; and n is 0, 1, 2 or 3;

with the proviso that when $R^6$ is hydrogen or methyl, and $R^4$ and $R^5$ together form =O or $R^4$ is hydrogen and $R^5$ is hydroxy, and $R^1$ is —C(O)$OR^9$, then $R^2$ is not —OH or —$OCH_3$.

72. A process for preparing a combinatorial library of benzobicyclooctane compounds, wherein said library comprises a plurality of compounds of formula (I) as recited in claim 1, said process comprising the steps:

(a) providing a compound bound to a solid support according to formula (II)

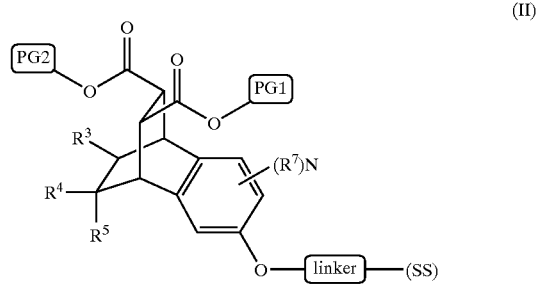

(II)

wherein PG1 and PG2 refer to first and second protecting groups, respectively, where the first protecting group can be removed in the continued presence of the second protecting group, and the second protecting group can be removed in the continued presence of the linker, and (SS) refers to a solid support;

(b) removing the first protecting group but not the second protecting group, to provide a first deprotected product;

(c) reacting the first deprotected product with a plurality of amines of the formula HNRR' to provide a plurality of compounds bound to a solid support, each according to formula (IIa)

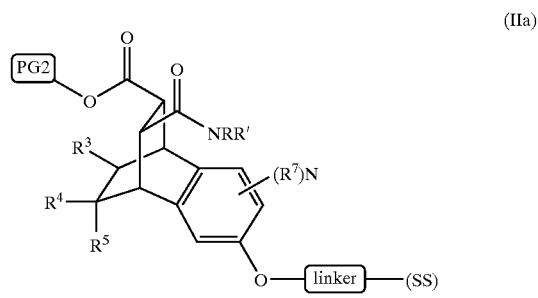

(IIa)

where R and R' are each independently selected from $R^9$;

(d) removing the second protecting group from (IIa) to provide a second deprotected product;

(e) reacting the second deprotected product with a plurality of amines of the formula HNR"R'" to provide a plurality of compounds bound to a solid support, each according to formula (IIb)

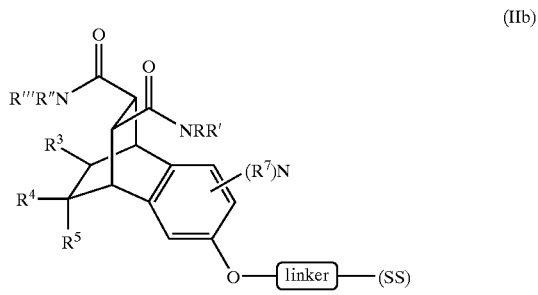

(IIb)

where R' and R'" are each independently selected from $R^9$;

(f) removing the scaffold from the linker to provide a library of compounds according to formula (IIc)

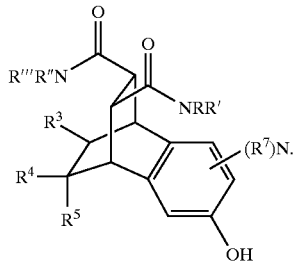

73. The process of claim 72 wherein PG1 is —CH$_2$—CH=CH$_2$.

74. The process of claim 72 wherein PG2 is —CH$_2$CH$_2$—Si(CH$_3$)$_3$.

75. The process of claim 72 wherein linker is

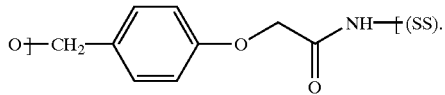

76. The process of claim 72 wherein PG1 is —CH$_2$—CH=CH$_2$; PG2 is —CH$_2$CH$_2$—Si(CH$_3$)$_3$; and linker is

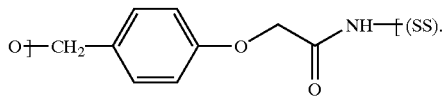

77. The process of claim 72 wherein removing the first protecting group but not the second protecting group, to provide a first deprotected product according to step (b), is accomplished by reacting (II) with Pd(PPh$_3$)$_4$ and N-methylaniline.

78. The process of claim 72 wherein removing the second protecting group from (IIa) to provide a second deprotected product according to step (d) is accomplished by treating (IIa) with tetrabutylammonium fluoride solution.

79. The process of claim 72 wherein removing the scaffold from the solid support to provide a library of compounds according to formula (IIc) is accomplished by treating (IIb) with aqueous trifluoroacetic acid.

80. The process of claim 72 wherein R$^3$ is H, R$^4$ and R$^5$ collectively form =O, and n is zero.

81. A method for identifying a binding partner to a compound of claim 1, wherein the method comprises:
  a. immoblizing proteins known to be involved in the TNF-a signaling pathway onto a suitable carrier; and
  b. passing a solution of said compounds in isolation or mixture over said proteins and analyzing for compound:protein complex formation using surface plasmon resonance.

82. A method for identifying a binding partner to a compound of claim 1, wherein the method comprises:
  a. providing said compound(s) bound to a solid support to provide solid phase compounds;
  b. contacting a cell or cell components with said solid phase compounds in isolation or mixture; and
  c. removing uncomplexed cellular material from said solid phase compounds; and
  d. recovering said binding partner from said solid phase compounds.

* * * * *

UNITED STATES PATENT AND TRADEMARK OFFICE
CERTIFICATE OF CORRECTION

PATENT NO. : 6,906,046 B2
DATED : June 14, 2005
INVENTOR(S) : Randy W. Jackson et al.

It is certified that error appears in the above-identified patent and that said Letters Patent is hereby corrected as shown below:

Title page,
Item [74], *Attorney, Agent, or Firm*, should read -- Jane E. Potter --.
Item [56], References Cited, OTHER PUBLICATIONS,
"Van Broeck et al." reference, should read -- pyran-3-ones and their Diesl-Alder Reactions with Olefinic --.

Signed and Sealed this

Twenty-seventh Day of September, 2005

JON W. DUDAS
*Director of the United States Patent and Trademark Office*